US012630528B2

(12) United States Patent
Yoon et al.

(10) Patent No.: US 12,630,528 B2
(45) Date of Patent: May 19, 2026

(54) AMINO ARYL DERIVATIVE USEFUL AS DIACYLGLYCEROL ACYLTRANSFERASE 2 INHIBITOR AND USE THEREOF

(71) Applicant: LG CHEM, LTD., Seoul (KR)

(72) Inventors: Seung Hyun Yoon, Seoul (KR); Hyun Woo Joo, Seoul (KR); Bo Kyung Seo, Seoul (KR); Eun Jin Lee, Seoul (KR); Jin Young Jung, Seoul (KR); Su Young Yoon, Seoul (KR); Woo Young Cho, Seoul (KR)

(73) Assignee: LG CHEM, LTD., Seoul (KR)

( * ) Notice: Subject to any disclaimer, the term of this patent is extended or adjusted under 35 U.S.C. 154(b) by 125 days.

(21) Appl. No.: 17/788,385

(22) PCT Filed: Dec. 22, 2020

(86) PCT No.: PCT/KR2020/018929

§ 371 (c)(1),
(2) Date: Jun. 23, 2022

(87) PCT Pub. No.: WO2021/133035

PCT Pub. Date: Jul. 1, 2021

(65) Prior Publication Data

US 2023/0078941 A1 Mar. 16, 2023

(30) Foreign Application Priority Data

Dec. 23, 2019 (KR) ........................ 10-2019-0173487

(51) Int. Cl.

| | |
|---|---|
| ***C07D 401/14*** | (2006.01) |
| ***A61P 3/00*** | (2006.01) |
| ***C07D 401/04*** | (2006.01) |
| ***C07D 413/14*** | (2006.01) |
| ***C07D 417/14*** | (2006.01) |
| *A61K 31/4545* | (2006.01) |
| *A61K 31/497* | (2006.01) |
| *A61K 31/506* | (2006.01) |

(52) U.S. Cl.

CPC ......... *C07D 401/14* (2013.01); *C07D 401/04* (2013.01); *C07D 413/14* (2013.01); *C07D 417/14* (2013.01)

(58) Field of Classification Search

CPC .. C07D 401/14; C07D 401/04; C07D 413/14; C07D 417/14

See application file for complete search history.

(56) References Cited

U.S. PATENT DOCUMENTS

| | | | |
|---|---|---|---|
| 2010/0113782 A1 | 5/2010 | Bolin et al. | |
| 2013/0131035 A1 | 5/2013 | Bregman et al. | |
| 2015/0259323 A1 | 9/2015 | Cabral et al. | |
| 2018/0051012 A1 | 2/2018 | Boehm et al. | |

FOREIGN PATENT DOCUMENTS

| | | | | |
|---|---|---|---|---|
| CL | 2014002541 A1 | 1/2015 | | |
| CL | 2022000835 A1 | 1/2023 | | |
| JP | 2013-519732 A | 5/2013 | | |
| JP | 2017-507979 A | 3/2017 | | |
| JP | 2019-524831 A | 9/2019 | | |
| KR | 10-2016-0115997 A | 10/2016 | | |
| KR | 10-2019-0035798 A | 4/2019 | | |
| KR | 2019-0035897 A | 4/2019 | | |
| NC | 20160001992 A | 9/2016 | | |
| NC | 20190001421 A | 2/2019 | | |
| NC | 20220004286 A | 4/2022 | | |
| WO | 2007126957 A2 | 11/2007 | | |
| WO | 2009126624 A1 | 10/2009 | | |
| WO | WO-2010022055 A2 * | 2/2010 | .............. | A61P 25/04 |
| WO | 2010-056506 A1 | 5/2010 | | |
| WO | 2011103196 A1 | 8/2011 | | |
| WO | 2011139107 A2 | 11/2011 | | |
| WO | 2013-068328 A1 | 5/2013 | | |
| WO | 2013150416 A1 | 10/2013 | | |
| WO | 2014074761 A2 | 5/2014 | | |
| WO | 2015140658 A1 | 9/2015 | | |
| WO | 2016187384 A1 | 11/2016 | | |
| WO | 2018033832 A1 | 2/2018 | | |
| WO | 2019220101 A1 | 11/2019 | | |
| WO | 2021064590 A1 | 4/2021 | | |

OTHER PUBLICATIONS

Bluestone JA, Herold K, Eisenbarth G. Genetics, pathogenesis and clinical interventions in type 1 diabetes. Nature. Apr. 29, 2010; 464(7293):1293-300. doi: 10.1038/nature08933. PMID: 20432533; PMCID: PMC4959889. (Year: 2010).*

Examination Report issued for AU Application No. 2020414202 on May 18, 2023, 3 pages.

Extended European Search Report issued for EP Application No. 20906835.2 on Dec. 15, 2022, 6 pages.

Notice of Reasons for Refusal issued for JP Application No. 2022-539025 on Jul. 20, 2023, 4 pages.

International Search Report issued for International Application No. PCT/KR2020/018929 on Apr. 8, 2021, 8 pages.

CAS Registry No. 1211864-69-5, Mar. 19, 2010, (1 page).

* cited by examiner

*Primary Examiner* — Jeffrey H Murray

*Assistant Examiner* — Kevin S Martin

(74) *Attorney, Agent, or Firm* — ROTHWELL, FIGG, ERNST & MANBECK, P.C.

(57) ABSTRACT

The present invention relates to an amino aryl derivative compound, represented by chemical formula (1) and exhibiting the activity of a diacylglycerol acyltransferase 2 (DGAT2) inhibitor, a pharmaceutical composition comprising same as an active ingredient, and a use thereof.

5 Claims, No Drawings

Specification includes a Sequence Listing.

AMINO ARYL DERIVATIVE USEFUL AS DIACYLGLYCEROL ACYLTRANSFERASE 2 INHIBITOR AND USE THEREOF

CROSS REFERENCE TO RELATED APPLICATION(S)

This application is a 35 U.S.C. 371 National Phase Entry Application from PCT/KR2020/018929 filed on Dec. 22, 2020, which claims priority to and the benefits of Korean Patent Application No. 10-2019-0173487, filed with the Korean Intellectual Property Office on Dec. 23, 2019, the entire contents of which are incorporated herein by reference.

The instant application contains a Sequence Listing which has been submitted and is hereby incorporated by reference in its entirety. Said Sequence Listing, created on Jun. 10, 2025, is named OPP20240195US.txt and is 727 bytes in size.

TECHNICAL FIELD

The present invention relates to an amino aryl derivative compound represented by Formula (1) showing inhibitory activity against diacylglycerol acyltransferase 2 (DGAT2), a pharmaceutical composition comprising the same as an active ingredient, and use thereof.

BACKGROUND ART

The improvement of living standards according to economic development, frequent consumption of instant foods, and changes to meat-based dietary habits caused excessive accumulation of caloric energy in the body. These changes in the dietary life of modern people have also led to a reduction in caloric energy consumption due to lack of exercise, leading to a serious prevalence of metabolic diseases such as obesity, hyperlipidemia, diabetes, cardiovascular disease and coronary artery disease. Specifically, obesity is one of the rapidly increasing diseases and is reported to be the cause of metabolic diseases such as diabetes. The development of therapeutic agents for metabolic diseases by controlling the functions of enzymes involved in the biosynthetic pathway of triglycerides—which is the main cause of obesity—is drawing attention.

Neutral fats, such as triglycerides (TG), play a very important role in the storage function as an energy source in the body. However, when neutral fats are excessively accumulated in organs or tissues, they cause obesity, hypertriglyceridemia, fatty liver, etc., thereby causing serious diseases such as diabetes, arteriosclerosis, metabolic abnormalities and hypofunction of organs. Diacylglycerol acyltransferase—which is a crucial enzyme in the biosynthesis of triglycerides—is found in various tissues of mammals, and is an enzyme that synthesizes TG by binding fatty acyl-CoA to the hydroxyl group of diacylglycerol in the final step of the glycerol phosphate pathway which is the main pathway for triglyceride synthesis. At present, two isoforms—DGAT1 and DGAT2—are known. Although their biochemical functions are similar, there is a difference in that DGAT1 is mainly expressed in the small intestine and adipose tissue, and DGAT2 is mainly expressed in the liver and adipose tissue. In addition, with respect to the gene family, DGAT1 belongs to the ACAT family, and DGAT2 belongs to the MGAT family. As such, it is expected that their role in TG biosynthesis is also different.

Several studies, including animal studies, have shown that DGAT2 primarily contributes to the biosynthesis of TG in vivo. Unlike DGAT2 knockout mice—which hardly synthesize TG and die shortly after birth due to an abnormal skin layer, DGAT1 knockout mice showed a slight decrease in TG levels and no problems with the survival of the mice (Stone S J et al., 2000. Nat. Genet. 25: 87-90). In addition, as a result of reducing the expression level of DGAT1 or DGAT2 by using antisense oligonucleotide (ASO) in an animal model of fatty liver, fatty liver symptoms were alleviated and the rate of glucose production in the liver was significantly reduced only when the amount of DGAT2 was reduced (Choi C S et al., 2007. Hepatology. 45: 1366-74).

The underlying molecular mechanisms have not been fully elucidated, but it has been thought that the inhibition of DGAT2 results in down-regulation of the expression of multiple genes encoding proteins involved in lipid production, such as sterol regulatory element-binding proteins 1c (SREBP1c) and stearoyl CoA-desaturase 1 (SCD1). At the same time, it has been thought that the oxidative pathway was induced by an increase in genes such as carnitine palmitoyltransferase 1 (CPT1). This change in turn leads to a decrease in hepatic DAG and TAG lipid levels, and thus improved insulin responsiveness in the liver. In addition, the inhibition of DGAT2 inhibited hepatic VLDL TAG secretion and reduced circulating cholesterol levels. Finally, plasma apolipoprotein B (APOB) levels were suppressed, which was thought to be due to the reduced supply of TAG in the lipidation of the newly synthesized APOB protein. That is, when DGAT2 is inhibited, beneficial effects on both glycemic control and plasma cholesterol profile showed, which means that the inhibition of DGAT2 can be applied to the treatment of metabolic disorders.

DISCLOSURE OF INVENTION

Technical Problem

An object of the present invention is to provide a novel amino aryl derivative compound represented by Formula (1) showing inhibitory activity against diacylglycerol acyltransferase 2 (DGAT2).

Another object of the present invention is to provide a method of preparing the amino aryl derivative compound.

Still another object of the present invention is to provide a pharmaceutical composition for the treatment of metabolic diseases associated with DGAT2 comprising the amino aryl derivative compound as an active ingredient, and a method for preparing thereof.

Still another object of the present invention is to provide a method for treating metabolic diseases associated with DGAT2 in a subject in which efficacy in animal models of diseases is improved as well as efficacy and convenience in taking in the subject are improved by using the amino aryl derivative compound as an active ingredient having improve physical and chemical properties compared to conventional compounds.

Solution to Problem

In order to achieve the above object, the present invention provides a compound of the following Formula (1), or a pharmaceutically acceptable salt or isomer:

[Formula (1) ]

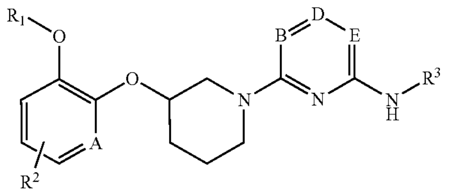

wherein

A and D are each independently CH or N;

B and E are each independently CH, C-halogen, C-haloalkyl or N;

$R^1$ is alkyl, cycloalkyl or haloalkyl;

$R^2$ is hydrogen, halogen or alkyl;

$R^3$ is -G-J;

wherein G is aryl, arylene, arylene-alkylene, heteroaryl or heteroarylene;

J is hydrogen, amino, aminocarbonyl, alkoxy-alkyl, cycloalkyl, cycloalkyl-oxy, heterocycloalkyl, aryl, aryl-oxy, aryl-alkoxy, heteroaryl, heteroaryl-amino, carboxyalkyl, carboxyalkenyl, carboxyalkyl-aryl, carboxyalkoxy-aryl, carboxyalkyl-heterocycloalkyl, carboxyalkenyl-heterocycloalkyl, carboxyalkoxy-heterocycloalkyl, carboxyalkyl-amino-aryl, carboxyalkyl-aryl-oxy or carboxyalkyl-heteroaryl;

wherein the alkyl, alkoxy, cycloalkyl, aryl, heterocycloalkyl, heteroaryl or heteroarylene is optionally substituted with one or more substituents selected from halo, —COOH, alkyl, alkoxy, haloalkyl, alkylsulfonyl and heteroaryl-alkyl; and the heterocycloalkyl, heteroaryl and heteroarylene include one or more heteroatoms selected from N, O and S.

The compound of Formula (1) according to the present invention may form a pharmaceutically acceptable salt. A pharmaceutically acceptable salt may include an acid-addition salt which is formed from an inorganic acid such as hydrochloric acid, sulfuric acid, nitric acid, phosphoric acid, hydrobromic acid and hydroiodic acid; an organic acid such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acid such as methanesulfonic acid, ethanesulfonic acid, benzenesulfonic acid and p-toluenesulfonic acid, which form non-toxic acid-addition salt including pharmaceutically acceptable anion. In addition, a pharmaceutically acceptable carboxylic acid salt includes the salt with alkali metal or alkali earth metal such as lithium, sodium, potassium, calcium and magnesium; salts with amino acid such as lysine, arginine and guanidine; an organic salt such as dicyclohexylamine, N-methyl-D-glucamine, tris(hydroxymethyl)methylamine, diethanolamine, choline and triethylamine. The compound of Formula (1) according to the present invention may be converted into their salts by conventional methods.

Meanwhile, since the compound of Formula (1) according to the present invention can have an asymmetric carbon center and asymmetric axis or plane, they can exist as E- or Z-isomer, R- or S-isomer, racemic mixtures or diastereoisomer mixtures and each diastereoisomer, all of which are within the scope of the present invention.

Herein, unless indicated otherwise, the term “the compound of Formula (1)” is used to mean all the compounds of Formula (1), including the pharmaceutically acceptable salts and isomers thereof.

Herein, the following concepts defined to the substituents are used to define the compound of Formula (1).

The term “halogen” or “halo” means fluoride (F), chlorine (Cl), bromine (Br) or iodine (I).

The term “alkyl” or “alkylene” means straight or branched hydrocarbons, may include a single bond, a double bond or a triple bond, and is preferably $C_1$-$C_{10}$ alkyl or $C_1$-$C_{10}$ alkylene, or $C_1$-$C_7$ alkyl or $C_1$-$C_7$ alkylene. Examples of alkyl include, but are not limited to, methyl, ethyl, n-propyl, i-propyl, n-butyl, i-butyl, tert-butyl, acetylene, vinyl, trifluoromethyl and the like.

The term “alkenyl” means straight or branched hydrocarbons having at least one carbon-carbon double bond, and is preferably $C_2$-$C_{10}$ alkenyl or $C_2$-$C_7$ alkenyl. Examples of alkenyl include, but are not limited to, vinyl, allyl, butenyl, isopropenyl, isobutenyl and the like.

The term “cycloalkyl” means partially or fully saturated single or fused ring hydrocarbons, and is preferably $C_3$-$C_{10}$-cycloalkyl. Examples of cycloalkyl include, but are not limited to, cyclopropyl, cyclobutyl, cyclopentyl, cyclohexyl, cycloheptyl and the like.

Unless otherwise defined, the term “alkoxy” means alkyloxy having 1 to 10 carbon atoms.

The term “aryl” or “arylene” means aromatic hydrocarbons, preferably $C_5$-$C_{12}$ aryl or $C_5$-$C_{12}$ arylene, more preferably $C_6$-$C_{10}$ aryl or $C_6$-$C_{10}$ arylene, and includes, but is not limited to, phenyl, naphthyl and the like.

The term “heteroaryl” or “heteroarylene” means 3- to 12-membered, more preferably 5- to 12-membered aromatic hydrocarbons which form a single or fused ring—which may be fused with benzo or $C_3$-$C_8$ cycloalkyl—including one or more heteroatoms selected from N, O and S as a ring member. Examples of heteroaryl include, but are not limited to, pyridinyl, pyrimidinyl, pyridazinyl, pyrazinyl, oxadiazolyl, isoxadiazolyl, tetrazolyl, triazolyl, indolyl, indazolyl, isoxazolyl, oxazolyl, thiazolyl, isothiazolyl, furanyl, benzofuranyl, imidazolyl, thiophenyl, benzthiazole, benzimidazole, quinolinyl, indolinyl, 1,2,3,4-tetrahydroisoquinolyl, 3,4-dihydroisoquinolinyl, thiazolopyridyl, 2,3-dihydrobenzofuran, 2,3-dihydrothiophene, 2,3-dihydroindole, benzo[1,3]dioxin, chroman, thiochroman, 1,2,3,4-tetrahydroquinoline, 4H-benzo[1,3]dioxin, 2,3-dihydrobenzo[1,4]-dioxin, 6,7-dihydro-5H-cyclopenta[d]pyrimidine and the like.

The term “heterocycloalkyl” means partially or fully saturated hydrocarbons which form a single or fused ring including one or more heteroatoms selected from N, O and S, and is preferably 3- to 12-membered heterocycloalkyl or 5- to 12-membered heterocycloalkyl. Examples of heterocycloalkyl include, but are not limited to, pyrrolidinyl, piperidinyl, morpholinyl, imidazolinyl, piperazinyl, tetrahydrofuran, tetrahydrothiofuran and the like.

Aryl-alkoxy, alkyl-aryl, heteroaryl-alkyl and alkyl-heteroaryl mean groups which are formed by the combination of the above-mentioned aryl or heteroaryl with alkyl or alkoxy. Examples include, but are not limited to, benzyl, methoxyphenyl, thiophenemethyl, pyrimidine methyl and the like.

According to one embodiment of the present invention, in the above Formula (1)

A and D are each independently CH or N;

B and E are each independently CH, C-halogen, C-halo-$C_1$-$C_7$ alkyl or N;

$R^1$ is $C_1$-$C_7$ alkyl, $C_3$-$C_7$ cycloalkyl or halo-$C_1$-$C_7$ alkyl;

$R^2$ is hydrogen, halogen or $C_1$-$C_7$ alkyl;

$R^3$ is -G-J;

wherein G is $C_6$-$C_{10}$ aryl, $C_6$-$C_{10}$ arylene, $C_6$-$C_{10}$ arylene-$C_1$-$C_7$ alkylene, 5- to 12-membered heteroaryl or 5- to 12-membered heteroarylene;

J is hydrogen, amino, aminocarbonyl, $C_1$-$C_7$ alkoxy-$C_1$-$C_7$ alkyl, $C_3$-$C_{10}$ cycloalkyl, $C_3$-$C_{10}$ cycloalkyl-oxy, 5- to 12-membered heterocycloalkyl, $C_6$-$C_{10}$ aryl, $C_6$-$C_{10}$ aryl-oxy, $C_6$-$C_{10}$ aryl-$C_1$-$C_7$ alkoxy, 5- to 12-membered heteroaryl, 5- to 12-membered heteroaryl-amino, carboxy-$C_1$-$C_7$ alkyl, carboxy-$C_2$-$C_7$ alkenyl, carboxy-$C_1$-$C_7$ alkyl-$C_6$-$C_{10}$ aryl, carboxy-$C_1$-$C_7$ alkoxy-$C_6$-$C_{10}$ aryl, carboxy-$C_1$-$C_7$ alkyl-5- to 12-membered heterocycloalkyl, carboxy-$C_2$-$C_7$ alkenyl-5- to 12-membered heterocycloalkyl, carboxy-$C_1$-$C_7$ alkoxy-5- to 12-membered heterocycloalkyl, carboxy-$C_1$-$C_7$ alkyl-amino-$C_6$-$C_{10}$ aryl, carboxy-$C_1$-$C_7$ alkyl-$C_6$-$C_{10}$ aryl-oxy or carboxy-$C_1$-$C_7$ alkyl-5- to 12-membered heteroaryl;

wherein the alkyl, alkoxy, cycloalkyl, aryl, heterocycloalkyl, heteroaryl or heteroarylene is optionally substituted with 1 to 4 substituents selected from halo, —COOH, $C_1$-$C_7$ alkyl, $C_1$-$C_7$ alkoxy, halo-$C_1$-$C_7$ alkyl, $C_1$-$C_7$ alkylsulfonyl and 5- to 12-membered heteroaryl-$C_1$-$C_7$ alkyl; and the heterocycloalkyl, heteroaryl and heteroarylene include 1 to 5 heteroatoms selected from N, O and S.

Representative compounds of Formula (1) according to the present invention include, but are not limited to, the following compounds:

(R)-2-((6-(3-(2-ethoxyphenoxy)piperidin-1-yl)pyrazin-2-yl)amino)thiazole-5-carboxylic acid;

(R)—N-(6-(3-(2-ethoxyphenoxy)piperidin-1-yl)pyrazin-2-yl)-4,5-dimethylthiazol-2-amine;

(R)—N-(6-(3-(2-ethoxyphenoxy)piperidin-1-yl)pyrazin-2-yl)thiazol-2-amine;

(R)—N-(6-(3-(2-ethoxyphenoxy)piperidin-1-yl)pyrazin-2-yl)-4-phenylthiazol-2-amine;

(R)—N-(6-(3-(2-ethoxyphenoxy)piperidin-1-yl)pyrazin-2-yl)benzo[d]thiazol-2-amine;

(R)—N-(6-(3-(2-ethoxyphenoxy)piperidin-1-yl)pyrazin-2-yl)-6-methoxybenzo[d]thiazol-2-amine;

(R)—N-(6-(3-(2-ethoxyphenoxy)piperidin-1-yl)pyrazin-2-yl)-6-(methanesulfonyl)benzo[d]thiazol-2-amine;

(R)—N-(6-(3-(2-ethoxyphenoxy)piperidin-1-yl)pyrazin-2-yl)-3-(1-(2-methoxyethoxy)-2-methylpropan-2-yl)isooxazol-5-amine;

(R)—N-(6-(3-(2-ethoxyphenoxy)piperidin-1-yl)pyrazin-2-yl)-4-phenyloxazol-2-amine;

(R)—N-(6-(3-(2-ethoxyphenoxy)piperidin-1-yl)pyrazin-2-yl)benzo[d]oxazol-2-amine;

(R)-5-chloro-N-(6-(3-(2-ethoxyphenoxy)piperidin-1-yl)pyrazin-2-yl)benzo[d]oxazol-2-amine;

(R)-2-(2-((6-(3-(2-ethoxyphenoxy)piperidin-1-yl)pyrazin-2-yl)amino)benzo[d]oxazol-5-yl)acetic acid;

(R)-2-(2-((6-(3-(2-ethoxyphenoxy)piperidin-1-yl)pyrazin-2-yl)amino)benzo[d]oxazol-5-yl)-2-methylpropanoic acid;

(R)-3-(2-((6-(3-(2-ethoxyphenoxy)piperidin-1-yl)pyrazin-2-yl)amino)benzo[d]oxazol-5-yl)-2,2-dimethylpropanoic acid;

(R,E)-3-(2-((6-(3-(2-ethoxyphenoxy)piperidin-1-yl)pyrazin-2-yl)amino)benzo[d]oxazol-5-yl)acrylic acid;

(R)-3-(2-((6-(3-(2-ethoxyphenoxy)piperidin-1-yl)pyrazin-2-yl)amino)benzo[d]oxazol-5-yl)propanoic acid;

(R)-2-(2-((6-(3-(2-ethoxyphenoxy)piperidin-1-yl)pyrazin-2-yl)amino)benzo[d]oxazol-6-yl)-2-methylpropanoic acid;

(R)-3-(2-((6-(3-(2-ethoxyphenoxy)piperidin-1-yl)pyrazin-2-yl)amino)benzo[d]oxazol-6-yl)propanoic acid;

(R)-6-(3-(2-ethoxyphenoxy)piperidin-1-yl)-N-(1H-pyrazol-3-yl)pyrazin-2-amine;

(R)-2-(3-((6-(3-(2-ethoxyphenoxy)piperidin-1-yl)pyrazin-2-yl)amino)-1H-pyrazol-1-yl)acetic acid;

(R)-3-(3-((6-(3-(2-ethoxyphenoxy)piperidin-1-yl)pyrazin-2-yl)amino)-1H-pyrazol-1-yl)-2,2-dimethylpropanoic acid;

(R)-3-(3-(6-((4-(3-(2-ethoxyphenoxy)piperidin-1-yl)-5-fluoropyrimidin-2-yl)amino)pyridin-2-yl)phenyl)-2,2-dimethylpropanoic acid;

(R)-6-(3-(2-ethoxyphenoxy)piperidin-1-yl)-N-(1-methyl-1H-tetrazol-5-yl)pyrazin-2-amine;

(R)—N-6-(3-(2-ethoxyphenoxy)piperidin-1-yl)-N-phenylpyrazin-2-amine;

(R)—N-(4-((6-(3-(2-ethoxyphenoxy)piperidin-1-yl)pyrazin-2-yl)amino)phenyl)methanesulfonamide;

(R)-2-(4-((6-(3-(2-ethoxyphenoxy)piperidin-1-yl)pyrazin-2-yl)amino)phenyl)-N-(pyridin-4-ylmethyl)acetamide;

(R)-2-(4-((6-(3-(2-ethoxyphenoxy)piperidin-1-yl)pyrazin-2-yl)amino)phenyl)-2-methylpropanoic acid;

(R)-2-(4-((6-(3-(2-ethoxyphenoxy)pyridin-1-yl)pyrazin-2-yl)amino)phenyl)-2-methylpropanoic acid;

(R)-2-(3-((6-(3-(2-ethoxyphenoxy)piperidin-1-yl)pyrazin-2-yl)amino)phenyl)-2-methylpropanoic acid;

(R)-3-(3'-((6-(3-(2-ethoxyphenoxy)piperidin-1-yl)pyrazin-2-yl)amino)-[1,1'-biphenyl]-4-yl)-2,2-dimethylpropanoic acid;

(R)-6-(3-(2-ethoxyphenoxy)piperidin-1-yl)-N-(pyridin-2-yl)pyrazin-2-amine;

(R)-6-((6-(3-(2-ethoxyphenoxy)piperidin-1-yl)pyrazin-2-yl)amino)nicotinic acid;

(R)-2-((6-(3-(2-ethoxyphenoxy)piperidin-1-yl)pyrazin-2-yl)amino)isonicotinic acid;

(R)-2-((6-(3-(2-ethoxyphenoxy)piperidin-1-yl)pyrazin-2-yl)amino)nicotinic acid;

(R)-2-(2-((6-(3-(2-ethoxyphenoxy)piperidin-1-yl)pyrazin-2-yl)amino)pyridin-4-yl)-2-methylpropanoic acid;

(R)-2-(6-((6-(3-(2-ethoxyphenoxy)piperidin-1-yl)pyrazin-2-yl)amino)pyridin-3-yl)acetic acid;

(R,E)-3-(6-((6-(3-(2-ethoxyphenoxy)piperidin-1-yl)pyrazin-2-yl)amino)pyridin-3-yl)acrylic acid;

(R)-3-(6-((6-(3-(2-ethoxyphenoxy)piperidin-1-yl)pyrazin-2-yl)amino)pyridin-3-yl)propanoic acid;

(R)-3-(2-((6-(3-(2-ethoxyphenoxy)piperidin-1-yl)pyrazin-2-yl)amino)pyridin-4-yl)-2,2-dimethylpropanoic acid;

(R)-6-(3-(2-ethoxyphenoxy)piperidin-1-yl)-N-(5-phenylpyridin-2-yl)pyrazin-2-amine;

(R)-6-(3-(2-ethoxyphenoxy)piperidin-1-yl)-N-(4-phenylpyridin-2-yl)pyrazin-2-amine;

(R)-2-(3-(2-((6-(3-(2-ethoxyphenoxy)piperidin-1-yl)pyrazin-2-yl)amino)pyridin-4-yl)phenyl)-2-methylpropanoic acid;

(R)-2-(3-(2-((6-(3-(2-ethoxyphenoxy)piperidin-1-yl)pyrazin-2-yl)amino)pyridin-4-yl)phenyl)-2-methylpropanoic acid;

(R)-3-(3-(2-((6-(3-(2-ethoxyphenoxy)piperidin-1-yl)pyrazin-2-yl)amino)pyridin-4-yl)phenyl)-2,2-dimethylpropanoic acid;

(R)-3-(4-(2-((6-(3-(2-ethoxyphenoxy)piperidin-1-yl)pyrazin-2-yl)amino)pyridin-4-yl)phenyl)-2,2-dimethylpropanoic acid;

(R)-3-(3-(2-((6-(3-(2-ethoxyphenoxy)piperidin-1-yl)pyrazin-2-yl)amino)pyridin-4-yl)phenyl)propanoic acid;
(R)-3-(3-(5-((6-(3-(2-ethoxyphenoxy)piperidin-1-yl)pyrazin-2-yl)amino)pyridin-3-yl)phenyl)-2,2-dimethylpropanoic acid;
(R)-3-(3-(5-((6-(3-(2-ethoxyphenoxy)piperidin-1-yl)pyrazin-2-yl)amino)pyridin-2-yl)phenyl)-2,2-dimethylpropanoic acid;
(R)-2-(6-((6-(3-(2-ethoxyphenoxy)piperidin-1-yl)pyrazin-2-yl)amino)pyridin-3-yl)phenyl)-2-methylpropanoic acid;
(R)-2-(6-((6-(3-(2-ethoxyphenoxy)piperidin-1-yl)pyrazin-2-yl)amino)pyridin-2-yl)-2-methylpropanoic acid;
(R)-3-(6-((6-(3-(2-ethoxyphenoxy)piperidin-1-yl)pyrazin-2-yl)amino)pyridin-2-yl)-2,2-dimethylpropanoic acid;
1-(6-((6-((R)-3-(2-ethoxyphenoxy)piperidin-1-yl)pyrazin-2-yl)amino)pyridin-2-yl)pyrrolidine-3-carboxylic acid;
1-(6-((6-((R)-3-(2-ethoxyphenoxy)piperidin-1-yl)pyrazin-2-yl)amino)pyridin-2-yl)-3-methylpyrrolidine-3-carboxylic acid;
1-(6-((6-((R)-3-(2-ethoxyphenoxy)piperidin-1-yl)pyrazin-2-yl)amino)pyridin-2-yl)piperidine-3-carboxylic acid;
(R)-1-(6-((6-((R)-3-(2-ethoxyphenoxy)piperidin-1-yl)pyrazin-2-yl)amino)pyridin-2-yl)piperidine-3-carboxylic acid;
(R)-1-(6-((6-(3-(2-ethoxyphenoxy)piperidin-1-yl)pyrazin-2-yl)amino)pyridin-2-yl)piperidine-4-carboxylic acid;
(R)-2-(1-(6-((6-(3-(2-ethoxyphenoxy)piperidin-1-yl)pyrazin-2-yl)amino)pyridin-2-yl)piperidin-4-yl)acetic acid;
(R)-2-(1-(6-((6-(3-(2-ethoxyphenoxy)piperidin-1-yl)pyrazin-2-yl)amino)pyridin-2-yl)piperidin-4-yl)-2-methylpropanoic acid;
2-(((S)-1-(6-((6-((R)-3-(2-ethoxyphenoxy)piperidin-1-yl)pyrazin-2-yl)amino)pyridin-2-yl)piperidin-3-yl)acetic acid;
(R)-2-(3-(6-((6-(3-(2-ethoxyphenoxy)piperidin-1-yl)pyrazin-2-yl)amino)pyridin-2-yl)phenyl)-2-methylpropanoic acid;
(R)-2-(4-(6-((6-(3-(2-ethoxyphenoxy)piperidin-1-yl)pyrazin-2-yl)amino)pyridin-2-yl)phenyl)-2-methylpropanoic acid;
(R)-2-(4-(6-((6-(3-((3-ethoxypyridin-2-yl)oxy)piperidin-1-yl)pyrazin-2-yl)amino)pyridin-2-yl)phenyl)-2-methylpropanoic acid;
(R)-3-(3-(6-((6-(3-(2-ethoxyphenoxy)piperidin-1-yl)pyrazin-2-yl)amino)pyridin-2-yl)phenyl)-2,2-dimethylpropanoic acid;
(R)-3-(3-(6-((6-(3-((3-ethoxypyridin-2-yl)oxy)piperidin-1-yl)pyrazin-2-yl)amino)pyridin-2-yl)phenyl)-2,2-dimethylpropanoic acid;
(R)-3-(3-(6-((6-(3-(2-ethoxyphenoxy)piperidin-1-yl)pyridin-2-yl)amino)pyridin-2-yl)phenyl)-2,2-dimethylpropanoic acid;
(R)-3-(3-(6-((2-(3-(2-ethoxyphenoxy)piperidin-1-yl)pyrimidin-4-yl)amino)pyridin-2-yl)phenyl)-2,2-dimethylpropanoic acid;
(R)-3-(3-(6-((6-(3-(2-ethoxyphenoxy)piperidin-1-yl)pyrimidin-2-yl)amino)pyridin-2-yl)phenyl)-2,2-dimethylpropanoic acid;
(R)-3-(3-(6-((4-(3-((3-ethoxypyridin-2-yl)oxy)piperidin-1-yl)pyrimidin-2-yl)amino)pyridin-2-yl)phenyl)-2,2-dimethylpropanoic acid;
(R)-3-(3-((6-(3-(2-ethoxyphenoxy)piperidin-1-yl)pyrazin-2-yl)amino)-1H-pyrazol-1-yl)phenyl)-2,2-dimethylpropanoic acid;
(R)-3-(3-(6-((2-(3-(2-ethoxyphenoxy)piperidin-1-yl)-5-(trifluoromethyl)pyrimidin-4-yl)amino)pyridin-2-yl)phenyl)-2,2-dimethylpropanoic acid;
(R)-3-(3-(6-((4-(3-(2-ethoxyphenoxy)piperidin-1-yl)-5-(trifluoromethyl)pyrimidin-2-yl)amino)pyridin-2-yl)phenyl)-2,2-dimethylpropanoic acid;
(R)-3-(4-(6-((6-(3-(2-ethoxyphenoxy)piperidin-1-yl)pyrazin-2-yl)amino)pyridin-2-yl)phenyl)-2,2-dimethylpropanoic acid;
(R)-(4-(6-((6-(3-(2-ethoxyphenoxy)piperidin-1-yl)pyrazin-2-yl)amino)pyridin-2-yl)phenyl)glycine;
(R)-(4-(6-((6-(3-((3-ethoxypyridin-2-yl)oxy)piperidin-1-yl)pyrazin-2-yl)amino)pyridin-2-yl)phenyl)glycine;
(R)-(4-(6-((2-(3-(2-ethoxyphenoxy)piperidin-1-yl)pyrimidin-4-yl)amino)pyridin-2-yl)phenyl)glycine;
(R)-(4-(6-((4-(3-(2-ethoxyphenoxy)piperidin-1-yl)pyrazin-2-yl)amino)pyridin-2-yl)phenyl)glycine;
(R)-2-((4-(6-((6-(3-(2-ethoxyphenoxy)piperidin-1-yl)pyrazin-2-yl)amino)pyridin-2-yl)phenyl)amino)-2-methylpropanoic acid;
(R)-3-(3-(6-((6-(3-(2-ethoxyphenoxy)piperidin-1-yl)pyrazin-2-yl)amino)pyridin-2-yl)-4-fluorophenyl)-2,2-dimethylpropanoic acid;
(R)-3-(3-(6-((6-(3-((3-ethoxypyridin-2-yl)oxy)piperidin-1-yl)pyrazin-2-yl)amino)pyridin-2-yl)-4-fluorophenyl)-2,2-dimethylpropanoic acid;
(R)-2-(3-(6-((6-(3-(2-ethoxyphenoxy)piperidin-1-yl)pyrazin-2-yl)amino)pyridin-2-yl)phenoxy)-2-methylpropanoic acid;
(R)-2-(3-(6-((6-(3-((3-ethoxypyridin-2-yl)oxy)piperidin-1-yl)pyrazin-2-yl)amino)pyridin-2-yl)phenoxy)-2-methylpropanoic acid;
(R)-2-(4-(6-((6-(3-(2-ethoxyphenoxy)piperidin-1-yl)pyrazin-2-yl)amino)pyridin-2-yl)phenoxy)-2-methylpropanoic acid;
(R)-2-(4-(6-((6-(3-((3-ethoxypyridin-2-yl)oxy)piperidin-1-yl)pyrazin-2-yl)amino)pyridin-2-yl)phenoxy)-2-methylpropanoic acid;
(R)-2-(3-(6-((6-(3-(2-ethoxyphenoxy)piperidin-1-yl)pyrazin-2-yl)amino)pyridin-2-yl)-4-fluorophenoxy)-2-methylpropanoic acid;
(R)-2-(3-(6-((6-(3-((3-ethoxypyridin-2-yl)oxy)piperidin-1-yl)pyrazin-2-yl)amino)pyridin-2-yl)-4-fluorophenoxy)-2-methylpropanoic acid;
(R)-3-(4-(6-((6-(3-(2-ethoxyphenoxy)piperidin-1-yl)pyrazin-2-yl)amino)pyridin-2-yl)-1H-pyrazol-1-yl)-2,2-dimethylpropanoic acid;
(R)-3-((6-((6-(3-(2-ethoxyphenoxy)piperidin-1-yl)pyrazin-2-yl)amino)pyridin-2-yl)oxy)benzoic acid;
(R)-3-((6-((6-(3-((3-ethoxypyridin-2-yl)oxy)piperidin-1-yl)pyrazin-2-yl)amino)pyridin-2-yl)oxy)benzoic acid;
(R)-4-((6-((6-(3-(2-ethoxyphenoxy)piperidin-1-yl)pyrazin-2-yl)amino)pyridin-2-yl)oxy)benzoic acid;
(R)-4-((6-((6-(3-((3-ethoxypyridin-2-yl)oxy)piperidin-1-yl)pyrazin-2-yl)amino)pyridin-2-yl)oxy)benzoic acid;
(R)-2-(3-((6-((6-(3-(2-ethoxyphenoxy)piperidin-1-yl)pyrazin-2-yl)amino)pyridin-2-yl)oxy)phenyl)-2-methylpropanoic acid;
(R)-2-(3-((6-((6-(3-((3-ethoxypyridin-2-yl)oxy)piperidin-1-yl)pyrazin-2-yl)amino)pyridin-2-yl)oxy)phenyl)-2-methylpropanoic acid;
(R)-2-(4-((6-((6-(3-(2-ethoxyphenoxy)piperidin-1-yl)pyrazin-2-yl)amino)pyridin-2-yl)oxy)phenyl)-2-methylpropanoic acid;
(R)-2-(4-((6-((6-(3-((3-ethoxypyridin-2-yl)oxy)piperidin-1-yl)pyrazin-2-yl)amino)pyridin-2-yl)oxy)phenyl)-2-methylpropanoic acid;

(R)-2-(3-((6-((6-(3-(2-ethoxyphenoxy)piperidin-1-yl)pyrazin-2-yl)amino)pyridin-2-yl)oxy)phenyl)acetic acid;

(R)-2-(3-((6-((6-(3-((3-ethoxypyridin-2-yl)oxy)piperidin-1-yl)pyrazin-2-yl)amino)pyridin-2-yl)oxy)phenyl)acetic acid;

(R)-2-(4-((6-((6-(3-(2-ethoxyphenoxy)piperidin-1-yl)pyrazin-2-yl)amino)pyridin-2-yl)oxy)phenyl)acetic acid;

(R)-2-(4-((6-((6-(3-((3-ethoxypyridin-2-yl)oxy)piperidin-1-yl)pyrazin-2-yl)amino)pyridin-2-yl)oxy)phenyl)acetic acid;

(R)-4-(((6-((6-(3-(2-ethoxyphenoxy)piperidin-1-yl)pyrazin-2-yl)amino)pyridin-2-yl)oxy)methyl)benzoic acid;

(R)-3-(3-(6-((6-(3-(2-ethoxyphenoxy)piperidin-1-yl)pyrazin-2-yl)amino)-5-fluoropyridin-2-yl)phenyl)-2,2-dimethylpropanoic acid;

(R)-3-(3-(6-((6-(3-((3-ethoxypyridin-2-yl)oxy)piperidin-1-yl)pyrazin-2-yl)amino)-5-fluoropyridin-2-yl)phenyl)-2,2-dimethylpropanoic acid;

(R)-3-(3-(6-((6-(3-(2-ethoxyphenoxy)piperidin-1-yl)pyrazin-2-yl)amino)-3-fluoropyridin-2-yl)phenyl)-2,2-dimethylpropanoic acid;

(R)-3-(3-(6-((6-(3-((3-ethoxypyridin-2-yl)oxy)piperidin-1-yl)pyrazin-2-yl)amino)-3-fluoropyridin-2-yl)phenyl)-2,2-dimethylpropanoic acid;

(R)-2-(3-(6-((6-(3-((3-ethoxypyridin-2-yl)oxy)piperidin-1-yl)pyrazin-2-yl)amino)-5-fluoropyridin-2-yl)phenoxy)-2-methylpropanoic acid;

(R)-2-(3-(6-((6-(3-((3-ethoxypyridin-2-yl)oxy)piperidin-1-yl)pyrazin-2-yl)amino)-3-fluoropyridin-2-yl)phenoxy)-2-methylpropanoic acid;

(R)-3-(3-(6-((6-(3-((3-ethoxypyridin-2-yl)oxy)piperidin-1-yl)pyrazin-2-yl)amino)-3-fluoropyridin-2-yl)-4-fluorophenyl)-2,2-dimethylpropanoic acid;

(R)-3-(3-(6-((6-(3-(2-ethoxyphenoxy)piperidin-1-yl)pyrazin-2-yl)amino)-5-fluoropyridin-2-yl)-4-fluorophenyl)-2,2-dimethylpropanoic acid;

(R)-3-(3-(6-((6-(3-((3-ethoxypyridin-2-yl)oxy)piperidin-1-yl)pyrazin-2-yl)amino)-5-fluoropyridin-2-yl)-4-fluorophenyl)-2,2-dimethylpropanoic acid;

(R)-2-(4-(6-((6-(3-(2-ethoxyphenoxy)piperidin-1-yl)pyrazin-2-yl)amino)-3-(trifluoromethyl)pyridin-2-yl)phenyl)-2-methylpropanoic acid;

(R)-3-(3-(6-((6-(3-(2-ethoxyphenoxy)piperidin-1-yl)pyrazin-2-yl)amino)-4-(trifluoromethyl)pyridin-2-yl)phenyl)-2,2-dimethylpropanoic acid;

(R)-3-(3-(6-((6-(3-(2-ethoxyphenoxy)piperidin-1-yl)pyrazin-2-yl)amino)-3-methylpyridin-2-yl)phenyl)-2,2-dimethylpropanoic acid;

(R)-3-(3-(6-((6-(3-(2-ethoxyphenoxy)piperidin-1-yl)pyrazin-2-yl)amino)pyrazin-2-yl)phenyl)-2,2-dimethylpropanoic acid;

(R)—N-(6-(3-(2-ethoxyphenoxy)piperidin-1-yl)pyrazin-2-yl)pyrimidin-2-amine;

(R)-2-((6-(3-(2-ethoxyphenoxy)piperidin-1-yl)pyrazin-2-yl)amino)pyrimidine-5-carboxylic acid;

(R)-2-(2-((6-(3-(2-ethoxyphenoxy)piperidin-1-yl)pyrazin-2-yl)pyrimidin-4-yl)-2-methylpropanoic acid;

(R)-2-(2-((4-(3-((3-ethoxypyridin-2-yl)oxy)piperidin-1-yl)pyrimidin-2-yl)pyrimidin-4-yl)-2-methylpropanoic acid;

(2-((6-((R)-3-(2-ethoxyphenoxy)piperidin-1-yl)pyrazin-2-yl)amino)pyrimidin-4-yl)-L-proline;

1-(2-((6-((R)-3-(2-ethoxyphenoxy)piperidin-1-yl)pyrazin-2-yl)amino)pyrimidin-4-yl)pyrrolidine-3-carboxylic acid;

1-(2-((6-((R)-3-(2-ethoxyphenoxy)piperidin-1-yl)pyrazin-2-yl)amino)pyrimidin-4-yl)-3-methylpyrrolidine-3-carboxylic acid;

1-(2-((6-((R)-3-(2-ethoxyphenoxy)piperidin-1-yl)pyrazin-2-yl)amino)pyrimidin-4-yl)piperidine-3-carboxylic acid;

(R)-1-(2-((6-((R)-3-(2-ethoxyphenoxy)piperidin-1-yl)pyrazin-2-yl)amino)pyrimidin-4-yl)piperidine-3-carboxylic acid;

1-(2-((6-((R)-3-(2-ethoxyphenoxy)piperidin-1-yl)pyrazin-2-yl)amino)pyrimidin-4-yl)-3-methylpiperidine-3-carboxylic acid;

(R)-1-(2-((6-(3-(2-ethoxyphenoxy)piperidin-1-yl)pyrazin-2-yl)amino)pyrimidin-4-yl)piperidine-4-carboxylic acid;

5-(2-((6-((R)-3-(2-ethoxyphenoxy)piperidin-1-yl)pyrazin-2-yl)amino)pyrimidin-4-yl)bicyclo[2.2.1]heptane-2-carboxylic acid;

(R)-2-(1-(2-((6-(3-(2-ethoxyphenoxy)piperidin-1-yl)pyrazin-2-yl)amino)pyrimidin-4-yl)piperidin-4-yl)acetic acid;

(R)-2-(1-(2-((6-(3-(2-ethoxyphenoxy)piperidin-1-yl)pyrazin-2-yl)amino)pyrimidin-4-yl)piperidin-4-yl)-2-methylpropanoic acid;

(R)-2-(4-(2-((6-(3-(2-ethoxyphenoxy)piperidin-1-yl)pyrazin-2-yl)amino)pyrimidin-4-yl)piperazin-1-yl)acetic acid;

2-((S)-1-(2-((6-((R)-3-(2-ethoxyphenoxy)piperidin-1-yl)pyrazin-2-yl)amino)pyrimidin-4-yl)piperidin-3-yl)acetic acid;

(E)-3-((S)-1-(2-((6-((R)-3-(2-ethoxyphenoxy)piperidin-1-yl)pyrazin-2-yl)amino)pyrimidin-4-yl)piperidin-3-yl)acrylic acid;

3-((S)-1-(2-((6-((R)-3-(2-ethoxyphenoxy)piperidin-1-yl)pyrazin-2-yl)amino)pyrimidin-4-yl)piperidin-3-yl)propanoic acid;

2-(((S)-1-(2-((6-((R)-3-(2-ethoxyphenoxy)piperidin-1-yl)pyrazin-2-yl)amino)pyrimidin-4-yl)piperidin-3-yl)oxy)acetic acid;

2-(((R)-1-(2-((6-((R)-3-(2-ethoxyphenoxy)piperidin-1-yl)pyrazin-2-yl)amino)pyrimidin-4-yl)piperidin-3-yl)oxy)acetic acid;

2-(((R)-1-(2-((6-((R)-3-(2-ethoxyphenoxy)piperidin-1-yl)pyrazin-2-yl)amino)pyrimidin-4-yl)piperidin-3-yl)oxy)-2-methylpropanoic acid;

(R)-4-(2-((6-(3-(2-ethoxyphenoxy)piperidin-1-yl)pyrazin-2-yl)amino)pyrimidin-4-yl)oxy)cyclohexane-1-carboxylic acid;

(1R,4r)-4-((2-((6-((R)-3-(2-ethoxyphenoxy)piperidin-1-yl)pyrazin-2-yl)amino)pyrimidin-4-yl)oxy)cyclohexane-1-carboxylic acid;

(1R,4r)-4-((2-((6-((R)-3-((3-ethoxypyridin-2-yl)oxy)piperidin-1-yl)pyrazin-2-yl)amino)pyrimidin-4-yl)oxy)cyclohexane-1-carboxylic acid;

(1S,4s)-4-((2-((6-((R)-3-(2-ethoxyphenoxy)piperidin-1-yl)pyrazin-2-yl)amino)pyrimidin-4-yl)oxy)cyclohexane-1-carboxylic acid;

(1S,4s)-4-((2-((6-((R)-3-((3-ethoxypyridin-2-yl)oxy)piperidin-1-yl)pyrazin-2-yl)amino)pyrimidin-4-yl)oxy)cyclohexane-1-carboxylic acid;

(R)-6-(2-((6-(3-(2-ethoxyphenoxy)piperidin-1-yl)pyrazin-2-yl)amino)pyrimidin-4-yl)picolinic acid;

(R)-2-(3-(2-((6-(3-(2-ethoxyphenoxy)piperidin-1-yl)pyrazin-2-yl)amino)pyrimidin-4-yl)phenyl)acetic acid;

(R)-2-(3-(2-((6-(3-(2-ethoxyphenoxy)piperidin-1-yl)pyrazin-2-yl)amino)pyrimidin-4-yl)phenyl)-2-methylpropanoic acid;

(R)-2-(3-(2-((6-(3-((3-ethoxypyridin-2-yl)oxy)piperidin-1-yl)pyrazin-2-yl)amino)pyrimidin-4-yl)phenyl)-2-methylpropanoic acid;

(R)-2-(4-(2-((6-(3-(2-ethoxyphenoxy)piperidin-1-yl) pyrazin-2-yl)amino)pyrimidin-4-yl)phenyl)-2-methylpropanoic acid;
(R)-2-(4-(2-((6-(3-((3-ethoxypyridin-2-yl)oxy)piperidin-1-yl)pyrazin-2-yl)amino)pyrimidin-4-yl)phenyl)-2-methylpropanoic acid;
(R)-3-(3-(2-((6-(3-(2-ethoxyphenoxy)piperidin-1-yl) pyrazin-2-yl)amino)pyrimidin-4-yl)phenyl)propanoic acid;
(R)-3-(3-(2-((6-(3-(2-ethoxyphenoxy)piperidin-1-yl) pyrazin-2-yl)amino)pyrimidin-4-yl)phenyl)-2,2-dimethylpropanoic acid;
(R)-3-(3-(2-((6-(3-((3-ethoxypyridin-2-yl)oxy)piperidin-1-yl)pyrazin-2-yl)amino)pyrimidin-4-yl)phenyl)-2,2-dimethylpropanoic acid;
(R)-3-(3-(2-((6-(3-(2-ethoxyphenoxy)piperidin-1-yl)pyridin-2-yl)amino)pyrimidin-4-yl)phenyl)-2,2-dimethylpropanoic acid;
(R)-3-(3-(2-((2-(3-(2-ethoxyphenoxy)piperidin-1-yl)pyrimidin-4-yl)amino)pyrimidin-4-yl)phenyl)-2,2-dimethylpropanoic acid;
(R)-3-(3-(2-((4-(3-(2-ethoxyphenoxy)piperidin-1-yl)pyrimidin-2-yl)amino)pyrimidin-4-yl)phenyl)-2,2-dimethylpropanoic acid;
(R)-2-(4-(2-((6-(3-(2-ethoxyphenoxy)piperidin-1-yl) pyrazin-2-yl)amino)pyrimidin-4-yl)phenyl)acetic acid;
(R)-2-(4-(2-((6-(3-((3-ethoxypyridin-2-yl)oxy)piperidin-1-yl)pyrazin-2-yl)amino)pyrimidin-4-yl)phenyl)acetic acid;
(R)-3-(4-(2-((6-(3-(2-ethoxyphenoxy)piperidin-1-yl) pyrazin-2-yl)amino)pyrimidin-4-yl)phenyl)-2,2-dimethylpropanoic acid;
(R)-3-(4-(2-((6-(3-((3-ethoxypyridin-2-yl)oxy)piperidin-1-yl)pyrazin-2-yl)amino)pyrimidin-4-yl)phenyl)-2,2-dimethylpropanoic acid;
(R)-3-(4-(2-((2-(3-(2-ethoxyphenoxy)piperidin-1-yl)pyrimidin-4-yl)amino)pyrimidin-4-yl)phenyl)-2,2-dimethylpropanoic acid;
(R)-3-(4-(2-((4-(3-(2-ethoxyphenoxy)piperidin-1-yl)pyrimidin-2-yl)amino)pyrimidin-4-yl)phenyl)-2,2-dimethylpropanoic acid;
(R)-3-(4-(2-((4-(3-((3-ethoxypyridin-2-yl)oxy)piperidin-1-yl)pyrimidin-2-yl)amino)pyrimidin-4-yl)phenyl)-2,2-dimethylpropanoic acid;
(R)-2-(3-(2-((6-(3-(2-ethoxyphenoxy)piperidin-1-yl) pyrazin-2-yl)amino)pyrimidin-4-yl)phenoxy)-2-methylpropanoic acid;
(R)-2-(3-(2-((6-(3-((3-ethoxypyridin-2-yl)oxy)piperidin-1-yl)pyrazin-2-yl)amino)pyrimidin-4-yl)phenoxy)-2-methylpropanoic acid;
(R)-2-(4-(2-((6-(3-(2-ethoxyphenoxy)piperidin-1-yl) pyrazin-2-yl)amino)pyrimidin-4-yl)phenoxy)-2-methylpropanoic acid;
(R)-2-((4-(2-((6-(3-(2-ethoxyphenoxy)piperidin-1-yl) pyrazin-2-yl)amino)pyrimidin-4-yl)phenyl)amino)-2-methylpropanoic acid;
(R)-2-(4-((2-((6-(3-(2-ethoxyphenoxy)piperidin-1-yl) pyrazin-2-yl)amino)pyrimidin-4-yl)oxy)phenyl)acetic acid;
(R)-2-(4-((2-((6-(3-((3-ethoxypyridin-2-yl)oxy)piperidin-1-yl)pyrazin-2-yl)amino)pyrimidin-4-yl)phenyl)acetic acid;
(R)-3-(3-(2-((6-(3-(2-ethoxyphenoxy)piperidin-1-yl) pyrazin-2-yl)amino)-5-fluoropyrimidin-4-yl)phenyl)-2,2-dimethylpropanoic acid;
(R)-3-(3-(2-((6-(3-((3-ethoxypyridin-2-yl)oxy)piperidin-1-yl)pyrazin-2-yl)amino)-5-(trifluoromethyl)pyrimidin-4-yl)phenyl)-2,2-dimethylpropanoic acid;
(R)-3-(3-(2-((6-(3-((3-ethoxypyridin-2-yl)oxy)piperidin-1-yl)pyrazin-2-yl)amino)-6-(trifluoromethyl)pyrimidin-4-yl)phenyl)-2,2-dimethylpropanoic acid;
(R)-3-(3-(2-((6-(3-(2-ethoxyphenoxy)piperidin-1-yl) pyrazin-2-yl)amino)-6-(trifluoromethyl)pyrimidin-4-yl) phenyl)-2,2-dimethylpropanoic acid;
(R)-2-(3-(4-((6-(3-(2-ethoxyphenoxy)piperidin-1-yl) pyrazin-2-yl)amino)pyrimidin-2-yl)phenyl)-2-methylpropanoic acid;
(R)-2-(4-(4-((6-(3-(2-ethoxyphenoxy)piperidin-1-yl) pyrazin-2-yl)amino)pyrimidin-2-yl)phenyl)-2-methylpropanoic acid;
(R)-3-(3-(4-((6-(3-(2-ethoxyphenoxy)piperidin-1-yl) pyrazin-2-yl)amino)pyrimidin-2-yl)phenyl)-2,2-dimethylpropanoic acid;
(R)-3-(3-(4-((6-(3-((3-ethoxypyridin-2-yl)oxy)piperidin-1-yl)pyrazin-2-yl)amino)pyrimidin-2-yl)phenyl)-2,2-dimethylpropanoic acid;
(R)-3-(4-(4-((6-(3-(2-ethoxyphenoxy)piperidin-1-yl) pyrazin-2-yl)amino)pyrimidin-2-yl)phenyl)-2,2-dimethylpropanoic acid;
(R)-3-(4-(4-((6-(3-((3-ethoxypyridin-2-yl)oxy)piperidin-1-yl)pyrazin-2-yl)amino)pyrimidin-2-yl)phenyl)-2,2-dimethylpropanoic acid;
(R)-2-(3-(4-((6-(3-(2-ethoxyphenoxy)piperidin-1-yl) pyrazin-2-yl)amino)pyrimidin-2-yl)phenoxy)-2-methylpropanoic acid;
(R)-2-(3-(4-((6-(3-((3-ethoxypyridin-2-yl)oxy)piperidin-1-yl)pyrazin-2-yl)amino)pyrimidin-2-yl)phenoxy)-2-methylpropanoic acid;
(R)-2-(3-(2-((6-(3-(2-ethoxyphenoxy)piperidin-1-yl) pyrazin-2-yl)amino)pyrimidin-4-yl)phenoxy)-2-methylpropanoic acid;
(R)-2-(4-(6-((6-(3-(2-ethoxy-4-fluorophenoxy)piperidin-1-yl)pyrazin-2-yl)amino)pyridin-2-yl)phenoxy)-2-methylpropanoic acid;
(R)-2-(4-(4-((6-(3-(2-ethoxyphenoxy)piperidin-1-yl) pyrazin-2-yl)amino)pyrimidin-2-yl)phenoxy)-2-methylpropanoic acid; and
(R)-2-(4-(4-((6-(3-((3-ethoxypyridin-2-yl)oxy)piperidin-1-yl)pyrazin-2-yl)amino)pyrimidin-2-yl)phenoxy)-2-methylpropanoic acid.

The terms and abbreviations used herein retain their original meanings unless indicated otherwise.

The present invention also provides a method for preparing the compound of Formula (1). Hereinafter, the method for preparing the compound of Formula (1) is explained based on exemplary reactions in order to illustrate the present invention. However, a person skilled in the art could prepare the compound of Formula (1) by various methods based on the structure of Formula (1), and such methods should be interpreted as being within the scope of the present invention. That is, the compound of Formula (1) may be prepared by the methods described herein or by combining various methods disclosed in the prior art, which should be interpreted as being within the scope of the present invention. Accordingly, a method for preparing the compound of Formula (1) is not limited to the following methods.

As represented in the following Reaction Scheme 1, the compound of formula (1) may be prepared by directly introducing a substituted amine group into compound (2), or through a cross-coupling reaction using a palladium catalyst to compound (3) which is prepared by introducing a protected amine to compound (2) and removing a protecting group.

[Reaction Scheme 1]

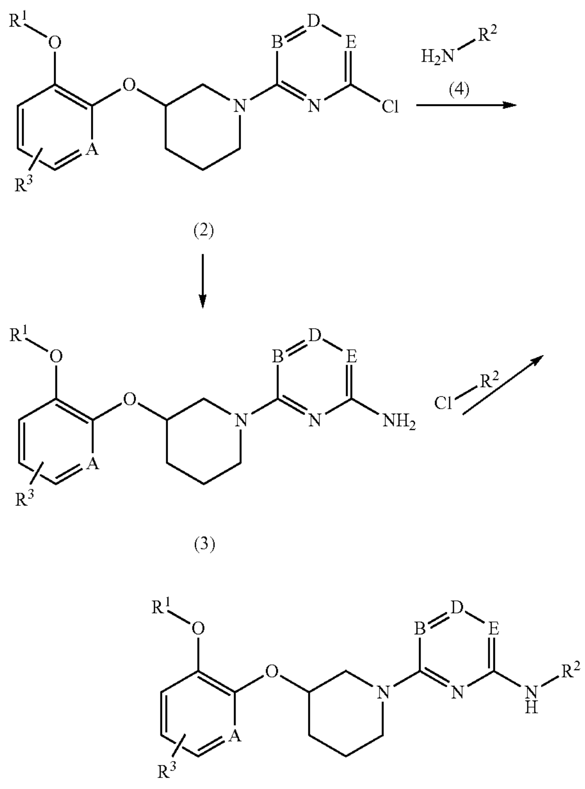

(2)

(3)

(1)

Compound (2) may be prepared from tert-butyl-3-hydroxypiperidine-1-carboxylate as a starting material according to the method of following Reaction Scheme 2.

[Reaction Scheme 2]

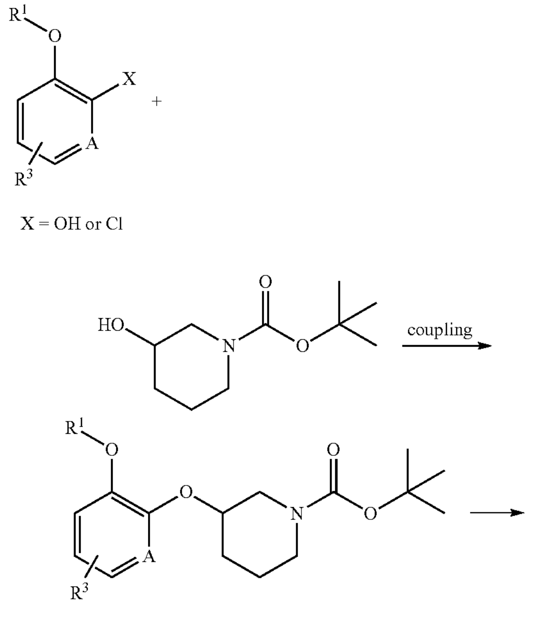

-continued

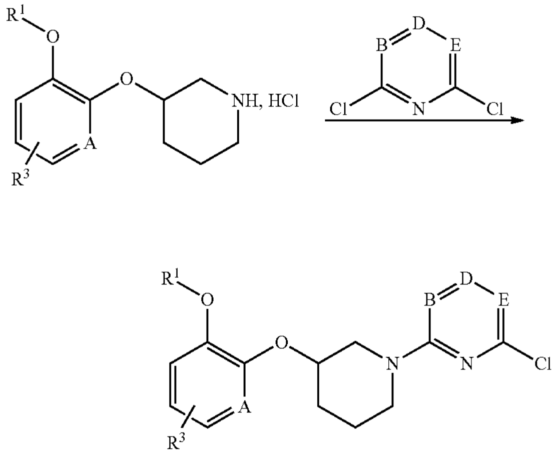

(2)

In addition, compound (3) may be prepared according to the method of following Reaction Scheme 3.

[Reaction Scheme 3]

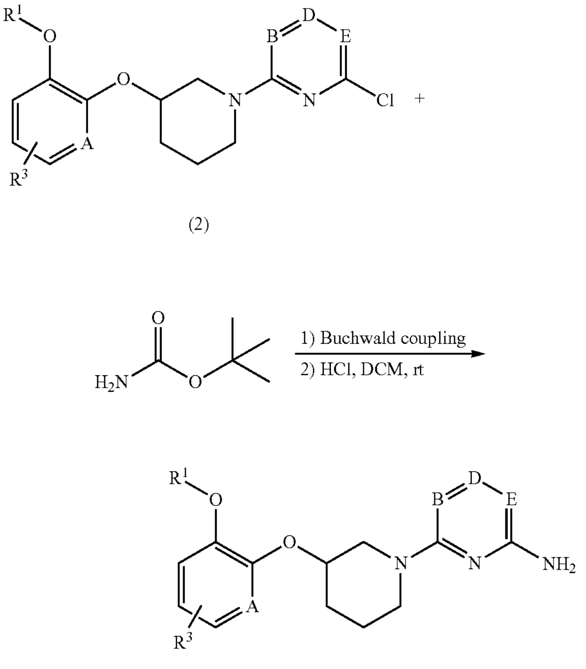

(2)

(3)

In addition, amino aryl intermediates were synthesized by introducing an amino group to a compound obtained through a cross-coupling reaction of a dioxaborolane core intermediate and various types of chloro aryl compounds. For example, methyl 2-(4-(2-aminopyrimidin-4-yl)phenyl)-2-methylpropanoate may be prepared according to the method of following Reaction Scheme 4 by using methyl 2-(4-bromophenyl)-2-methylpropanoate as a starting material.

[Reaction Scheme 4]

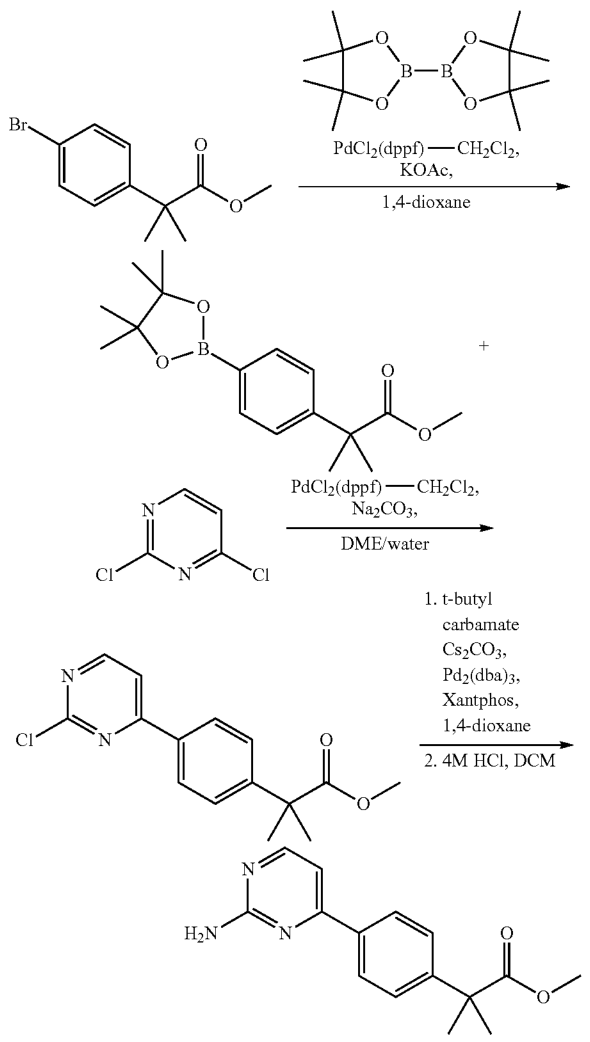

A compound not specifically described in the preparation method of the present specification is a known compound or a compound that can be easily synthesized from a known compound by a known synthesis method or a similar method.

The compound of Formula (1) obtained by the above methods can be separated or purified from the reaction products by conventional methods such as recrystallization, ionospheresis, silica gel column chromatography or ion-exchange chromatography.

As explained above, the compounds according to the present invention, starting materials or intermediates for the preparation thereof can be prepared by a variety of methods, which should be interpreted as being within the scope of the present invention in respect to the preparation of the compound of Formula (1).

The compound of Formula (1) according to the present invention exhibits inhibitory activity against diacylglycerol acyltransferase 2 (DGAT2). Accordingly, the present invention provides a pharmaceutical composition for the treatment of diseases associated with DGAT2 comprising the compound of Formula (1), or a pharmaceutically acceptable salt or isomer thereof, together with a pharmaceutically acceptable carrier. Various kinds of prodrugs, which are converted into the compound of Formula (1) in vivo, are also within the scope of the present invention.

Exemplary diseases associated with DGAT2 which can be treated by the pharmaceutical composition according to the present invention include, but are not limited to, that selected from the group consisting of fatty liver, nonalcoholic steatohepatitis (NASH), nonalcoholic fatty liver disease (NAFLD), diabetes, obesity, hyperlipidemia, atherosclerosis and hypercholesterolemia.

In the present invention, a "pharmaceutical composition" may include other components such as carriers, diluents, excipients, etc., in addition to the active ingredient of the present invention. Accordingly, the pharmaceutical composition may include pharmaceutically acceptable carriers, diluents, excipients or combinations thereof, if necessary. The pharmaceutical composition facilitates the administration of compounds into the body. Various methods for administering the compounds include, but are not limited to, oral, injection, aerosol, parenteral and local administration.

Herein, a "carrier" means a compound that facilitates the addition of compounds into the cell or tissue. For example, dimethylsulfoxide (DMSO) is a conventional carrier facilitating the administration of many organic compounds into living cells or tissues.

Herein, a "diluent" means a compound that not only stabilizes a biologically active form but is diluted in solvent dissolving the compounds. A dissolved salt in buffer is used as a diluent in this field. A conventionally used buffer is a phosphate buffer saline mimicking salt form in body fluid. Since a buffer solution can control the pH of the solution at low concentration, a buffer diluent hardly modifies the biological activity of compounds.

Herein, "pharmaceutically acceptable" means such property that does not impair the biological activity and physical property of compounds.

The compounds according to the present invention can be formulated as various pharmaceutically administered dosage forms. In the preparation of the pharmaceutical composition of the present invention, an active component—specifically, the compound of Formula (1) or a pharmaceutically acceptable salt or isomer thereof—is mixed with selected pharmaceutically acceptable carriers considering the dosage form to be prepared. For example, the pharmaceutical composition of the present invention can be formulated as injections, oral preparations and the like, as needed.

The compound of the present invention can be formulated by conventional methods using known pharmaceutical carriers and excipients, and inserted into a unit or multi-unit containers. The formulations may be solution, suspension or emulsion in oil or aqueous solvent and include conventional dispersing agents, suspending agents or stabilizing agents. In addition, the compound may be, for example, dry powder form which is dissolved in sterilized pyrogen-free water before use. The compound of the present invention can be formulated into suppositories by using a conventional suppository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the compounds of the present invention with at least one carrier selected from inert diluents such as sucrose, lactose or starch, lubricants such as magnesium stearate, disintegrating agents, binders and the like.

The compound or a pharmaceutical composition comprising the same according to the present invention can be administered in combination with other drugs—for example, other metabolic disorder therapeutic agents—as required.

The dose of the compound of Formula (1) according to the present invention is determined by a physician's prescription considering the patient's body weight, age and disease condition. A typical dose for adults is in the range of about 0.3 to 500 mg per day according to the frequency and intensity of administration. A typical daily dose of intramuscular or intravenous administration for adults is in the range of about 1 to 300 mg per day which can be administered in divided unit dosages. Some patients need a higher daily dose.

Herein, the term "treatment" is used to mean deterring, delaying or ameliorating the progress of diseases in a subject exhibiting symptoms of diseases.

Advantageous Effects of Invention

The novel amino aryl derivative compound of Formula (1) according to the present invention exhibits excellent inhibitory activity against diacylglycerol acyltransferase 2 (DGAT2), and thus can be usefully used in the prevention, alleviation or treatment of metabolic disorders associated with DGAT2. In addition, the novel amino aryl derivative compound of Formula (1) according to the present invention exhibits increased lipophilicity and liver selectivity, thereby improving efficacy through increased exposure to the liver, as well as expecting the advantages of convenience in taking because the half-life is relatively long in disease animal models and clinical practice.

MODE FOR THE INVENTION

Hereinafter, the present invention will be described in more detail through preparation examples and examples. However, these examples are only illustrative, and the scope of the present invention is not limited thereto.

In the following examples, M refers to molar concentration, and N refers to normal concentration. In addition, the descriptions of abbreviations and terms used in the Reaction Scheme, Preparation Examples and Examples are as follows:

DCM: dichloromethane
DIPEA: diisopropylethylamine
DME: dimethoxyethane
DMF: N,N-dimethylformamide
HCl: hydrochloric acid
Pd/C: palladium/charcoal
TEA: triethylamine
TFA: trifluoroacetic acid
THF: tetrahydrofuran

Preparation Example 1: (R)-2-chloro-6-(3-(2-ethoxyphenoxy)piperidin-1-yl)pyrazine

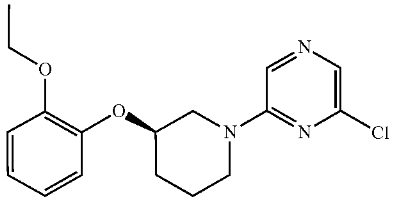 [SMILES: CCOc1ccccc1O[C@@H]1CCCN(c2cncc(Cl)n2)C1]

Step 1: tert-butyl-(R)-3-(2-ethoxyphenoxy)piperidine-1-carboxylate (S)-tert-butyl-3-hydroxypiperidine-1-carboxylate (30.0 g, 149 mmol), 2-ethoxyphenol (20.6 g, 149 mmol), triphenylphosphine (43.8 g, 167 mmol) were dissolved in 500 ml of toluene and stirred at room temperature. Diethylazodicarboxylate (30.4 ml) was diluted in 50 ml of toluene and slowly added dropwise to the reaction mixture. After stirring at room temperature for 15 hours, it was filtered, washed with 300 ml of diethyl ether, washed with 100 ml of 3N sodium hydroxide solution, the organic solvent was dried over magnesium sulfate, and the organic solvent was removed under reduced pressure. The desired product was obtained by purification with silica gel column (ethyl acetate:hexane=1:6). (Yield 47%)

$^1$H NMR (300 MHz, CHLOROFORM-D): δ 6.89-6.95 (m, 4H), 4.07 (m, 3H), 3.9 (bs, 1H), 3.66 (bs, 1H), 3.16 (m, 2H), 2.07 (bs, 1H), 1.76-1.83 (m, 2H), 1.45 (m+s, 3H)

Step 2: (R)-3-(2-ethoxyphenoxy)piperidine Hydrochloride

Tert-butyl-(R)-3-(2-ethoxyphenoxy)piperidine-1-carboxylate (10.0 g, 31.1 mmol) obtained in step 1 was dissolved in 100 ml of dichloromethane and 4 M hydrochloric acid solution was added dropwise at room temperature. After stirring at room temperature for 4 hours, it was confirmed that the reaction was complete by TLC experiment, and the organic solvent was removed under reduced pressure. After diluting with ethyl acetate and washing with an aqueous sodium hydrogen carbonate solution, the organic solvent was dried over magnesium sulfate, and the crude compound obtained through distillation under reduced pressure was used in the next reaction without further purification.

m/z $(M+H)^+$ calculated for $C_{13}H_{19}NO_2$: 221. found 222.

Step 3: (R)-2-chloro-6-(3-(2-ethoxyphenoxy)piperidin-1-yl)pyrazine (R)-3-(2-ethoxyphenoxy)piperidine hydrochloride obtained in step 2, 2,6-dichloropyrazine (5.10 g, 34.2 mmol) and triethylamine (13 ml, 93 mmol) were mixed with 100 ml of ethanol and stirred at room temperature. After stirring at room temperature for 24 hours, it was confirmed that the reaction was complete through a TLC experiment, and the organic solvent was removed under reduced pressure, dissolved in ethyl acetate, and washed with brine. The organic solvent was dried over magnesium sulfate and the organic solvent was removed under reduced pressure. The desired product was obtained by purification with silica gel column. (Yield 91%)

$^1$H-NMR (500 MHz, CHLOROFORM-D) δ 7.93 (s, 1H), 7.74 (s, 1H), 7.04-6.93 (m, 2H), 6.92-6.80 (m, 2H), 4.35-4.24 (m, 1H), 4.07-3.89 (m, 3H), 3.82-3.68 (m, 1H), 3.67-3.46 (m, 2H), 2.09 (q, J=4.3 Hz, 1H), 2.02-1.97 (m, 1H), 1.93 (q, J=4.3 Hz, 1H), 1.68-1.58 (m, 1H), 1.38 (t, J=7.0 Hz, 3H)

Preparation Example 2: (R)-6-(3-(2-ethoxyphenoxy)piperidin-1-yl)pyrazin-2-amine

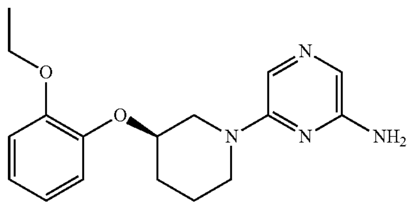 [SMILES: CCOc1ccccc1O[C@@H]1CCCN(c2cncc(N)n2)C1]

Step 1: tert-butyl (R)-(6-(3-(2-ethoxyphenoxy)piperidin-1-yl)pyrazin-2-yl)carbamate After dissolving (R)-2-chloro-6-(3-(2-ethoxyphenoxy)piperidin-1-yl)pyrazine (1.41 g, 4.22 mmol) obtained in Preparation Example 1, tert-butyl carbamate (0.55 g, 4.65 mmol), cesium carbonate (3.44 g, 10.56 mmol), 4,5-bis(diphenylphosphino)-9,9-dimethylxanthine (220 mg, 0.38 mmol) and tris(dibenzylideneacetone) dipalladium (0) (232 mg, 0.25 mmol) in 50 ml of 1,4-dioxane, the dissolved oxygen was removed through nitrogen bubbling under stirring, and the inflow of outside air was blocked in a sealed container. The reaction was stirred at 110° C. for 5 hours and then cooled to room temperature. After filtering through a Celite pad and removing the organic solvent under reduced pressure, the reaction was dissolved in ethyl acetate and washed with brine. The organic solvent was dried over magnesium sulfate and the organic solvent was removed under reduced pressure. The desired product was obtained by purification with silica gel column (ethyl acetate: hexane=3:1). (Yield 89%)

$^1$H-NMR (500 MHz, CHLOROFORM-D) δ 8.40 (s, 1H), 7.78 (s, 1H), 6.96 (t, J=7.0 Hz, 2H), 6.91-6.77 (m, 2H), 6.66 (s, 1H), 4.48-4.15 (m, 1H), 4.14-3.85 (m, 3H), 3.84-3.69 (m, 1H), 3.52-3.41 (1H), 3.40-3.23 (m, 1H), 2.11 (t, J=6.1 Hz, 1H), 2.01-1.92 (m, 1H), 1.88 (q, J=4.3 Hz, 1H), 1.57 (dt, J=13.4, 4.0 Hz, 1H), 1.52 (s, 9H), 1.37 (t, J=7.0 Hz, 3H)

Step 2: (R)-6-(3-(2-ethoxyphenoxy)piperidin-1-yl)pyrazin-2-amine

Tert-butyl (R)-(6-(3-(2-ethoxyphenoxy)piperidin-1-yl)pyrazin-2-yl) carbamate obtained in step 1 was dissolved in 10 ml of dichloromethane, stirred and 2 ml of trifluoroacetic acid was added dropwise thereto. After confirming that the reaction was complete by TLC, the organic solvent was removed under reduced pressure, diluted with ethyl acetate, and washed with an aqueous sodium hydrogen carbonate solution. The organic solvent was dried over magnesium sulfate and the organic solvent was removed under reduced pressure to obtain a crude product, and the next reaction was carried out without further purification.

$^1$H NMR (300 MHz, CHLOROFORM-D): δ 7.49 (s, 1H), 7.28 (s, 1H), 7.27 (d, 1H), 6.90-7.05 (m, 3H), 3.80-4.25 (m, 7H), 3.25 (m, 2H), 2.18 (m, 1H), 1.75-1.98 (m, 2H), 1.91 (m, 1H), 1.43 (t, 3H), 1.27 (m, 1H)

Preparation Example 3: (R)-2-chloro-6-(3-((3-ethoxypyridin-2-yl)oxy)piperidin-1-yl)pyrazine

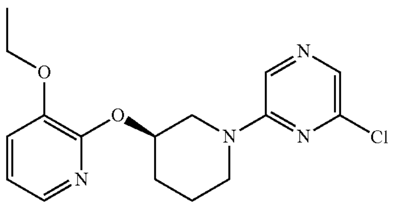 [SMILES: CCOc1cccnc1O[C@@H]1CCCN(c2cncc(Cl)n2)C1]

Step 1: 2-chloro-3-ethoxypyridine

2-Chloropyridin-3-ol (10.0 g, 77 mmol), iodoethane (14.45 g, 93 mmol) and potassium carbonate (21.34 g, 154 mmol) were added to 77 mL of DMF and stirred at room temperature for 48 hours. The reaction mixture was filtered and water was added, followed by extraction with ethyl acetate. After washing with water and brine, the organic layer was dried over magnesium sulfate and concentrated under reduced pressure. The desired product was obtained by purification with column chromatography. (Yield 99%)

$^1$H NMR (400 MHz, CHLOROFORM-D): δ 7.96 (t, J=3.0 Hz, 1H), 7.17 (d, J=3.2 Hz, 2H), 4.10 (q, J=7.0 Hz, 2H), 1.48 (t, J=7.1 Hz, 3H)

Step 2: tert-butyl (R)-3-((3-ethoxypyridin-2-yl)oxy)piperidine-1-carboxylate

Sodium hydride (3.38 g, 84 mmol) was added to 96 mL of anhydrous DMF, and tert-butyl (R)-3-hydroxypiperidine-1-carboxylate (17.00 g, 84 mmol) was further added. The temperature was raised to 60° C., stirred for 1 hour, and 2-chloro-3-ethoxypyridine (12.1 g, 77 mmol) obtained in step 1 was added, followed by stirring for 24 hours. Water was added to the reaction mixture, followed by extraction with ethyl acetate. After washing with water and brine, the organic layer was dried over magnesium sulfate and concentrated under reduced pressure. The desired product was obtained by purification with column chromatography. (yield 75%)

$^1$H NMR (400 MHz, CHLOROFORM-D): δ 7.68 (td, J=3.2, 1.7 Hz, 1H), 7.03 (dt, J=7.8, 1.4 Hz, 1H), 6.82-6.72 (m, 1H), 5.06 (s, 1H), 4.03 (q, J=7.0 Hz, 2H), 3.55 (d, J=100.2 Hz, 4H), 2.16-1.96 (m, 1H), 1.96-1.70 (m, 2H), 1.68-1.50 (m, 1H), 1.50-1.27 (m, 12H)

Step 3: (R)-2-chloro-6-(3-((3-ethoxypyridin-2-yl)oxy)piperidin-1-yl)pyrazine

The title compound was obtained in a similar manner to Step 3 of Preparation Example 1 by using tert-butyl (R)-3-((3-ethoxypyridin-2-yl)oxy)piperidine-1-carboxylate (31.5 g, 98 mmol) obtained in step 2, (R)-3-ethoxy-2-(piperidin-3-yloxy)pyridine hydrochloride (30 g, 116 mmol) obtained by using in a similar manner to Step 2 of Preparation Example 1 and 2,6-dichloropyrazine (19 g, 128 mmol). (Yield 80%)

$^1$H NMR (400 MHz, CHLOROFORM-D): δ 7.96 (d, J=11.0 Hz, 1H), 7.74-7.66 (m, 2H), 7.04 (dd, J=7.8, 1.4 Hz, 1H), 6.83 (dd, J=7.8, 5.0 Hz, 1H), 5.24 (td, J=7.0, 3.4 Hz, 1H), 4.05-3.83 (m, 3H), 3.83-3.70 (m, 2H), 3.67-3.53 (m,

1H), 2.22-2.09 (m, 1H), 2.07-1.93 (m, 2H), 1.75-1.60 (m, 1H), 1.35-1.27 (t, J=7.1 Hz, 3H)

Preparation Example 4: (R)-2-chloro-6-(3-(2-ethoxyphenoxy)piperidin-1-yl)pyridine

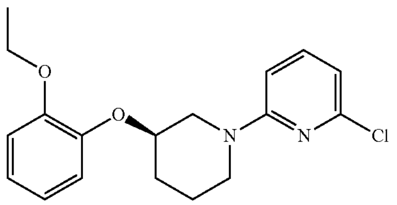

The desired product was obtained in a similar manner to step 3 of Preparation Example 1 by using (R)-3-(2-ethoxyphenoxy)piperidine hydrochloride (10 g, 45.2 mmol) obtained in step 2 of Preparation Example 1 and 2,6-dichloropyridine (11.37 g, 77 mmol). (Yield 41%)

$^1$H-NMR (400 MHz, CHLOROFORM-D): δ 7.44-7.29 (m, 1H), 7.17-7.05 (m, 1H), 6.94-6.86 (m, 3H), 6.73-6.49 (m, 1H), 6.49-6.32 (m, 1H), 4.30-4.17 (m, 2H), 4.04-3.96 (m, 2H), 3.95-3.78 (m, 1H), 3.35-3.18 (m, 2H), 2.22-2.07 (m, 1H), 1.97-1.75 (m, 2H), 1.64-1.52 (m, 1H), 1.40 (q, J=6.9 Hz, 3H)

Preparation Example 5: (R)-4-chloro-2-(3-(2-ethoxyphenoxy)piperidin-1-yl)pyrimidine

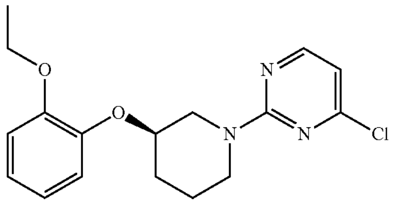 [SMILES: CCOc1ccccc1O[C@@H]1CCCN(c2nccc(Cl)n2)C1]

The title compound was synthesized in a similar manner to Preparation Example 1 (Step 2, Step 3) by using tert-butyl-(R)-3-(2-ethoxyphenoxy)piperidine-1-carboxylate (15.0 g, 46.7 mmol) obtained in step 1 of Preparation Example 1 and 2,4-dichloropyrimidine (13.9 g, 93 mmol). (Yield 19%)

$^1$H-NMR (400 MHz, CHLOROFORM-D): δ 8.11 (d, 1H), 7.03 (m, 1H), 6.95 (m, 1H), 6.89 (m, 2H), 6.45 (d, 1H), 4.44 (dd, 1H), 4.22 (m, 1H), 4.10 (m, 1H), 4.02 (m, 2H), 3.63 (m, 1H), 3.51 (m, 1H), 2.12 (m, 1H), 1.92 (m, 2H), 1.55 (m, 1H), 1.40 (t, 3H)

Preparation Example 6: (R)-2-chloro-4-(3-(2-ethoxyphenoxy)piperidin-1-yl)pyrimidine

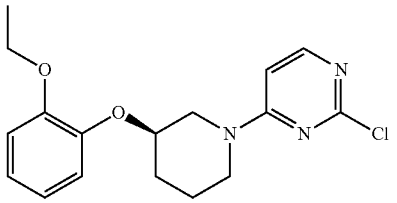 [SMILES: CCOc1ccccc1O[C@@H]1CCCN(c2ccnc(Cl)n2)C1]

The title compound was synthesized in a similar manner to Preparation Example 1 (Step 2, Step 3) by using tert-butyl-(R)-3-(2-ethoxyphenoxy)piperidine-1-carboxylate (15.0 g, 46.7 mmol) obtained in step 1 of Preparation Example 1 and 2,4-dichloropyrimidine (13.9 g, 93 mmol). (Yield 72%)

$^1$H-NMR (400 MHz, CHLOROFORM-D): δ 7.97 (d, 1H), 6.98 (m, 2H), 6.89 (m, 2H), 6.32 (d, 1H), 4.31 (m, 1H), 4.01 (m, 3H), 3.71 (m, 3H), 2.01 (m, 3H), 1.61 (m, 1H), 1.38 (t, 3H)

Preparation Example 7: (R)-2-chloro-4-(3-((3-ethoxypyridin-2-yl)oxy)piperidin-1-yl)pyrimidine

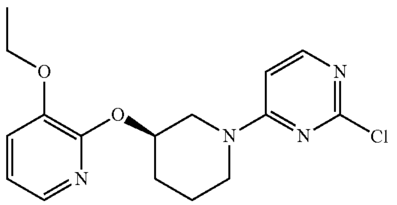 [SMILES: CCOc1cccnc1O[C@@H]1CCCN(c2ccnc(Cl)n2)C1]

It was used in a similar manner to Step 3 of Preparation Example 1 to obtain the desired product by using (R)-3-ethoxy-2-(piperidin-3-yloxy)pyridine hydrochloride (5.90 g, 22.80 mmol) obtained in step 3 of Preparation Example 3 and 2,4-dichloropyrimidine (3.74 g, 25.08 mmol). (Yield 26%)

$^1$H-NMR (400 MHz, CHLOROFORM-D): δ 7.91 (d, J=6.4 Hz, 1H), 7.70 (dd, J=4.8, 1.6 Hz, 1H), 7.03 (dd, J=7.8, 1.4 Hz, 1H), 6.82 (q, J=4.1 Hz, 1H), 6.32 (d, J=5.9 Hz, 1H), 5.19 (s, 1H), 4.05-3.59 (m, 6H), 2.25-1.90 (m, 3H), 1.76-1.57 (m, 1H), 1.31 (t, J=6.9 Hz, 3H)

Preparation Example 8: (R)-2-chloro-4-(3-(2-ethoxyphenoxy)piperidin-1-yl)-5-fluoropyrimidine

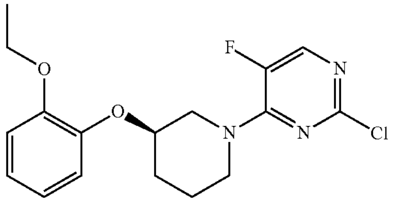 [SMILES: CCOc1ccccc1O[C@@H]1CCCN(c2nc(Cl)ncc2F)C1]

The title compound was synthesized in a similar manner to Step 3 of Preparation Example 1 by using (R)-3-(2-ethoxyphenoxy)piperidine hydrochloride (4 g, 18.08 mmol) synthesized in step 2 of Preparation Example 1 and 2,4-dichloro-5-fluoropyrimidine (7.54 g, 45.2 mmol). (Yield 81%)

$^1$H-NMR (CHLOROFORM-D): δ 7.96-7.83 (m, 1H), 7.09-6.83 (m, 4H), 4.44-4.31 (m, 1H), 4.11 (d, J=9.8 Hz, 1H), 4.08-3.95 (m, 2H), 3.93 (s, 1H), 3.82 (dd, J=24.6, 7.5 Hz, 2H), 2.15-1.95 (m, 3H), 1.63 (d, J=7.9 Hz, 1H), 1.40 (q, J=6.9 Hz, 3H)

Preparation Example 9: (R)-4-chloro-2-(3-(2-ethoxyphenoxy)piperidin-1-yl)-5-(trifluoromethyl) pyrimidine

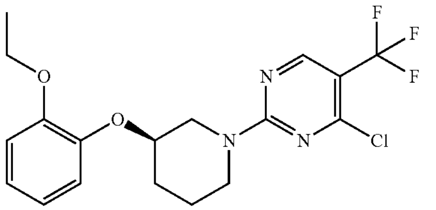 [SMILES: CCOc1ccccc1O[C@@H]1CCCN(c2ncc(C(F)(F)F)c(Cl)n2)C1]

The title compound was synthesized in a similar manner to Step 3 of Preparation Example 1 by using (R)-3-(2-ethoxyphenoxy)piperidine hydrochloride (1 g, 4.52 mmol) synthesized in step 2 of Preparation Example 1 and 2,4-dichloro-5-(trifluoromethyl) pyrimidine (2.45 g, 11.3 mmol). (Yield 38%)

$^1$H-NMR (400 MHz, CHLOROFORM-D): δ 8.37 (d, J=21.0 Hz, 1H), 6.96 (t, J=7.5 Hz, 2H), 6.87 (t, J=5.5 Hz, 2H), 4.28 (td, J=6.6, 3.4 Hz, 1H), 4.19 (s, 1H), 4.06-3.89 (m, 4H), 3.89-3.72 (1H), 2.16-1.88 (m, 3H), 1.67 (s, 1H), 1.62-1.48 (m, 1H), 1.48-1.30 (m, 3H)

Preparation Example 10: (R)-2-chloro-4-(3-(2-ethoxyphenoxy)piperidin-1-yl)-5-(trifluoromethyl) pyrimidine

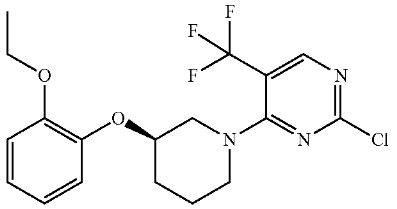 [SMILES: CCOc1ccccc1O[C@@H]1CCCN(c2nc(Cl)ncc2C(F)(F)F)C1]

The title compound was synthesized in a similar manner to Step 3 of Preparation Example 1 by using (R)-3-(2-ethoxyphenoxy)piperidine hydrochloride (1 g, 4.52 mmol) synthesized in step 2 of Preparation Example 1 and 2,4-dichloro-5-(trifluoromethyl)pyrimidine (2.45 g, 11.3 mmol). (Yield 28%)

$^1$H-NMR (400 MHz, CHLOROFORM-D): δ 8.36 (s, 1H), 7.12-7.01 (m, 1H), 7.01-6.91 (m, 1H), 6.90-6.78 (m, 2H), 4.32 (td, J=7.5, 3.7 Hz, 1H), 4.16 (dd, J=13.5, 3.0 Hz, 1H), 4.01 (td, J=7.3, 6.3 Hz, 2H), 3.76 (dd, J=13.5, 5.7 Hz, 1H), 3.68-3.47 (m, 2H), 2.19-1.84 (m, 4H), 1.71-1.57 (m, 1H), 1.39 (t, J=7.1 Hz, 3H)

Preparation Example 11: 4-Phenylpyridin-2-amine

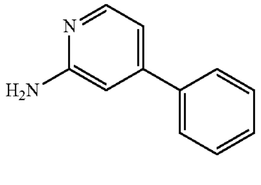 [SMILES: Nc1cc(-c2ccccc2)ccn1]

Phenylboronic acid (0.14 g, 1.16 mmol), 4-bromopyridin-2-amine (0.2 g, 1.16 mmol), [1,1'-bis(diphenylphosphino) ferrocene]dichloropalladium dichloromethane adduct (0.09 g, 0.12 mmol) was dissolved in 3 ml of 1,2-dimethoxyethane, and 1 M saturated aqueous sodium hydrogen carbonate solution (3.47 ml, 3.47 mmol) was added dropwise, followed by stirring at 90° C. for 5 hours. After cooling to room temperature, filtering through a Celite pad and washing with dichloromethane, the organic solvent was dried over magnesium sulfate, and removed under reduced pressure. The desired product was obtained by purification with silica gel column (Biotage 40 M column). (Yield 97%).

$^1$H-NMR (500 MHz, CHLOROFORM-D) δ 8.25 (d, J=5.5 Hz, 1H), 8.00-7.77 (m, 2H), 7.41 (t, J=7.3 Hz, 2H), 7.36 (t, J=7.3 Hz, 1H), 7.04-6.78 (m, 1H), 6.42 (q, J=2.6 Hz, 1H), 4.57 (s, 1H)

Preparation Example 12: Methyl 2-(6-aminopyridine)acetate

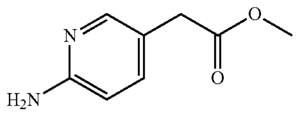

Step 1: 2-(6-chloropyridin-3-yl)acetonitrile

2-Chloro-5-(chloromethyl)pyridine (5.0 g, 30.9 mmol) was dissolved in 20 ml of ethanol, and potassium cyanide (2.21 g, 33.9 mmol) was dissolved in 9 ml of water and added dropwise at 0° C. The reaction was stirred at reflux for 2 hours and then stirred at room temperature for 18 hours. After diluting in 500 ml of dichloromethane and washing with brine, the organic solvent was dried over magnesium sulfate, and removed under reduced pressure. The desired product was obtained by purification with silica gel column (dichloromethane:hexane=7:3). (Yield 83%)

$^1$H-NMR (500 MHz, CHLOROFORM-D) δ 8.36 (d, J=2.4 Hz, 1H), 7.77-7.60 (m, 1H), 7.38 (d, J=8.6 Hz, 1H), 3.87-3.63 (2H)

Step 2: Methyl 2-(6-chloropyridin-3-yl)acetate 2-(6-chloropyridin-3-yl)acetonitrile (3.92 g, 25.7 mmol) obtained in step 1 was dissolved in 5 ml of concentrated hydrochloric acid and stirred at 80° C. for 24 hours. The reaction was poured into ice water, extracted with 500 ml of dichloromethane, washed with brine, and then the organic solvent was dried over magnesium sulfate, and removed under reduced pressure. The desired product was obtained by purification with silica gel column (ethyl acetate: hexane=1:1). (Yield 90%)

$^1$H-NMR (500 MHz, CHLOROFORM-D) δ 8.28 (d, J=2.4 Hz, 1H), 7.61 (dd, J=7.9, 2.4 Hz, 1H), 7.29 (d, J=8.6 Hz, 1H), 3.71 (s, 3H), 3.61 (s, 2H)

Step 3: Methyl 2-(6-aminopyridine)acetate

The desired product was obtained in a similar manner to Preparation Example 2 (Step 1, Step 2) by using methyl 2-(6-chloropyridin-3-yl)acetate (2.0 g, 10.8 mmol) obtained in step 2 and tert-butyl carbamate (3.8 g, 32.3 mmol). (Yield 26.8%)

$^1$H-NMR (500 MHz, CHLOROFORM-D) δ 7.93 (d, J=2.4 Hz, 1H), 7.39 (dd, J=7.9, 2.4 Hz, 1H), 6.48 (d, J=8.6 Hz, 1H), 4.49 (s, 2H), 3.68 (s, 3H), 3.47 (s, 2H)

Preparation Example 13: Methyl (E)-3-(6-aminopyridin-3-yl)acrylate

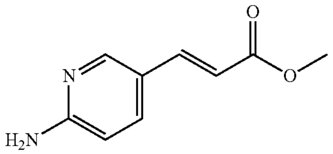

To a solution of 2-amino-5-bromopyridine (2.70 g, 15.61 mmol), palladium (II) acetate (0.16 g, 0.70 mmol), tris(o-tolyl)phosphine (0.48 g, 1.56 mmol), TEA (2.61 ml, 18.73 mmol) in 30 ml of DMF was added methyl acrylate (1.48 g, 17.17 mmol), and the mixture was stirred at 100° C. for 6 h. The reaction was quenched by the addition of water and the whole was extracted with ethyl acetate. The combined organic layer was washed with brine, dried over $MgSO_4$, and concentrated under reduced pressure. The residue was purified by silica gel column chromatography (DCM/EA/MeOH=4:1:0 to 2:1:0 to 2:1:0.1) to give the desired product as a yellow solid. (Yield 83%)

$^1$H-NMR (500 MHz, CHLOROFORM-D) δ 8.18 (d, J=1.8 Hz, 1H), 7.74-7.63 (m, 1H), 7.56 (s, 1H), 6.50 (d, J=8.6 Hz, 1H), 6.25 (d, J=15.9 Hz, 1H), 4.73 (s, 2H), 3.78 (s, 3H)

Preparation Example 14: Methyl 2-(4-aminophenyl)-2-methylpropanoate

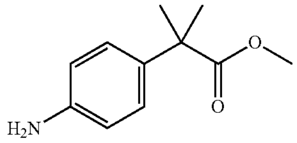

Step 1: Methyl 2-(4-nitrophenyl)acetate

Concentrated sulfuric acid (34 ml, 0.64 mol) was added to water (34 ml), and 4-nitrophenylacetonitrile (11.8 g, 73 mmol) was added to this mixture. The reaction mixture was refluxed for 30 min, diluted with 34 ml of water, and cooled to 0° C. when colorless crystalline solid separated. The solid was filtered off, washed with ice-cold water to remove trace of acid, and dried to yield the acid. And then the solid was treated with THF/diazomethane at 0° C. The product was obtained via evaporation and column chromatography. (Yield 56%)

$^1$H-NMR (500 MHz, CHLOROFORM-D) δ 8.18 (d, J=8.6 Hz, 2H), 7.45 (d, J=8.6 Hz, 2H), 3.73 (s, 2H), 3.71 (s, 3H)

Step 2: methyl 2-methyl-2-(4-nitrophenyl)propanoate

To a suspension of sodium hydride (60 percent in oil, 1.47 g, 37 mmol) in DMF (50 mL) at 0° C. was added methyl 2-(4-nitrophenyl)acetate (3.25 g, 16.7 mmol) obtained in step 1. The mixture was stirred for 15 minutes at 0° C. and iodomethane (4.2 ml, 6.6 mmol) was added. The mixture was stirred for further 5 minutes at 0° C. and at room temperature for 12 hours, then quenched with 1 N aqueous hydrochloric acid (1 mL) and extracted with EtOAc (30×2 mL). The organic layer washed with water (30×2 mL) and brine (20 mL), dried over MgSO4, filtered and concentrated under reduced pressure. The residue was purified by silica-gel chromatography (EtOAc:Hexane=1:3) to give desired product. (Yield 57%)

$^1$H-NMR (400 MHz, CHLOROFORM-D) δ 8.17 (d, J=8.7 Hz, 2H), 7.49 (d, J=8.7 Hz, 2H), 3.66 (s, 3H), 1.61 (s, 6H)

Step 3: Methyl 2-(4-aminophenyl)-2-methylpropanoate

A mixture of methyl 2-methyl-2-(4-nitrophenyl)propanoate (2.11 g, 9.45 mmol) and Pd/C (0.2 g) in MeOH (30 ml) were stirred under balloon of $H_2$ at room temperature for 4 hours, then filtered through celite to give the product (Yield 95%).

$^1$H-NMR (400 MHz, CHLOROFORM-D) δ 7.12 (d, J=8.2 Hz, 2H), 6.64 (d, J=8.7 Hz, 2H), 3.62 (s, 3H), 1.52 (d, J=0.9 Hz, 6H)

Preparation Example 15: Methyl 2-(3-aminophenyl)-2-methylpropanoate

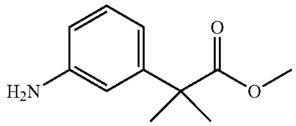

The desired product was obtained in a similar manner to Preparation Example 14 by using 2-(3-nitrophenyl)acetic acid (4 g, 22.08 mmol). (3 step yield 30%)

$^1$H-NMR (400 MHz, CHLOROFORM-D) δ 7.15-7.03 (m, 1H), 6.78-6.67 (m, 1H), 6.67-6.59 (1H), 6.58-6.51 (m, 1H), 3.65 (q, J=14.9 Hz, 3H), 1.61-1.45 (m, 6H)

Preparation Example 16: Methyl 2-(2-aminobenzo[d]oxazol-5-yl)acetate

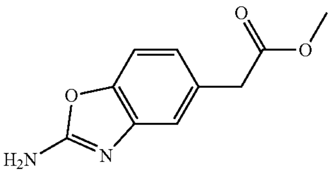

The desired product was obtained in a similar manner to Preparation Example 18 (Step 1, Step 2, Step 3, Step 5, Step 6) by using 2-(4-hydroxyphenyl)acetic acid (20 g, 131 mmol). (5 steps yield 48%)

$^1$H-NMR (400 MHz, CHLOROFORM-D) δ 7.27 (s, 1H), 7.21 (d, J=8.2 Hz, 1H), 6.98 (d, J=8.2 Hz, 1H), 5.46 (s, 2H), 3.69 (s, 3H), 3.67 (s, 2H)

Preparation Example 17: Methyl 2-(2-aminobenzo[d]oxazol-5-yl)-2-methylpropanoate

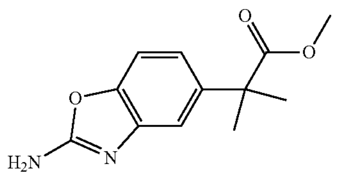 [SMILES: COC(=O)C(C)(C)c1ccc2oc(N)nc2c1]

The desired product was prepared in a similar manner to Preparation Example 18 (Step 1, Step 2, Step 3, Step 4, Step 5, Step 6) by using 2-(4-hydroxyphenyl)acetic acid (20 g, 131 mmol). (6 step yield 43%)

$^1$H-NMR (400 MHz, CHLOROFORM-D) δ 7.34 (d, J=1.8 Hz, 1H), 7.20 (d, J=8.7 Hz, 1H), 7.04 (dd, J=8.7, 1.8 Hz, 1H), 5.58 (s, 2H), 3.65 (s, 3H), 1.61 (s, 6H)

Preparation Example 18: Methyl 2-(2-aminobenzo[d]oxazol-6-yl)-2-methylpropanoate

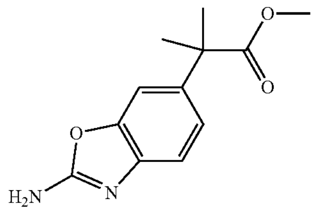 [SMILES: COC(=O)C(C)(C)c1ccc2nc(N)oc2c1]

Step 1: 2-(3-hydroxy-4-nitrophenyl)acetic Acid 2-(3-Hydroxyphenyl)acetic acid (2 g, 13.15 mmol) and 4 ml of 70% nitric acid were stirred at room temperature for 30 minutes. After confirming that the reaction was complete by TLC, the organic solvent was removed under reduced pressure. After extraction with ethyl acetate (2×20 ml), it was washed with brine (20 ml), and the organic solvent was dried over magnesium sulfate, and removed under reduced pressure. The next reaction was carried out without an additional column.

m/z $(M+H)^+$ calculated for $C_8H_7NO_5$: 198. found 198.

Step 2: Methyl 2-(3-hydroxy-4-nitrophenyl)acetate 2-(3-hydroxy-4-nitrophenyl)acetic acid (2.59 g, 13.14 mmol) obtained in step 1 and 0.245 ml of sulfuric acid were dissolved in 50 ml of methanol and stirred at 70° C. for 4 hours. After confirming that the reaction was complete by TLC, the organic solvent was removed under reduced pressure. After extraction with ethyl acetate (2×20 ml), it was washed with brine (20 ml), and the organic solvent was dried over magnesium sulfate, and removed under reduced pressure. The desired product was obtained by purification with silica gel column (ethyl acetate:hexane=1:9). (Yield 26.8%)

$^1$H-NMR (400 MHz, CHLOROFORM-D) δ 10.57 (s, 1H), 8.05 (d, J=8.7 Hz, 1H), 7.10-7.03 (m, 1H), 6.90 (dd, J=8.7, 1.8 Hz, 1H), 3.71 (s, 3H), 3.65 (s, 2H)

Step 3: Methyl 2-(3-(benzyloxy)-4-nitrophenyl)acetate

Methyl 2-(3-hydroxy-4-nitrophenyl)acetate (0.744 g, 3.52 mmol) obtained in step 2, 0.461 ml of benzyl bromide and potassium carbonate (1.315 g, 9.52 mmol) were added to 30 ml of DMF and stirred at room temperature for 15 hours. After confirming that the reaction was complete by TLC, the organic solvent was removed under reduced pressure. After extraction with ethyl acetate (2×20 ml), it was washed with brine (20 ml), and the organic solvent was dried over magnesium sulfate and removed under reduced pressure. The desired product was obtained by purification with silica gel column (ethyl acetate:hexane=1:9). (Yield 30.1%)

$^1$H-NMR (400 MHz, CHLOROFORM-D) δ 7.90-7.73 (m, 1H), 7.45 (dd, J=16.5, 9.1 Hz, 2H), 7.42-7.35 (m, 2H), 7.35-7.28 (m, 1H), 7.12-7.04 (m, 1H), 6.93 (dd, J=8.2, 1.4 Hz, 1H), 5.28-5.18 (m, 2H), 3.71-3.66 (m, 3H), 3.66-3.59 (m, 2H)

Step 4: Methyl 2-(3-(benzyloxy)-4-nitrophenyl)-2-methylpropanoate

Sodium hydride (0.076 g, 3.19 mmol) was dissolved in 10.6 ml of DMF in the presence of nitrogen, methyl 2-(3-(benzyloxy)-4-nitrophenyl)acetate (0.32 g, 1.062 mmol) obtained in step 3 was dissolved in DMF and slowly added dropwise, followed by stirring at 0° C. for 15 minutes. Then, 0.166 ml of methyl iodide was added and stirred at room temperature for 4 hours. After confirming that the reaction was complete by TLC, the organic solvent was removed under reduced pressure. After extraction with ethyl acetate (2×20 ml), it was washed with brine (20 ml), and the organic solvent was dried over magnesium sulfate, and removed under reduced pressure. The desired product was obtained by purification with silica gel column (ethyl acetate: hexane=1:9). (Yield 85%)

$^1$H-NMR (CHLOROFORM-D) δ 7.86 (d, J=8.5 Hz, 1H), 7.48 (d, J=7.3 Hz, 2H), 7.42 (t, J=7.5 Hz, 2H), 7.35 (t, J=7.2 Hz, 1H), 7.07 (s, 1H), 7.02 (d, J=8.5 Hz, 1H), 5.26 (s, 2H), 3.69-3.58 (m, 3H), 1.58-1.53 (m, 6H)

Step 5: Methyl 2-(4-amino-3-hydroxyphenyl)-2-methylpropanoate

The desired product was obtained in a similar manner to step 3 of Preparation Example 94 by using methyl 2-(3-(benzyloxy)-4-nitrophenyl)-2-methylpropanoate (0.297 g, 0.902 mmol) obtained in step 4. (Yield 89%)

$^1$H-NMR (400 MHz, CHLOROFORM-D) δ 6.78-6.65 (m, 3H), 3.76-3.60 (m, 3H), 1.49 (d, J=15.1 Hz, 6H)

Step 6: Methyl 2-(2-aminobenzo[d]oxazol-6-yl)-2-methylpropanoate

Methyl 2-(4-amino-3-hydroxyphenyl)-2-methylpropanoate (0.167 g, 0.798 mmol) obtained in step 5 and cyanogen bromide (0.423 g, 3.99 mmol) were dissolved with 5.7 ml of methanol and 5.7 ml of water and stirred at room temperature for 6 hours. After confirming that the reaction was complete by TLC, the organic solvent was removed under reduced pressure. After extraction with ethyl acetate (2×20 ml), it was washed with brine (20 ml), and the organic solvent was dried over magnesium sulfate, and removed under reduced pressure. The next reaction was carried out without an additional purification.

$^1$H-NMR (400 MHz, CHLOROFORM-D) δ 7.29-7.26 (m, 1H), 7.25 (d, J=2.7 Hz, 1H), 7.16 (dd, J=8.7, 1.8 Hz, 1H), 5.44 (s, 1H), 3.66-3.61 (m, 3H), 1.64-1.55 (m, 6H)

Preparation Example 19: Methyl 2-(6-aminopyridin-3-yl)-2-methylpropanoate

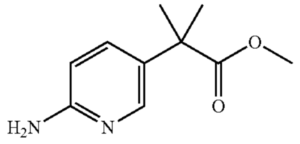

Step 1: Methyl 2-(6-chloropyridin-3-yl)acetate

At 0° C., acetyl chloride was added dropwise to 48.6 ml of methanol, followed by stirring for 15 minutes. After adding 2-(6-chloropyridin-3-yl)acetic acid (2.50 g, 14.6 mmol), the mixture was stirred at 100° C. for 5 hours, and the organic solvent was removed under reduced pressure. It was diluted with ethyl acetate, washed with brine, and the organic solvent was dried over magnesium sulfate, and removed under reduced pressure to obtain the desired product. (Yield 96%)

$^1$H-NMR (400 MHz, CHLOROFORM-D) δ 8.29 (d, J=2.3 Hz, 1H), 7.62 (dd, J=8.2, 2.7 Hz, 1H), 7.31 (d, J=7.8 Hz, 1H), 3.72 (s, 3H), 3.62 (s, 2H)

Step 2: Methyl 2-(6-chloropyridin-3-yl)-2-methylpropanoate

DMF in which sodium hydride (60%, 0.948 g, 23.7 mmol) was dissolved was lowered to 0° C., and methyl 2-(6-chloropyridin-3-yl)acetate synthesized in step 1 was added. After stirring for 15 minutes at 0° C., iodomethane (2.70 ml, 43.1 mmol) was added dropwise thereto. After stirring for an additional 5 minutes at 0° C., the mixture was stirred at room temperature for 15 hours. After washing with ethyl acetate, it was washed with 1 N hydrochloric acid solution, and the organic solvent was dried over magnesium sulfate, and removed under reduced pressure. The desired product was obtained by purification with silica gel column (ethyl acetate:hexane). (Yield 59%)

$^1$H-NMR (400 MHz, CHLOROFORM-D) δ 8.38 (d, J=2.7 Hz, 1H), 7.63 (dd, J=8.2, 2.7 Hz, 1H), 7.29 (d, J=8.2 Hz, 1H), 3.67 (s, 3H), 1.61 (s, 6H)

Step 3: Methyl 2-(6-((tert-butoxycarbonyl)amino)pyridin-3-yl)-2-methylpropanoate After dissolving methyl 2-(6-chloropyridin-3-yl)-2-methylpropanoate (0.47 g, 2.2 mmol) synthesized in step 2, tert-butyl carbamate (0.77 g, 6.6 mmol), cesium carbonate (1.08 g, 3.30 mmol), 4,5-bis(diphenylphosphino)-9,9-dimethylxanthine (255 mg, 0.440 mmol) and tris(dibenzylideneacetone)dipalladium(0) (201 mg, 0.220 mmol) in 1,4-dioxane 11.0 ml, the dissolved oxygen was removed through nitrogen bubbling under stirring, and the inflow of outside air was blocked in a sealed container. The reaction was stirred at 140° C. for 15 hours and then cooled to room temperature. After filtering through a Celite pad and removing the organic solvent under reduced pressure, it was dissolved in ethyl acetate and washed with brine. The organic solvent was dried over magnesium sulfate and removed under reduced pressure. The desired product was obtained by purification with silica gel column (ethyl acetate:hexane). (Yield 26%)

$^1$H-NMR (400 MHz, CHLOROFORM-D) δ 8.22 (d, J=2.3 Hz, 1H), 7.95-7.79 (1H), 7.63 (dd, J=8.9, 2.5 Hz, 1H), 7.47-7.36 (1H), 3.65 (s, 3H), 1.66-1.58 (6H), 1.52 (s, 9H)

Step 4: Methyl 2-(6-aminopyridin-3-yl)-2-methylpropanoate

After dissolving methyl 2-(6-((tert-butoxycarbonyl)amino)pyridin-3-yl)-2-methylpropanoate (169 mg, 0.574 mmol) synthesized in step 3 in 3.00 ml of DCM, 4 N solution of hydrogen chloride in dioxane was added dropwise. After stirring at room temperature overnight, the organic solvent was removed under reduced pressure, neutralized, extracted with ethyl acetate, and purified by a silica gel column (DCM: methanol) to obtain the desired product. (Yield 71%)

$^1$H-NMR (400 MHz, CHLOROFORM-D) δ 7.81-7.62 (m, 2H), 7.43 (s, 2H), 7.18 (d, J=9.1 Hz, 1H), 3.68 (s, 3H), 1.55 (s, 6H)

Preparation Example 20: Ethyl 2-(2-aminopyrimidin-4-yl)-2-methylpropanoate

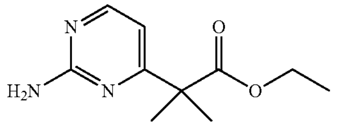

Step 1: Diethyl 2-(2-chloropyrimidin-4-yl)-malonate

Sodium hydride (60%, 7.89 g, 197 mmol) was added to 300 ml of THF in which diethyl malonate (15.8 g, 99.0 mmol) was dissolved at 0° C. After stirring at the same temperature for 30 minutes, 2,4-dichloropyrimidine (9.80 g, 65.8 mmol) was added, followed by reflux stirring at 90° C. for 3 hours. The reaction was terminated by adding saturated aqueous ammonium chloride solution to the reaction solution, followed by extraction with ethyl acetate. The organic solvent was dried over magnesium sulfate and removed under reduced pressure. The desired product was obtained by purification with silica gel column (ethyl acetate:hexane). (Yield 96%)

$^1$H-NMR (400 MHz, CHLOROFORM-D) δ 8.66 (d, J=5.0 Hz, 1H), 7.56 (d, J=5.0 Hz, 1H), 4.85 (s, 1H), 4.37-4.17 (m, 4H), 1.29 (q, J=7.0 Hz, 6H)

Step 2: Ethyl 2-(2-chloropyrimidin-4yl)acetate

Diethyl 2-(2-chloropyrimidin-4-yl)-malonate (17.3 g, 63.4 mmol) synthesized in step 1 and sodium ethoxide (20%, 6.48 g, 19.0 mmol) were dissolved in 150 ml of ethanol and reflux stirred for 3 hours. The pH was adjusted to pH 7 with 1 N aqueous hydrochloric acid, extracted with ethyl acetate, dried over magnesium sulfate, and purified by silica gel column (ethyl acetate:hexane) to obtain the desired product. (Yield 68%)

$^1$H-NMR (400 MHz, CHLOROFORM-D) δ 8.59 (d, J=5.0 Hz, 1H), 7.34 (d, J=5.0 Hz, 1H), 4.31-4.12 (2H), 3.83 (s, 2H), 1.38-1.19 (m, 3H)

Step 3: Ethyl 2-(2-aminopyrimidin-4-yl)-2-methylpropanoate

The desired product was obtained in a similar manner to Preparation Example 19 (Step 2, Step 3, Step 4) by using ethyl 2-(2-chloropyrimidin-4yl)acetate (5.70 g, 28.4 mmol) synthesized in Step 2. (3 step yield 36%)

m/z $(M+H)^+$ calculated for $C_{10}H_{16}N_3O_2$: 210. found 210.

Preparation Example 21: Methyl 3-(2-aminobenzo[d]oxazol-5-yl)-2,2-dimethylpropanoate

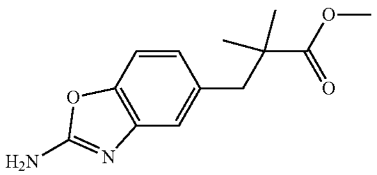 [SMILES: COC(=O)C(C)(C)Cc1ccc2oc(N)nc2c1]

Step 1: Methyl 3-(4-hydroxyphenyl)-2,2-dimethylpropanoate

Indium(III) bromide (0.41 g, 1.16 mmol) and dimethylketene trimethylsilyl methyl acetal (6.08 g, 34.9 mmol) were dissolved in dichloromethane, and then 1-(benzyloxy)-4-(bromomethyl)benzene (6.44 g, 23.2 mmol) was slowly added. After stirring at room temperature for 2 hours, the reaction solution was poured into a saturated aqueous sodium bicarbonate solution. After the mixture was extracted with ethyl acetate, the organic solvent was dried over magnesium sulfate, and the organic solvent was removed under reduced pressure. The desired product was obtained by purification with silica gel column (ethyl acetate:hexane=1:3). (Yield 60%)

$^1$H-NMR (400 MHz, CHLOROFORM-D) δ 6.96 (d, J=8.7 Hz, 2H), 6.75-6.68 (2H), 4.86-4.71 (1H), 3.65 (s, 3H), 2.78 (s, 2H), 1.20-1.13 (m, 6H)

Step 2: Methyl 3-(4-hydroxy-3-nitrophenyl)-2,2-dimethylpropanoate

Methyl 3-(4-hydroxyphenyl)-2,2-dimethylpropanoate (2.9 g, 13.9 mmol) synthesized in step 1 was dissolved in acetic acid, lowered to 0° C., and nitric acid (70%, 1.02 ml, 16.01 mmol) was added slowly, and the reaction temperature was gradually raised to room temperature for 1 hour, followed by stirring. After completion of the reaction, it was extracted with ethyl acetate, and the organic solvent was dried over magnesium sulfate, and the organic solvent was removed under reduced pressure. The desired product was obtained by purification with silica gel column (ethyl acetate:hexane=1:3). (Yield 56%)

$^1$H-NMR (400 MHz, CHLOROFORM-D) δ 10.47 (s, 1H), 7.85 (d, J=2.3 Hz, 1H), 7.34 (dd, J=8.5, 2.1 Hz, 1H), 7.06 (d, J=8.2 Hz, 1H), 3.68 (t, J=15.1 Hz, 3H), 2.82 (d, J=15.1 Hz, 2H), 1.20 (s, 6H)

Step 3: Methyl 3-(3-amino-4-hydroxyphenyl)-2,2-dimethylpropanoate

Methyl 3-(4-hydroxy-3-nitrophenyl)-2,2-dimethylpropanoate (1.97 g, 7.78 mmol) prepared in step 2 was dissolved in methanol, Pd/C (207 mg, 0.19 mmol)) was added, and then a hydrogen balloon was connected and stirred at room temperature for 4 hours. After completion of the reaction, the desired compound was synthesized by Celite filter. (Yield 98%)

$^1$H-NMR (400 MHz, CHLOROFORM-D) δ 6.84 (s, 1H), 6.72 (d, J=8.2 Hz, 1H), 6.62-6.54 (1H), 5.44 (s, 2H), 3.62 (s, 3H), 2.65 (s, 2H), 1.12 (d, J=7.8 Hz, 6H)

Step 4: Methyl 3-(2-aminobenzo[d]oxazol-5-yl)-2,2-dimethylpropanoate

Methyl 3-(3-amino-4-hydroxyphenyl)-2,2-dimethylpropanoate (1.7 g, 7.61 mmol) synthesized in step 3 was dissolved in methanol, lowered to 5° C., and Cyanogen bromide (3.1 ml, 9.14 mmol) dissolved in 10 ml of water was slowly added while stirring vigorously. After stirring at room temperature for 2 hours, sodium bicarbonate (640 mg, 7.61 mmol) was added over 1 hour to adjust the pH of the reaction solution from 6.5 to 7.0, followed by stirring at room temperature for an additional 1 hour. The resulting solid was filtered, washed with cold water, and recrystallized in ethanol to obtain the desired compound. (Yield 65%)

$^1$H-NMR (400 MHz, CHLOROFORM-D) δ 7.15 (d, J=8.2 Hz, 1H), 7.09 (d, J=0.9 Hz, 1H), 6.81 (s, 1H), 5.39 (s, 2H), 3.66 (s, 3H), 2.90 (s, 2H), 1.17 (d, J=13.3 Hz, 6H)

Preparation Example 22: Methyl (E)-3-(2-amino-benzo[d]oxazol-5-yl)acrylate

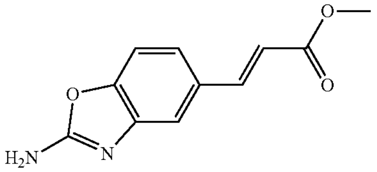 [SMILES: COC(=O)/C=C/c1ccc2oc(N)nc2c1]

Step 1: Methyl (E)-3-(4-hydroxy-3-nitrophenyl)acrylate

Sodium hydride (2.154 g, 90 mmol) was dissolved in 6 ml of DMF in the presence of nitrogen, and methyl-2-(diethoxyphosphoryl)acetate (11.32 g, 53.9 mmol) was dissolved in THF, slowly added dropwise, and then stirred for 15 minutes at 0° C. Then, 4-hydroxy-3-nitrobenzaldehyde (3 g, 17.95 mmol) was added and stirred at room temperature for 4 hours. After confirming that the reaction was complete by TLC, the organic solvent was removed under reduced pressure. After extraction with ethyl acetate (2×20 ml), it was washed with brine (20 ml), and the organic solvent was dried over magnesium sulfate, and removed under reduced pressure. The next reaction was carried out without further purification.

Step 2: Methyl (E)-3-(3-amino-4-hydroxyphenyl)acrylate

Methyl (E)-3-(4-hydroxy-3-nitrophenyl)acrylate (4 g, 17.92 mmol) synthesized in step 1, iron (3.5 g, 62.7 mmol) and 3.08 ml of acetic acid were dissolved in 60 ml of ethanol and stirred at 75° C. for 4 hours. After confirming that the reaction was complete by TLC, the organic solvent was removed under reduced pressure. After extraction with ethyl acetate (2×30 ml), it was washed with brine (20 ml), and the organic solvent was dried over magnesium sulfate, and removed under reduced pressure. The desired product was obtained by purification with silica gel column (ethyl acetate:hexane=1:9). (Yield 20%)

$^1$H-NMR (400 MHz, METHANOL-D4) δ 7.59-7.42 (m, 1H), 7.07-6.88 (m, 1H), 6.88-6.74 (m, 1H), 6.73-6.58 (m, 1H), 6.29-6.10 (m, 1H), 3.82-3.63 (m, 3H), 3.35-3.21 (m, 2H)

Step 3: Methyl (E)-3-(2-aminobenzo[d]oxazol-5-yl) acrylate

The desired product was obtained in a similar manner to step 6 of Preparation Example 18 by using methyl (E)-3-(3-amino-4-hydroxyphenyl)acrylate (0.7 g, 3.62 mmol) synthesized in step 2. (Yield 67%)

$^1$H-NMR (400 MHz, METHANOL-D4) δ 7.82-7.58 (m, 1H), 7.55-7.38 (m, 1H), 7.36-7.19 (m, 2H), 6.53-6.35 (m, 1H), 3.86-3.62 (3H)

Preparation Example 23: Methyl 3-(2-aminobenzo[d]oxazol-5-yl)propanoate

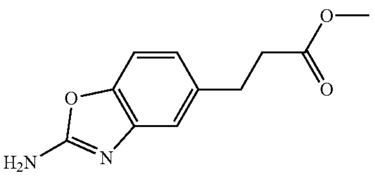 [SMILES: COC(=O)CCc1ccc2oc(N)nc2c1]

Step 1: Methyl 3-(3-amino-4-hydroxyphenyl)propanoate

The desired product was obtained in a similar manner to Step 3 of Preparation Example 94 by using the methyl (E)-3-(4-hydroxy-3-nitrophenyl)acrylate (5.34 g, 23.93 mmol) obtained in Step 1 of Preparation Example 22. The next reaction was carried out without further purification.

Step 2: Methyl 3-(2-aminobenzo[d]oxazol-5-yl)propanoate

The desired product was obtained in a similar manner to step 6 of Preparation Example 18 by using methyl 3-(3-amino-4-hydroxyphenyl)propanoate (4.67 g, 23.92 mmol) synthesized in step 1. (Yield 40%)

m/z $(M+H)^+$ calculated for $C_{11}H_{13}N_2O_3$: 221. found 221.

Preparation Example 24: Methyl 3-(2-aminobenzo[d]oxazol-6-yl)propanoate

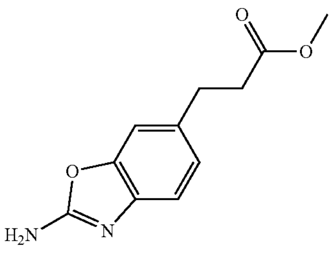 [SMILES: COC(=O)CCc1ccc2nc(N)oc2c1]

Step 1: Methyl 3-(4-amino-3-hydroxyphenyl)propanoate

The desired product was obtained in a similar manner to Preparation Example 22 (Step 1) and Preparation Example 94 (Step 3) by using 3-hydroxy-4-nitrobenzaldehyde (1.8 g, 10.77 mmol). (2 step yield 36%)

$^1$H-NMR (400 MHz, METHANOL-D4) δ 6.74-6.57 (m, 1H), 6.57-6.50 (m, 1H), 6.50-6.35 (m, 1H), 3.65-3.49 (m, 3H), 2.82-2.59 (m, 2H), 2.59-2.39 (2H)

Step 2: Methyl 3-(2-aminobenzo[d]oxazol-6-yl)propanoate

The desired product was obtained in a similar manner to Preparation Example 18 (step 6) by using methyl 3-(4-amino-3-hydroxyphenyl)propanoate (0.75 g, 3.87 mmol) synthesized in step 1. (Yield 51.7%)

m/z $(M+H)^+$ calculated for $C_{11}H_{13}N_2O_3$: 221. found 221.

Preparation Example 25: 4-phenyloxazol-2-amine

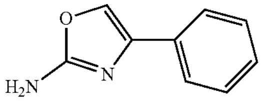 [SMILES: Nc1nc(-c2ccccc2)co1]

2-Bromo-1-phenylethane-1-one (0.100 g, 0.502 mmol) was dissolved in acetonitrile (5.02 ml), stirred at room temperature, and urea (0.302 g, 5.02 mmol) was added. After stirring at 80° C. for 16 hours, the solvent was removed under reduced pressure. The desired product was obtained by purification with silica gel column. (Yield 19.8%)

$^1$H-NMR (500 MHz, CHLOROFORM-D) δ 7.74-7.55 (m, 2H), 7.55-7.44 (m, 1H), 7.44-7.34 (m, 2H), 7.30 (t, J=7.5 Hz, 1H), 5.15 (d, J=42.1 Hz, 2H)

Preparation Example 26: Methyl 2-(4-(2-aminopyridin-4-yl)phenyl)-2-methylpropanoate

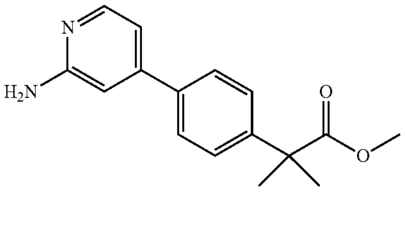

Step 1: Methyl 2-methyl-2-(4-(4,4,5,5-tetramethyl-1,3,2-dioxophorolein-2-yl)phenyl)propanoate Methyl 2-(4-bromophenyl)-2-methylpropanoate (1 g, 3.89 mmol) and bis(pinacolato)diborone (1.481 g, 5.83 mmol) were dissolved in toluene (19.45 ml), [1,1'-bis(diphenylphosphino)ferrocene]dichloropalladium dichloromethane complex (0.159 g, 0.194 mmol) and potassium acetate (1.527 g, 15.56 mmol) were added. The mixture was reflux stirred for 16 hours at 110° C. It was filtered through a Celite pad and the organic solvent was removed under reduced pressure. The desired product was obtained by purification with silica gel column. (Yield 72%)

$^1$H-NMR (400 MHz, CHLOROFORM-D) δ 7.76 (d, J=8.2 Hz, 2H), 7.32 (d, J=8.2 Hz, 2H), 3.62 (s, 3H), 1.55 (d, J=13.7 Hz, 7H), 1.32 (s, 12H)

Step 2: Methyl 2-(4-(2-aminopyridin-4-yl)phenyl)-2-methylpropanoate

The desired product was obtained in a similar manner to Preparation Example 11 by using methyl 2-methyl-2-(4-(4,4,5,5-tetramethyl-1,3,2-dioxophorolein-2-yl)phenyl)propanoate (0.851 g, 2.80 mmol) obtained in step 1 and 4-bromopyridin-2-amine (0.484 g, 2.80 mmol). (yield 100%)

$^1$H-NMR (400 MHz, CHLOROFORM-D) δ 8.10 (d, J=5.5 Hz, 1H), 7.54 (d, J=8.2 Hz, 2H), 7.44-7.38 (m, 2H), 6.86 (dd, J=5.5, 1.4 Hz, 1H), 6.68 (s, 2H), 4.46 (s, 1H), 3.67 (s, 3H), 1.60 (s, 6H)

Preparation Example 27: Methyl 2-(3-(2-aminopyridin-4-yl)phenyl)-2-methylpropanoate

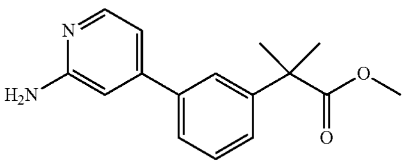

The desired product was obtained in a similar manner to Preparation Example 26 by using methyl 2-(3-bromophenyl)-2-methylpropanoate (1 g, 3.89 mmol). (2 step yield 90%)

$^1$H-NMR (400 MHz, CHLOROFORM-D) δ 8.15 (d, J=5.5 Hz, 1H), 7.55 (s, 1H), 7.50-7.39 (m, 3H), 6.89 (dd, J=5.2, 1.5 Hz, 1H), 6.71 (s, 1H), 4.51 (s, 2H), 3.70 (s, 3H), 1.65 (s, 6H)

Preparation Example 28: Ethyl 1-(2-aminopyrimidin-4-yl)piperidine-4-carboxylate

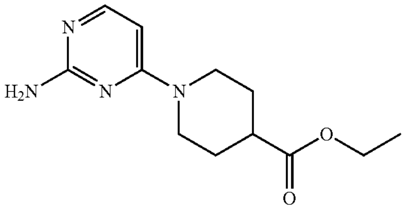 [SMILES: CCOC(=O)C1CCN(c2ccnc(N)n2)CC1]

Step 1: Ethyl 1-(2-chloropyrimidin-4-yl)piperidine-4-carboxylate 2,4-Dichloropyrimidine (0.1 g, 0.671 mmol) was dissolved in ethanol (6.71 ml), and ethyl piperidine-4-carboxylate (0.124 ml, 0.806 mmol) and TEA (0.187 ml, 1.343 mmol) were added. It was stirred at 85° C. for 3 hours. After removing the solvent under reduced pressure, it was dissolved in ethyl acetate and washed with water. The desired product was obtained by purification with silica gel column. (Yield 80%)

$^1$H-NMR (CHLOROFORM-D) δ 8.05 (d, J=6.4 Hz, 1H), 6.42 (d, J=6.1 Hz, 1H), 4.27 (s, 2H), 4.22-4.16 (2H), 3.22-3.06 (2H), 2.63 (tt, J=10.6, 4.1 Hz, 1H), 2.06-1.96 (m, 2H), 1.86-1.67 (2H), 1.29 (td, J=7.2, 4.5 Hz, 3H)

Step 2: Ethyl 1-(2-((tert-butoxycarbonyl)amino)pyrimidin-4-yl)piperidine-4-carboxylate The desired product was obtained in a similar manner to Step 1 of Preparation Example 2 by using ethyl 1-(2-chloropyrimidin-4-yl)piperidine-4-carboxylate (1.43 g, 5.30 mmol) obtained in step 1 and tert-butyl carbamate (0.683 g, 5.83 mmol). (Yield 37%)

$^1$H-NMR (500 MHz, CHLOROFORM-D) δ 7.88 (d, J=6.1 Hz, 1H), 6.04-5.92 (1H), 4.76-4.70 (1H), 4.26 (d, J=13.1 Hz, 2H), 4.22-4.09 (m, 2H), 3.09-2.93 (m, 2H), 2.66-2.50 (m, 1H), 1.98 (dd, J=13.6, 3.8 Hz, 2H), 1.82-1.68 (2H), 1.64 (s, 9H), 1.31-1.22 (m, 3H)

Step 3: Ethyl 1-(2-aminopyrimidin-4-yl)piperidine-4-carboxylate

Ethyl 1-(2-((tert-butoxycarbonyl)amino)pyrimidin-4-yl)piperidine-4-carboxylate (0.480 g, 1.370 mmol) obtained in step 2 was dissolved in DCM (12.3 ml), and then trifluoroacetic acid (1.37 ml) dissolved in DCM was added and stirred at room temperature for 2 hours. After removing the solvent under reduced pressure, it was dissolved in DCM and washed with water. The desired product was obtained by purification with silica gel column. (Yield 100%)

$^1$H-NMR (CHLOROFORM-D) δ 10.02-9.49 (1H), 7.56 (d, J=7.3 Hz, 1H), 6.10 (d, J=7.6 Hz, 1H), 4.90-4.54 (1H), 4.20 (q, J=7.1 Hz, 2H), 4.00-3.77 (1H), 3.28 (d, J=16.5 Hz, 2H), 2.74-2.62 (m, 1H), 2.07 (d, J=12.5 Hz, 2H), 1.91-1.69 (2H), 1.30 (t, J=7.2 Hz, 3H)

Preparation Example 29: Ethyl 1-(6-aminopyridin-2-yl)piperidine-4-carboxylate

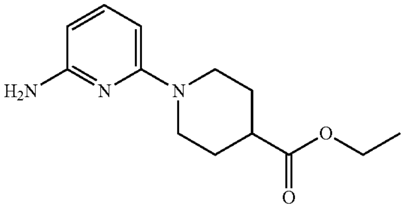 [SMILES: CCOC(=O)C1CCN(c2cccc(N)n2)CC1]

Step 1: Ethyl 1-(6-chloropyridin-2-yl)piperidine-4-carboxylate 2,6-dichloropyridine (0.565 g, 3.82 mmol) was dissolved in ethanol (6.71 ml), and ethyl piperidine-4-carboxylate (0.500 g, 3.18 mmol) and DIPEA (1.11 ml, 6.36 mmol) were added. It was stirred at 100° C. for 16 hours. After the reaction was terminated by adding water, it was dissolved in diethyl ether and washed with water. The desired product was obtained by purification with silica gel column. (Yield 53%)

$^1$H-NMR (CHLOROFORM-D) δ 7.40 (t, J=7.8 Hz, 1H), 6.59 (d, J=7.6 Hz, 1H), 6.52 (d, J=8.2 Hz, 1H), 4.38-4.04 (m, 4H), 3.13-2.91 (m, 2H), 2.55 (tt, J=11.0, 3.9 Hz, 1H), 2.01 (dd, J=13.4, 3.4 Hz, 2H), 1.88-1.68 (m, 2H), 1.29 (t, J=7.2 Hz, 3H)

Step 2: Ethyl 1-(6-aminopyridin-2-yl) piperidine-4-carboxylate

The desired product was obtained in a similar manner to Preparation Example 28 (step 2, step 3) by using ethyl 1-(6-chloropyridin-2-yl)piperidine-4-carboxylate obtained in step 1. (2 step yield 36%)

$^1$H-NMR (500 MHz, CHLOROFORM-D) δ 7.49 (t, J=8.2 Hz, 1H), 5.95 (dd, J=8.4, 5.0 Hz, 2H), 4.19 (q, J=7.0 Hz, 2H), 3.94 (d, J=13.7 Hz, 2H), 3.22 (t, J=10.8 Hz, 2H), 2.69-2.54 (m, 1H), 2.08 (dd, J=13.9, 3.5 Hz, 2H), 1.98-1.79 (m, 2H), 1.29 (t, J=7.0 Hz, 3H)

Preparation Example 30: Ethyl (R)-1-(2-aminopyrimidin-4-yl)piperidine-3-carboxylate

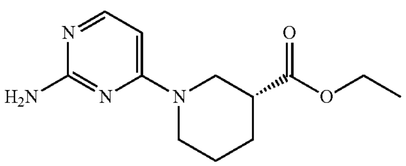 [SMILES: CCOC(=O)[C@@H]1CCCN(c2ccnc(N)n2)C1]

The desired product was obtained in a similar manner to Preparation Example 28 by using ethyl (R)-piperidine-3-carboxylate (0.621 ml, 4.03 mmol). (3 step yield 6%)

$^1$H-NMR (500 MHz, CHLOROFORM-D) δ 7.68 (d, J=6.7 Hz, 1H), 6.49-6.21 (1H), 6.07 (d, J=6.7 Hz, 1H), 4.31 (d, J=13.1 Hz, 1H), 4.16 (q, J=7.1 Hz, 2H), 4.01 (d, J=13.1 Hz, 1H), 3.43-3.30 (1H), 3.30-3.16 (1H), 2.63-2.47 (m, 1H), 2.19-2.03 (m, 1H), 1.91-1.76 (m, 2H), 1.65-1.46 (m, 1H), 1.26 (t, J=7.0 Hz, 3H)

Preparation Example 31: Ethyl (R)-1-(6-aminopyridin-2-yl)piperidine-3-carboxylate

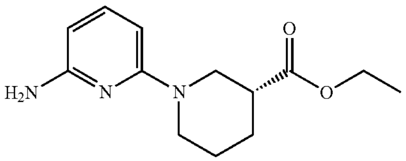

The desired product was obtained in a similar manner to Preparation Example 29 by using ethyl (R)-piperidine-3-carboxylate (0.500 g, 3.18 mmol). (3 step yield 37%)

$^1$H-NMR (500 MHz, CHLOROFORM-D) δ 7.49 (t, J=8.2 Hz, 1H), 5.95 (dd, J=8.4, 5.0 Hz, 2H), 4.19 (q, J=7.0 Hz, 2H), 3.94 (d, J=13.7 Hz, 2H), 3.22 (t, J=10.8 Hz, 2H), 2.69-2.54 (m, 1H), 2.08 (dd, J=13.9, 3.5 Hz, 2H), 1.98-1.79 (m, 2H), 1.29 (t, J=7.0 Hz, 3H)

Preparation Example 32: Ethyl 2-(1-(2-aminopyrimidin-4-yl)piperidin-4-yl)acetate

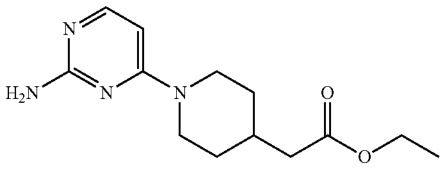 [SMILES: CCOC(=O)CC1CCN(c2ccnc(N)n2)CC1]

Step 1: Ethyl 2-(1-(2-chloropyrimidin-4-yl)piperidin-4-yl)acetate

The desired product was obtained in a similar manner to Step 4 of Preparation Example 36 by using ethyl 2-(piperidin-4-yl)acetate (0.315 g, 1.84 mmol) obtained in Step 3, 2,6-dichloropyrimidine (2.023 mmol) and 0.77 ml of triethylamine. (Yield 86%)

$^1$H-NMR (400 MHz, CHLOROFORM-D) δ 7.90-7.72 (m, 1H), 6.34-6.17 (m, 1H), 4.65-4.02 (m, 2H), 3.98 (q, J=7.2 Hz, 2H), 2.94-2.62 (m, 2H), 2.21-2.04 (m, 2H), 2.04-1.81 (m, 1H), 1.81-1.55 (m, 2H), 1.23-0.93 (m, 5H)

Step 2: Ethyl 2-(1-(2-aminopyrimidin-4-yl)piperidin-4-yl)acetate

The desired product was obtained in a similar manner to Preparation Example 19 (Step 3, Step 4) by using ethyl 2-(1-(2-chloropyrimidin-4-yl)piperidin-4-yl)acetate (0.45 g, 1.586 mmol) synthesized in Step 1. (2-step yield 61%)

$^1$H-NMR (400 MHz, CHLOROFORM-D) δ 7.92-7.74 (m, 1H), 5.93 (d, J=6.4 Hz, 1H), 4.88-4.57 (2H), 4.32 (d, J=13.3 Hz, 2H), 4.13 (q, J=7.2 Hz, 2H), 3.00-2.71 (m, 2H), 2.41-2.11 (m, 2H), 2.06 (qt, J=11.2, 3.8 Hz, 1H), 1.87-1.63 (m, 2H), 1.37-1.04 (m, 5H)

Preparation Example 33: Methyl 2-(1-(2-aminopyrimidin-4-yl)piperidin-4-yl)-2-methylpropanoate

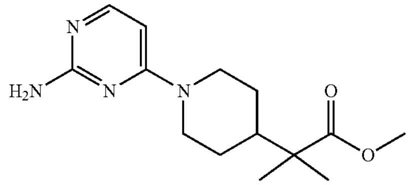 [SMILES: COC(=O)C(C)(C)C1CCN(c2ccnc(N)n2)CC1]

Step 1: Methyl 2-(1-(2-chloropyrimidin-4-yl)piperidin-4-yl)-2-methylpropanoate

The desired product was obtained in a similar manner to Step 4 of Preparation Example 36 by using methyl 2-methyl-2-(piperidin-4-yl)propanoate (0.26 g, 1.403 mmol) obtained in Step 4 of Preparation Example 34 and 2,4-dichloropyrimidine (0.23 g, 1.544 mmol. (Yield 81%)

$^1$H-NMR (400 MHz, CHLOROFORM-D) δ 8.13-7.81 (m, 1H), 6.44-6.26 (m, 1H), 4.41 (s, 1H), 3.72-3.52 (m, 3H), 2.82 (d, J=9.1 Hz, 2H), 2.32-1.74 (m, 2H), 1.63 (d, J=8.7 Hz, 2H), 1.43-1.16 (m, 2H), 1.16-0.91 (m, 6H)

Step 2: Methyl 2-(1-(2-aminopyrimidin-4-yl)piperidin-4-yl)-2-methylpropanoate

The desired product was obtained in a similar manner to Preparation Example 19 (Step 3 and Step 4) by using methyl 2-(1-(2-chloropyrimidin-4-yl)piperidin-4-yl)-2-methylpropanoate (0.344 g, 1.155 mmol) obtained in step 1. (2 step yield 59%)

$^1$H-NMR (400 MHz, CHLOROFORM-D) δ 7.92-7.67 (m, 1H), 5.96-5.77 (m, 1H), 4.83 (d, J=43.0 Hz, 2H), 4.50-4.27 (m, 2H), 3.72-3.58 (m, 3H), 2.81-2.59 (m, 2H), 1.93-1.70 (m, 1H), 1.68-1.42 (m, 2H), 1.31-1.15 (m, 2H), 1.15-0.96 (m, 6H)

Preparation Example 34: Methyl 2-(1-(6-aminopyridin-2-yl)piperidin-4-yl)-2-methylpropanoate

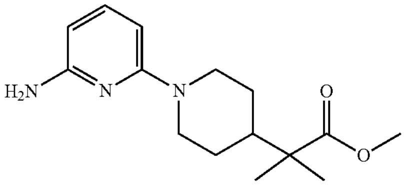 [SMILES: COC(=O)C(C)(C)C1CCN(c2cccc(N)n2)CC1]

Step 1: tert-butyl 4-(2-methoxy-2-oxoethylidine) piperidine-1-carboxylate

Methyl 2-(triphenyl-$\lambda^5$-phosphanylidene)acetate (15.6 g, 46.7 mmol) and tert-butyl 4-oxopiperidine-1-carboxylate (5 g, 25.09 mmol) were dissolved in 50 ml of toluene and stirred at room temperature for 4 hours. After confirming that the starting material disappeared by TLC, the organic solvent was removed under reduced pressure. After extraction with ethyl acetate (2×30 ml), the mixture was washed with brine (20 ml), the organic solvent was dried over magnesium sulfate, and then the organic solvent was removed under reduced pressure. The desired product was obtained by purification with silica gel column (ethyl acetate:hexane=1:9). (Yield 94%)

$^1$H-NMR (400 MHz, CHLOROFORM-D) δ 5.70 (s, 1H), 3.74-3.63 (3H), 3.56-3.38 (m, 4H), 2.92 (t, J=5.7 Hz, 2H), 2.36-2.20 (m, 2H), 1.51-1.37 (m, 9H)

Step 2: tert-butyl 4-(2-methoxy-2-oxoethyl)piperidine-1-carboxylate

The desired product was obtained in a similar manner to Step 3 of Preparation Example 94 by using tert-butyl 4-(2-methoxy-2-oxoethylidine)piperidine-1-carboxylate (1 g, 3.92 mmol) obtained in Step 1. (Yield 99%)

$^1$H-NMR (CHLOROFORM-D) δ 4.20-3.96 (m, 2H), 3.75-3.64 (m, 3H), 2.73 (t, J=11.1 Hz, 2H), 2.30-2.21 (2H), 2.00-1.89 (m, 1H), 1.70 (d, J=13.1 Hz, 2H), 1.51-1.41 (m, 9H), 1.17 (qd, J=12.3, 4.2 Hz, 2H)

Step 3: tert-butyl 4-(1-methoxy-2-methyl-1-oxopropan-2-yl)piperidine-1-carboxylate 1.67 ml of diisopropylamine was dissolved in 7.5 ml of THF in the presence of nitrogen, and 4.66 ml of n-butyllithium was slowly added dropwise at 0° C., followed by stirring for 30 minutes. Then, tert-butyl 4-(2-methoxy-2-oxoethyl) piperidine-1-carboxylate (1 g, 3.89 mmol) synthesized in step 2 was dissolved in 5 ml of THF in the presence of nitrogen, slowly added dropwise, and stirred for 30 minutes. After that, 1.22 ml of methyl iodide was added and stirred at −78° C. for 1 hour. This was repeated once more, and after stirring at room temperature for 4 hours, it was confirmed that the reaction was complete by TLC. The reaction was terminated with ammonium chloride, extracted with ethyl acetate (2×20 ml), washed with brine (10 ml), and the organic solvent was dried over magnesium sulfate, and the organic solvent was removed under reduced pressure. The desired product was obtained by purification with silica gel column (ethyl acetate:hexane=1:9). (Yield 68%)

$^1$H-NMR (CHLOROFORM-D) δ 4.14 (q, J=7.1 Hz, 2H), 3.70 (q, J=4.1 Hz, 3H), 2.66 (d, J=12.5 Hz, 2H), 1.77-1.67 (m, 1H), 1.66-1.59 (m, 2H), 1.47 (s, 9H), 1.31-1.18 (m, 2H), 1.18-1.08 (m, 6H)

Step 4: Methyl 2-methyl-2-(piperidin-4-yl)propanoate

The desired product was obtained in a similar manner to step 3 of Preparation Example 36 by using tert-butyl 4-(1-methoxy-2-methyl-1-oxopropan-2-yl) piperidine-1-carboxylate (0.35 g, 1.226 mmol) synthesized in step 3. (Yield 99%)

m/z $(M+H)^+$ calculated for $C_{10}H_{20}NO_2$: 186. found 186.

Step 5: Methyl 2-(1-(6-chloropyridin-2-yl)piperidin-4-yl)-2-methylpropanoate

The desired product was obtained in a similar manner to step 4 of Preparation Example 36 by using methyl 2-methyl-2-(piperidin-4-yl)propanoate (0.227 g, 1.225 mmol) synthesized in step 4. (Yield 42%)

$^1$H-NMR (400 MHz, CHLOROFORM-D) δ 7.48-7.29 (m, 1H), 6.60-6.48 (1H), 6.48-6.37 (1H), 4.44-4.23 (m, 2H), 3.73-3.54 (m, 3H), 2.83-2.62 (m, 2H), 1.90-1.71 (m, 1H), 1.71-1.47 (m, 2H), 1.47-1.19 (m, 2H), 1.19-1.05 (m, 6H)

Step 6: Methyl 2-(1-(6-aminopyridin-2-yl)piperidin-4-yl)-2-methylpropanoate

The desired product was obtained in a similar manner to Preparation Example 19 (Step 3 and Step 4) by using methyl 2-(1-(6-chloropyridin-2-yl)piperidin-4-yl)-2-methylpropanoate (0.16 g, 0.539 mmol) synthesized in step 5. (2 step yield 43%)

$^1$H-NMR (400 MHz, CHLOROFORM-D) δ 7.30-7.17 (m, 1H), 6.07-5.91 (m, 1H), 5.91-5.73 (m, 1H), 4.29 (d, J=12.8 Hz, 2H), 4.12 (d, J=18.8 Hz, 2H), 3.66 (dd, J=15.8, 14.9 Hz, 3H), 2.75-2.50 (2H), 1.85-1.70 (m, 1H), 1.61-1.43 (m, 2H), 1.43-1.26 (m, 2H), 1.18-1.04 (m, 6H)

Preparation Example 35: Ethyl 2-(4-(2-aminopyrimidin-4-yl)piperazin-1-yl)acetate

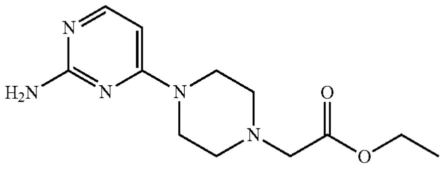 [SMILES: CCOC(=O)CN1CCN(c2ccnc(N)n2)CC1]

Step 1: tert-butyl 4-(2-chloropyrimidin-4-yl)piperazine-1-carboxylate 2,4-dichloropyrimidine (0.200 g, 1.343 mmol) was dissolved in DCM (6.71 ml) and then tert-butyl piperazine-1-carboxylate (0.300 g, 1.611 mmol) and DIPEA (0.586 ml, 3.36 mmol) was added. The mixture was stirred at room temperature for 16 hours. After removing the solvent under reduced pressure, it was dissolved in ethyl acetate and washed with water. The desired product was obtained by purification with silica gel column. (Yield 83%)

$^1$H-NMR (400 MHz, CHLOROFORM-D) δ 8.06 (d, J=5.9 Hz, 1H), 6.38 (d, J=5.9 Hz, 1H), 3.71-3.59 (3H), 3.57-3.45 (m, 4H), 1.52-1.43 (9H)

Step 2: 2-Chloro-4-(piperazin-1-yl)pyrimidine Hydrochloride

The desired product was obtained in a similar manner to step 3 of Preparation Example 28 by using tert-butyl 4-(2-chloropyrimidin-4-yl)piperazine-1-carboxylate (0.332 g, 1.11 mmol) obtained in step 1. (Yield 100%)

$^1$H-NMR (400 MHz, METHANOL-D4) δ 8.25 (d, J=6.9 Hz, 1H), 7.13 (dd, J=7.1, 1.1 Hz, 1H), 4.15 (t, J=4.8 Hz, 4H), 3.40 (t, J=5.3 Hz, 4H)

Step 3: Ethyl 2-(4-(2-chloropyrimidin-4-yl)piperazin-1-yl)acetate

2-Chloro-4-(piperazin-1-yl)pyrimidine hydrochloride (0.095 g, 0.404 mmol) obtained in step 2 was dissolved in acetonitrile (4 ml), followed by ethyl 2-bromoacetate (0.067 ml, 0.606 mmol) and potassium carbonate (0.168 g, 1.212 mmol) were added. It was stirred at 60° C. for 16 hours. After removing the solvent under reduced pressure, it was dissolved in ethyl acetate and washed with water. The organic solvent was dried over magnesium sulfate and the organic solvent was removed under reduced pressure. The desired product was obtained by purification with silica gel column. (Yield 33%)

$^1$H-NMR (500 MHz, CHLOROFORM-D) δ 8.04 (d, J=6.1 Hz, 1H), 6.39 (d, J=6.1 Hz, 1H), 4.20 (q, J=7.1 Hz, 2H), 3.72 (s, 4H), 3.27 (s, 2H), 2.67 (t, J=5.0 Hz, 4H), 1.28 (t, J=7.0 Hz, 3H)

Step 4: ethyl 2-(4-(2-aminopyrimidin-4-yl)piperazin-1-yl)acetate

The desired product was obtained in a similar manner to Preparation Example 2 by using ethyl 2-(4-(2-chloropyrimidin-4-yl)piperazin-1-yl)acetate (0.038 g, 133 mmol) obtained in step 3. (2 step yield 33%)

$^1$H-NMR (400 MHz, CHLOROFORM-D) δ 7.84 (d, J=5.9 Hz, 1H), 5.91 (d, J=5.9 Hz, 1H), 4.73 (s, 2H), 4.18 (q, J=7.2 Hz, 2H), 3.62 (t, J=4.8 Hz, 4H), 3.24 (d, J=7.8 Hz, 2H), 2.60 (t, J=5.0 Hz, 4H), 1.31-1.23 (m, 3H)

Preparation Example 36: Ethyl 2-(1-(6-aminopyridin-2-yl)piperidin-4-yl)acetate

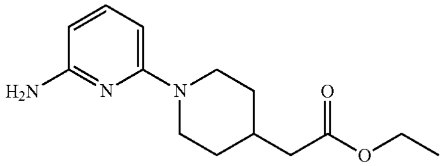 [SMILES: CCOC(=O)CC1CCN(c2cccc(N)n2)CC1]

Step 1: tert-butyl 4-(2-ethoxy-2-oxoethylidine)piperidine-1-carboxylate

Ethyl 2-(diethoxyphosphoryl)acetate (6.75 g, 30.1 mmol) was dissolved in 40 ml of THF in the presence of nitrogen, sodium hydride (1.204 g, 50.2 mmol) was added at 0° C., and tert-butyl 4-oxopiperidine-1-carboxylate (5 g, 25.09 mmol) was dissolved in 10 ml of THF and slowly added dropwise. After stirring at room temperature for 15 hours, it was confirmed that the starting material disappeared by TLC. The reaction was terminated with ammonium chloride, extracted with ethyl acetate (2×30 ml) and washed with brine (20 ml), and the organic solvent was dried over magnesium sulfate, and removed under reduced pressure. The desired product was obtained by purification with silica gel column (ethyl acetate:hexane=1:9). (Yield 25%)

$^1$H-NMR (400 MHz, CHLOROFORM-D) δ 5.51 (s, 1H), 4.19-4.01 (m, 2H), 3.95-3.78 (m, 2H), 3.56-3.43 (m, 2H), 3.08-2.91 (2H), 2.07 (d, J=38.4 Hz, 2H), 1.55-1.36 (9H), 1.31-1.18 (m, 3H)

Step 2: tert-butyl 4-(2-ethoxy-2-oxoethyl)piperidine-1-carboxylate

The desired product was obtained in a similar manner to Step 3 of Preparation Example 94 by using tert-butyl 4-(2-ethoxy-2-oxoethylidine)piperidine-1-carboxylate (0.6 g, 2.228 mmol) obtained in Step 1. (Yield 99%)

$^1$H-NMR (400 MHz, CHLOROFORM-D) δ 4.26-3.90 (m, 4H), 2.84-2.58 (m, 2H), 2.21 (d, J=7.3 Hz, 2H), 2.01-1.78 (m, 1H), 1.73-1.59 (2H), 1.48-1.39 (m, 9H), 1.32-1.19 (m, 3H), 1.19-1.02 (m, 2H)

Step 3: Ethyl 2-(piperidin-4-yl)acetate

Tert-butyl 4-(2-ethoxy-2-oxoethyl)piperidine-1-carboxylate (0.6 g, 2.248 mmol) obtained in step 2 was dissolved in 10 ml of dichloromethane, 2.76 ml of 4.0 M hydrochloric acid solution (1,4-dioxane) was added dropwise and stirred at room temperature for 15 hours. The reaction was terminated with a 1 N aqueous sodium hydroxide solution, extracted with ethyl acetate (2×15 ml), and washed with brine (10 ml), the organic solvent was dried over magnesium sulfate, and the organic solvent was removed under reduced pressure. The desired product was obtained by purification with silica gel column (ethyl acetate:hexane=1:9). (Yield 99%)

m/z $(M+H)^+$ calculated for $C_9H_{18}NO_2$: 172. found 172.

Step 4: Ethyl 2-(1-(6-chloropyridin-2-yl)piperidin-4-yl)acetate

Ethyl 2-(piperidin-4-yl)acetate (0.385 g, 2.247 mmol) obtained in step 3, 2,6-dichloropyridine (0.399 g, 2.7 mmol) and 0.982 ml of DIPEA were dissolved in 8 ml of DMF and stirred at 100° C. for 15 hours. After confirming that the reaction was completed by TLC, the organic solvent was removed under reduced pressure. After extraction with ethyl acetate (2×15 ml), it was washed with brine (20 ml), and the organic solvent was dried over magnesium sulfate, and removed under reduced pressure. The desired product was obtained by purification with silica gel column (ethyl acetate:hexane=1:9). (Yield 35%)

$^1$H-NMR (CHLOROFORM-D) δ 7.38 (t, J=7.9 Hz, 1H), 6.57 (d, J=7.3 Hz, 1H), 6.51 (d, J=8.5 Hz, 1H), 4.38-4.23 (2H), 4.17 (q, J=7.1 Hz, 2H), 2.88 (td, J=12.7, 2.3 Hz, 2H), 2.36-2.19 (m, 2H), 2.17-1.98 (m, 1H), 1.88-1.75 (2H), 1.37-1.19 (m, 5H)

Step 5: Ethyl 2-(1-(6-aminopyridin-2-yl)piperidin-4-yl)acetate

The desired product was obtained in a similar manner to Preparation Example 19 (Step 3, Step 4) by using ethyl 2-(1-(6-chloropyridin-2-yl)piperidin-4-yl)acetate (0.22 g, 0.778 mmol) obtained in Step 4. (2 step yield 69%)

$^1$H-NMR (CHLOROFORM-D) δ 7.30 (s, 1H), 6.03 (d, J=8.2 Hz, 1H), 5.86 (d, J=7.9 Hz, 1H), 4.33-4.22 (2H), 4.17 (q, J=7.2 Hz, 2H), 2.80 (t, J=12.2 Hz, 2H), 2.28 (t, J=7.6 Hz, 2H), 2.02 (tt, J=11.3, 3.8 Hz, 1H), 1.80 (d, J=12.8 Hz, 2H), 1.41-1.21 (m, 5H)

Preparation Example 37: Methyl (2-aminopyrimidin-4-yl)-L-prolinate

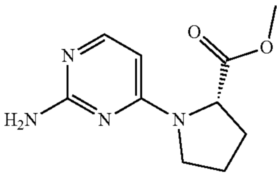 [SMILES: COC(=O)[C@@H]1CCCN1c1ccnc(N)n1]

The desired product was obtained in a similar manner to Preparation Example 28 by using methyl L-prolinate hydrochloride (0.267 g, 1.611 mmol). (3 step yield 40%)

$^1$H-NMR (400 MHz, CHLOROFORM-D) δ 7.88 (d, J=6.1 Hz, 1H), 6.03-5.72 (1H), 4.70 (s, 2H), 4.65-4.41 (1H), 3.88-3.70 (3H), 3.70-3.55 (1H), 3.55-3.30 (1H), 2.52-2.22 (1H), 2.22-2.00 (m, 3H)

Preparation Example 38: Methyl 1-(6-aminopyridin-2-yl)pyrrolidine-3-carboxylate

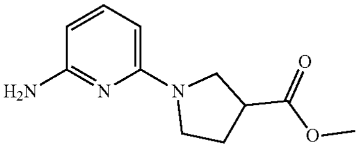 [SMILES: COC(=O)C1CCN(c2cccc(N)n2)C1]

The desired product was obtained in a similar manner to Preparation Example 29 by using methyl pyrrolidine-3-carboxylate hydrochloride (0.500 g, 3.02 mmol). (3 step yield 10%)

$^1$H-NMR (400 MHz, CHLOROFORM-D) δ 7.26 (m, 1H), 5.83 (d, J=7.6 Hz, 1H), 5.77 (d, J=7.9 Hz, 1H), 4.26-4.07 (m, 2H), 3.85-3.70 (m, 4H), 3.70-3.53 (m, 2H), 3.53-3.37 (m, 1H), 3.18 (t, J=7.6 Hz, 1H), 2.37-2.20 (m, 2H)

Preparation Example 39: Methyl 1-(2-aminopyrimidin-4-yl)pyrrolidine-3-carboxylate

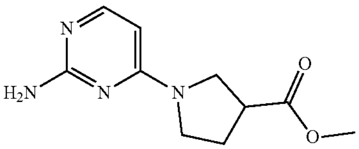 [SMILES: COC(=O)C1CCN(c2ccnc(N)n2)C1]

The desired product was obtained in a similar manner to Preparation Example 28 by using methyl pyrrolidine-3-carboxylate hydrochloride (0.667 g, 4.03 mmol). (3 step yield 14%)

$^1$H-NMR (500 MHz, CHLOROFORM-D) δ 7.77 (d, J=6.1 Hz, 1H), 5.69 (d, J=6.1 Hz, 1H), 5.22 (s, 2H), 3.79-3.65 (m, 4H), 3.65-3.46 (m, 2H), 3.40 (s, 1H), 3.13 (t, J=7.0 Hz, 1H), 2.21 (d, J=7.0 Hz, 2H)

Preparation Example 40: Ethyl 1-(2-aminopyrimidin-4-yl)-3-methylpiperidine-3-carboxylate

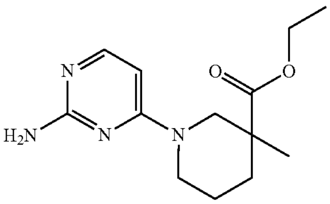 [SMILES: CCOC(=O)C1(C)CCCN(c2ccnc(N)n2)C1]

Step 1: 1-(tert-butyl) 3-ethyl piperidine-1,3-dicarboxylate

Ethyl piperidine-3-carboxylate (1.0 g, 6.36 mmol) was dissolved in DCM (50 ml), and then di-tert-butyl dicarbonate (1.754 ml, 7.63 mmol) and TEA (1.733 ml, 12.72 mmol) were added. It was stirred at room temperature for 4 hours. After the reaction was terminated by adding water, it was dissolved in DCM and washed with water. The organic solvent was dried over magnesium sulfate and the organic solvent was removed under reduced pressure. The desired product was obtained by purification with silica gel column. (Yield 70%)

$^1$H-NMR (500 MHz, CHLOROFORM-D) δ 4.16 (q, J=7.1 Hz, 3H), 3.94 (d, J=12.8 Hz, 1H), 2.93 (s, 1H), 2.87-2.75 (m, 1H), 2.45 (t, J=10.5 Hz, 1H), 2.06 (dd, J=13.1, 4.0 Hz, 1H), 1.72 (dt, J=13.1, 3.7 Hz, 1H), 1.68-1.59 (m, 1H), 1.51-1.45 (m, 10H), 1.32-1.17 (m, 3H)

Step 2: 1-(tert-butyl) 3-ethyl 3-methylpiperidine-1,3-dicarboxylate

Diisopropylamine (1.277 ml, 8.96 mmol) was dissolved in THF (22.4 ml), and then n-butyllithium (3.58 ml, 8.96 mmol) was added at −78° C. The mixture was stirred at −78° C. for 10 minutes, and stirred at room temperature for 10 minutes, and then lowered the temperature to −78° C. To the reaction mixture, 1-(tert-butyl) 3-ethyl piperidine-1,3-dicarboxylate (1.153 g, 4.48 mmol) obtained in step 1 was dissolved in THF (22.40 ml) and added. After stirring at −78° C. for 1 hour, iodomethane (0.336 ml, 5.37 mmol) was added and stirred at room temperature for 1 hour. After the reaction was terminated with aqueous ammonium chloride solution, it was dissolved in ethyl acetate and washed with water. The organic solvent was dried over magnesium sulfate and the organic solvent was removed under reduced pressure. The desired product was obtained by purification with silica gel column. (Yield 21%)

$^1$H-NMR (400 MHz, CHLOROFORM-D) δ 4.21-4.03 (m, 2H), 3.82 (d, J=13.3 Hz, 1H), 3.48-3.36 (m, 1H), 3.32-3.18 (m, 1H), 3.17-3.07 (1H), 2.07-1.95 (m, 1H), 1.58 (d, J=7.3 Hz, 1H), 1.56 (s, 1H), 1.52 (dd, J=9.6, 4.1 Hz, OH), 1.48-1.38 (m, 11H), 1.29-1.20 (m, 3H), 1.14 (s, 3H)

Step 3: Ethyl 3-methylpiperidine-3-carboxylate hydrochloride

The desired product was obtained in a similar manner to Step 2 of Preparation Example 1 by using 1-(tert-butyl)

3-ethyl 3-methylpiperidine-1,3-dicarboxylate (0.250 g, 0.921 mmol) obtained in step 2 and the next step was used immediately without further purification.

m/z $(M+H)^+$ calculated for $C_9H_{18}NO_2$: 172. found 172.

Step 4: Ethyl 1-(2-aminopyrimidin-4-yl)-3-methylpiperidine-3-carboxylate

The desired product was obtained in a similar manner to Preparation Example 28 by using ethyl 3-methylpiperidine-3-carboxylate hydrochloride (0.191 g, 0.921 mmol) obtained in step 3. (3 step yield 45%)

$^1$H-NMR (500 MHz, CHLOROFORM-D) δ 7.83 (q, J=6.2 Hz, 1H), 6.01 (d, J=6.4 Hz, 1H), 4.84 (d, J=17.1 Hz, 2H), 4.31-4.02 (m, 3H), 3.98 (d, J=12.2 Hz, 1H), 3.24-2.93 (m, 2H), 2.18 (dt, J=13.2, 5.0 Hz, 1H), 1.69-1.53 (m, 2H), 1.53-1.41 (m, 1H), 1.20-0.94 (m, 6H)

Preparation Example 41: Benzyl (S)-2-(1-(2-aminopyrimidin-4-yl)piperidin-3-yl)acetate

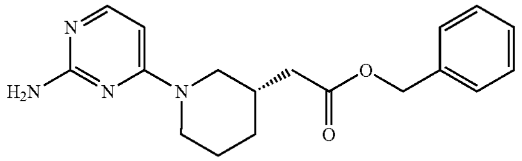 [SMILES: Nc1nccc(N2CCC[C@@H](CC(=O)OCc3ccccc3)C2)n1]

Step 1: (R)-1-(2-chloropyrimidin-4-yl)piperidine-3-carboxylic Acid

The intermediate obtained in Preparation Example 30, ethyl (R)-1-(2-chloropyrimidin-4-yl)piperidine-3-carboxylate (0.950 g, 3.52 mmol) was added to THF (17.6 ml) and ethanol (17.6 ml), and then 6 N aqueous sodium hydroxide solution (2.94 ml, 17.61 mmol) was added and stirred at room temperature for 4 hours. After removing the solvent under reduced pressure, it was dissolved in ethyl acetate and washed with water. The desired product was obtained by purification with silica gel column. (Yield 66%)

$^1$H-NMR (400 MHz, CHLOROFORM-D) δ 8.02 (d, J=6.4 Hz, 1H), 6.43 (d, J=5.9 Hz, 1H), 4.40-4.18 (1H), 4.18-4.11 (2H), 4.02 (s, 1H), 3.39 (dd, J=13.5, 9.4 Hz, 1H), 3.25 (t, J=10.5 Hz, 1H), 2.61-2.44 (m, 1H), 2.16-2.04 (m, 1H), 1.93-1.70 (m, 2H), 1.63-1.54 (m, 1H), 1.25 (td, J=7.1, 2.7 Hz, 3H)

Step 2: Benzyl (S)-2-(1-(2-chloropyrimidin-4-yl)piperidin-3-yl)acetate (R)-1-(2-chloropyrimidin-4-yl)piperidine-3-carboxylic acid (0.300 g, 1.241 mmol) obtained in step 1 was dissolved in DCM (12.4 ml), and then oxalyl chloride (0.543 ml, 6.21 mmol) and DMF (0.481 µl, 6.21 µmol) were sequentially added dropwise. After stirring at room temperature for 1 hour, the solvent was removed under reduced pressure. The reaction was dissolved in acetonitrile (10.3 ml) and THF (10.3 ml), and then trimethylsilyldiazomethane (1.86 ml, 3.72 mmol) dissolved in 2 Min diethyl ether at 0° C. was added. After stirring at room temperature for 16 hours, the solvent was removed under reduced pressure. The reaction was dissolved in 2,4,6-trimethylpyridine (8.26 ml), benzyl alcohol (0.271 ml, 2.61 mmol) was added, followed by stirring at 180° C. for 7 minutes. After the reaction was terminated by adding water, it was dissolved in diethyl ether, washed with water, and dried over magnesium sulfate. The desired product was obtained by purification with silica gel column. (Yield 52%)

$^1$H-NMR (500 MHz, CHLOROFORM-D) δ 8.07 (t, J=5.6 Hz, 1H), 6.49 (d, J=6.4 Hz, 1H), 4.49-4.17 (1H), 4.06 (t, J=6.1 Hz, 1H), 3.45 (dd, J=13.3, 9.3 Hz, 1H), 3.40-3.26 (m, 1H), 2.73-2.59 (m, 1H), 2.17 (dd, J=17.7, 4.6 Hz, 1H), 2.01-1.79 (m, 2H), 1.73-1.54 (m, 1H)

Step 3: Benzyl (S)-2-(1-(2-aminopyrimidin-4-yl)piperidin-3-yl)acetate

The desired product was obtained in a similar manner to Preparation Example 2 by using benzyl (S)-2-(1-(2-chloropyrimidin-4-yl)piperidin-3-yl)acetate (0.224 g, 0.648 mmol) obtained in step 2. (2 step yield 40%)

$^1$H-NMR (500 MHz, CHLOROFORM-D) δ 7.82 (d, J=6.4 Hz, 1H), 7.43-7.35 (m, 5H), 5.89 (d, J=6.1 Hz, 1H), 5.17 (t, J=12.8 Hz, 2H), 4.66 (s, 2H), 4.18 (d, J=11.6 Hz, 2H), 3.03-2.92 (m, 1H), 2.77 (dd, J=13.1, 10.1 Hz, 1H), 2.44-2.25 (m, 2H), 2.07 (dd, J=10.7, 7.3 Hz, 1H), 1.96-1.86 (m, 1H), 1.72 (dt, J=13.4, 4.0 Hz, 1H), 1.60-1.47 (m, 1H), 1.39-1.22 (m, 1H)

Preparation Example 42: Ethyl (S,E)-3-(1-(2-aminopyrimidin-4-yl)piperidin-3-yl)acrylate

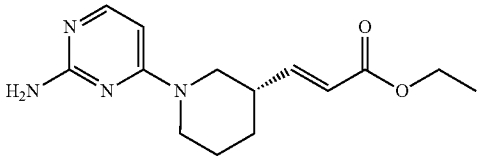 [SMILES: CCOC(=O)/C=C/[C@@H]1CCCN(c2ccnc(N)n2)C1]

Step 1: tert-butyl (R)-3-formylpiperidine-1-carboxylate 1-(tert-butyl) 3-ethyl piperidine-1,3-dicarboxylate (1.73 g, 6.72 mmol) obtained in step 1 of Preparation Example 40 was dissolved in toluene (67.2 ml) and then 1 M diisobutylaluminum hydride (16.81 ml, 16.81 mmol) was added dropwise at −78° C. and stirred for 3 hours and 30 minutes. The reaction was terminated by slowly adding ethyl acetate (10 ml) and methanol (5 ml) at −78° C. After 15 minutes, 1 M aqueous solution of sodium potassium tartrate was added and stirred for 1 hour, and then diluted with ethyl acetate and filtered to remove the precipitate. The organic solvent was removed under reduced pressure and then purified by a silica gel column to obtain the desired product. (Yield 20%)

$^1$H-NMR (400 MHz, CHLOROFORM-D) δ 9.69 (s, 1H), 3.91 (d, J=13.3 Hz, 1H), 3.64 (d, J=12.3 Hz, 1H), 3.31 (dd, J=13.5, 8.5 Hz, 1H), 3.14-2.99 (m, 1H), 2.41 (s, 1H), 1.93 (d, J=3.7 Hz, 1H), 1.76-1.59 (m, 2H), 1.52-1.46 (m, 1H), 1.46-1.36 (9H)

Step 2: tert-butyl (S,E)-3-(3-ethoxy-3-oxoprop-1-en-1-yl)piperidine-1-carboxylate Tert-butyl (R)-3-formylpiperidine-1-carboxylate (0.283 g, 1.327 mmol) obtained in step 1 was dissolved in DCM (6.63 ml), and ethyl 2-(triphenyl-15-phosphanylidene) acetate (0.601 g, 1.725 mmol) was added, and stirred at room temperature for 16 hours. The organic solvent was removed under reduced pressure and then purified by a silica gel column to obtain the desired product. (Yield 96%)

$^1$H-NMR (400 MHz, CHLOROFORM-D) δ 6.83 (dd, J=15.8, 6.6 Hz, 1H), 5.85 (dd, J=16.0, 1.4 Hz, 1H), 4.18 (q, J=7.0 Hz, 2H), 3.89 (td, J=8.6, 4.3 Hz, 2H), 2.81 (t, J=11.2 Hz, 2H), 2.43-2.22 (m, 1H), 1.87 (dd, J=13.0, 3.9 Hz, 1H), 1.67 (dt, J=13.0, 3.9 Hz, 1H), 1.48 (s, 1H), 1.43 (d, J=14.6 Hz, 9H), 1.41-1.31 (m, 1H), 1.27 (dd, J=13.5, 6.2 Hz, 3H)

Step 3: Ethyl (S,E)-3-(1-(2-chloropyrimidin-4-yl)piperidin-3-yl)acrylate

Ethyl (S,E)-3-(piperidin-3-yl)acrylate hydrochloride was obtained in a similar manner to Step 2 of Preparation Example 1 by using tert-butyl (S,E)-3-(3-ethoxy-3-oxopro-1-phen-1-yl)piperidine-1-carboxylate obtained in step 2, and then the desired product was obtained in a similar manner to Step 1 of Preparation Example 28 without further purification. (Yield 91%)

$^1$H-NMR (400 MHz, CHLOROFORM-D) δ 8.02 (d, J=6.4 Hz, 1H), 6.86 (dd, J=15.8, 7.1 Hz, 1H), 6.39 (d, J=5.9 Hz, 1H), 5.89 (dd, J=16.0, 1.4 Hz, 1H), 4.51-4.15 (m, 3H), 3.06-2.92 (m, 1H), 2.86 (dd, J=13.0, 10.7 Hz, 1H), 2.51-2.31 (m, 1H), 2.01-1.92 (1H), 1.90-1.78 (1H), 1.65-1.55 (m, 1H), 1.54 (s, 3H), 1.52-1.41 (m, 1H), 1.29 (t, J=7.1 Hz, 3H)

Step 4: Ethyl (S,E)-3-(1-(2-aminopyrimidin-4-yl)piperidin-3-yl)acrylate

The desired product was prepared in a similar manner to Preparation Example 2 by using ethyl (S,E)-3-(1-(2-chloropyrimidin-4-yl)piperidin-3-yl)acrylate obtained in step 3. (2 step yield 49%)

$^1$H-NMR (500 MHz, CHLOROFORM-D) δ 7.94-7.81 (m, 1H), 6.91 (dd, J=15.9, 7.0 Hz, 1H), 5.97 (t, J=6.0 Hz, 1H), 5.95-5.84 (1H), 4.73 (d, J=18.0 Hz, 2H), 4.41 (s, 1H), 4.23 (q, J=7.1 Hz, 2H), 4.20-4.06 (m, 1H), 3.00-2.85 (m, 1H), 2.78 (dd, J=13.1, 10.4 Hz, 1H), 2.48-2.31 (1H), 1.98 (d, J=12.5 Hz, 1H), 1.87-1.77 (m, 1H), 1.62-1.53 (m, 1H), 1.53-1.42 (m, 1H), 1.32 (t, J=7.2 Hz, 3H)

Preparation Example 43: Ethyl 1-(2-aminopyrimidin-4-yl)piperidine-3-carboxylate

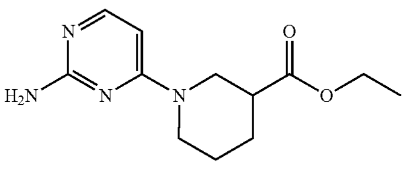 [SMILES: CCOC(=O)C1CCCN(c2ccnc(N)n2)C1]

The desired product was obtained in a similar manner to Preparation Example 28 by using ethyl piperidine-3-carboxylate (0.626 ml, 4.03 mmol). (3 step yield 14%)

$^1$H-NMR (500 MHz, CHLOROFORM-D) δ 7.86 (d, J=6.1 Hz, 1H), 6.01 (d, J=6.4 Hz, 1H), 4.93 (s, 2H), 4.58-4.29 (1H), 4.29-4.14 (2H), 4.14-4.01 (1H), 3.33-3.12 (1H), 3.12-2.98 (1H), 2.67-2.43 (m, 1H), 2.23-1.96 (1H), 1.82 (d, J=4.0 Hz, 1H), 1.74-1.61 (1H), 1.56 (s, 1H), 1.39-1.23 (3H)

Preparation Example 44: tert-butyl (S)-2-((1-(2-aminopyrimidin-4-yl)piperidin-3-yl)oxy)acetate

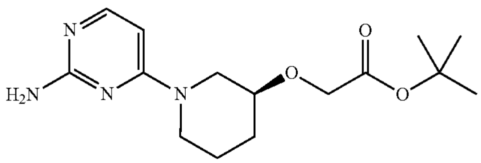 [SMILES: CC(C)(C)OC(=O)CO[C@H]1CCCN(c2ccnc(N)n2)C1]

Step 1: Benzyl (S)-3-hydroxypiperidine-1-carboxylate (S)-piperidin-3-ol hydrochloride (1.0 g, 7.27 mmol) was dissolved in DCM (14.5 ml), TEA (2.026 ml, 14.53 mmol) was added, and benzyl carbonochloridate (1.025 ml, 7.27) mmol) was added dropwise at 0° C. for 2 hours and 30 minutes. The mixture was further stirred at 0° C. for 30 minutes, diluted with DCM, and washed with 1 N HCl aqueous solution. The organic solvent was dried over magnesium sulfate and then the organic solvent was removed under reduced pressure. It was used in the next reaction immediately without further purification.

$^1$H-NMR (500 MHz, CHLOROFORM-D) δ 7.57-7.31 (m, 5H), 5.27-5.09 (2H), 3.90-3.70 (m, 2H), 3.61 (s, 1H), 3.38-3.15 (m, 2H), 2.00-1.87 (m, 1H), 1.87-1.73 (1H), 1.73-1.46 (m, 3H)

Step 2: Benzyl (S)-3-(2-(tert-butoxy)-2-oxoethoxy)piperidine-1-carboxylate

After dissolving the benzyl (S)-3-hydroxypiperidine-1-carboxylate (7.27 mmol) obtained in step 1 in toluene (14.5 ml), tert-butyl 2-bromoacetate (1.611 ml, 10.91 mmol) and tetra-n-butylammonium hydrogen sulfate (0.074 g, 0.218 mmol) dissolved in 5 ml of water were added. Sodium hydroxide (7.27 g, 182 mmol) dissolved in 7.27 ml of water was added dropwise to the reaction. After stirring at room temperature for 16 hours, it was dissolved in ethyl acetate and washed with brine. The organic solvent was dried over magnesium sulfate and the organic solvent was removed under reduced pressure. The desired product was obtained by purification with silica gel column (yield 59%)

$^1$H-NMR (400 MHz, CHLOROFORM-D) δ 7.46-7.26 (5H), 5.11 (s, 2H), 3.96 (s, 2H), 3.88 (d, J=11.4 Hz, 1H), 3.66 (d, J=12.8 Hz, 1H), 3.41 (s, 1H), 3.21-3.07 (2H), 1.96 (s, 1H), 1.77 (d, J=3.7 Hz, 1H), 1.59 (d, J=9.6 Hz, 1H), 1.45 (s, 9H)

Step 3: tert-butyl (S)-2-(piperidin-3-yloxy)acetate

Benzyl (S)-3-(2-(tert-butoxy)-2-oxoethoxy)piperidine-1-carboxylate obtained in step 2 was dissolved in ethanol (21.2 ml), and then Pd/C (0.1485 g, 1.395 mmol) was added and a deprotection reaction was performed using a hydrogen balloon. After filtration through Celite pad, the solvent was removed under reduced pressure, and purified by silica gel column to obtain the desired product. (Yield 100%)

$^1$H-NMR (500 MHz, CHLOROFORM-D) δ 4.03 (dd, J=25.9, 16.5 Hz, 2H), 3.45-3.31 (m, 1H), 3.09 (dd, J=12.4, 2.6 Hz, 1H), 2.90-2.78 (m, 1H), 2.78-2.62 (2H), 2.04-1.91 (m, 1H), 1.79-1.70 (1H), 1.61 (tt, J=12.8, 4.4 Hz, 1H), 1.56-1.39 (m, 11H)

Step 4: tert-butyl (S)-2-((1-(2-aminopyrimidin-4-yl)piperidin-3-yl)oxy)acetate

The desired product was obtained in a similar manner to Preparation Example 28 by using tert-butyl (S)-2-(piperidin-3-yloxy)acetate (0.517 g, 1.577 mmol) obtained in step 3. (3 step yield 50%)

$^1$H-NMR (400 MHz, CHLOROFORM-D) δ 7.83 (t, J=3.2 Hz, 1H), 5.96 (d, J=6.4 Hz, 1H), 4.64 (s, 2H), 4.15 (d, J=11.9 Hz, 1H), 4.06-4.00 (2H), 3.87 (s, 1H), 3.41 (t, J=4.1 Hz, 1H), 3.21-3.04 (m, 2H), 2.05 (s, 1H), 1.83 (s, 1H), 1.53-1.38 (m, 11H)

Preparation Example 45: tert-butyl (S)-2-((1-(6-aminopyridin-2-yl)piperidin-3-yl)oxy)acetate

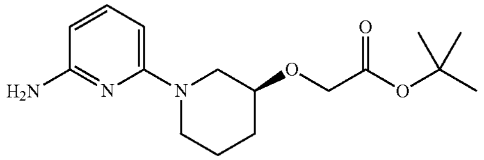 [SMILES: CC(C)(C)OC(=O)CO[C@H]1CCCN(c2cccc(N)n2)C1]

The desired product was obtained in a similar manner to Step 1 of Preparation Example 29 and Preparation Example 2 by using tert-butyl (S)-2-(piperidin-3-yloxy)acetate (0.503 g, 2.336 ml) prepared in Step 3 of Preparation Example 44. (3 step yield 6%)

$^1$H-NMR (400 MHz, CHLOROFORM-D) δ 7.22 (d, J=7.8 Hz, 1H), 6.01 (d, J=8.2 Hz, 1H), 5.82 (d, J=7.8 Hz, 1H), 4.25 (dd, J=12.3, 4.1 Hz, 1H), 4.22-4.09 (m, 2H), 4.05 (s, 2H), 3.94-3.85 (m, 1H), 3.45 (td, J=9.1, 4.4 Hz, 1H), 2.92-2.80 (m, 2H), 2.09 (d, J=3.7 Hz, 1H), 1.89-1.74 (m, 1H), 1.55-1.49 (m, 2H), 1.47 (s, 9H)

Preparation Example 46: tert-butyl (R)-2-((1-(2-aminopyrimidin-4-yl)piperidin-3-yl)oxy)acetate

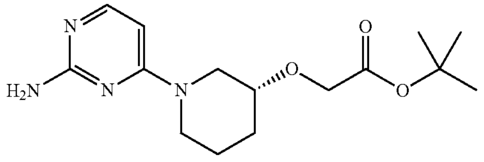 [SMILES: CC(C)(C)OC(=O)CO[C@@H]1CCCN(c2ccnc(N)n2)C1]

The desired product was obtained in a similar manner to Preparation Example 44 by using (R)-piperidin-3-ol hydrochloride (1.0 g, 7.27 mmol). (5-step yield 23%)

$^1$H-NMR (400 MHz, CHLOROFORM-D) δ 7.80 (d, J=6.4 Hz, 1H), 5.96 (d, J=6.4 Hz, 1H), 4.91 (s, 1H), 4.21-4.08 (1H), 4.08-3.96 (2H), 3.84 (d, J=12.8 Hz, 1H), 3.55-3.37 (m, 1H), 3.27-3.08 (2H), 2.29-1.89 (m, 1H), 1.90-1.75 (m, 1H), 1.69-1.57 (m, 1H), 1.57-1.48 (m, 1H), 1.47 (s, 9H)

Preparation Example 47: tert-butyl (R)-2-((1-(2-aminopyrimidin-4-yl)piperidin-3-yl)oxy)-2-methylpropanoate

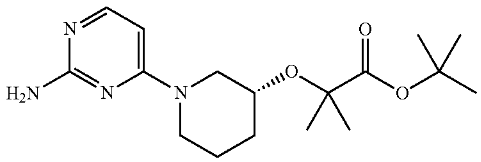 [SMILES: CC(C)(C)OC(=O)C(C)(C)O[C@@H]1CCCN(c2ccnc(N)n2)C1]

Step 1: (R)-1-benzylpiperidin-3-ol (R)-piperidin-3-ol hydrochloride (1.0 g, 7.27 mmol) was dissolved in DMF (14.5 ml) and potassium carbonate (2.210 g, 15.99 mmol) and benzyl bromide (0.951 ml, 7.99 mmol) were added. The reaction was stirred at 60° C. for 3 days. After filtering potassium carbonate, the DMF solvent was removed under reduced pressure. The desired product was obtained by purification with silica gel column. (Yield 57%)

$^1$H-NMR (500 MHz, CHLOROFORM-D) δ 7.33 (td, J=8.0, 6.1 Hz, 4H), 7.28-7.23 (m, 1H), 3.84 (t, J=3.8 Hz, 1H), 3.53 (s, 2H), 2.50 (d, J=14.0 Hz, 3H), 2.27 (s, 1H), 1.95-1.74 (1H), 1.75-1.46 (m, 3H)

Step 2: tert-butyl (R)-2-((1-benzylpiperidin-3-yl)oxy)acetate

The desired product was obtained in a similar manner to Step 2 of Preparation Example 44 by using (R)-1-benzylpiperidin-3-ol (0.785 g, 4.10 mmol) prepared in Step 1. (Yield 40%)

$^1$H-NMR (400 MHz, CHLOROFORM-D) δ 7.39-7.26 (m, 4H), 7.24-7.20 (m, 1H), 3.96 (s, 2H), 3.52 (s, 2H), 3.49-3.39 (m, 1H), 3.06-2.91 (m, 1H), 2.65 (d, J=11.0 Hz, 1H), 2.07-1.90 (3H), 1.71 (dt, J=13.7, 3.7 Hz, 1H), 1.55-1.46 (1H), 1.46-1.40 (m, 9H), 1.28 (ddd, J=22.1, 12.2, 4.5 Hz, 1H)

Step 3: tert-butyl (R)-2-((1-benzylpiperidin-3-yl)oxy)-2-methylpropanoate

After dissolving tert-butyl (R)-2-((1-benzylpiperidin-3-yl)oxy)acetate (0.507 g, 1.660 mmol) prepared in step 2 in THF (10 ml), lithium bis(trimethylsilyl)amide (1.938 ml, 2.52 mmol) was added at −78° C. After stirring at room temperature for 1 hour, the mixture was cooled to −78° C., and then iodomethane (0.068 ml, 1.109 mmol) dissolved in THF (0.7 ml) was added. It was stirred again at room temperature for 1 hour. Tert-butyl 2-(((R)-1-benzylpiperidin-3-yl)oxy)propanoate to which one methyl group was added was obtained by purification with silica gel column. The same method was repeated to obtain the desired product. (Yield 38%)

$^1$H-NMR (400 MHz, CHLOROFORM-D) δ 57.28 (d, J=4.6 Hz, 4H), 7.24-7.15 (m, 1H), 3.48 (d, J=3.7 Hz, 2H), 3.46-3.37 (m, 1H), 3.01 (dt, J=10.5, 2.1 Hz, 1H), 2.76-2.64 (m, 1H), 2.04-1.81 (m, 4H), 1.64 (tt, J=10.2, 3.4 Hz, 1H), 1.58-1.45 (m, 1H), 1.37 (d, J=6.9 Hz, 9H), 1.34 (s, 3H), 1.33-1.29 (m, 3H), 1.29-1.14 (m, 1H)

Step 4: tert-butyl (R)-2-((1-(2-aminopyrimidin-4-yl)piperidin-3-yl)oxy)-2-methylpropanoate The desired product was obtained in a similar manner to Preparation Example 44 (Step 3, Step 4) by using tert-butyl (R)-2-((1-benzylpiperidin-3-yl)oxy)-2-methylpropanoate prepared in Step 3. (4 step yield 43%)

$^1$H-NMR (400 MHz, CHLOROFORM-D) δ 8.14 (d, J=95.6 Hz, 1H), 6.29 (s, 1H), 4.45 (s, 2H), 3.54 (s, 1H), 3.13 (s, 2H), 2.33-2.01 (m, 3H), 1.46 (s, 9H), 1.38 (d, J=14.2 Hz, 6H)

Preparation Example 48: Methyl 1-(2-aminopyrimidin-4-yl)-3-methylpyrrolidine-3-carboxylate

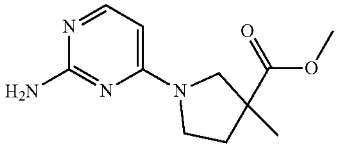 [SMILES: COC(=O)C1(C)CCN(c2ccnc(N)n2)C1]

The desired product was obtained in a similar manner to Preparation Example 40 by using methyl pyrrolidine-3-carboxylate hydrochloride (1.0 g, 6.04 mmol). (6 step yield 30%)

$^1$H-NMR (400 MHz, CHLOROFORM-D) δ 7.82 (d, J=5.9 Hz, 1H), 5.72 (d, J=5.9 Hz, 1H), 4.68 (s, 2H), 3.99-3.76 (1H), 3.71 (s, 3H), 3.52 (s, 1H), 2.54-2.36 (1H), 1.95-1.81 (m, 1H), 1.63 (m, 2H), 1.38 (s, 3H)

Preparation Example 49: Methyl 1-(6-aminopyridin-2-yl)-3-methylpyrrolidine-3-carboxylate

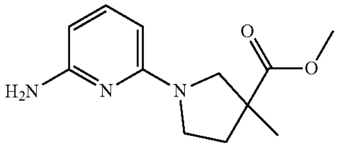 [SMILES: COC(=O)C1(C)CCN(c2cccc(N)n2)C1]

The desired product was obtained in a similar manner to Preparation Example 29 by using the intermediate, methyl 3-methylpyrrolidine-3-carboxylate hydrochloride (0.390 g, 2.171 mmol) prepared in Preparation Example 48. (3 step yield 10%)

$^1$H-NMR (400 MHz, CHLOROFORM-D) δ 7.22 (t, J=8.0 Hz, 1H), 5.78 (d, J=7.3 Hz, 1H), 5.71 (d, J=8.2 Hz, 1H), 4.13 (s, 2H), 3.83 (d, J=10.5 Hz, 1H), 3.69 (s, 3H), 3.57-3.41 (m, 2H), 3.32 (d, J=10.5 Hz, 1H), 2.51-2.36 (m, 1H), 1.92-1.80 (m, 1H), 1.37 (s, 3H)

Preparation Example 50: Methyl (1r,4r)-4-((2-aminopyrimidin-4-yl)oxy)cyclohexane-1-carboxylate

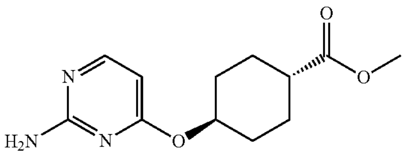 [SMILES: COC(=O)[C@H]1CC[C@H](Oc2ccnc(N)n2)CC1]

Step 1: Methyl (1r,4r)-4-hydroxycyclohexane-1-carboxylate (1r,4r)-4-hydroxycyclohexane-1-carboxylic acid (0.300 g, 2.081 mmol) was dissolved in methanol (10 ml) and sulfuric acid (0.017 ml, 0.312 mmol) was added. After stirring at 60° C. for 16 hours, the organic solvent was removed under reduced pressure and purified by silica gel column to obtain the desired product. (Yield 100%)

$^1$H-NMR (400 MHz, CHLOROFORM-D) δ 8.25 (d, J=5.9 Hz, 1H), 6.64-6.50 (m, 1H), 5.16-5.05 (1H), 3.73-3.62 (m, 3H), 2.35 (tt, J=11.4, 3.7 Hz, 1H), 2.18 (dt, J=12.8, 3.5 Hz, 2H), 2.07 (dd, J=14.2, 3.7 Hz, 2H), 1.74-1.56 (m, 2H), 1.49 (ddd, J=23.0, 12.7, 3.5 Hz, 2H)

Step 2: Methyl (1r,4r)-4-((2-aminopyrimidin-4-yl)oxy)cyclohexane-1-carboxylate

The desired product was obtained in a similar manner to Preparation Example 117 by using methyl (1r,4r)-4-hydroxycyclohexane-1-carboxylate (0.333 g, 2.105 mmol). (2 step yield 28%)

$^1$H-NMR (400 MHz, CHLOROFORM-D) δ 7.98 (d, J=5.9 Hz, 1H), 6.01 (d, J=5.5 Hz, 1H), 5.02-4.89 (m, 1H), 4.82 (s, 2H), 3.68 (dd, J=7.3, 2.7 Hz, 5H), 2.44-2.26 (m, 1H), 2.20-1.99 (m, 4H), 1.71-1.57 (m, 2H), 1.52 (s, 1H), 1.41 (dd, J=12.6, 3.4 Hz, 1H)

Preparation Example 51: Methyl (1s,4s)-4-((2-aminopyrimidin-4-yl)oxy)cyclohexane-1-carboxylate

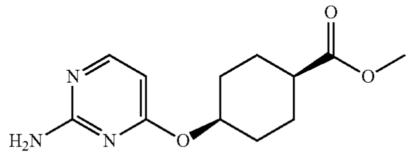 [SMILES: COC(=O)[C@H]1CC[C@@H](Oc2ccnc(N)n2)CC1]

The desired product was obtained in a similar manner to Preparation Example 50 by using (1s,4s)-4-hydroxycyclohexane-1-carboxylic acid (1.000 g, 6.94 mmol). (3 step yield 20%) 1H-NMR (400 MHz, CHLOROFORM-D) δ 7.93 (t, J=5.7 Hz, 1H), 6.00 (t, J=5.7 Hz, 1H), 5.20-4.97 (m, 3H), 3.64 (s, 3H), 2.45-2.31 (m, 1H), 2.04-1.81 (m, 4H), 1.79-1.52 (m, 4H)

Preparation Example 52: Methyl 2-(3-(6-aminopyridin-2-yl)phenyl)-2-methylpropanoate

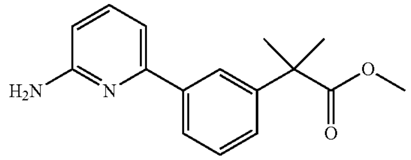 [SMILES: COC(=O)C(C)(C)c1cccc(-c2cccc(N)n2)c1]

Step 1: Methyl 2-methyl-2-(3-(4,4,5,5-tetramethyl-1,3,2-dioxaborolan-2-yl)phenyl)propanoate After dissolving methyl 2-(3-bromophenyl)-2-methylpropanoate (250 mg, 0.972 mmol), 4,4,4,4,5,5,5,5-octamethyl-2,2-bi(1,3,2-dioxaborolane) (296 mg, 1.17 mmol), potassium acetate (286 mg, 2.92 mmol) and 1,1'-bis(diphenylphosphino)ferrocene-palladium(II)dichloride dichloromethane complex (39.7 mg, 0.0490 mmol) in 9.72 ml of 1,4-dioxane, the dissolved oxygen was removed through nitrogen bubbling under stirring, and the inflow of outside air was blocked in a sealed container. The reaction was stirred at 110° C. for 15 hours and then cooled to room temperature. After filtering through Celite pad and removing the organic solvent under reduced pressure, the desired product was obtained by purification with silica gel column (ethyl acetate:hexane). (Yield 94%)

$^1$H-NMR (400 MHz, CHLOROFORM-D) δ 7.77 (s, 1H), 7.69 (d, J=7.3 Hz, 1H), 7.46-7.37 (1H), 7.33 (t, J=7.5 Hz, 1H), 3.65 (s, 3H), 1.60 (s, 6H), 1.34 (s, 12H)

Step 2: Methyl 2-(3-(6-((tert-butoxycarbonyl)amino)pyridin-2-yl)phenyl)2-methylpropanoate Methyl 2-methyl-2-(3-(4,4,5,5-tetramethyl-1,3,2-dioxaborolan-2-yl)phenyl)propanoate (279 mg, 0.917 mmol) synthesized in step 1 and tert-butyl (6-bromopyridin-2-yl)carbamate (251 mg, 0.917 mmol) obtained in Preparation Example 73, 2 M aqueous sodium carbonate solution (1.38 ml, 2.75 mmol) and bis(triphenylphosphino)dichloropalladium (64 mg, 0.092 mmol) were dissolved in 7.64 ml of dimethoxyethane, and dissolved oxygen was removed through nitrogen bubbling under stirring, and the inflow of outside air was blocked in a sealed container. The reaction was stirred at 100° C. for 15 hours and then cooled to room temperature. After filtering through a Celite pad and removing the organic solvent under reduced pressure, dissolved in ethyl acetate and washed with brine. The organic solvent was dried over magnesium sulfate and the organic solvent was removed under reduced pressure. The desired product was obtained by purification with silica gel column (ethyl acetate:hexane). (Yield 72%)

$^1$H-NMR (400 MHz, CHLOROFORM-D) δ 7.95 (d, J=1.8 Hz, 1H), 7.86 (d, J=8.2 Hz, 1H), 7.80 (dt, J=7.3, 1.6 Hz, 1H), 7.76-7.66 (1H), 7.42-7.33 (m, 3H), 7.31 (s, 1H), 3.66 (s, 3H), 1.64 (s, 6H), 1.55 (s, 9H)

Step 3: Methyl 2-(3-(6-aminopyridin-2-yl)phenyl)-2-methylpropanoate

The desired product was obtained in a similar manner to Step 4 of Preparation Example 19 by using methyl 2-(3-(6-((tert-butoxycarbonyl)amino)pyridin-2-yl)phenyl)2-methylpropanoate (244 mg, 0.659 mmol) synthesized in step 2. (Yield 81%)

$^1$H-NMR (400 MHz, CHLOROFORM-D) δ 7.92 (t, J=1.8 Hz, 1H), 7.84-7.70 (m, 1H), 7.50 (t, J=8.0 Hz, 1H), 7.39 (t, J=7.5 Hz, 1H), 7.34 (dt, J=7.9, 1.6 Hz, 1H), 7.07 (d, J=7.3 Hz, 1H), 6.54-6.39 (1H), 4.49 (s, 2H), 3.66 (s, 3H), 1.64 (s, 6H)

Preparation Example 53: Methyl 2-(3-(2-aminopyrimidin-4-yl)phenyl)-2-methylpropanoate

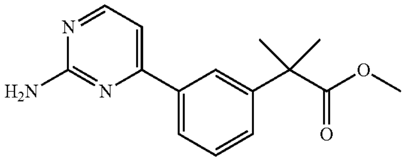 [SMILES: COC(=O)C(C)(C)c1cccc(-c2ccnc(N)n2)c1]

Step 1: Methyl 2-methyl-2-(3-(4,4,5,5-tetramethyl-1,3,2-dioxaborolan-2-yl)phenyl)propanoate Methyl 2-(3-bromophenyl)-2-methylpropanoate (0.5 g, 1.944 mmol) and 4,4,4,4,5,5,5,5-oxamethyl-2,2-bis(1,3,2-dioxaborolane) (0.494 g, 1.944 mmol), potassium acetate (0.478 g, 4.862 mmol), 1,1'-bis(diphenylphosphino)ferrocenedichloro-palladium(II)dichloromethane complex (0.08 g, 0.098 mmol) was dissolved in 8 ml of 1,4-dioxane and stirred at 110° C. for 4 hours. After confirming that the reaction was completed by TLC, the organic solvent was removed under reduced pressure. After extraction with ethyl acetate (2×15 ml), it was washed with brine (20 ml), and the organic solvent was dried over magnesium sulfate, and removed under reduced pressure. The desired product was obtained by purification with silica gel column (ethyl acetate:hexane=1:9). (Yield 85%)

$^1$H-NMR (400 MHz, CHLOROFORM-D) δ 7.76 (d, J=0.9 Hz, 1H), 7.72-7.65 (m, 1H), 7.43-7.37 (m, 1H), 7.31 (t, J=7.5 Hz, 1H), 3.71-3.53 (m, 3H), 1.59 (s, 6H), 1.33 (s, 12H)

Step 2: Methyl 2-(3-(2-chloropyrimidin-4-yl)phenyl)-2-methylpropanoate

Methyl 2-methyl-2-(3-(4,4,5,5-tetramethyl-1,3,2-dioxaborolan-2-yl)phenyl)propanoate obtained in step 1 (0.25 g, 0.822 mmol), 2,4-dichloropyrimidine (0.147 g, 0.986 mmol), 1 ml of sodium carbonate and bis(triphenylphosphine)palladium(II) dichloride (0.058 g, 0.082 mmol) were dissolved in 4 ml of DME and stirred at 100° C. for 4 hours. After confirming that the reaction was completed by TLC, the organic solvent was removed under reduced pressure. After extraction with ethyl acetate (2×15 ml), it was washed with brine (20 ml), and the organic solvent was dried over magnesium sulfate, and removed under reduced pressure. The desired product was obtained by purification with silica gel column (ethyl acetate:hexane=1:9). (Yield 80%)

$^1$H-NMR (400 MHz, CHLOROFORM-D) δ 8.66-8.55 (m, 1H), 8.05 (dd, J=15.1, 1.8 Hz, 1H), 7.98-7.85 (m, 1H), 7.66-7.56 (m, 1H), 7.56-7.38 (m, 2H), 3.70-3.59 (3H), 1.67-1.58 (m, 6H)

Step 3: Methyl 2-(3-(2-aminopyrimidin-4-yl)phenyl)-2-methylpropanoate

The desired product was obtained in a similar manner to Preparation Example 19 (Step 3, Step 4) by using methyl 2-(3-(2-chloropyrimidin-4-yl)phenyl)-2-methylpropanoate (0.19 g, 0.653 mmol) obtained in Step 2. (2 step yield 64%)

$^1$H-NMR (400 MHz, CHLOROFORM-D) δ 8.31 (d, J=5.5 Hz, 1H), 8.00 (t, J=1.6 Hz, 1H), 7.84 (dt, J=7.3, 1.6 Hz, 1H), 7.50-7.38 (2H), 7.06 (t, J=5.3 Hz, 1H), 5.43 (s, 2H), 3.65 (t, J=15.3 Hz, 3H), 1.63 (s, 6H)

Preparation Example 54: Methyl 2-(4-(6-aminopyridin-2-yl)phenyl)-2-methylpropanoate

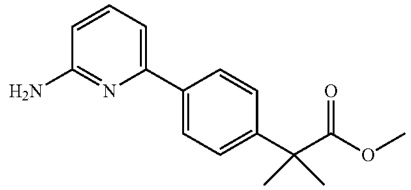 [SMILES: COC(=O)C(C)(C)c1ccc(-c2cccc(N)n2)cc1]

Step 1: Methyl 2-methyl-2-(4-(4,4,5,5-tetramethyl-1,3,2-dioxaborolan-2-yl)phenyl)propanoate The desired product was obtained in a similar manner to Step 1 of Preparation Example 53 by using methyl 2-(4-bromophenyl)-2-methylpropanoate (1 g, 3.89 mmol). (Yield 95%)

$^1$H-NMR (CHLOROFORM-D) δ 7.80 (d, J=8.2 Hz, 2H), 7.39-7.31 (m, 2H), 3.74-3.59 (m, 3H), 1.60 (s, 6H), 1.37-1.32 (m, 12H)

Step 2: Methyl 2-(4-(6-((tert-butoxycarbonyl) amino)pyridin-2-yl)phenyl)-2-methylpropanoate The desired product was obtained in a similar manner to Step 2 of Preparation Example 53 by using methyl 2-methyl-2-(4-(4,4,5,5-tetramethyl-1,3,2-dioxaborolan-2-yl)phenyl) propanoate (0.62 g, 2.038 mmol) obtained in Step 1 and tert-butyl (6-chloropyridin-2-yl)carbamate (0.559 g, 2.446 mmol). (Yield 62%)

$^1$H-NMR (400 MHz, CHLOROFORM-D) δ 7.88 (dt, J=8.5, 2.1 Hz, 2H), 7.84 (d, J=8.2 Hz, 1H), 7.70 (t, J=8.0 Hz, 1H), 7.44-7.38 (m, 2H), 7.36 (d, J=7.3 Hz, 1H), 7.31 (d, J=11.4 Hz, 1H), 3.65 (s, 3H), 1.60 (s, 6H), 1.52 (s, 9H)

Step 3: Methyl 2-(4-(6-aminopyridin-2-yl)phenyl)-2-methylpropanoate

The desired product was obtained in a similar manner to Step 4 of Preparation Example 19 by using methyl 2-(4-(6-((tert-butoxycarbonyl)amino)pyridin-2-yl)phenyl)-2-methylpropanoate (0.467 g, 1.263 mmol) obtained in step 2. (Yield 78%)

$^1$H-NMR (400 MHz, CHLOROFORM-D) δ 7.99-7.75 (m, 2H), 7.57-7.44 (m, 1H), 7.44-7.33 (m, 2H), 7.16-6.94 (m, 1H), 6.51-6.35 (m, 1H), 4.61 (s, 2H), 3.72-3.51 (m, 3H), 1.73-1.51 (m, 6H)

Preparation Example 55: Methyl 2-(4-(2-aminopyrimidin-4-yl)phenyl)-2-methylpropanoate

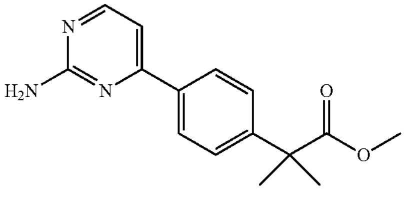 [SMILES: COC(=O)C(C)(C)c1ccc(-c2ccnc(N)n2)cc1]

Step 1: Methyl 2-(4-(2-chloropyrimidin-4-yl)phenyl)-2-methylpropanoate

The desired product was obtained in a similar manner to Step 2 of Preparation Example 53 by using methyl 2-methyl-2-(4-(4,4,5,5-tetramethyl-1,3,2-dioxaborolan-2-yl)phenyl) propanoate (0.7 g, 2.301 mmol) obtained in step 1 of Preparation Example 54 and 2,4-dichloropyrimidine (0.411 g, 2.76 mmol). (Yield 99%)

$^1$H-NMR (400 MHz, CHLOROFORM-D) δ 8.65-8.56 (m, 1H), 8.09-8.01 (m, 2H), 7.61 (d, J=5.5 Hz, 1H), 7.53-7.43 (m, 2H), 3.66 (d, J=5.5 Hz, 3H), 1.62 (d, J=9.6 Hz, 6H)

Step 2: Methyl 2-(4-(2-aminopyrimidin-4-yl)phenyl)-2-methylpropanoate

The desired product was obtained in a similar manner to Preparation Example 19 (Step 3, Step 4) by using methyl 2-(4-(2-chloropyrimidin-4-yl)phenyl)-2-methylpropanoate (0.59 g, 2.029 mmol) obtained in Step 1. (2 step yield 44%)

$^1$H-NMR (400 MHz, CHLOROFORM-D) δ 8.43-8.20 (m, 1H), 8.05-7.83 (m, 2H), 7.54-7.34 (2H), 7.06-6.89 (m, 1H), 5.36 (s, 2H), 3.70-3.55 (m, 3H), 1.69-1.51 (m, 6H)

Preparation Example 56: Methyl 3-(3-(2-aminopyridin-4-yl)phenyl)propanoate

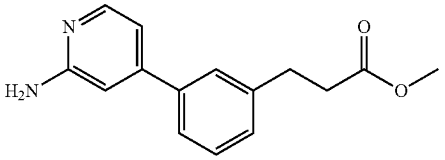 [SMILES: COC(=O)CCc1cccc(-c2ccnc(N)c2)c1]

The desired product was obtained in a similar manner to Preparation Example 26 by using methyl 3-(3-bromophenyl) propanoate (1 g, 4.11 mmol). (2 step yield 69%)

$^1$H-NMR (500 MHz, CHLOROFORM-D) δ 8.13 (d, J=5.2 Hz, 1H), 7.45 (d, J=7.9 Hz, 2H), 7.40 (t, J=7.6 Hz, 1H), 7.27 (s, 1H), 6.89 (d, J=5.5 Hz, 1H), 6.72 (s, 1H), 4.64-4.42 (2H), 3.70 (s, 3H), 3.04 (t, J=7.8 Hz, 2H), 2.70 (t, J=7.8 Hz, 2H)

Preparation Example 57: Methyl 3-(3-(2-aminopyrimidin-4-yl)phenyl)propanoate

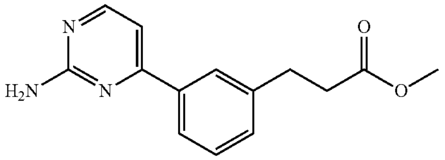 [SMILES: COC(=O)CCc1cccc(-c2ccnc(N)n2)c1]

The desired product was obtained in a similar manner to Step 1 of Preparation Example 28 and Preparation Example 2 by using the intermediate, methyl 3-(3-(4,4,5,5-tetramethyl-1,3,2-dioxaborolan-2-yl)phenyl)propanoate (0.200 g, 0.689 mmol) prepared in Preparation Example 56. (3 step yield 43%)

$^1$H-NMR (500 MHz, CHLOROFORM-D) δ 8.33 (d, J=5.2 Hz, 1H), 7.86 (s, 1H), 7.84-7.74 (m, 1H), 7.47-7.37 (1H), 7.32 (d, J=7.3 Hz, 1H), 7.01 (d, J=5.2 Hz, 1H), 5.57-5.31 (2H), 3.70 (d, J=22.6 Hz, 3H), 3.03 (t, J=7.8 Hz, 2H), 2.69 (t, J=7.8 Hz, 2H)

Preparation Example 58: Methyl 3-(3-(2-aminopyridin-4-yl)phenyl)-2,2-dimethylpropanoate

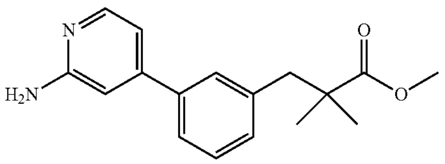 [SMILES: COC(=O)C(C)(C)Cc1cccc(-c2ccnc(N)c2)c1]

Step 1: Methyl 3-(3-bromophenyl)-2,2-dimethylpropanoate

Diisopropylamine (20.5 ml, 144 mmol) was added to 400 ml of anhydrous tetrahydrofuran, and 2.5 M n-butyllithium (57.6 ml, 144 mmol) was slowly added dropwise at −78° C. The reaction solution was stirred at the same temperature for 20 minutes. The temperature was raised to room temperature and stirred for 10 minutes, then lowered to −78° C. and stirred for 10 minutes. The reaction solution was added dropwise to methyl isobutyrate (16.5 ml, 144 mmol) dissolved in 100 ml of anhydrous tetrahydrofuran. The reaction solution was stirred at −78° C. for 1 hour, and 1-bromo-3-(bromomethyl)benzene (30.0 g, 120 mmol) dissolved in 100 ml of anhydrous tetrahydrofuran was slowly added dropwise. The reaction solution was raised to room temperature and stirred for 20 minutes. The reaction was terminated by adding 1 N aqueous hydrochloric acid solution to the reaction solution, followed by extraction with diethyl ether. The organic layer was concentrated under reduced pressure and then purified by a silica gel column (ethyl acetate: hexane) to obtain the desired product. (Yield 72%).

$^1$H-NMR (CHLOROFORM-D) δ 7.35 (d, J=7.9 Hz, 1H), 7.26-7.20 (1H), 7.13 (t, J=7.8 Hz, 1H), 7.03 (d, J=7.6 Hz, 1H), 3.67 (s, 3H), 2.81 (s, 2H), 1.18 (s, 6H)

Step 2: Methyl 2,2-dimethyl-3-(3-(4,4,5,5-tetramethyl-1,3,2-dioxaborolan-2-yl)phenyl)propanoate The desired product was obtained in a similar manner to Step 1 of Preparation Example 52 by using methyl 3-(3-bromophenyl)-2,2-dimethylpropanoate obtained in Step 1. (Yield 73%)

$^1$H-NMR (CHLOROFORM-D) δ 7.65 (d, J=7.3 Hz, 1H), 7.54 (s, 1H), 7.29-7.23 (m, 1H), 7.19 (d, J=7.6 Hz, 1H), 3.66 (s, 3H), 2.86 (s, 2H), 1.33 (s, 12H), 1.18 (s, 6H)

Step 3: Methyl 3-(3-(2-aminopyridin-4-yl)phenyl)2,2-dimethylpropanoate

The desired product was obtained in a similar manner to Step 2 of Preparation Example 52 by using 4-bromopyridin-2-amine (109 mg, 0.628 mmol) and methyl 2,2-dimethyl-3-(3-(4,4,5,5-tetramethyl-1,3,2-dioxaborolan-2-yl)phenyl-propanoate (200 mg, 0.628 mmol) obtained in step 2, and the next reaction was carried out without purification.

$^1$H-NMR (CHLOROFORM-D) δ 8.11 (d, J=5.5 Hz, 1H), 7.43 (d, J=7.6 Hz, 1H), 7.37-7.29 (m, 2H), 7.15 (d, J=7.6 Hz, 1H), 6.85 (d, J=4.0 Hz, 1H), 6.67 (s, 1H), 4.56-4.43 (2H), 3.66 (s, 3H), 2.92 (s, 2H), 1.21 (s, 6H)

Preparation Example 59: Methyl 3-(3-(2-aminopyrimidin-4-yl)phenyl)-2,2-dimethylpropanoate

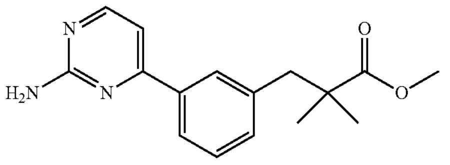 [SMILES: COC(=O)C(C)(C)Cc1cccc(-c2ccnc(N)n2)c1]

Step 1: Methyl 3-(3-(2-chloropyrimidin-4-yl)phenyl)-2,2-dimethylpropanoate

The desired product was obtained in a similar manner to Step 2 of Preparation Example 52 by using 2,4-dichloropyrimidine (1.40 g, 9.43 mmol) and methyl 2,2-dimethyl-3-(3-(4,4,5,5-tetramethyl-1,3,2-dioxaborolan-2-yl)phenyl-propanoate (3.00 g, 9.43 mmol) obtained in step 2 of Preparation Example 58. (Yield 76%)

$^1$H-NMR (CHLOROFORM-D) δ 8.62 (d, J=5.2 Hz, 1H), 7.91 (d, J=7.9 Hz, 1H), 7.87 (s, 1H), 7.62 (d, J=5.5 Hz, 1H), 7.41 (t, J=7.6 Hz, 1H), 7.29 (d, J=7.6 Hz, 1H), 3.70 (s, 3H), 2.96 (s, 2H), 1.22 (s, 6H)

Step 2: Methyl 3-(3-(2-aminopyrimidin-4-yl)phenyl)-2,2-dimethylpropanoate

The desired product was obtained in a similar manner to Step 3, 4 of Preparation Example 19 by using methyl 3-(3-(2-chloropyrimidin-4-yl)phenyl)-2,2-dimethylpropanoate (2.18 g, 7.15 mmol) obtained in Step 1. (2 step yield 44%)

$^1$H-NMR (400 MHz, CHLOROFORM-D) δ 8.32 (d, J=5.5 Hz, 1H), 7.85 (d, J=7.8 Hz, 1H), 7.80-7.69 (1H), 7.38 (t, J=7.8 Hz, 1H), 7.23 (d, J=7.8 Hz, 1H), 7.12-6.97 (1H), 5.31 (d, J=22.0 Hz, 2H), 3.67 (s, 3H), 2.94 (s, 2H), 1.21 (s, 6H)

Preparation Example 60: Methyl 2-(2-aminopyridin-4-yl)-2-methylpropanoate

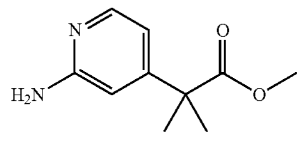

The desired product was obtained in a similar manner to Preparation Example 19 by using 2-(2-chloropyridin-4-yl) acetic acid (5.00 g, 29.1 mmol). (4 step yield 5%)

$^1$H-NMR (CHLOROFORM-D) δ 8.00 (d, J=4.6 Hz, 1H), 6.66-6.54 (m, 1H), 6.44 (s, 1H), 4.45 (s, 2H), 3.67 (s, 3H), 1.52 (s, 6H)

Preparation Example 61: Ethyl 2-(6-aminopyridin-2-yl)-2-methylpropanoate

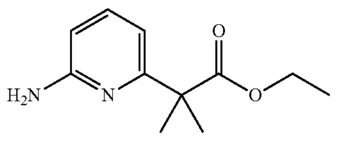

Step 1: Ethyl 2-(6-chloropyridin-2-yl)acetate

Diisopropylamine (1.77 ml, 12.4 mmol) was added to 20 ml of anhydrous tetrahydrofuran, and 2.5 M n-butyllithium (4.97 ml, 12.4 mmol) was slowly added dropwise at −78° C. The reaction solution was stirred at the same temperature for 20 minutes. The temperature was raised to room temperature and stirred for 10 minutes, then lowered to −78° C. and stirred for 10 minutes. 2-chloro-6-methylpyridine (0.57 ml, 5.2 mmol) dissolved in 100 ml of anhydrous tetrahydrofuran was added dropwise to the reaction solution. The reaction solution was stirred at −78° C. for 1 hour, and diethyl carbonate (0.75 ml, 6.2 mmol) dissolved in 100 ml of anhydrous tetrahydrofuran was slowly added dropwise. The reaction solution was raised to 0° C. and stirred for 4 hours. The reaction was terminated by adding saturated aqueous ammonium chloride solution to the reaction solution, followed by extraction with ethyl acetate. The organic layer was concentrated under reduced pressure and then purified by a silica gel column (ethyl acetate:hexane) to obtain the desired product. (Yield 88%)

$^1$H-NMR (CHLOROFORM-D) δ 7.61 (t, J=7.8 Hz, 1H), 7.22 (d, J=7.6 Hz, 2H), 4.16 (q, J=7.1 Hz, 2H), 3.80 (s, 2H), 1.29-1.20 (m, 3H)

Step 2: Ethyl 2-(6-aminopyridin-2-yl)-2-methylpropanoate

The desired product was obtained in a similar manner to Preparation Example 19 (Step 2, Step 3, Step 4) by using ethyl 2-(6-chloropyridin-2-yl)acetate (903 mg, 4.52 mmol) obtained in Step 1. (3 step yield 5%)

$^1$H-NMR (CHLOROFORM-D) δ 7.38 (t, J=7.9 Hz, 1H), 6.62 (d, J=7.3 Hz, 1H), 6.34 (d, J=7.9 Hz, 1H), 4.34 (s, 2H), 4.19-4.12 (m, 2H), 1.53 (s, 6H), 1.19 (t, J=7.0 Hz, 3H)

Preparation Example 62: tert-butyl 3-(6-aminopyridin-2-yl)-2,2-dimethylpropanoate

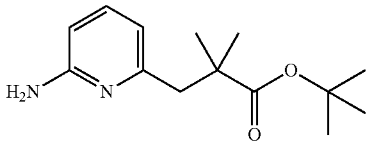 [SMILES: CC(C)(C)OC(=O)C(C)(C)Cc1cccc(N)n1]

Step 1: 2-(Bromomethyl)-6-chloropyridine

2-Chloro-6-methylpyridine (3.00 g, 23.5 mmol), N-bromosuccinimide (4.19 g, 23.5 mmol) and 2,2'-azobis(2-methylpropionitryl) (0.077 g, 0.47 mmol) were dissolved in 50 ml of 1,2-dichloroethane, heated at 80° C. for 3 hours, and washed with brine. The organic solvent was dried over magnesium sulfate and the organic solvent was removed under reduced pressure. The desired product was obtained by purification with silica gel column (ethyl acetate:hexane). (Yield 25%)

$^1$H-NMR (400 MHz, CHLOROFORM-D) δ 7.67 (t, J=7.8 Hz, 1H), 7.39 (d, J=7.8 Hz, 1H), 7.28 (s, 1H), 4.50 (s, 2H)

Step 2: tert-butyl 3-(6-chloropyridin-2-yl)-2,2,-dimethylpropanoate

The desired product was obtained in a similar manner to step 1 of Preparation Example 58 by using 2-(bromomethyl)-6-chloropyridine (1.23 g, 5.96 mmol) obtained in step 1 and tert-butyl isobutyrate (1.03 g, 7.15 mmol). (Yield 84%)

$^1$H-NMR (400 MHz, CHLOROFORM-D) δ 7.52 (t, J=7.5 Hz, 1H), 7.15 (d, J=7.8 Hz, 1H), 7.06 (d, J=7.8 Hz, 1H), 3.00 (s, 2H), 1.44 (s, 9H), 1.18 (s, 6H)

Step 3: tert-butyl 3-(6-aminopyridin-2-yl)-2,2-dimethylpropanoate

The desired product was obtained in a similar manner to Preparation Example 19 (Step 3, Step 4) by using tert-butyl 3-(6-chloropyridin-2-yl)-2,2-dimethylpropanoate (1.35 g, 5.00 mmol) obtained in Step 2. (2 step yield 9%)

$^1$H-NMR (CHLOROFORM-D) δ 7.31 (t, J=7.8 Hz, 1H), 6.48 (d, J=7.3 Hz, 1H), 6.34-6.29 (1H), 4.27 (s, 2H), 2.84 (s, 2H), 1.44 (s, 9H), 1.20-1.13 (6H)

Preparation Example 63: tert-butyl 3-(2-aminopyridin-4-yl)-2,2-dimethylpropanoate

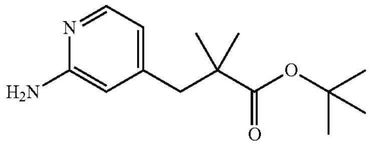 [SMILES: CC(C)(C)OC(=O)C(C)(C)Cc1ccnc(N)c1]

The desired product was obtained in a similar manner to Preparation Example 62 by using 2-chloro-4-methylpyridine (3.00 g, 23.5 mmol). (4 step yield 3%)

$^1$H-NMR (400 MHz, CHLOROFORM-D) δ 7.94 (d, J=5.5 Hz, 1H), 6.47 (d, J=5.5 Hz, 1H), 6.30 (s, 1H), 4.30 (s, 2H), 2.70 (s, 2H), 1.44 (s, 9H), 1.14 (s, 6H)

Preparation Example 64: tert-butyl 3-amino-1H-pyrazole-1-carboxylate

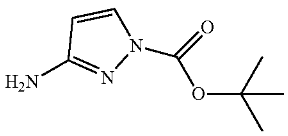

After dissolving 1H-pyrazol-3-amine (0.500 g, 6.02 mmol), TEA (1.677 ml, 12.03 mmol) and 4-dimethylaminopyridine (0.049 g, 0.403 mmol) in 1,4-dioxane (20.06 ml), di-tert-butyl dicarbonate (1.590 ml, 6.92 mmol) was added dropwise at room temperature. After stirring at room temperature for 4 hours, the organic solvent was removed under reduced pressure. The mixture was diluted with ethyl acetate and washed with brine. The organic solvent was dried over magnesium sulfate and used in the next reaction without further purification. (Yield 84%)

$^1$H-NMR (500 MHz, CHLOROFORM-D) δ 7.86 (d, J=2.7 Hz, 1H), 5.84 (d, J=2.7 Hz, 1H), 4.01 (s, 2H), 1.64 (s, 9H)

Preparation Example 65: Ethyl 1-(6-aminopyridin-2-yl)piperidine-3-carboxylate

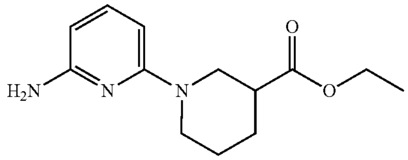 [SMILES: CCOC(=O)C1CCCN(c2cccc(N)n2)C1]

The desired product was obtained in a similar manner to Preparation Example 29 by using ethyl piperidine-3-carboxylate (0.500 g, 3.18 mmol). (3 step yield 24%)

$^1$H-NMR (500 MHz, CHLOROFORM-D) δ 7.49 (t, J=8.4 Hz, 1H), 5.97 (dd, J=20.1, 8.2 Hz, 2H), 4.18 (q, J=7.1 Hz,

2H), 4.05-3.93 (m, 1H), 3.86 (d, J=13.1 Hz, 1H), 3.38 (dd, J=13.1, 9.8 Hz, 1H), 3.19 (dd, J=13.0, 9.9 Hz, 1H), 2.84-2.59 (m, 1H), 2.16 (d, J=9.5 Hz, 1H), 1.89 (s, 1H), 1.83-1.65 (m, 2H), 1.28 (t, J=7.2 Hz, 3H)

Preparation Example 66: Methyl 3-(3-amino-1H-pyrazol-1-yl)-2,2-dimethylpropanoate

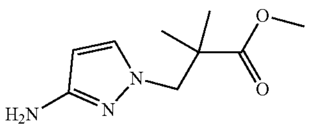

By using methyl 3-hydroxy-2,2-dimethylpropanoate (0.70 g, 5.31 mmol) and 3-nitro-1H-pyrazole (0.50 g, 4.42 mmol), a method similar to Step 1 of Preparation Example 1 and Step 3 of Preparation Example 94 was sequentially used to obtain a desired product. (Yield 63%)

$^1$H-NMR (400 MHz, CHLOROFORM-D): δ 7.09 (d, J=2.3 Hz, 1H), 5.55 (d, J=2.3 Hz, 1H), 4.07 (s, 2H), 3.69 (s, 3H), 1.19 (s, 6H)

Preparation Example 67: Methyl 3-(3-(3-amino-1H-pyrazol-1-yl)phenyl)-2,2-dimethylpropanoate

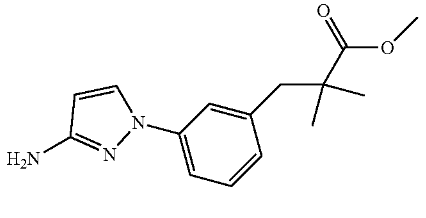 [SMILES: COC(=O)C(C)(C)Cc1cccc(-n2ccc(N)n2)c1]

1H-pyrazol-3-amine (0.20 g, 2.41 mmol), copper (I) iodide (0.046 g, 0.24 mmol), cesium carbonate (1.186 g, 3.61 mmol) and tert-Butyl 3-(3-bromophenyl)-2,2-dimethylpropanoate (0.75 g, 2.41 mmol) obtained in step 1 of Preparation Example 79 were added to DMF (2.4 mL) and stirred at 120° C. for 12 hours. Water was added to the reaction mixture, followed by extraction with ethyl acetate. The organic layer was washed with brine and dried over magnesium sulfate. The solvent was removed under reduced pressure and purified by column chromatography to obtain the title compound. (Yield 59%)

$^1$H-NMR (400 MHz, CHLOROFORM-D): δ 7.66 (d, J=2.3 Hz, 1H), 7.48-7.33 (m, 2H), 7.30-7.25 (m, 1H), 6.99 (d, J=7.8 Hz, 1H), 5.83 (d, J=2.3 Hz, 1H), 3.31 (s, 2H), 2.86 (s, 2H), 1.43 (s, 9H), 1.15 (s, 6H)

Preparation Example 68: Ethyl 2-(3-(2-aminopyrimidin-4-yl)phenoxy)-2-methylpropanoate

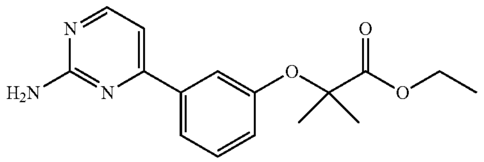 [SMILES: CCOC(=O)C(C)(C)Oc1cccc(-c2ccnc(N)n2)c1]

Step 1: Ethyl 2-(3-bromophenoxy)-2-methylpropanoate 3-bromophenol (1 g, 5.78 mmol), ethyl 2-bromo-2-methylpropanoate (1.24 g, 6.36 mmol) and potassium carbonate (1.598 g, 11.56 mmol) were dissolved in 10 ml of DMF and stirred at room temperature for 4 hours. After confirming that the reaction was completed by TLC, the organic solvent was removed under reduced pressure. After extraction with ethyl acetate (2×20 ml), it was washed with brine (20 ml), and the organic solvent was dried over magnesium sulfate, and removed under reduced pressure. The desired product was obtained by purification with silica gel column (ethyl acetate:hexane=1:9). (Yield 42%)

$^1$H-NMR (400 MHz, CHLOROFORM-D) δ 7.13-6.92 (m, 3H), 6.79-6.67 (m, 1H), 4.24-4.13 (m, 2H), 1.71-1.43 (m, 6H), 1.25-1.15 (m, 3H)

Step 2: Ethyl 2-(3-(2-aminopyrimidin-4-yl)phenoxy)-2-methylpropanoate

The desired product was obtained in a similar manner to Preparation Example 53 (Step 1, Step 2) and Preparation Example 19 (Step 3, Step 4) by using ethyl 2-(3-bromophenoxy)-2-methylpropanoate (0.7 g, 2.56 mmol) obtained in step 1. (4 step yield 34%)

$^1$H-NMR (400 MHz, CHLOROFORM-D) δ 8.39-8.25 (1H), 7.66-7.58 (m, 1H), 7.55-7.50 (m, 1H), 7.40-7.26 (m, 1H), 7.03-6.87 (2H), 5.01 (d, J=31.6 Hz, 2H), 4.34-4.16 (m, 2H), 1.62 (s, 6H), 1.28-1.19 (m, 3H)

Preparation Example 69: Ethyl 2-(4-(2-aminopyrimidin-4-yl)phenoxy)-2-methylpropanoate

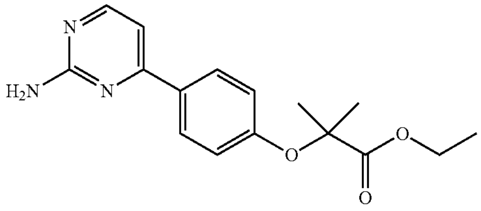 [SMILES: CCOC(=O)C(C)(C)Oc1ccc(-c2ccnc(N)n2)cc1]

The desired product was obtained in a similar manner to Step 1 of Preparation Example 68, Preparation 53 (Step 1, Step 2), and Preparation Example 19 (Step 3, Step 4) by using 4-bromophenol (1 g, 5.78 mmol). (5 step yield 21%)

$^1$H-NMR (400 MHz, CHLOROFORM-D) δ 8.32-8.19 (m, 1H), 7.96-7.81 (m, 2H), 6.98-6.89 (m, 1H), 6.89-6.77 (m, 2H), 5.34 (s, 2H), 4.29-4.14 (m, 2H), 1.63-1.54 (m, 6H), 1.25-1.14 (m, 3H)

Preparation Example 70: Methyl 2-(3-(2-aminopyrimidin-4-yl)phenyl)acetate

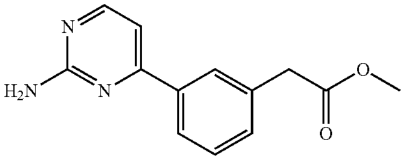 [SMILES: COC(=O)Cc1cccc(-c2ccnc(N)n2)c1]

Step 1: Methyl 2-(3-bromophenyl)acetate 2-(3-Bromophenyl)acetic acid (2 g, 9.30 mmol) and 2.79 ml of sulfuric acid were dissolved in 18.6 ml of methanol and stirred at 80° C. for 4 hours. After confirming that the reaction was completed by TLC, the organic solvent was removed under reduced pressure. After extraction with ethyl acetate (2×20 ml), it was washed with brine (20 ml), and the organic solvent was dried over magnesium sulfate, and removed under reduced pressure. The desired product was obtained by purification with silica gel column (ethyl acetate:hexane=1:9). (Yield 96%)

$^1$H-NMR (400 MHz, CHLOROFORM-D) δ 7.46-7.38 (m, 1H), 7.38-7.26 (m, 1H), 7.26-7.02 (m, 2H), 3.71-3.59 (m, 3H), 3.59-3.48 (m, 2H)

Step 2: Methyl 2-(3-(2-aminopyrimidin-4-yl)phenyl)acetate

The desired product was obtained in a similar manner to Preparation Example 53 (Step 1, Step 2) and Preparation Example 19 (Step 3, Step 4) by using methyl 2-(3-bromophenyl)acetate (2.042 g, 8.94 mmol) obtained in Step 1. (4 step yield 21%)

$^1$H-NMR (400 MHz, CHLOROFORM-D) δ 8.37-8.30 (m, 1H), 7.94 (d, J=14.6 Hz, 1H), 7.90-7.81 (m, 1H), 7.44-7.36 (m, 2H), 7.00 (t, J=5.7 Hz, 1H), 5.26 (t, J=43.7 Hz, 2H), 3.69 (s, 5H)

Preparation Example 71: tert-butyl 3-(4-(2-aminopyridin-4-yl)phenyl)-2,2-dimethylpropanoate

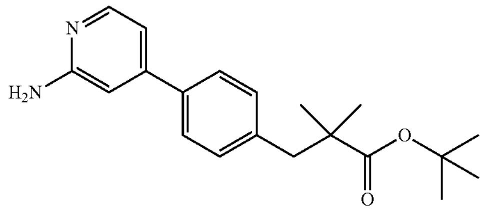

Step 1: tert-butyl 2,2-dimethyl-3-(4-(4,4,5,5-tetramethyl-1,3,2-dioxaborolan-2-yl)phenyl)propanoate The desired product was obtained in a similar manner to Preparation Example 58 (Step 1, Step 2) by using 1-bromo-4-(bromomethyl)benzene (2.00 g, 8.00 mmol) and tert-butyl isobutyrate (1.39 g, 9.60 mmol). (2 step yield 64%)

$^1$H-NMR (CHLOROFORM-D) δ 7.70 (d, J=7.6 Hz, 2H), 7.16 (d, J=7.9 Hz, 2H), 2.84 (s, 2H), 1.43 (s, 9H), 1.34 (s, 12H), 1.11 (s, 6H)

Step 2: tert-butyl 3-(4-(2-aminopyridin-4-yl)phenyl)-2,2-dimethylpropanoate

The desired product was obtained in a similar manner to Step 2 of Preparation Example 52 by using 4-bromopyridin-2-amine (106 mg, 0.611 mmol) and tert-butyl 2,2-dimethyl-3-(4-(4,4,5,5-tetramethyl-1,3,2-dioxaborolan-2-yl)phenyl) propanoate (220 mg, 0.611 mmol) obtained in Step 1. (Yield 86%)

$^1$H-NMR (CHLOROFORM-D) δ 8.11 (d, J=5.2 Hz, 1H), 7.49 (d, J=7.6 Hz, 2H), 7.24 (d, J=7.6 Hz, 2H), 6.88 (d, J=5.2 Hz, 1H), 6.70 (s, 1H), 4.46 (s, 2H), 2.87 (s, 2H), 1.52-1.36 (m, 9H), 1.21-1.07 (m, 6H)

Preparation Example 72: Ethyl 6-(2-aminopyrimidin-4-yl)picolinate

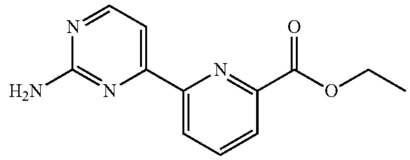 [SMILES: CCOC(=O)c1cccc(-c2ccnc(N)n2)n1]

Step 1: Ethyl 6-(tributylstannyl)picolinate

Ethyl 6-bromopicolinate (300 mg, 1.304 mmol) was dissolved in toluene, and bis(tributyltin) (791 μl, 1.57 mmol) and potassium acetate (384 mg, 3.91 mmol) were added. After removing the dissolved oxygen from the reaction mixture, it was filled with nitrogen and the inflow of outside air was blocked. 1,1'-bis(diphenylphosphino)ferrocene-palladium(II)dichloride dichloromethane complex (53.2 mg, 0.065 mmol) was added and reacted at 90° C. for 18 hours. After completion of the reaction, it was filtered through Celite and concentrated under reduced pressure, and the mixture was immediately used for the next reaction.

$^1$H-NMR (400 MHz, CHLOROFORM-D) δ 7.90 (dd, J=7.8, 1.4 Hz, 1H), 7.59 (t, J=7.5 Hz, 1H), 7.51 (dd, J=7.3, 1.4 Hz, 1H), 4.42 (q, J=7.2 Hz, 2H), 1.68-1.45 (m, 9H), 1.41 (t, J=7.1 Hz, 3H), 1.33 (td, J=14.8, 7.5 Hz, 6H), 1.25-1.02 (m, 6H), 0.88 (q, J=7.3 Hz, 10H)

Step 2: Ethyl 6-(2-chloropyrimidin-4-yl)picolinate

Ethyl 6-(tributylstannyl)picolinate synthesized in step 1 was dissolved in toluene, and 2,4-dichloropyrimidine (18.6 mg, 0.125 mmol) and sodium carbonate (39.7 mg, 0.375 mmol) were added. After removing the dissolved oxygen from the reaction mixture, it was filled with nitrogen and the inflow of outside air was blocked. (Triphenylphosphine) palladium (0) (14.4 mg, 0.012 mmol) was added, a reflux cooling device was connected at 130° C. and heated for 12 hours. After completion of the reaction, it was filtered through Celite and concentrated under reduced pressure, and the mixture was purified by column chromatography (hexane:ethyl acetate) to synthesize the desired compound. (Yield 49%)

$^1$H-NMR (400 MHz, CHLOROFORM-D) δ 8.76 (d, J=5.0 Hz, 1H), 8.66 (dd, J=7.8, 0.9 Hz, 1H), 8.47 (d, J=5.0 Hz, 1H), 8.23 (dd, J=7.5, 1.1 Hz, 1H), 8.02 (t, J=7.8 Hz, 1H), 4.58-4.40 (2H), 1.46 (t, J=7.1 Hz, 3H)

Step 3: Ethyl 6-(2-aminopyrimidin-4-yl)picolinate

The desired product was synthesized in a similar manner to Preparation Example 19 (Step 3, Step 4) by using ethyl 6-(2-chloropyrimidin-4-yl) picolinate (76 mg, 0.288 mmol) synthesized in Step 2. (2 step yield 24%)

$^1$H-NMR (400 MHz, CHLOROFORM-D) δ 8.52 (dd, J=7.8, 0.9 Hz, 1H), 8.46 (d, J=5.0 Hz, 1H), 8.17 (dd, J=7.8, 0.9 Hz, 1H), 7.96 (t, J=7.8 Hz, 1H), 7.81 (d, J=5.0 Hz, 1H), 5.19 (s, 2H), 4.48 (q, J=7.2 Hz, 2H), 1.46 (t, J=7.1 Hz, 3H)

Preparation Example 73: tert-butyl (6-bromopyridin-2-yl)carbamate

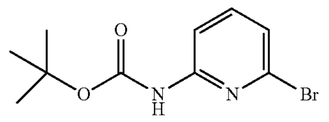

6-Bromopyridin-2-amine (15.0 g, 87.0 mmol) and 1.3 M lithium hexamethyldisilazide (147 ml, 191 mmol) were dissolved in THF 93 ml, and di-tert-butyl dicarbonate (21.9 ml, 95.0 mmol) which diluted in 100 ml of THF at −78° C. under nitrogen purge was added dropwise thereto. After stirring at room temperature overnight, the organic solvent was removed under reduced pressure, diluted with ethyl acetate, washed with 1 N aqueous hydrochloric acid solution, dried over magnesium sulfate, and purified by silica gel column (ethyl acetate:hexane) to obtain the desired product. (Yield 98%)

$^1$H-NMR (CHLOROFORM-D) δ 7.88 (d, J=8.2 Hz, 1H), 7.50 (t, J=7.9 Hz, 1H), 7.24-7.16 (1H), 7.12 (d, J=7.6 Hz, 1H), 1.52-1.50 (9H)

Preparation Example 74: Methyl 2-(4-(2-aminopyrimidin-4-yl)phenyl)acetate

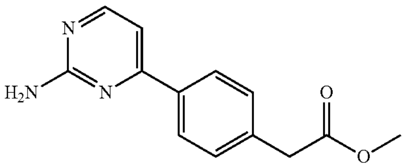 [SMILES: COC(=O)Cc1ccc(-c2ccnc(N)n2)cc1]

Step 1: Methyl 2-(4-(4,4,5,5-tetramethyl-1,3,2-dioxaborolan-2-yl)phenyl)acetate

The desired product was obtained in a similar manner to Step 1 of Preparation Example 53 by using methyl 2-(4-bromophenyl)acetate (2.07 g, 9.04 mmol). (Yield 96%)

$^1$H-NMR (400 MHz, CHLOROFORM-D) δ 7.76 (dd, J=23.1, 15.3 Hz, 2H), 7.34-7.26 (m, 2H), 3.67 (s, 3H), 3.61 (t, J=7.5 Hz, 2H), 1.43-1.29 (m, 12H)

Step 2: Methyl 2-(4-(2-chloropyrimidin-4-yl)phenyl)acetate

The desired product was obtained in a similar manner to Step 2 of Preparation Example 53 by using methyl 2-(4-(4,4,5,5-tetramethyl-1,3,2-dioxaborolan-2-yl)phenyl)acetate (2.4 g, 8.69 mmol) obtained in step 1. (Yield 14%)

$^1$H-NMR (400 MHz, CHLOROFORM-D) δ 8.62 (d, J=5.5 Hz, 1H), 8.13-7.97 (m, 2H), 7.62 (d, J=5.0 Hz, 1H), 7.43 (d, J=8.2 Hz, 2H), 3.71 (dd, J=15.8, 14.4 Hz, 5H)

Step 3: Methyl 2-(4-(2-aminopyrimidin-4-yl)phenyl)acetate

The desired product was obtained in a similar manner to Preparation Example 19 (Step 3, Step 4) by using methyl 2-(4-(2-chloropyrimidin-4-yl)phenyl)acetate (0.32 g, 1.218 mmol) obtained in Step 2. (2 step yield 28%)

$^1$H-NMR (400 MHz, CHLOROFORM-D) δ 8.63 (q, J=2.6 Hz, 1H), 8.04-7.96 (m, 2H), 7.79 (d, J=13.3 Hz, 1H), 7.39 (d, J=8.2 Hz, 2H), 7.36-7.29 (m, 2H), 3.69 (s, 3H), 3.68 (s, 2H)

Preparation Example 75: Methyl 2-(4-(6-amino-3-(trifluoromethyl)pyridin-2-yl)phenyl)-2-methylpropanoate

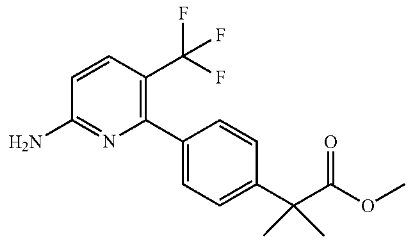 [SMILES: COC(=O)C(C)(C)c1ccc(-c2nc(N)ccc2C(F)(F)F)cc1]

Step 1: Methyl 2-(4-(6-chloro-3-(trifluoromethyl)pyridin-2-yl)phenyl)-2-methylpropanoate The desired product was obtained in a similar manner to Step 2 of Preparation Example 53 by using methyl 2-methyl-2-(4-(4,4,5,5-tetramethyl-1,3,2-dioxaborolan-2-yl)phenyl)propanoate (0.5 g, 1.644 mmol) obtained in step 1 of Preparation Example 54 and 2,6-dichloro-3-(trifluoromethyl)pyridine (0.426 g, 1.972 mmol). (Yield 78%)

$^1$H-NMR (400 MHz, CHLOROFORM-D) δ 8.08-8.01 (m, 1H), 7.99 (dt, J=8.7, 2.1 Hz, 2H), 7.72 (d, J=8.2 Hz, 1H), 7.48-7.41 (m, 2H), 3.66 (s, 3H), 1.66-1.61 (m, 6H)

Step 2: Methyl 2-(4-(6-amino-3-(trifluoromethyl)pyridin-2-yl)phenyl)-2-methylpropanoate The desired product was obtained in a similar manner to Preparation Example 19 (step 3, step 4) by using methyl 2-(4-(6-chloro-5-(trifluoromethyl)pyridin-2-yl)phenyl)-2-methylpropanoate (0.46 g, 1.286 mmol) obtained in step 1. (2 step yield 41%)

$^1$H-NMR (400 MHz, CHLOROFORM-D) δ 7.90 (d, J=8.7 Hz, 2H), 7.74 (d, J=8.2 Hz, 1H), 7.41 (dd, J=21.5, 12.8 Hz, 2H), 7.17-7.03 (m, 1H), 5.05 (d, J=43.0 Hz, 2H), 3.72-3.56 (m, 3H), 1.62 (d, J=15.1 Hz, 6H)

Preparation Example 76: Methyl 3-(4-(2-aminopyrimidin-4-yl)phenyl)-2,2-dimethylpropanoate

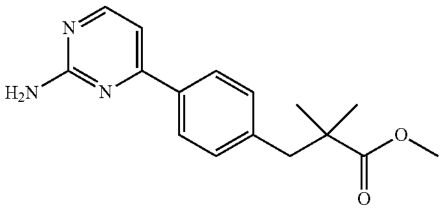 [SMILES: COC(=O)C(C)(C)Cc1ccc(-c2ccnc(N)n2)cc1]

Step 1: tert-butyl 3-(4-(2-((tert-butoxycarbonyl)amino)pyrimidin-4-yl)phenyl)-2,2-dimethylpropanoate The desired product was obtained in a similar manner to Step 2 of Preparation Example 52 and Step 3 of Preparation Example 19 by using 2,4-dichloropyrimidine (4.30 g, 28.9 mmol) and tert-butyl 2,2-dimethyl-3-(4-(4,4,5,5-tetramethyl-1,3,2-dioxaborolan-2-yl)phenyl)propanoate (10.4 g, 28.9 mmol) obtained in step 1 of Preparation Example 71. (2 step yield 9%)

m/z $(M+H)^+$ calculated for $C_{24}H_{34}N_3O_4$: 428. found 428.

Step 2: Methyl 3-(4-(2-aminopyrimidin-4-yl)phenyl)-2,2-dimethylpropanoate

Tert-butyl 3-(4-(2-((tert-butoxycarbonyl)amino)pyrimidin-4-yl)phenyl)-2,2-dimethylpropanoate (1.63 g, 3.81 mmol) obtained in step 1 was dissolved in 63.5 ml of methanol, and sulfuric acid (1.02 ml, 19.1 mmol) was slowly added dropwise. It was stirred under reflux at 100° C. for 2 hours, cooled, and washed with sodium hydrogen carbonate solution. The organic solvent was dried over magnesium sulfate and the organic solvent was removed under reduced pressure. The desired product was obtained by purification with silica gel column (ethyl acetate:hexane). (Yield 73%)

$^1$H-NMR (400 MHz, CHLOROFORM-D) δ 8.33 (d, J=5.0 Hz, 1H), 7.98-7.82 (m, 2H), 7.21 (d, J=8.2 Hz, 2H), 7.02 (d, J=5.5 Hz, 1H), 5.03 (s, 2H), 3.67 (s, 3H), 2.92 (s, 2H), 1.20 (s, 6H)

Preparation Example 77: tert-butyl 3-(4-(6-aminopyridin-2-yl)phenyl)-2,2-dimethylpropanoate

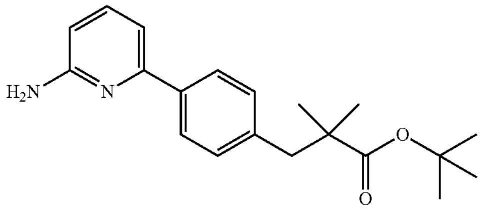

The desired product was obtained in a similar manner to Step 2 of Preparation Example 52 by using 6-chloropyridin-2-amine (143 mg, 1.11 mmol) and tert-butyl 2,2-dimethyl-3-(4-(4,4,5,5-tetramethyl-1,3,2-dioxaborolan-2-yl)phenyl) propanoate (500 mg, 1.39 mmol) obtained in step 1 of Preparation Example 71. (Yield 40%)

$^1$H-NMR (400 MHz, CHLOROFORM-D) δ 7.82 (d, J=8.7 Hz, 2H), 7.49 (t, J=7.8 Hz, 1H), 7.23 (d, J=6.4 Hz, 2H), 7.15-6.99 (1H), 6.44 (d, J=7.8 Hz, 1H), 4.46 (s, 2H), 2.87 (s, 2H), 1.45 (s, 9H), 1.13 (s, 6H)

Preparation Example 78: Methyl 3-(3-(6-aminopyridin-2-yl)phenyl)-2,2-dimethylpropanoate

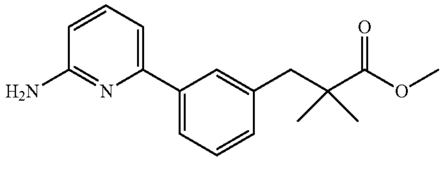 [SMILES: COC(=O)C(C)(C)Cc1cccc(-c2cccc(N)n2)c1]

Step 1: Methyl 3-(3-(6-((tert-butoxycarbonyl)amino)pyridin-2-yl)-phenyl)-2,2-dimethylpropanoate The desired product was obtained in a similar manner to step 2 of Preparation Example 52 by using tert-butyl (6-bromopyridin-2-yl)carbamate (17.3 g, 63.5 mmol) obtained in Preparation Example 73 and methyl 2,2-dimethyl-3-(3-(4,4,5,5-tetramethyl-1,3,2-dioxaborolan-2-yl)phenyl)propanoate (20.2 g, 63.5 mmol) obtained from Step 2 of Preparation Example 58. (Yield 66%).

$^1$H-NMR (400 MHz, CHLOROFORM-D) δ 7.85 (d, J=8.2 Hz, 1H), 7.79 (d, J=7.8 Hz, 1H), 7.75-7.67 (m, 2H), 7.35 (q, J=7.8 Hz, 2H), 7.14 (d, J=7.3 Hz, 1H), 3.66 (s, 3H), 2.93 (s, 2H), 1.54 (s, 9H), 1.22 (s, 6H)

Step 2: Methyl 3-(3-(6-aminopyridin-2-yl)phenyl)-2,2-dimethylpropanoate

The desired product was obtained in a similar manner to Step 4 of Preparation Example 19 by using methyl 3-(3-(6-((tert-butoxycarbonyl)amino)pyridin-2-yl)-phenyl)-2,2-dimethylpropanoate (16.2 g, 42.1 mmol) obtained in step 1. (Yield 86%)

$^1$H-NMR (400 MHz, CHLOROFORM-D) δ 7.78 (d, J=7.8 Hz, 1H), 7.67 (s, 1H), 7.57-7.40 (m, 1H), 7.32 (t, J=7.8 Hz, 1H), 7.11 (d, J=7.3 Hz, 1H), 7.08-6.99 (m, 1H), 6.53-6.37 (m, 1H), 4.45 (s, 2H), 3.67 (s, 3H), 3.00-2.85 (2H), 1.21 (s, 6H)

Preparation Example 79: tert-butyl 3-(3-(2-chloro-5-fluoropyrimidin-4-yl)phenyl)-2,2-dimethylpropanoate

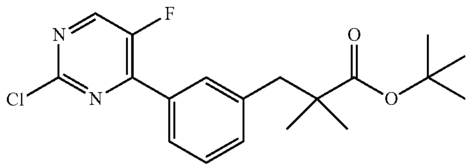 [SMILES: CC(C)(C)OC(=O)C(C)(C)Cc1cccc(-c2nc(Cl)ncc2F)c1]

Step 1: tert-butyl 3-(3-bromophenyl)-2,2-dimethylpropanoate

The title compound was synthesized in a similar manner to Step 1 of Preparation Example 58 by using 1-bromo-3-(bromomethyl)benzene (5 g, 20.01 mmol) and tert-butyl isobutyrate (4.00 ml, 24.01 mmol). (Yield 70%)

$^1$H-NMR (400 MHz, CHLOROFORM-D) δ 7.40-7.27 (m, 2H), 7.11 (t, J=7.3 Hz, 1H), 7.08-6.99 (m, 1H), 2.84-2.70 (2H), 1.43 (s, 9H), 1.12 (s, 6H)

Step 2: tert-butyl 2,2-dimethyl-3-(3-(4,4,5,5-tetramethyl-1,3,2-dioxaborolan-2-yl)phenyl)propanoate The title compound was synthesized in a similar manner to Step 2 of Preparation Example 58 by using tert-butyl 3-(3-bromophenyl)-2,2-dimethylpropanoate (4.38 g, 13.98 mmol) synthesized in Step 1. (Yield 72%)

$^1$H-NMR (400 MHz, CHLOROFORM-D) δ 7.69-7.54 (2H), 7.23 (d, J=1.4 Hz, 2H), 2.82 (s, 2H), 1.55 (d, J=1.4 Hz, 2H), 1.43 (s, 9H), 1.31 (s, 12H), 1.12 (s, 6H)

Step 3: tert-butyl 3-(3-(2-chloro-5-fluoropyrimidin-4-yl)phenyl)-2,2-dimethylpropanoate The title compound was synthesized in a similar manner to Step 2 of Preparation Example 52 by using tert-butyl 2,2-dimethyl-3-(3-(4,4,5,5-tetramethyl-1,3,2-dioxaborolan-2-yl)phenyl)propanoate (500 mg, 1.39 mmol) synthesized in step 2. (Yield 46%)

$^1$H-NMR (400 MHz, CHLOROFORM-D) δ 8.49 (d, J=3.2 Hz, 1H), 8.00-7.88 (m, 2H), 7.49-7.31 (m, 2H), 2.92 (s, 2H), 1.43 (s, 9H), 1.15 (s, 6H)

Preparation Example 80: tert-butyl 3-(3-(2-amino-pyrimidin-4-yl)phenyl)-2,2-dimethylpropanoate

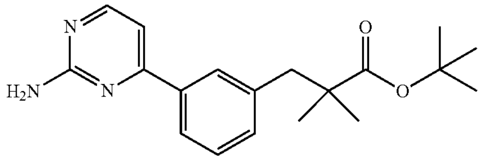 [SMILES: CC(C)(C)OC(=O)C(C)(C)Cc1cccc(-c2ccnc(N)n2)c1]

The desired product was obtained in a similar manner to step 2 of Preparation Example 52 and Preparation Example 19 (Step 3, Step 4) by using 2,4-dichloropyrimidine (0.620 g, 4.16 mmol) and tert-butyl 2,2-dimethyl-3-(3-(4,4,5,5-tetramethyl-1,3,2-dioxaborolan-2-yl)phenyl)propanoate (1.50 g, 4.16 mmol) obtained in step 2 of Preparation Example 79. (3 step yield 49%)

$^1$H-NMR (CHLOROFORM-D) δ 8.34 (s, 1H), 7.83 (d, J=8.8 Hz, 2H), 7.36 (s, 1H), 7.28 (s, 1H), 7.03 (s, 1H), 5.02 (s, 2H), 2.91 (s, 2H), 1.43 (s, 9H), 1.16 (s, 6H)

Preparation Example 81: tert-butyl 3-(4-(2-amino-pyrimidin-4-yl)phenyl)-2,2-dimethylpropanoate

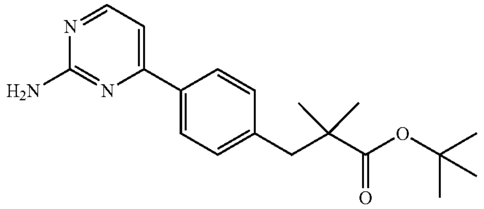 [SMILES: CC(C)(C)OC(=O)C(C)(C)Cc1ccc(-c2ccnc(N)n2)cc1]

The desired product was obtained in a similar manner to Step 2 of Preparation Example 52 and Preparation Example 19 (Step 3, Step 4) by using 2,4-dichloropyrimidine (182 mg, 1.22 mmol) and tert-butyl 2,2-dimethyl-3-(4-(4,4,5,5-tetramethyl-1,3,2-dioxaborolan-2-yl)phenyl)propanoate (440 mg, 1.22 mmol) obtained from step 1 of Preparation Example 71. (3 step yield 19%)

$^1$H-NMR (400 MHz, CHLOROFORM-D) δ 8.33 (d, J=5.5 Hz, 1H), 7.98-7.82 (m, 2H), 7.28 (s, 2H), 7.03 (d, J=5.5 Hz, 1H), 5.04 (s, 2H), 2.88 (d, J=9.1 Hz, 2H), 1.44 (s, 9H), 1.14 (s, 6H)

Preparation Example 82: tert-butyl 3-(3-(6-amino-pyrazin-2-yl)phenyl)-2,2-dimethylpropanoate

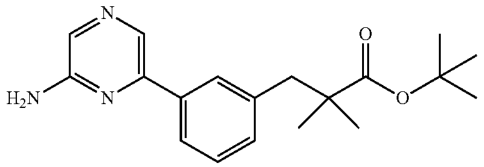 [SMILES: CC(C)(C)OC(=O)C(C)(C)Cc1cccc(-c2cncc(N)n2)c1]

Step 1: tert-butyl 3-(3-(6-chloropyrazin-2-yl)phenyl)-2,2-dimethylpropanoate

The desired product was obtained in a similar manner to Step 2 of Preparation Example 52 by using 2,6-dichloropyrazine (124 mg, 0.833 mmol) and tert-butyl 2,2-dimethyl-3-(3-(4,4,5,5-tetramethyl-1,3,2-dioxaborolan-2-yl)phenyl)propanoate (300 mg, 0.833 mmol) obtained in step 2 of Preparation Example 79. (Yield 52%)

$^1$H-NMR (400 MHz, CHLOROFORM-D) δ 8.90 (s, 1H), 8.50 (s, 1H), 7.93-7.78 (m, 2H), 7.49-7.34 (m, 1H), 7.30 (d, J=7.3 Hz, 1H), 2.93 (s, 2H), 1.45 (s, 9H), 1.24-1.10 (6H)

Step 2: tert-butyl 3-(3-(6-aminopyrazin-2-yl)phenyl)-2,2-dimethylpropanoate

The desired product was obtained in a similar manner to Preparation Example 19 (Step 3, Step 4) by using tert-butyl 3-(3-(6-chloropyrazin-2-yl)phenyl)-2,2-dimethylpropanoate (151 mg, 0.435 mmol) synthesized in step 1. (2 step yield 69%)

$^1$H-NMR (400 MHz, CHLOROFORM-D) δ 8.35 (s, 1H), 7.92 (s, 1H), 7.77 (t, J=7.3 Hz, 2H), 7.36 (t, J=7.8 Hz, 1H), 7.23 (d, J=7.8 Hz, 1H), 4.57 (s, 2H), 2.91 (s, 2H), 1.43 (s, 9H), 1.16 (s, 6H)

Preparation Example 83: Methyl 3-(3-(5-aminopyridin-3-yl)phenyl)-2,2-dimethylpropanoate

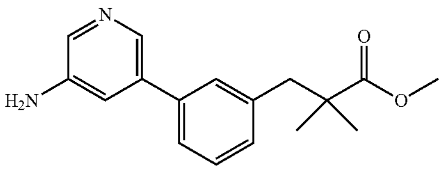 [SMILES: COC(=O)C(C)(C)Cc1cccc(-c2cncc(N)c2)c1]

Step 1: tert-butyl 3-(3-(5-bromopyridin-3-yl)phenyl)-2,2-dimethylpropanoate

The desired product was obtained in a similar manner to Step 2 of Preparation Example 52 by using 3,5-bromopyridine (197 mg, 0.833 mmol) and tert-butyl 2,2-dimethyl-3-(3-(4,4,5,5-tetramethyl-1,3,2-dioxaborolan-2-yl)phenyl)propanoate (300 mg, 0.833 mmol) obtained in step 2 of Preparation Example 79. (Yield 54%)

$^1$H-NMR (400 MHz, CHLOROFORM-D) δ 8.73 (d, J=1.8 Hz, 1H), 8.64 (d, J=2.3 Hz, 1H), 7.99 (t, J=2.1 Hz, 1H), 7.44-7.32 (m, 3H), 7.23 (d, J=6.9 Hz, 1H), 2.91 (s, 2H), 1.43 (s, 9H), 1.16 (s, 6H)

Step 2: Methyl 3-(3-(5-aminopyridin-3-yl)phenyl)-2,2-dimethylpropanoate

The desired product was obtained in a similar manner to Step 3 of Preparation Example 19 and Step 2 of Preparation Example 76 by using tert-butyl 3-(3-(5-bromopyridin-3-yl)phenyl)-2,2-dimethylpropanoate (176 mg, 0.451 mmol) synthesized in step 1. (2 step yield 13%)

$^1$H-NMR (400 MHz, CHLOROFORM-D) δ 8.23 (d, J=1.8 Hz, 1H), 8.14-8.00 (1H), 7.40 (dd, J=7.8, 1.4 Hz, 1H), 7.34 (t, J=7.5 Hz, 1H), 7.28 (s, 1H), 7.12 (q, J=2.3 Hz, 2H), 3.78 (s, 2H), 3.66 (s, 3H), 2.92 (s, 2H), 1.22 (s, 6H)

Preparation Example 84: tert-butyl 3-(3-(6-amino-4-(trifluoromethyl)pyridin-2-yl)phenyl)-2,2-dimethyl-propanoate

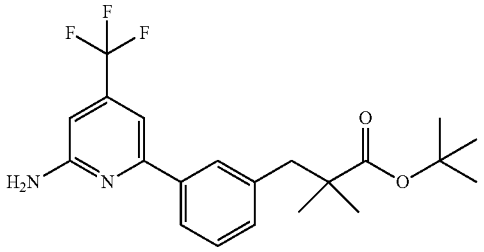 [SMILES: CC(C)(C)OC(=O)C(C)(C)Cc1cccc(-c2cc(C(F)(F)F)cc(N)n2)c1]

Step 1: tert-butyl 3-(3-(6-chloro-4-(trifluoromethyl) pyridin-2-yl)phenyl)-2,2-dimethylpropanoate The desired product was obtained in a similar manner to Step 2 of Preparation Example 52 by using 2,6-dichloro-4-(trifluoromethyl)pyridine (0.115 ml, 0.799 mmol) and tert-butyl 2,2-dimethyl-3-(3-(4,4,5,5-tetramethyl-1,3,2-dioxaborolan-2-yl)phenyl)propanoate (288 mg, 0.799 mmol) obtained in Step 2 of Preparation Example 79. (Yield 66%).

$^1$H-NMR (400 MHz, CHLOROFORM-D) δ 7.87 (d, J=8.7 Hz, 2H), 7.81 (s, 1H), 7.46 (s, 1H), 7.40 (t, J=7.5 Hz, 1H), 7.28 (d, J=7.8 Hz, 1H), 2.94 (s, 2H), 1.45 (s, 9H), 1.17 (s, 6H)

Step 2: tert-butyl 3-(3-(6-amino-4-(trifluoromethyl) pyridin-2-yl)phenyl)-2,2-dimethylpropanoate The desired product was obtained in a similar manner to Preparation Example 19 (Step 3, Step 4) by using tert-butyl 3-(3-(6-chloro-4-(trifluoromethyl)pyridin-2-yl)phenyl)-2,2-dimethylpropanoate (218 mg, 0.527 mmol) synthesized in step 1. (2 step yield 63%)

$^1$H-NMR (400 MHz, CHLOROFORM-D) δ 7.79 (dd, J=7.8, 1.4 Hz, 1H), 7.75 (s, 1H), 7.35 (t, J=7.5 Hz, 1H), 7.22 (d, J=8.2 Hz, 2H), 6.62 (s, 1H), 4.74 (s, 2H), 2.91 (s, 2H), 1.44 (s, 9H), 1.16 (s, 6H)

Preparation Example 85: tert-butyl 3-(3-(6-amino-5-fluoropyridin-2-yl)phenyl)-2,2-dimethylpropanoate

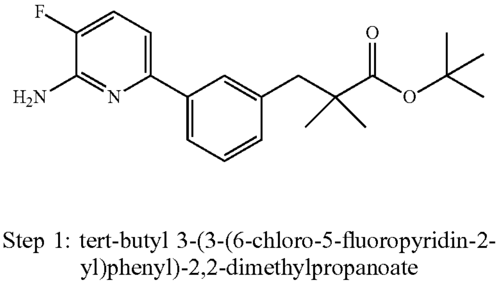

Step 1: tert-butyl 3-(3-(6-chloro-5-fluoropyridin-2-yl)phenyl)-2,2-dimethylpropanoate The title compound was synthesized in the same manner as in Step 2 of Preparation Example 52 by using tert-butyl 2,2-dimethyl-3-(3-(4,4,5,5-tetramethyl-1,3,2-dioxaborolan-2-yl)phenyl)propanoate (500 mg, 1.39 mmol) obtained in Step 2 of Preparation Example 79 and 2,6-dichloro-3-fluoropyridine (230 mg, 1.39 mmol). (Yield 10%)

$^1$H-NMR (CHLOROFORM-D) δ 7.79 (d, J=8.5 Hz, 2H), 7.66 (dd, J=8.4, 3.2 Hz, 1H), 7.60-7.46 (1H), 7.38 (t, J=7.5 Hz, 1H), 7.27-7.18 (1H), 2.94 (s, 2H), 1.45 (d, J=9.8 Hz, 9H), 1.19 (s, 6H)

Step 2: tert-butyl 3-(3-(6-amino-5-fluoropyridin-2-yl)phenyl)-2,2-dimethylpropanoate The title compound was synthesized in a similar manner to Preparation Example 19 (Step 3, Step 4) by using tert-butyl 3-(3-(6-chloro-5-fluoropyridin-2-yl)phenyl)-2,2-dimethylpropanoate (500 mg, 1.39 mmol) obtained in step 1. (2 step yield 49%)

$^1$H-NMR (CHLOROFORM-D) δ 7.74 (d, J=7.6 Hz, 1H), 7.70 (s, 1H), 7.34 (t, J=7.8 Hz, 1H), 7.32-7.25 (m, 1H), 7.19 (d, J=7.6 Hz, 1H), 7.04 (dd, J=7.9, 3.1 Hz, 1H), 4.83 (s, 2H), 2.92 (d, J=6.7 Hz, 2H), 1.49-1.41 (m, 9H), 1.18 (s, 6H)

Preparation Example 86: tert-butyl 3-(3-(2-amino-5-(trifluoromethyl)pyrimidin-4-yl)phenyl)-2,2-dimethylpropanoate

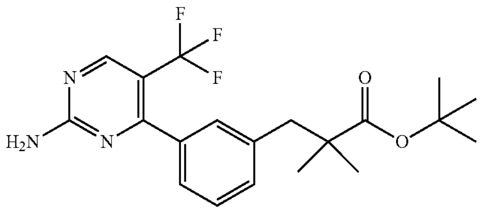 [SMILES: CC(C)(C)OC(=O)C(C)(C)Cc1cccc(-c2nc(N)ncc2C(F)(F)F)c1]

Step 1: tert-butyl 3-(3-(2-chloro-5-(trifluoromethyl) pyrimidin-4-yl)phenyl)-2,2-dimethylpropanoate The title compound was synthesized in the same manner as in Step 2 of Preparation Example 52 by using tert-butyl 2,2-dimethyl-3-(3-(4,4,5,5-tetramethyl-1,3,2-dioxaborolan-2-yl)phenylpropanoate (500 mg, 1.39 mmol) obtained in step 2 of Preparation Example 79 and 2,6-dichloro-5-(trifluoromethyl)pyrimidine (301 mg, 1.39 mmol). (Yield 13%)

$^1$H-NMR (CHLOROFORM-D) δ 7.79 (d, J=8.5 Hz, 2H), 7.66 (dd, J=8.4, 3.2 Hz, 1H), 7.60-7.46 (1H), 7.38 (t, J=7.5 Hz, 1H), 7.27-7.18 (1H), 2.94 (s, 2H), 1.45 (d, J=9.8 Hz, 9H), 1.19 (s, 6H)

Step 2: tert-butyl 3-(3-(2-amino-5-(trifluoromethyl) pyrimidin-4-yl)phenyl)-2,2-dimethylpropanoate The title compound was synthesized in the same manner as in Preparation Example 19 (Step 3, Step 4) by using tert-butyl 3-(3-(2-chloro-5-(trifluoromethyl)pyrimidin-4-yl) phenyl)-2,2-dimethylpropanoate (232 mg, 0.64 mmol) obtained in step 1. (2 step yield 43%)

m/z $(M+H)^+$ calculated for $C_{20}H_{25}F_3N_3O_2$: 396. found 396.

Preparation Example 87: tert-butyl 3-(3-(6-amino-3-fluoropyridin-2-yl)phenyl)-2,2-dimethylpropanoate

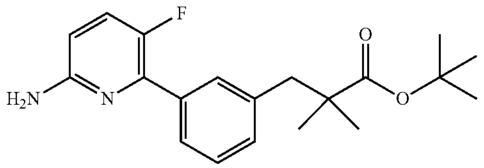 [SMILES: CC(C)(C)OC(=O)C(C)(C)Cc1cccc(-c2nc(N)ccc2F)c1]

Step 1: tert-butyl 3-(3-(6-chloro-3-fluoropyridin-2-yl)phenyl)-2,2-dimethylpropanoate The title compound was synthesized in the same manner as in Step 2 of Preparation Example 52 by using tert-butyl 2,2-dimethyl-3-(3-(4,4,5,5-tetramethyl-1,3,2-dioxaborolan-2-yl)phenyl)propanoate (500 mg, 1.39 mmol) obtained in step 2 of Preparation Example 79 and 2,6-dichloro-3-fluoropyridine (230 mg, 1.39 mmol). (Yield 68%)

$^1$H-NMR (400 MHz, CHLOROFORM-D) δ 7.81 (dd, J=7.9, 1.5 Hz, 1H), 7.78 (d, J=1.8 Hz, 1H), 7.44 (dd, J=10.1, 8.2 Hz, 1H), 7.36 (t, J=7.8 Hz, 1H), 7.24 (d, J=2.7 Hz, 1H), 7.22 (d, J=3.2 Hz, OH), 2.91 (s, 2H), 1.46-1.33 (m, 9H), 1.16 (d, J=8.2 Hz, 6H)

Step 2: tert-butyl 3-(3-(6-amino-3-fluoropyridin-2-yl)phenyl)-2,2-dimethylpropanoate The title compound was synthesized in a similar manner to Preparation Example 19 (Step 3, Step 4) by using tert-butyl 3-(3-(6-chloro-3-fluoropyridin-2-yl)phenyl)-2,2-dimethylpropanoate (192 mg, 0.53 mmol) synthesized in step 1. (2 step yield 12%)

$^1$H-NMR (CHLOROFORM-D) δ 7.85 (d, J=7.6 Hz, 1H), 7.82 (s, 1H), 7.57 (d, J=8.5 Hz, 1H), 7.46 (t, J=9.6 Hz, 1H), 7.41 (t, J=7.6 Hz, 2H), 7.26 (s, 1H), 2.96 (s, 2H), 1.50-1.43 (m, 11H), 1.22 (d, J=8.5 Hz, 6H)

Preparation Example 88: Ethyl 2-(3-(6-aminopyridin-2-yl)phenoxy)-2-methylpropanoate

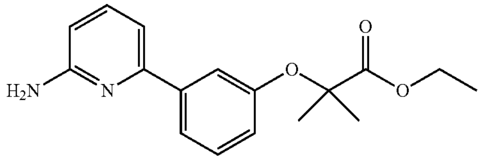 [SMILES: CCOC(=O)C(C)(C)Oc1cccc(-c2cccc(N)n2)c1]

Step 1: Ethyl 2-(3-bromophenoxy)-2-methylpropanoate

3-Bromophenol (2.00 g, 11.6 mmol), ethyl 2-bromo-2-methylpropanoate (2.48 g, 12.7 mmol) and potassium carbonate (3.20 g, 23.1 mmol) were dissolved in 23.1 ml of DMF and stirred at room temperature overnight. After extraction with ethyl acetate, the organic solvent was dried over magnesium sulfate, and the organic solvent was removed under reduced pressure. The desired product was obtained by purification with silica gel column (ethyl acetate:hexane). (Yield 42%)

$^1$H-NMR (400 MHz, CHLOROFORM-D) δ 7.16-7.05 (m, 2H), 7.03 (t, J=2.1 Hz, 1H), 6.76 (td, J=4.6, 2.6 Hz, 1H), 4.24 (q, J=7.0 Hz, 2H), 1.59 (s, 6H), 1.25 (t, J=7.1 Hz, 3H)

Step 2: ethyl 2-methyl-2-(3-(4,4,5,5-tetramethyl-1,3,2-dioxaborolan-2-yl)phenoxy)propanoate The desired product was obtained in a similar manner to step 1 of Preparation Example 52 by using ethyl 2-(3-bromophenoxy)-2-methylpropanoate (1.39 g, 4.84 mmol) synthesized in step 1. (Yield 80%)

$^1$H-NMR (400 MHz, CHLOROFORM-D) δ 7.43 (d, J=7.3 Hz, 1H), 7.30 (d, J=2.7 Hz, 1H), 7.23 (d, J=7.8 Hz, 1H), 6.94 (dq, J=8.2, 1.2 Hz, 1H), 4.25 (q, J=7.2 Hz, 2H), 1.58 (s, 6H), 1.32 (s, 12H), 1.27-1.25 (3H)

Step 3: Ethyl 2-(3-(6-aminopyridin-2-yl)phenoxy)-2-methylpropanoate

The desired product was obtained in a similar manner to Preparation Example 78 (step 1, step 2) by using tert-butyl (6-bromopyridin-2-yl) carbamate (1.06 g, 3.89 mmol) obtained in Preparation Example 73 and ethyl 2-methyl-2-(3-(4,4,5,5-tetramethyl-1,3,2-dioxaborolan-2-yl)phenoxy) propanoate (1.30 g, 3.89 mmol) synthesized in step 2. (2 step yield 53%)

$^1$H-NMR (400 MHz, CHLOROFORM-D) δ 7.57 (d, J=7.8 Hz, 1H), 7.53-7.40 (2H), 7.29 (t, J=7.8 Hz, 1H), 7.04 (d, J=7.3 Hz, 1H), 6.92-6.77 (m, 1H), 6.45 (d, J=8.2 Hz, 1H), 4.45 (s, 2H), 4.25 (q, J=7.2 Hz, 2H), 1.62 (s, 6H), 1.25 (t, J=7.1 Hz, 3H)

Preparation Example 89: tert-butyl 3-(3-(6-aminopyridin-2-yl)-4-fluorophenyl)-2,2-dimethylpropanoate

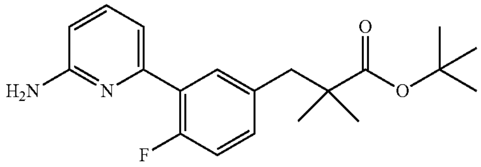 [SMILES: CC(C)(C)OC(=O)C(C)(C)Cc1ccc(F)c(-c2cccc(N)n2)c1]

Step 1: tert-butyl 3-(3-bromo-4-fluorophenyl)-2,2-dimethylpropanoate

The title compound was synthesized in a similar manner to Step 1 of Preparation Example 58 by using 2-bromo-4-(bromomethyl)-1-fluorobenzene (5 g, 18.66 mmol) and tert-butyl isobutyrate (3.73 ml, 22.39 mmol). (Yield 79%)

$^1$H-NMR (400 MHz, CHLOROFORM-D) δ 7.35 (dd, J=6.6, 2.1 Hz, 1H), 7.12-7.02 (1H), 6.98 (t, J=8.5 Hz, 1H), 2.75 (s, 2H), 1.47-1.34 (9H), 1.11 (s, 6H)

Step 2: tert-butyl 3-(4-fluoro-3-(4,4,5,5-tetramethyl-1,3,2-dioxaborolan-2-yl)phenyl)-2,2-dimethylpropanoate The title compound was synthesized in a similar manner to Step 2 of Preparation Example 58 by using tert-butyl 3-(3-bromo-4-fluorophenyl)-2,2-dimethylpropanoate (4.86 g, 14.67 mmol) synthesized in Step 1. (Yield 58%)

$^1$H-NMR (400 MHz, CHLOROFORM-D) δ 57.52 (q, J=2.7 Hz, 1H), 7.22-7.10 (m, 1H), 6.90 (t, J=8.7 Hz, 1H), 2.78 (s, 2H), 1.42 (d, J=6.4 Hz, 10H), 1.31 (d, J=15.1 Hz, 13H), 1.11 (d, J=4.1 Hz, 6H)

Step 3: tert-butyl 3-(3-(6-aminopyridin-2-yl)-4-fluorophenyl)-2,2-dimethylpropanoate The title compound was synthesized in a similar manner to Step 2 of Preparation Example 52 by using tert-butyl 3-(4-fluoro-3-(4,4,5,5-tetramethyl-1,3,2-dioxaborolan-2-yl)phenyl)-2,2-dimethylpropanoate (500 mg, 1.32 mmol) synthesized in Step 2 and 6-chloropyridin-2-amine (170 mg, 1.32 mmol). (Yield 76%)

1H-NMR (400 MHz, CHLOROFORM-D) δ 7.78 (d, J=7.3 Hz, 1H), 7.74-7.60 (m, 1H), 7.07 (dd, J=11.2, 8.5 Hz, 2H), 6.71 (d, J=8.7 Hz, 1H), 2.98-2.89 (2H), 1.42 (s, 11H), 1.15 (s, 6H)

Preparation Example 90: Methyl 3-(3-(4-aminopyrimidin-2-yl)phenyl)-2,2-dimethylpropanoate

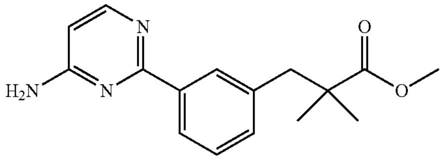 [SMILES: COC(=O)C(C)(C)Cc1cccc(-c2nccc(N)n2)c1]

Step 1: tert-butyl (2-chloropyrimidin-4-yl)carbamate

2-Chloropyrimidin-4-amine (15.0 g, 116 mmol) and di-tert-butyl dicarbonate (31.9 ml, 139 mmol) were dissolved in 257 ml of anhydrous DCM, and then 4-dimethylaminopyridine (2.83 g, 23.2 mmol) was added and stirred at room temperature overnight. After removing the organic solvent, it was purified by silica gel column (DCM) to obtain the desired product. (Yield 5%)

$^1$H-NMR (CHLOROFORM-D) δ 8.42 (d, J=5.8 Hz, 1H), 7.86 (d, J=5.8 Hz, 1H), 7.35 (s, 1H), 1.53 (s, 9H)

Step 2: Methyl 3-(3-(4-aminopyrimidin-2-yl)phenyl)-2,2-dimethylpropanoate

The desired product was obtained in a similar manner to Step 2 of Preparation Example 52 and Step 4 of Preparation Example 19 by using tert-butyl (2-chloropyrimidin-4-yl) carbamate (361 mg, 1.57 mmol) synthesized in step 1 and methyl 2,2-dimethyl-3-(3-(4,4,5,5-tetramethyl-1,3,2-dioxaborolan-2-yl)phenyl)propanoate (500 mg, 1.57 mmol) obtained in step 2 of Preparation Example 58. (2 step yield 14%)

$^1$H-NMR (400 MHz, CHLOROFORM-D) δ 8.34 (d, J=4.1 Hz, 1H), 8.26 (d, J=6.9 Hz, 1H), 8.16 (s, 1H), 7.44-7.35 (m, 1H), 7.20 (s, 1H), 6.46 (s, 1H), 5.30 (s, 2H), 3.68 (s, 3H), 2.96 (s, 2H), 1.22 (s, 6H)

Preparation Example 91: tert-butyl 3-(3-(6-amino-3-methylpyridin-2-yl)phenyl)-2,2-dimethylpropanoate

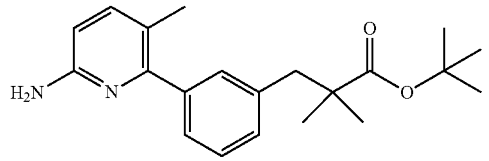 [SMILES: Cc1ccc(N)nc1-c1cccc(CC(C)(C)C(=O)OC(C)(C)C)c1]

Step 1: tert-butyl 3-(3-(6-chloro-3-methylpyridin-2-yl)phenyl)-2,2-dimethylpropanoate The title compound was synthesized in the same manner as in Step 2 of Preparation Example 52 by using tert-butyl 2,2-dimethyl-3-(3-(4,4,5,5-tetramethyl-1,3,2-dioxaborolan-2-yl)phenyl)propanoate (289 mg, 0.80 mmol) obtained in step 2 of Preparation Example 79 and 2,6-dichloro-3-methylpyridine (260 mg, 1.61 mmol). (Yield 16%)

$^1$H-NMR (400 MHz, CHLOROFORM-D) δ 7.51 (d, J=8.2 Hz, 1H), 7.42-7.26 (m, 3H), 7.18 (dd, J=7.5, 2.5 Hz, 2H), 2.87 (s, 2H), 2.30 (s, 3H), 1.40 (s, 9H), 1.12 (d, J=5.5 Hz, 6H)

Step 2: tert-butyl 3-(3-(6-amino-3-methylpyridin-2-yl)phenyl)-2,2-dimethylpropanoate The title compound was synthesized in a similar manner to Preparation Example 19 (Step 3, Step 4) by using tert-butyl 3-(3-(6-chloro-3-methylpyridin-2-yl)phenyl)-2,2-dimethylpropanoate (47 mg, 0.13 mmol) obtained in step 1. (2 step yield 54%)

$^1$H-NMR (CHLOROFORM-D) δ 7.39 (dd, J=8.2, 2.7 Hz, 1H), 7.36-7.29 (m, 2H), 7.19 (d, J=6.1 Hz, 1H), 6.56-6.40 (m, 1H), 4.70 (s, 2H), 2.90 (s, 2H), 2.20 (s, 3H), 1.46 (d, J=13.4 Hz, 9H), 1.24-1.08 (m, 6H)

Preparation Example 92: Ethyl 2-(3-(6-aminopyridin-2-yl)-4-fluorophenoxy)-2-methylpropanoate

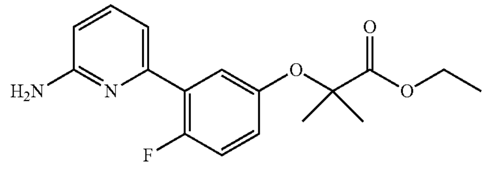 [SMILES: CCOC(=O)C(C)(C)Oc1ccc(F)c(-c2cccc(N)n2)c1]

Step 1: Ethyl 2-(3-bromo-4-fluorophenoxy)-2-methylpropanoate

3-Bromo-4-fluorophenol (2 g, 10.47 mmol) was dissolved in DMF, ethyl 2-bromo-2-methylpropanoate (2.25 g, 11.52 mmol) and cesium carbonate (6.82 g, 20.94 mmol) was added, and stirred at room temperature for 12 hours. After completion of the reaction, water was added, extracted with ethyl acetate, and washed with brine to remove excess DMF. After removing water with magnesium sulfate and distilling under reduced pressure, the mixture was purified by column chromatography (hexane:ethyl acetate) to obtain the desired compound. (Yield 58%)

$^1$H-NMR (400 MHz, CHLOROFORM-D) δ 7.09 (q, J=2.9 Hz, 1H), 6.98 (t, J=8.5 Hz, 1H), 6.86-6.70 (m, 1H), 4.23 (q, J=7.0 Hz, 2H), 1.55 (s, 6H), 1.26 (t, J=7.1 Hz, 3H)

Step 2: Ethyl 2-(4-fluoro-3-(4,4,5,5-tetramethyl-1,3,2-dioxaborolan-2-yl)phenoxy)-2-methylpropanoate The title compound was synthesized in a similar manner to Step 1 of Preparation Example 52 by using ethyl 2-(3-bromo-4-fluorophenoxy)-2-methylpropanoate (1.86 g, 6.10 mmol) synthesized in Step 1. (Yield 91%)

$^1$H-NMR (400 MHz, CHLOROFORM-D) δ 7.22 (dd, J=4.6, 3.2 Hz, 1H), 7.01-6.80 (2H), 4.23 (q, J=7.2 Hz, 2H), 1.54 (s, 6H), 1.32 (s, 12H), 1.24 (d, J=7.8 Hz, 7H)

Step 3: Ethyl 2-(3-(6-aminopyridin-2-yl)-4-fluorophenoxy)-2-methylpropanoate

The title compound was synthesized in a similar manner to Step 2 of Preparation Example 52 by using ethyl 2-(4-fluoro-3-(4,4,5,5-tetramethyl-1,3,2-dioxaborolan-2-yl)phenoxy)-2-methylpropanoate (400 mg, 1.136 mmol) synthesized in step 2. (Yield 59%)

$^1$H-NMR (400 MHz, CHLOROFORM-D) δ 7.57-7.39 (m, 2H), 7.10 (dd, J=7.5, 2.1 Hz, 1H), 6.98 (dd, J=10.5, 8.7 Hz, 1H), 6.90-6.75 (1H), 6.49 (d, J=8.2 Hz, 1H), 4.73 (s, 2H), 4.24 (q, J=7.2 Hz, 2H), 1.65-1.43 (6H), 1.26 (t, J=7.1 Hz, 3H)

Preparation Example 93: Methyl 3-(3-(2-amino-6-(trifluoromethyl)pyrimidin-4-yl)phenyl)-2,2-dimethylpropanoate

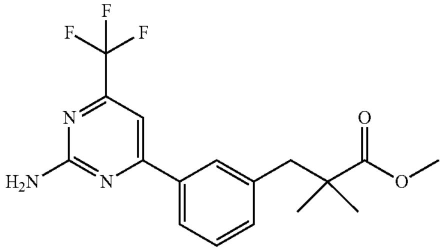 [SMILES: COC(=O)C(C)(C)Cc1cccc(-c2cc(C(F)(F)F)nc(N)n2)c1]

Step 1: Methyl 3-(3-(2-chloro-6-(trifluoromethyl)pyrimidin-4-yl)phenyl)-2,2-dimethylpropanoate The title compound was synthesized in the same manner as in Step 2 of Preparation Example 52 by using methyl 2,2-dimethyl-3-(3-(4,4,5,5-tetramethyl-1,3,2-dioxaborolan-2-yl)phenyl)propanoate (1 g, 3.14 mmol) obtained in step 2 of Preparation Example 58 and 2,4-dichloro-6-(trifluoromethyl)pyrimidine (682 mg, 3.14 mmol). (Yield 63%)

$^1$H-NMR (400 MHz, CHLOROFORM-D) δ 7.95 (dd, J=7.8, 1.8 Hz, 1H), 7.93-7.83 (2H), 7.44 (t, J=7.5 Hz, 1H), 7.34 (d, J=7.8 Hz, 1H), 3.77-3.58 (m, 3H), 2.96 (s, 2H), 1.21 (d, J=5.9 Hz, 6H)

Step 2: Methyl 3-(3-(2-amino-6-(trifluoromethyl)pyrimidin-4-yl)phenyl)-2,2-dimethylpropanoate The title compound was synthesized in a similar manner to Preparation Example 19 (Step 3, Step 4) by using methyl 3-(3-(2-chloro-6-(trifluoromethyl)pyrimidin-4-yl)phenyl)-2,2-dimethylpropanoate (735 mg, 1.97 mmol) obtained in step 1. (2 step yield 29%)

$^1$H-NMR (400 MHz, CHLOROFORM-D) δ 7.86 (d, J=7.8 Hz, 1H), 7.78 (d, J=6.9 Hz, 1H), 7.47-7.33 (m, 1H), 7.28 (s, 1H), 7.27 (s, 1H), 5.49 (s, 2H), 3.65 (d, J=6.4 Hz, 3H), 2.94 (s, 2H), 1.23 (q, J=7.8 Hz, 6H)

Preparation Example 94: tert-butyl 3-(3'-amino-[1,1'-biphenyl]-4-yl)-2,2-dimethylpropanoate

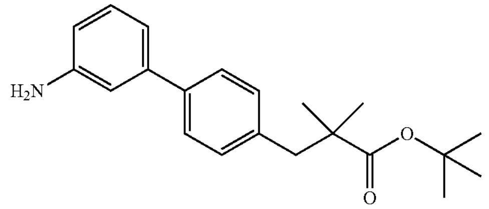 [SMILES: CC(C)(C)OC(=O)C(C)(C)Cc1ccc(-c2cccc(N)c2)cc1]

Step 1: tert-butyl 2,2-dimethyl-3-(4-(4,4,5,5-tetramethyl-1,3,2-dioxaborolan-2-yl)phenyl)propanoate The desired product was obtained in a similar manner to Step 1 of Preparation Example 71 by using 1-bromo-4-(bromomethyl)benzene (2 g, 8 mmol). (2 step yield 77%)

$^1$H-NMR (CHLOROFORM-D) δ 7.70 (d, J=7.6 Hz, 2H), 7.16 (d, J=7.9 Hz, 2H), 2.84 (s, 2H), 1.43 (s, 9H), 1.34 (s, 12H), 1.11 (s, 6H)

Step 2: tert-butyl 2,2-dimethyl-3-(3'-nitro-[1,1'-biphenyl]-4-yl)propanoate

Tert-butyl 2,2-dimethyl-3-(4-(4,4,5,5-tetramethyl-1,3,2-dioxaborolan-2-yl)phenyl)propanoate (0.15 g, 0.416 mmol) obtained in step 1, 1-bromo-3-nitrobenzene (0.084 g, 0.416 mmol), 1,1'-bis(diphenylphosphino)ferrocene dichloropalladium(II)dichloromethane complex (0.007 g, 8.33 μmol) and 0.555 ml of 2N sodium carbonate were dissolved in 1.4 ml of ethylene glycol dimethyl ether and stirred at 90° C. for 15 hours. After confirming that the reaction was completed by TLC, the organic solvent was removed under reduced pressure. After extraction with ethyl acetate (60 ml), it was washed with brine (20 ml) and dried over magnesium sulfate, the organic solvent was concentrated under reduced pressure. The desired product was obtained by purification with silica gel column (ethyl acetate:hexane=1:9). (Yield 88%)

$^1$H-NMR (400 MHz, CHLOROFORM-D) δ 8.43 (d, J=1.8 Hz, 1H), 8.21-8.13 (m, 1H), 7.90 (t, J=7.3 Hz, 1H), 7.64-7.55 (m, 1H), 7.55-7.48 (m, 2H), 7.32-7.26 (m, 2H), 2.90 (d, J=15.1 Hz, 2H), 1.45 (s, 9H), 1.16 (s, 6H)

Step 3: tert-butyl 3-(3'-amino-[1,1'-biphenyl]-4-yl)-2,2-dimethylpropanoate

Tert-butyl 2,2-dimethyl-3-(3'-nitro-[1,1'-biphenyl]-4-yl)propanoate (0.255 g, 0.717 mmol) obtained in step 2 was dissolved in 2 ml of methanol, Pd/C (3.82 mg, 0.036 mmol) was added, and then a reduction reaction was performed using a hydrogen balloon. After confirming that the reaction was completed, it was filtered with a Celite filter, and the organic solvent was removed under reduced pressure to obtain the desired product. (Yield 73%)

$^1$H-NMR (400 MHz, CHLOROFORM-D) δ 7.53-7.44 (m, 2H), 7.28-7.17 (m, 3H), 7.05-6.96 (1H), 6.94-6.87 (m, 1H), 6.72-6.62 (m, 1H), 3.73 (s, 2H), 2.96-2.74 (m, 2H), 1.54-1.38 (9H), 1.26-1.12 (m, 6H)

Preparation Example 95: Ethyl 2-(3-(4-aminopyrimidin-2-yl)phenoxy)-2-dimethylpropanoate

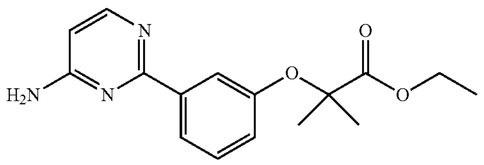 [SMILES: CCOC(=O)C(C)(C)Oc1cccc(-c2nccc(N)n2)c1]

The desired product was obtained in a similar manner to Step 2 of Preparation Example 52 and Step 4 of Preparation Example 19 by using tert-butyl (2-chloropyrimidin-4-yl) carbamate (344 mg, 1.50 mmol) obtained from Step 1 of Preparation Example 90 and ethyl 2-methyl-2-(3-(4,4,5,5-tetramethyl-1,3,2-dioxaborolan-2-yl)phenoxy)propanoate (500 mg, 1.50 mmol) obtained from Step 2 of Preparation Example 88. (2 step yield 22%)

$^1$H-NMR (CHLOROFORM-D) δ 8.33 (d, J=5.8 Hz, 1H), 8.01 (d, J=7.9 Hz, 1H), 7.92 (d, J=1.8 Hz, 1H), 7.33 (t, J=7.9 Hz, 1H), 6.96 (dd, J=8.1, 2.6 Hz, 1H), 6.34 (d, J=5.8 Hz, 1H), 4.90 (s, 2H), 4.27 (q, J=7.1 Hz, 2H), 1.64 (s, 6H), 1.27 (t, J=7.0 Hz, 3H)

Preparation Example 96: Methyl 3-(4-(4-aminopyrimidin-2-yl)phenyl)-2,2-dimethylpropanoate

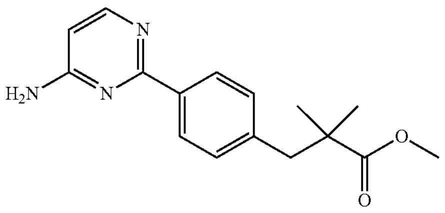 [SMILES: COC(=O)C(C)(C)Cc1ccc(-c2nccc(N)n2)cc1]

Step 1: Methyl 2,2-dimethyl-3-(4-(4,4,5,5-tetramethyl-1,3,2-dioxaborolan-2-yl)phenyl)propanoate The desired product was obtained in a similar manner to Preparation Example 58 (Step 1, Step 2) by using 1-bromo-4-(bromomethyl)benzene (30.0 g, 120 mmol). (2 step yield 75%)

$^1$H-NMR (400 MHz, CHLOROFORM-D) δ 7.70 (d, J=8.2 Hz, 2H), 7.10 (d, J=7.8 Hz, 2H), 3.64 (s, 3H), 2.86 (s, 2H), 1.34 (s, 12H), 1.17 (s, 6H)

Step 2: Methyl 3-(4-(4-aminopyrimidin-2-yl)phenyl)-2,2-dimethylpropanoate

The desired product was obtained in a similar manner to Step 2 of Preparation Example 52 and Step 4 of Preparation Example 19 by using tert-butyl (2-chloropyrimidin-4-yl) carbamate (578 mg, 2.51 mmol) obtained from Step 1 of Preparation Example 90 and methyl 2,2-dimethyl-3-(4-(4,4,5,5-tetramethyl-1,3,2-dioxaborolan-2-yl)phenyl)propanoate (800 mg, 2.51 mmol) synthesized in Step 1. (2 step yield 68%)

$^1$H-NMR (400 MHz, CHLOROFORM-D) δ 8.33 (d, J=5.9 Hz, 1H), 8.25 (d, J=8.2 Hz, 2H), 7.20 (d, J=8.2 Hz, 2H), 6.37 (d, J=5.9 Hz, 1H), 5.12 (s, 2H), 3.66 (s, 3H), 2.91 (s, 2H), 1.20 (s, 6H)

Preparation Example 97: Ethyl 2-(4-(6-aminopyridin-2-yl)phenoxy)-2-methylpropanoate

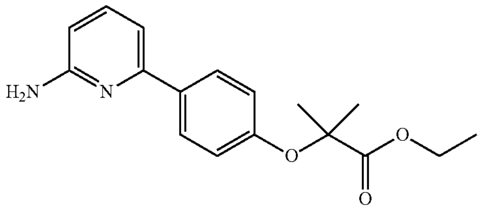 [SMILES: CCOC(=O)C(C)(C)Oc1ccc(-c2cccc(N)n2)cc1]

The desired product was obtained in a similar manner to Preparation Example 88 by using 4-bromophenol (2.00 g, 11.6 mmol). (4 step yield 24%)

$^1$H-NMR (400 MHz, CHLOROFORM-D) δ 7.82 (dt, J=9.6, 2.5 Hz, 2H), 7.55-7.38 (m, 1H), 7.10-6.96 (m, 1H), 6.89 (dt, J=9.5, 2.5 Hz, 2H), 6.49-6.33 (m, 1H), 4.44 (s, 2H), 4.24 (q, J=7.0 Hz, 2H), 1.62 (s, 6H), 1.25 (t, J=7.3 Hz, 3H)

Preparation Example 98: Ethyl 2-((4-(6-aminopyridin-2-yl)phenyl)amino)-2-methylpropanoate

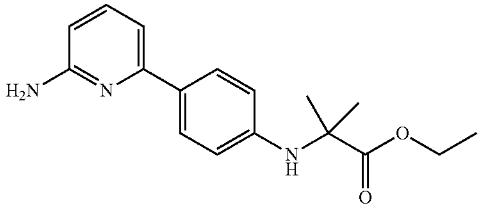 [SMILES: CCOC(=O)C(C)(C)Nc1ccc(-c2cccc(N)n2)cc1]

Step 1: Ethyl 2-((4-bromophenyl)amino)-2-methylpropanoate

4-Bromoaniline (3.00 g, 17.44 mmol) was dissolved in DMF, ethyl 2-bromo-2-methylpropanoate (3.40 g, 17.44 mmol) and potassium carbonate (3.62 g, 26.2 mmol) were added and stirred at 100° C. for 6 hours. After completion of the reaction, it was cooled to room temperature, and water was added, extracted with ethyl acetate, washed with brine, and removed excess DMF. After removing water with magnesium sulfate and distilling under reduced pressure, the mixture was purified by column chromatography (hexane: ethyl acetate) to obtain the desired compound. (Yield 22%)

$^1$H-NMR (CHLOROFORM-D) δ 7.25 (d, J=8.5 Hz, 2H), 6.50 (d, J=8.5 Hz, 2H), 4.19 (q, J=7.0 Hz, 2H), 1.59 (d, J=22.3 Hz, 7H), 1.22 (t, J=7.2 Hz, 3H)

Step 2: Ethyl 2-methyl-2-((4-(4,4,5,5-tetramethyl-1,3,2-dioxaborolan-2-yl)phenyl)amino)propanoate The title compound was synthesized in a similar manner to Step 1 of Preparation Example 52 by using ethyl 2-((4- bromophenyl)amino)-2-methylpropanoate (1.82 g, 6.36 mmol) synthesized in Step 1. (Yield 65%)

$^1$H-NMR (400 MHz, CHLOROFORM-D) δ 7.64-7.49 (2H), 6.58-6.38 (2H), 4.44-4.20 (1H), 4.20-4.11 (2H), 1.32-1.27 (12H), 1.19-1.07 (3H)

Step 3: Ethyl 2-((4-(6-aminopyridin-2-yl)phenyl) amino)-2-methylpropanoate

The title compound was synthesized in a similar manner to Step 2 of Preparation Example 52 by using ethyl 2-methyl-2-((4-(4,4,5,5-tetramethyl-1,3,2-dioxaborolan-2-yl)phenyl)amino)propanoate (500 mg, 1.50 mmol) synthesized in step 2 and 6-chloropyridin-2-amine (183 mg, 1.422 mmol). (Yield 34%)

$^1$H-NMR (CHLOROFORM-D) δ 7.83 (d, J=8.5 Hz, 2H), 7.54 (t, J=7.9 Hz, 1H), 6.99 (d, J=7.6 Hz, 1H), 6.65 (d, J=8.5 Hz, 2H), 6.45 (d, J=8.2 Hz, 1H), 4.63-4.33 (1H), 4.20 (q, J=7.0 Hz, 2H), 1.61 (s, 6H), 1.22 (t, J=7.2 Hz, 3H)

Preparation Example 99: Ethyl 2-((4-(2-aminopyrimidin-4-yl)phenyl)amino)-2-methylpropanoate

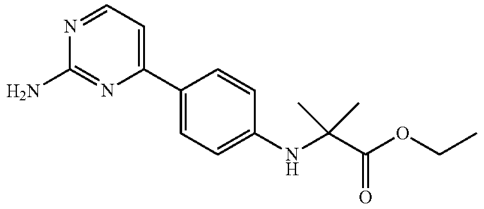 [SMILES: CCOC(=O)C(C)(C)Nc1ccc(-c2ccnc(N)n2)cc1]

Step 1: Ethyl 2-((4-(2-chloropyrimidin-4-yl)phenyl) amino)-2-methylpropanoate

The title compound was synthesized in a similar manner to Step 2 of Preparation Example 52 by using ethyl 2-methyl-2-((4-(4,4,5,5-tetramethyl-1,3,2-dioxaborolan-2-yl)phenyl)amino)propanoate (400 mg, 1.20 mmol) obtained in step 2 of Preparation Example 98 and 2,4-dichloropyrimidine (179 mg, 1.20 mmol). (Yield 59%)

$^1$H-NMR (400 MHz, METHANOL-D4) δ 8.47-8.38 (1H), 8.00-7.88 (2H), 7.74-7.66 (1H), 6.64-6.49 (2H), 4.21-4.02 (2H), 1.58-1.48 (6H), 1.22-1.07 (3H)

Step 2: Ethyl 2-((4-(2-aminopyrimidin-4-yl)phenyl) amino)-2-methylpropanoate

The title compound was synthesized in a similar manner to Preparation Example 19 (Step 3, Step 4) by using ethyl 2-((4-(2-chloropyrimidin-4-yl)phenyl)amino)-2-methylpropanoate (83 mg, 0.21 mmol) synthesized in Step 1. (2 step yield 27%)

m/z $(M+H)^+$ calculated for $C_{16}H_{21}N_4O_2$: 301. found 301.

Preparation Example 100: Ethyl (4-(6-aminopyridin-2-yl)phenyl)glycinate

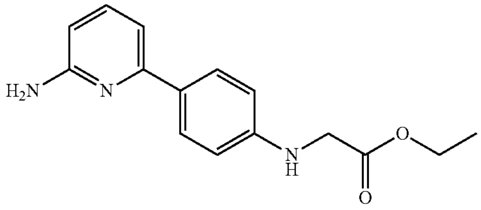 [SMILES: CCOC(=O)CNc1ccc(-c2cccc(N)n2)cc1]

Step 1: Ethyl (4-bromophenyl)glycinate

The title compound was synthesized in a similar manner to Step 1 of Preparation Example 98 by using 4-bromoaniline (3.00 g, 17.44 mmol). (Yield 44%)

$^1$H-NMR (CHLOROFORM-D) δ 7.32-7.23 (m, 2H), 6.59-6.45 (m, 2H), 4.34-4.19 (m, 2H), 4.12 (s, 1H), 3.89 (s, 2H), 1.39-1.23 (m, 3H)

Step 2: Ethyl (4-(4,4,5,5-tetramethyl-1,3,2-dioxaborolan-2-yl)phenyl)glycinate

The title compound was synthesized in a similar manner to Step 1 of Preparation Example 52 by using ethyl (4-bromophenyl)glycinate (1.99 g, 7.71 mmol) synthesized in Step 1. (Yield 44%)

$^1$H-NMR (400 MHz, CHLOROFORM-D) δ 7.73-7.58 (m, 2H), 6.63 (d, J=8.2 Hz, 2H), 4.24 (t, J=7.1 Hz, 2H), 4.22-4.04 (m, 1H), 3.93 (d, J=1.4 Hz, 2H), 1.31 (s, 12H), 1.28 (t, J=7.1 Hz, 3H)

Step 3: Ethyl (4-(6-aminopyridin-2-yl)phenyl)glycinate

The title compound was synthesized in a similar manner to Step 2 of Preparation Example 52 by using ethyl (4-(4,4,5,5-tetramethyl-1,3,2-dioxaborolan-2-yl)phenyl)glycinate (700 mg, 2.30 mmol) synthesized in step 2 and 6-chloropyridin-2-amine (295 mg, 2.30 mmol). (Yield 32%)

$^1$H-NMR (400 MHz, METHANOL-D4) δ 7.63 (dt, J=9.3, 2.3 Hz, 2H), 7.42 (t, J=7.8 Hz, 1H), 6.87 (d, J=6.9 Hz, 1H), 6.63 (dt, J=9.3, 2.3 Hz, 2H), 6.47-6.32 (1H), 4.18 (q, J=7.2 Hz, 2H), 3.93 (s, 2H), 1.24 (t, J=7.1 Hz, 3H)

Preparation Example 101: Methyl 5-(2-aminopyrimidin-4-yl)bicyclo[2.2.1]heptane-2-carboxylate

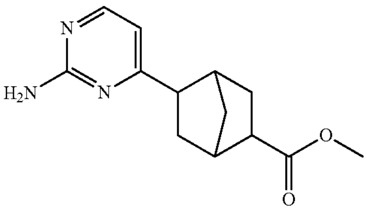 [SMILES: COC(=O)C1CC2CC1CC2c1ccnc(N)n1]

Step 1: Methyl bicyclo[2.2.1]hept-5-ene-2-carboxylate

The desired product was obtained in a similar manner to Step 1 of Preparation Example 50 by using bicyclo[2.2.1]hept-5-ene-2-carboxylic acid (1 g, 7.24 mmol). (Yield 100%)

$^1$H-NMR (400 MHz, CHLOROFORM-D) δ 6.18 (q, J=3.0 Hz, 1H), 5.91 (q, J=2.9 Hz, 1H), 3.61 (s, 3H), 3.18 (d, J=1.4 Hz, 1H), 2.98-2.76 (m, 2H), 1.97-1.81 (m, 1H), 1.57 (t, J=1.6 Hz, 1H), 1.45-1.37 (2H)

Step 2: Methyl 5-(2-chloropyrimidin-4-yl)bicyclo[2.2.1]heptane-2-carboxylate 2,4-dichloropyrimidine (0.775 g, 5.20 mmol) was dissolved in THF (23.6 ml) and methyl bicyclo[2.2.1]hept-5-ene-2-carboxylate (0.720 g, 4.73 mmol) prepared in step 1 was added. Palladium(II) acetate (0.212 g, 0.946 mmol), triphenylphosphine (0.496 g, 1.892 mmol) and formic acid (0.907 ml, 23.65 mmol) were added to the reaction solution, and TEA (4.29 ml, 30.8 mmol) was added dropwise thereto. After stirring at 60° C. for 16 hours, the reaction was terminated with water, diluted with ethyl acetate, washed with brine, and the organic solvent was dried over magnesium sulfate. The desired product was obtained by purification with silica gel column. (Yield 24%)

$^1$H-NMR (400 MHz, CHLOROFORM-D) δ 8.42 (q, J=2.6 Hz, 1H), 7.08 (q, J=4.9 Hz, 1H), 3.77-3.62 (m, 3H), 3.01-2.80 (m, 2H), 2.80-2.66 (m, 1H), 2.52-2.39 (m, 1H), 2.10-1.85 (m, 1H), 1.85-1.67 (m, 4H), 1.41-1.31 (m, 1H)

Step 3: Methyl 5-(2-aminopyrimidin-4-yl)bicyclo[2.2.1]heptane-2-carboxylate

The desired product was obtained in a similar manner to Preparation Example 2 by using methyl 5-(2-chloropyrimidin-4-yl)bicyclo[2.2.1]heptane-2-carboxylate (0.428 g, 1.605 mmol) prepared in step 2. (2 step yield 13%)

$^1$H-NMR (500 MHz, CHLOROFORM-D) δ 8.48 (q, J=5.3 Hz, 1H), 7.49 (s, 1H), 6.81 (td, J=14.5, 5.2 Hz, 1H), 4.51 (s, 1H), 3.73 (d, J=11.3 Hz, 3H), 2.93-2.80 (m, 2H), 2.80-2.61 (m, 1H), 2.53-2.35 (m, 1H), 2.11-1.97 (m, 1H), 1.85-1.77 (m, 2H), 1.77-1.67 (m, 2H), 1.40-1.20 (m, 1H)

Preparation Example 102: Methyl 3-(3-(5-aminopyridin-2-yl)phenyl)-2,2-dimethylpropanoate

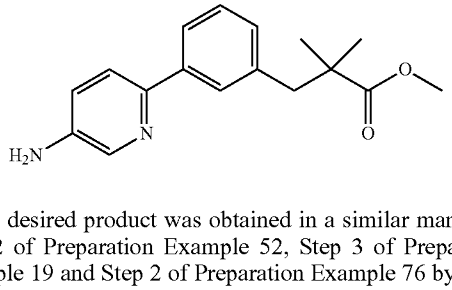

The desired product was obtained in a similar manner to Step 2 of Preparation Example 52, Step 3 of Preparation Example 19 and Step 2 of Preparation Example 76 by using 2,5-dibromopyridine (189 mg, 0.799 mmol) and tert-butyl 2,2-dimethyl-3-(3-(4,4,5,5-tetramethyl-1,3,2-dioxaborolan-2-yl)phenyl)propanoate (288 mg, 0.799 mmol) obtained in step 2 of Preparation Example 79. (3 step yield 20%).

$^1$H-NMR (400 MHz, CHLOROFORM-D) δ 8.17 (d, J=2.7 Hz, 1H), 7.74 (dt, J=7.8, 1.4 Hz, 1H), 7.65 (d, J=1.8 Hz, 1H), 7.51 (d, J=7.8 Hz, 1H), 7.31 (t, J=7.9 Hz, 1H), 7.14-6.97 (m, 2H), 3.72 (s, 2H), 3.66 (s, 3H), 2.99-2.85 (2H), 1.21 (s, 6H)

Preparation Example 103: Methyl 2-(4-((2-aminopyrimidin-4-yl)oxy)phenyl)acetate

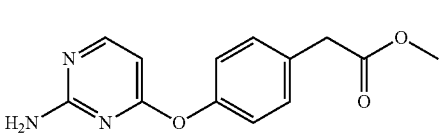 [SMILES: COC(=O)Cc1ccc(Oc2ccnc(N)n2)cc1]

The desired product was obtained in a similar manner to Step 1 of Preparation Example 104 and Preparation Example 19 (Step 3, Step 4) by using methyl 2-(4-hydroxyphenyl)acetate (1 g, 6.02 mmol). (3 step yield 57%)

$^1$H-NMR (400 MHz, CHLOROFORM-D) δ 8.11 (d, J=5.5 Hz, 1H), 7.30 (dd, J=8.9, 2.5 Hz, 2H), 7.08 (dt, J=9.1, 2.4 Hz, 2H), 6.18-6.02 (1H), 5.01 (s, 2H), 3.77-3.67 (3H), 3.62 (d, J=16.0 Hz, 2H)

Preparation Example 104: Methyl 4-((6-aminopyridin-2-yl)oxy)benzoate

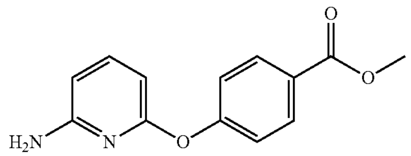 [SMILES: COC(=O)c1ccc(Oc2cccc(N)n2)cc1]

Step 1: Methyl 4-((6-chloropyridin-2-yl)oxy)benzoate

Methyl 4-hydroxybenzoate (1 g, 6.57 mmol), 2,6-dichloropyridine (0.875 g, 5.92 mmol) and cesium carbonate (2.57 g, 7.89 mmol) were dissolved in 27.4 ml of DMF and stirred at 120° C. for 4 hours. After confirming that the reaction was completed by TLC, the organic solvent was removed under reduced pressure. After extraction with ethyl acetate (2×20 ml), it was washed with brine (20 ml), and the organic solvent was dried over magnesium sulfate, and removed under reduced pressure. The desired product was obtained by purification with silica gel column (ethyl acetate: hexane=1:9). (Yield 75%)

$^1$H-NMR (400 MHz, CHLOROFORM-D) δ 8.14-7.94 (m, 2H), 7.74-7.52 (m, 1H), 7.20-7.10 (m, 2H), 7.10-6.96 (m, 1H), 6.89-6.76 (m, 1H), 3.95-3.80 (m, 3H)

Step 2: Methyl 4-((6-aminopyridin-2-yl)oxy)benzoate

The desired product was obtained in a similar manner to Preparation Example 19 (step 3, step 4) by using methyl 4-((6-chloropyridin-2-yl)oxy)benzoate (1.3 g, 4.93 mmol) synthesized in step 1. (2 step yield 76%)

$^1$H-NMR (400 MHz, CHLOROFORM-D) δ 8.15-7.89 (m, 2H), 7.52-7.37 (m, 1H), 7.12 (dt, J=9.3, 2.3 Hz, 2H), 6.33-6.10 (2H), 4.58-4.26 (m, 2H), 3.97-3.72 (m, 3H)

Preparation Example 105: Methyl 2-(4-((6-amino-pyridin-2-yl)oxy)phenyl)acetate

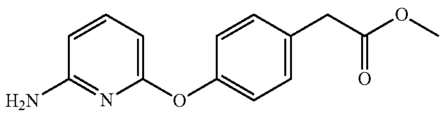

Step 1: Methyl 2-(4-((6-chloropyridin-2-yl)oxy) phenyl)acetate 2,6-Dichloropyridine (2.67 g, 18.1 mmol), methyl 2-(4-hydroxyphenyl)acetate (3.00 g, 18.1 mmol) and cesium carbonate (7.06 g, 21.7 mmol) were dissolved in 75.0 ml of DMF and stirred at 120° C. overnight. It was extracted with DCM and the organic solvent was dried over magnesium sulfate, and removed under reduced pressure. The desired product was obtained by purification with silica gel column (ethyl acetate:hexane). (Yield 50%)

$^1$H-NMR (400 MHz, CHLOROFORM-D) δ 7.61 (t, J=7.8 Hz, 1H), 7.39-7.28 (2H), 7.10 (td, J=5.7, 3.2 Hz, 2H), 7.03 (d, J=7.8 Hz, 1H), 6.75 (d, J=8.2 Hz, 1H), 3.72 (s, 3H), 3.64 (s, 2H)

Step 2: Methyl 2-(4-((6-aminopyridin-2-yl)oxy) phenyl)acetate

The desired product was obtained in a similar manner to Preparation Example 19 (Step 3, Step 4) by using methyl 2-(4-((6-chloropyridin-2-yl)oxy)phenyl)acetate (1.25 g, 4.50 mmol) synthesized in Step 1. (2 step yield 5%)

$^1$H-NMR (400 MHz, CHLOROFORM-D) δ 7.46 (t, J=8.0 Hz, 1H), 7.30 (d, J=8.7 Hz, 2H), 7.09 (dd, J=6.6, 2.1 Hz, 2H), 6.28-6.22 (1H), 6.02 (d, J=8.2 Hz, 1H), 3.72 (s, 3H), 3.66-3.60 (2H)

Preparation Example 106: Methyl 2-(4-((6-amino-pyridin-2-yl)oxy)phenyl)-2-methylpropanoate

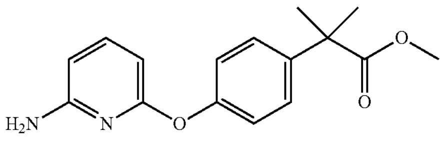 [SMILES: COC(=O)C(C)(C)c1ccc(Oc2cccc(N)n2)cc1]

The desired product was obtained in a similar manner to Preparation Example 19 (Step 2, Step 3, Step 4) by using methyl 2-(4-((6-chloropyridin-2-yl)oxy)phenyl)acetate (1.25 g, 4.50 mmol) obtained from Step 1 of Preparation 105. (3 step yield 41%)

$^1$H-NMR (CHLOROFORM-D) δ 7.40 (t, J=7.6 Hz, 1H), 7.37-7.29 (m, 2H), 7.09-7.00 (m, 2H), 6.23-6.14 (m, 1H), 6.06 (dd, J=7.9, 5.2 Hz, 1H), 3.67 (s, 3H), 1.59 (s, 6H)

Preparation Example 107: Methyl 3-((6-aminopyridin-2-yl)oxy)benzoate

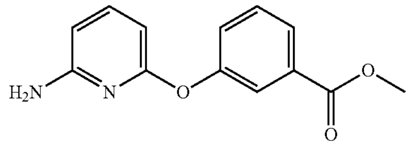 [SMILES: COC(=O)c1cccc(Oc2cccc(N)n2)c1]

Step 1: Methyl 3-((6-chloropyridin-2-yl)oxy)benzoate

The desired product was obtained in a similar manner to Step 1 of Preparation Example 104 by using methyl 3-hydroxybenzoate (0.2 g, 1.315 mmol). (Yield 75%)

$^1$H-NMR (400 MHz, CHLOROFORM-D) δ 7.99-7.82 (m, 1H), 7.82-7.72 (m, 1H), 7.72-7.54 (m, 1H), 7.54-7.39 (m, 1H), 7.39-7.28 (1H), 7.08-6.95 (1H), 6.87-6.65 (1H), 3.96-3.81 (3H)

Step 2: Methyl 3-((6-aminopyridin-2-yl)oxy)benzoate

The desired product was obtained in a similar manner to Preparation Example 19 (step 3, step 4) by using methyl 3-((6-chloropyridin-2-yl)oxy)benzoate (0.26 g, 0.986 mmol) synthesized in step 1. (2 step yield 54%)

$^1$H-NMR (400 MHz, CHLOROFORM-D) δ 7.84 (dd, J=7.8, 1.4 Hz, 1H), 7.76 (t, J=1.8 Hz, 1H), 7.42 (td, J=7.9, 3.4 Hz, 2H), 7.30 (dq, J=8.0, 1.2 Hz, 1H), 6.21 (d, J=8.2 Hz, 1H), 6.10 (d, J=7.8 Hz, 1H), 3.89 (d, J=3.2 Hz, 3H)

Preparation Example 108: Methyl 2-(3-((6-amino-pyridin-2-yl)oxy)phenyl)acetate

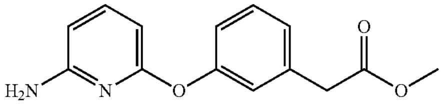 [SMILES: COC(=O)Cc1cccc(Oc2cccc(N)n2)c1]

Step 1: Methyl 2-(3-hydroxyphenyl)acetate

The desired product was obtained in a similar manner to Step 2 of Preparation Example 76 by using 2-(3-hydroxyphenyl)acetic acid (3.00 g, 19.7 mmol). (Yield 99%)

$^1$H-NMR (400 MHz, CHLOROFORM-D) δ 7.19 (t, J=7.8 Hz, 1H), 6.84 (d, J=7.3 Hz, 1H), 6.80-6.66 (m, 2H), 5.10-4.91 (m, 1H), 3.70 (s, 3H), 3.58 (s, 2H)

Step 2: Methyl 2-(3-((6-aminopyridin-2-yl)oxy) phenyl)acetate

The desired product was obtained in a similar manner to Preparation Example 105 by using 2,6-dichloropyridine (2.90 g, 19.6 mmol) and methyl 2-(3-hydroxyphenyl)acetate (3.26 g, 19.6 mmol) synthesized in step 1. (3 step yield 12%)

$^1$H-NMR (400 MHz, CHLOROFORM-D) δ 7.44 (t, J=8.0 Hz, 1H), 7.33 (t, J=7.8 Hz, 1H), 7.11 (d, J=7.8 Hz, 1H), 7.09-6.96 (m, 2H), 6.23 (d, J=8.2 Hz, 1H), 6.05 (d, J=7.8 Hz, 1H), 3.70 (s, 3H), 3.65-3.62 (2H)

Preparation Example 109: Methyl 2-(3-((6-amino-pyridin-2-yl)oxy)phenyl)-2-methylpropanoate

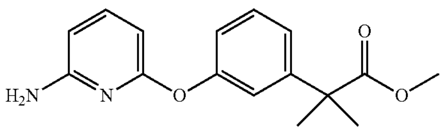 [SMILES: COC(=O)C(C)(C)c1cccc(Oc2cccc(N)n2)c1]

The desired product was obtained in a similar manner to Preparation Example 106 by using methyl 2-(3-hydroxyphenyl)acetate (1.45 g, 5.22 mmol) obtained from Step 1 of Preparation Example 108. (3 step yield 35%)

$^1$H-NMR (400 MHz, CHLOROFORM-D) δ 7.49-7.35 (m, 1H), 7.35-7.27 (m, 1H), 7.17-7.07 (m, 2H), 7.04-6.90 (m, 1H), 6.25-6.15 (m, 1H), 6.06 (d, J=7.8 Hz, 1H), 4.44 (s, 2H), 3.65 (s, 3H), 1.44-1.40 (6H)

Preparation Example 110: Methyl 4-(((6-aminopyridin-2-yl)oxy)methyl)benzoate

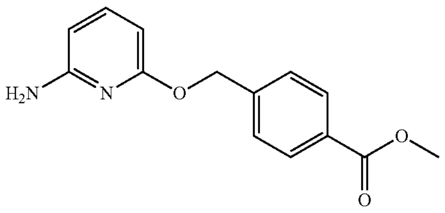 [SMILES: COC(=O)c1ccc(COc2cccc(N)n2)cc1]

Step 1: Methyl 4-(((6-chloropyridin-2-yl)oxy)methyl)benzoate

Methyl 4-(hydroxymethyl)benzoate (0.5 g, 3.01 mmol) and 2,6-dichloropyridine (0.445 g, 3.01 mmol), cesium carbonate (1.176 g, 3.61 mmol), 4,5-bis(diphenylphosphino)-9,9-dimethylxanthine (0.244 g, 0.421 mmol) and palladium(II)acetate (0.054 g, 0.241 mmol) were dissolved in 12 ml of toluene and stirred at 120° C. for 4 hours. After confirming that the reaction was completed by TLC, the organic solvent was removed under reduced pressure. After extraction with ethyl acetate (2×20 ml), it was washed with brine (20 ml), and the organic solvent was dried over magnesium sulfate, and removed under reduced pressure. The desired product was obtained by purification with silica gel column (ethyl acetate:hexane=1:9). (Yield 24%)

$^1$H-NMR (400 MHz, CHLOROFORM-D) δ 8.07-7.98 (m, 2H), 7.53 (q, J=7.8 Hz, 3H), 7.00-6.83 (m, 1H), 6.82-6.66 (m, 1H), 5.52-5.34 (m, 2H), 3.89 (d, J=16.0 Hz, 3H)

Step 2: Methyl 4-(((6-aminopyridin-2-yl)oxy)methyl)benzoate

The method was obtained in a similar manner to Preparation Example 19 (step 3, step 4) by using methyl 4-(((6-chloropyridin-2-yl)oxy)methyl)benzoate (0.2 g, 0.72 mmol) synthesized in step 1. (2 step yield 19%)

$^1$H-NMR (400 MHz, CHLOROFORM-D) δ 8.12-7.91 (m, 2H), 7.60-7.42 (m, 2H), 7.42-7.30 (m, 1H), 6.26-6.11 (m, 1H), 6.11-5.99 (m, 1H), 5.46-5.28 (m, 2H), 3.96-3.81 (m, 3H)

Preparation Example 111: Methyl 2-(3-(4-aminopyrimidin-2-yl)phenyl)-2-methylpropanoate

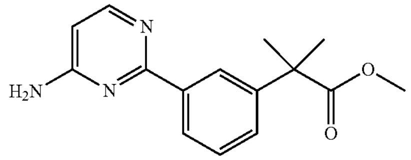 [SMILES: COC(=O)C(C)(C)c1cccc(-c2nccc(N)n2)c1]

The desired product was obtained in a similar manner to Preparation Example 53 (Step 1, Step 2) and Preparation Example 19 (Step 3, Step 4) by using methyl 2-(3-bromophenyl)-2-methylpropanoate (0.25 g, 0.972 mmol). (4 step yield 36%)

$^1$H-NMR (400 MHz, CHLOROFORM-D) δ 8.40-8.27 (m, 2H), 8.27-8.16 (m, 1H), 7.45-7.35 (m, 2H), 6.32 (d, J=5.9 Hz, 1H), 5.14 (s, 2H), 3.70-3.49 (m, 3H), 1.72-1.56 (m, 6H)

Preparation Example 112: Methyl 2-(4-(4-aminopyrimidin-2-yl)phenyl)-2-methylpropanoate

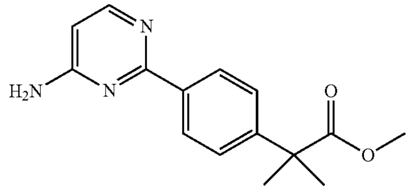 [SMILES: COC(=O)C(C)(C)c1ccc(-c2nccc(N)n2)cc1]

The desired product was obtained in a similar manner to Preparation Example 53 (Step 1, Step 2) and Preparation Example 19 (Step 3, Step 4) by using methyl 2-(4-bromophenyl)-2-methylpropanoate (5 g, 19.45 mmol). (4 step yield 36%)

$^1$H-NMR (400 MHz, CHLOROFORM-D) δ 8.37-8.28 (m, 1H), 8.26 (d, J=8.2 Hz, 2H), 7.46-7.34 (m, 2H), 6.35-6.23 (m, 1H), 4.99 (s, 2H), 3.77-3.46 (m, 3H), 1.67-1.52 (m, 6H)

Preparation Example 113: tert-butyl 3-(3-(6-amino-pyridin-2-yl)phenyl)-2,2-dimethylpropanoate

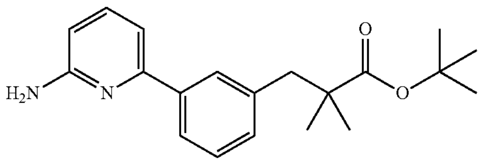 [SMILES: CC(C)(C)OC(=O)C(C)(C)Cc1cccc(-c2cccc(N)n2)c1]

The title compound was synthesized in a similar manner to Step 2 of Preparation Example 52 by using tert-butyl 2,2-dimethyl-3-(3-(4,4,5,5-tetramethyl-1,3,2-dioxaborolan-2-yl)phenyl)propanoate (500 mg, 1.39 mmol) obtained in step 2 of Preparation Example 79 and 6-chloropyridin-2-amine (178 mg, 1.39 mmol). (Yield 66%)

$^1$H-NMR (400 MHz, CHLOROFORM-D) δ 7.86 (t, J=7.3 Hz, 1H), 7.71 (s, 1H), 7.66 (d, J=16.0 Hz, 1H), 7.38-7.30 (m,

1H), 7.02 (d, J=7.8 Hz, 1H), 6.64 (d, J=7.3 Hz, 2H), 6.36 (d, J=8.2 Hz, 1H), 4.52 (s, 2H), 2.91 (s, 2H), 1.40 (d, J=6.9 Hz, 9H), 1.14 (t, J=4.6 Hz, 6H)

Preparation Example 114: tert-butyl 3-(3-(6-amino-3-fluoropyridin-2-yl)-4-fluorophenyl)-2,2-dimethylpropanoate

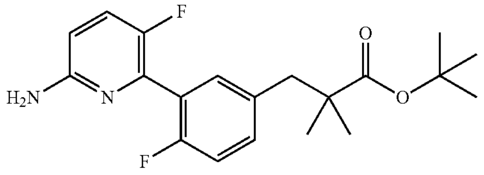 [SMILES: CC(C)(C)OC(=O)C(C)(C)Cc1ccc(F)c(-c2nc(N)ccc2F)c1]

Step 1: tert-butyl 3-(3-(6-chloro-3-fluoropyridin-2-yl)-4-fluorophenyl)-2,2-dimethylpropanoate The title compound was synthesized in a similar manner to Step 2 of Preparation Example 52 by using tert-butyl 3-(4-fluoro-3-(4,4,5,5-tetramethyl-1,3,2-dioxaborolan-2-yl)phenyl)-2,2-dimethylpropanoate (1.52 g, 4.01 mmol) obtained in Step 2 of Preparation Example 89 and 2,6-dichloro-3-fluoropyridine (799 mg, 4.81 mmol). (Yield 21%)

m/z $(M+H)^+$ calculated for $C_{20}H_{23}ClF_2NO_2$: 382. found 382.

Step 2: tert-butyl 3-(3-(6-amino-3-fluoropyridin-2-yl)-4-fluorophenyl)-2,2-dimethylpropanoate The title compound was synthesized in a similar manner to Preparation Example 19 (Step 3, Step 4) by using tert-butyl 3-(3-(6-chloro-3-fluoropyridin-2-yl)-4-fluorophenyl)-2,2-dimethylpropanoate (327 mg, 0.86 mmol) obtained in step 1. (2 step yield 17%)

$^1$H-NMR (400 MHz, CHLOROFORM-D) δ 7.66 (dd, J=7.5, 2.5 Hz, 1H), 7.34-7.15 (m, 1H), 7.15-7.04 (m, 2H), 7.04-6.90 (1H), 4.89-4.60 (2H), 2.84 (s, 2H), 1.40 (d, J=6.9 Hz, 9H), 1.17-1.03 (m, 6H)

Preparation Example 115: tert-butyl 3-(3-(6-amino-5-fluoropyridin-2-yl)-4-fluorophenyl)-2,2-dimethylpropanoate

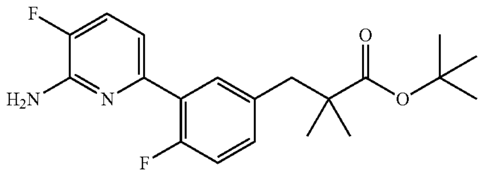 [SMILES: CC(C)(C)OC(=O)C(C)(C)Cc1ccc(F)c(-c2ccc(F)c(N)n2)c1]

Step 1: tert-butyl 3-(3-(6-chloro-5-fluoropyridin-2-yl)-4-fluorophenyl)-2,2-dimethylpropanoate The title compound was synthesized in a similar manner to Step 2 of Preparation Example 52 by using tert-butyl 3-(4-fluoro-3-(4,4,5,5-tetramethyl-1,3,2-dioxaborolan-2-yl)phenyl)-2,2-dimethylpropanoate (1.52 g, 4.01 mmol) obtained in Step of Preparation Example 89 and 2,6-dichloro-3-fluoropyridine (799 mg, 4.81 mmol). (Yield 49%)

$^1$H-NMR (400 MHz, CHLOROFORM-D) δ 7.46 (t, J=8.5 Hz, 1H), 7.38 (dd, J=7.1, 2.5 Hz, 1H), 7.32 (dd, J=8.7, 3.2 Hz, 1H), 7.22 (td, J=5.5, 2.7 Hz, 1H), 7.04 (dd, J=9.8, 8.5 Hz, 1H), 2.85 (s, 2H), 1.54 (s, 2H), 1.40 (d, J=7.8 Hz, 9H), 1.14 (s, 6H)

Step 2: tert-butyl 3-(3-(6-amino-5-fluoropyridin-2-yl)-4-fluorophenyl)-2,2-dimethylpropanoate The title compound was synthesized in a similar manner to Preparation Example 19 (Step 3, Step 4) by using tert-butyl 3-(3-(6-chloro-3-fluoropyridin-2-yl)-4-fluorophenyl)-2,2-dimethylpropanoate (756 mg, 1.98 mmol) obtained in step 1. (2 step yield 38%)

$^1$H-NMR (400 MHz, CHLOROFORM-D) δ 7.57-7.41 (m, 2H), 7.39 (dd, J=6.9, 1.8 Hz, 1H), 7.22-7.11 (m, 1H), 7.06 (t, J=9.1 Hz, 1H), 6.70 (dd, J=8.9, 3.0 Hz, 1H), 4.38 (d, J=22.9 Hz, 1H), 2.86 (s, 2H), 1.42-1.34 (9H), 1.16-1.06 (6H)

Preparation Example 116: Methyl 3-(4-(6-aminopyridin-2-yl)-1H-pyrazol-1-yl)-2,2-dimethylpropanoate

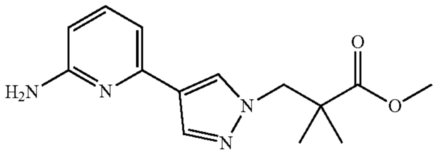 [SMILES: COC(=O)C(C)(C)Cn1cc(-c2cccc(N)n2)cn1]

By using methyl 3-hydroxy-2,2-dimethylpropanoate (1.08 g, 8.16 mmol) and 4-bromo-1H-pyrazole (1.00 g, 6.80 mmol), the method similar to Step 1 of Preparation Example 1, Step 2 of Preparation Example 58, and Preparation Example 19 (Step 3 and Step 4) was sequentially used to obtain the desired product. (4 step yield 0.3%)

$^1$H-NMR (400 MHz, CHLOROFORM-D): δ 7.84 (d, J=7.8 Hz, 2H), 7.43-7.30 (m, 1H), 6.84-6.75 (m, 1H), 6.30 (d, J=7.8 Hz, 1H), 4.52 (s, 2H), 4.27 (s, 2H), 3.70 (s, 3H), 1.21 (s, 6H)

Preparation Example 117: Ethyl 4-((2-aminopyrimidin-4-yl)oxy)cyclohexane-1-carboxylate

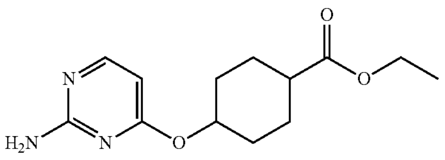 [SMILES: CCOC(=O)C1CCC(Oc2ccnc(N)n2)CC1]

Step 1: Ethyl 4-((2-chloropyrimidin-4-yl)oxy)cyclohexane-1-carboxylate 2,4-dichloropyrimidine (0.300 g, 2.014 mmol) was dissolved in DMF (10 ml), and then ethyl 4-hydroxycyclohexane-1-carboxylate (0.357 ml, 2.215 mmol) and cesium carbonate (1.640 g, 5.03 mmol) was added. After stirring at 80° C. for 3 hours, it was diluted with diethyl ether and washed with water. After drying the organic solvent with magnesium sulfate, it was purified by silica gel column to obtain the desired product. (Yield 29%)

$^1$H-NMR (400 MHz, CHLOROFORM-D) δ 8.29-8.17 (m, 1H), 6.64-6.46 (m, 1H), 5.46-4.97 (m, 1H), 4.18-4.00 (m, 2H), 2.46-2.21 (m, 1H), 2.14 (dt, J=9.0, 3.5 Hz, 1H), 2.08-1.89 (m, 2H), 1.89-1.79 (m, 1H), 1.79-1.70 (1H), 1.70-1.51 (m, 2H), 1.51-1.32 (m, 1H), 1.29-1.12 (m, 3H)

Step 2: Ethyl 4-((2-aminopyrimidin-4-yl)oxy)cyclohexane-1-carboxylate

The desired product was obtained in a similar manner to Preparation Example 2 by using ethyl 4-((2-chloropyrimidin-4-yl)oxy)cyclohexane-1-carboxylate (0.165 g, 0.579 mmol) prepared in step 1. (2 step yield 98%)

m/z $(M+H)^+$ calculated for $C_{13}H_{20}N_3O_3$: 266.32. found 266.1.

Preparation Example 118: (R)-2-chloro-6-(3-(2-ethoxy-4-fluorophenoxy)piperidin-1-yl)pyrazine

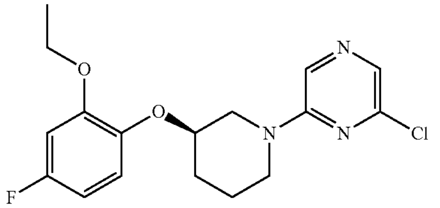 [SMILES: CCOc1cc(F)ccc1O[C@@H]1CCCN(c2cncc(Cl)n2)C1]

Step 1: 1-(Benzyloxy)-2-ethoxy-4-fluorobenzene 2-(Benzyloxy)-5-fluorophenol (1.00 g, 4.58 mmol), iodoethane (0.44 mL, 5.5 mmol) and cesium carbonate (2.24 g, 6.87 mmol) were added to 6.74 mL of acetone and stirred for 24 hours at room temperature. The reaction mixture was filtered and water was added, followed by extraction with ethyl acetate. After washing with water and brine, the organic layer was dried over magnesium sulfate and concentrated under reduced pressure. The desired product was obtained by purification with silica gel column. (Yield 82%)

$^1$H-NMR (400 MHz, CHLOROFORM-D) δ 7.43 (d, J=7.3 Hz, 2H), 7.40-7.33 (m, 2H), 7.33-7.27 (m, 1H), 6.82 (dd, J=9.1, 5.5 Hz, 1H), 6.64 (dd, J=10.1, 2.7 Hz, 1H), 6.51 (td, J=8.3, 3.0 Hz, 1H), 5.09 (s, 2H), 4.08 (q, J=7.0 Hz, 2H), 1.47 (t, J=7.1 Hz, 3H)

Step 2: 2-Ethoxy-4-fluorophenol 1-(benzyloxy)-2-ethoxy-4-fluorobenzene (921 mg, 3.74 mmol) obtained in step 1 was dissolved in methanol, and Pd/C (19.9 mg, 0.187 mmol) was added, followed by stirring under hydrogen conditions. After completion of the reaction, it was filtered through Celite to obtain the desired product. (Yield 92%)

$^1$H-NMR (400 MHz, CHLOROFORM-D) δ 6.83 (dd, J=8.7, 5.5 Hz, 1H), 6.68-6.48 (m, 2H), 5.45-5.31 (1H), 4.09 (q, J=7.0 Hz, 2H), 1.50-1.37 (3H)

Step 3: (R)-2-chloro-6-(3-(2-ethoxy-4-fluorophenoxy)piperidin-1-yl)pyrazine

The desired product was obtained in a similar manner to Preparation Example 1 (step 1, step 2, step 3) by using 2-ethoxy-4-fluorophenol (539 mg, 3.45 mmol) obtained in step 2. (3 step yield 37%)

$^1$H-NMR (400 MHz, CHLOROFORM-D) δ 7.95 (s, 1H), 7.74 (d, J=5.0 Hz, 1H), 6.92 (dd, J=8.7, 5.9 Hz, 1H), 6.70-6.47 (m, 2H), 4.28-4.14 (1H), 4.07-3.89 (3H), 3.72 (q, J=6.4 Hz, 1H), 3.67-3.46 (m, 2H), 2.15-1.85 (m, 3H), 1.59 (qd, J=8.5, 4.3 Hz, 1H), 1.41 (t, J=7.1 Hz, 3H)

Preparation Example 119: Methyl 2-(4-(4-aminopyrimidin-2-yl)phenoxy)-2-methylpropanoate

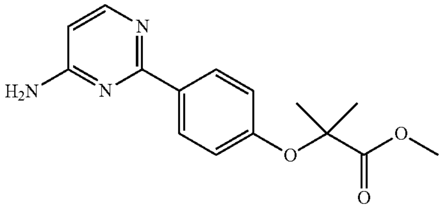

The desired product was obtained in a similar manner to Step 1 of Preparation Example 68, Preparation Example 53 (Step 1, Step 2), and Preparation Example 19 (Step 4) by using 4-bromophenol (1 g, 5.78 mmol). (4 step yield 6%)

$^1$H-NMR (400 MHz, CHLOROFORM-D) δ 8.31-8.00 (m, 3H), 6.96-6.60 (m, 2H), 6.33-6.07 (m, 1H), 5.26 (d, J=44.4 Hz, 2H), 4.22-4.09 (m, 2H), 1.63-1.50 (m, 6H), 1.29-1.07 (m, 3H)

Example 1: (R)-2-((6-(3-(2-ethoxyphenoxy)piperidin-1-yl)pyrazin-2-yl)amino)thiazole-5-carboxylic Acid

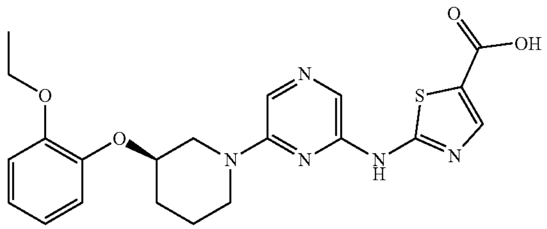 [SMILES: CCOc1ccccc1O[C@@H]1CCCN(c2cncc(Nc3ncc(C(=O)O)s3)n2)C1]

(R)-2-chloro-6-(3-(2-ethoxyphenoxy)piperidin-1-yl) pyrazine (20 mg, 0.06 mmol) prepared in Preparation Example 1 and methyl 2-aminothiazole-5-carboxylate (0.011 g, 0.072 mmol) were dissolved in 1,4-dioxane, cesium carbonate (49 mg, 0.150 mmol), tris(dibenzylideneacetone)dipalladium(0) (4.39 mg, 0.005 mmol) and 4,5-bis(diphenylphosphino)-9,9-dimethylxanthine (3.47 mg, 0.006 mmol) were added, and then reflux stirred for 4 hours. After the reaction was completed, the reaction mixture was cooled to room temperature, diluted with ethyl acetate, washed with an aqueous sodium hydrogen carbonate solution and brine, and then dried over magnesium sulfate, and the organic solvent was removed under reduced pressure. The desired product was obtained by purification with silica gel column (hexane:ethyl acetate=2:1). (Yield 81%)

The obtained ester compound (22 mg, 0.05 mmol) was dissolved in THF:water:methanol=1:1:1, and lithium hydroxide (2 mg, 0.074 mmol) was added, followed by stirring at 60° C. for 12 hours. After cooling the reaction to room temperature, the pH was adjusted to 4.5, followed by extraction with an organic solvent. The organic layer was dried over magnesium sulfate, removed under reduced pressure, and then synthesized by purification with silica gel column chromatography.

$^1$H NMR (300 MHz, Methanol-D): δ 11.5 (bs, 1H), 7.77 (s, 1H), 7.70 (s, 1H), 7.01 (d, 1H), 6.78-6.87 (m, 3H), 4.36 (bs, 1H), 3.75-3.91 (m, 8H), 1.82-1.97 (m, 4H), 1.55 (m, 1H), 1.18 (m, 5H)

Example 2: (R)—N-(6-(3-(2-ethoxyphenoxy)piperidin-1-yl)pyrazin-2-yl)-4,5-dimethylthiazol-2-amine

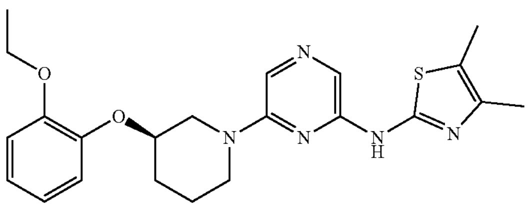 [SMILES: CCOc1ccccc1O[C@@H]1CCCN(c2cncc(Nc3nc(C)c(C)s3)n2)C1]

The title compound was obtained in a similar manner to Example 1 by using (R)-2-chloro-6-(3-(2-ethoxyphenoxy)piperidin-1-yl)pyrazine (0.10 g, 0.30 mmol) prepared in Preparation Example 1 and 2-amino-4,5-dimethylthiazole (0.038 g, 0.30 mmol). (Yield 63%)

$^1$H-NMR (400 MHz, CHLOROFORM-D): δ 8.80 (brs, 1H), 7.61 (s, 1H), 7.41 (s, 1H), 6.82-7.01 (m, 4H), 4.30-4.36 (m, 2H), 3.98-4.05 (m, 3H), 3.49 (m, 1H), 3.38 (m, 1H), 2.21 (s, 3H), 2.19 (s, 3H), 2.20 (m, 1H), 1.78 (m, 1H), 1.61-1.69 (m, 2H), 1.39 (t, 3H)

Example 3: (R)—N-(6-(3-(2-ethoxyphenoxy)piperidin-1-yl)pyrazin-2-yl)thiazol-2-amine

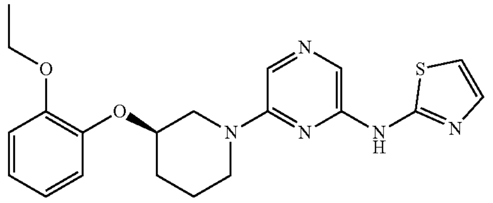 [SMILES: CCOc1ccccc1O[C@@H]1CCCN(c2cncc(Nc3nccs3)n2)C1]

The title compound was obtained in a similar manner to Example 1 by using (R)-2-chloro-6-(3-(2-ethoxyphenoxy)piperidin-1-yl)pyrazine (0.10 g, 0.30 mmol) prepared in Preparation Example 1 and 2-aminothiazole (0.03 g, 0.30 mmol). (Yield 25%)

$^1$H-NMR (400 MHz, CHLOROFORM-D): δ 10.97 (s, 1H), 7.64 (s, 1H), 7.59 (s, 1H), 7.45 (s, 1H), 7.02 (m, 2H), 6.86 (m, 2H), 6.71 (s, 1H), 4.46 (m, 1H), 4.34 (m, 1H), 4.03 (m, 3H), 3.34-3.45 (m, 2H), 2.24 (m, 1H), 2.02 (m, 1H), 1.91 (m, 1H), 1.71 (m, 1H), 1.39 (t, 3H)

Example 4: (R)—N-(6-(3-(2-ethoxyphenoxy)piperidin-1-yl)pyrazin-2-yl)-4-phenylthiazol-2-amine

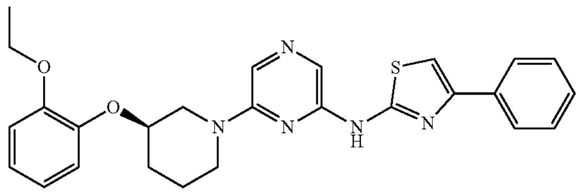 [SMILES: CCOc1ccccc1O[C@@H]1CCCN(c2cncc(Nc3nc(-c4ccccc4)cs3)n2)C1]

The title compound was obtained in a similar manner to Example 1 by using (R)-2-chloro-6-(3-(2-ethoxyphenoxy)piperidin-1-yl)pyrazine (0.10 g, 0.30 mmol) prepared in Preparation Example 1 and 2-amino-4-benzothiazole (0.053 g, 0.30 mmol). (Yield 28%)

$^1$H-NMR (400 MHz, CHLOROFORM-D): δ 8.72 (brs, 1H), 7.85 (d, 2H), 7.63 (s, 1H), 7.40 (t, 2H), 7.35 (s, 1H), 7.29 (t, 1H), 7.02 (m, 2H), 6.87 (m, 3H), 4.44 (m, 1H), 4.33 (m, 1H), 3.95-4.06 (m, 3H), 3.35-3.47 (m, 2H), 2.23 (m, 1H), 2.02 (m, 1H), 1.89 (m, 1H), 1.70 (m, 1H), 1.39 (t, 3H)

Example 5: (R)—N-(6-(3-(2-ethoxyphenoxy)piperidin-1-yl)pyrazin-2-yl)benzo[d]thiazol-2-amine

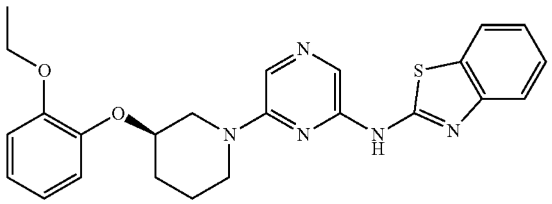 [SMILES: CCOc1ccccc1O[C@@H]1CCCN(c2cncc(Nc3nc4ccccc4s3)n2)C1]

The title compound was obtained in a similar manner to Example 1 by using (R)-2-chloro-6-(3-(2-ethoxyphenoxy)piperidin-1-yl)pyrazine (0.10 g, 0.30 mmol) prepared in Preparation Example 1 and 2-aminobenzothiazole (0.045 g, 0.30 mmol). (Yield 37%)

$^1$H-NMR (400 MHz, CHLOROFORM-D): δ 9.20 (brs, 1H), 7.73 (s, 1H), 7.64-7.71 (m, 2H), 7.42 (s, 1H), 7.38 (m, 1H), 7.22 (m, 1H), 7.04 (d, 1H), 6.83-6.93 (m, 3H), 4.31-4.40 (m, 2H), 4.03 (m, 3H), 3.63 (m, 1H), 3.59 (m, 1H), 2.21 (m, 1H), 2.09 (m, 1H), 1.97 (m, 1H), 1.74 (m, 1H), 1.39 (t, 3H)

Example 6: (R)—N-(6-(3-(2-ethoxyphenoxy)piperidin-1-yl)pyrazin-2-yl)-6-methoxybenzo[d]thiazol-2-amine

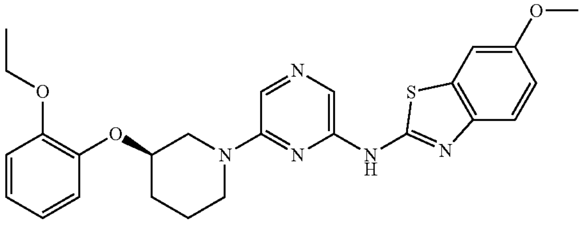 [SMILES: CCOc1ccccc1O[C@@H]1CCCN(c2cncc(Nc3nc4ccc(OC)cc4s3)n2)C1]

The title compound was obtained in a similar manner to Example 1 by using (R)-2-chloro-6-(3-(2-ethoxyphenoxy)piperidin-1-yl)pyrazine (0.10 g, 0.30 mmol) prepared in Preparation Example 1 and 2-amino-(6-methoxy)benzothiazole (0.054 g, 0.30 mmol). (Yield 28%)

$^1$H-NMR (400 MHz, CHLOROFORM-D): δ 9.90 (brs, 1H), 7.70 (s, 1H), 7.61 (d, 1H), 7.52 (s, 1H), 7.15 (s, 1H), 6.82-7.06 (m, 4H), 4.40 (m, 2H), 3.99-4.06 (m, 3H), 3.86 (s, 3H), 3.60 (m, 1H), 3.48 (m, 1H), 2.20 (m, 1H), 2.07 (m, 1H), 1.96 (m, 1H), 1.73 (m, 1H), 1.39 (t, 3H)

Example 7: (R)—N-(6-(3-(2-ethoxyphenoxy)piperidin-1-yl)pyrazin-2-yl)-6-(methanesulfonyl)benzo[d]thiazol-2-amine

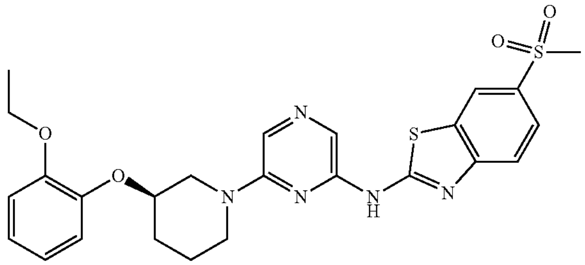 [SMILES: CCOc1ccccc1O[C@@H]1CCCN(c2cncc(Nc3nc4ccc(S(C)(=O)=O)cc4s3)n2)C1]

The title compound was obtained in a similar manner to Example 1 by using (R)-2-chloro-6-(3-(2-ethoxyphenoxy)piperidin-1-yl)pyrazine (0.10 g, 0.3 mmol) prepared in Preparation Example 1 and 2-amino-(6-methylsulfonyl)benzothiazole (0.068 g, 0.30 mmol). (Yield 19%)

$^1$H-NMR (400 MHz, CHLOROFORM-D): δ 9.70 (brs, 1H), 8.24 (s, 1H), 7.89 (m, 1H), 7.80 (s, 1H), 7.76 (m, 1H), 7.53 (s, 1H), 7.03 (d, 1H), 6.96 (m, 2H), 6.83 (m, 1H), 4.45 (m, 1H), 4.29 (m, 1H), 4.03 (m, 3H), 3.89 (m, 1H), 3.72 (m, 1H), 3.59 (m, 1H), 3.11 (s, 3H), 2.19 (m, 1H), 2.11 (m, 1H), 2.01 (m, 1H), 1.76 (m, 1H), 1.39 (t, 3H)

Example 8: (R)—N-(6-(3-(2-ethoxyphenoxy)piperidin-1-yl)pyrazin-2-yl)-3-(1-(2-methoxyethoxy)-2-methylpropan-2-yl)isooxazol-5-amine

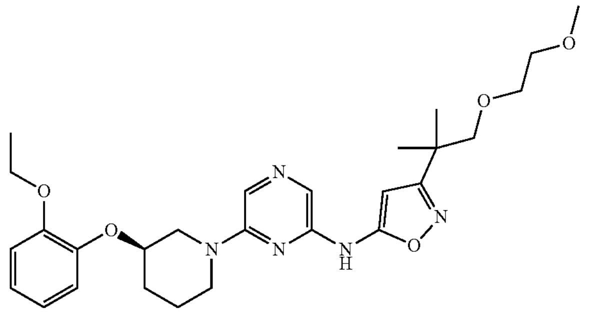 [SMILES: CCOc1ccccc1O[C@@H]1CCCN(c2cncc(Nc3cc(C(C)(C)COCCOC)no3)n2)C1]

The title compound was obtained in a similar manner to Example 1 by using (R)-2-chloro-6-(3-(2-ethoxyphenoxy)piperidin-1-yl)pyrazine (0.15 g, 0.45 mmol) prepared in Preparation Example 1 and 3-(1-(2-methoxyethoxy)-2-methylpropan-2-yl)isooxazol-5-amine (0.1 g, 0.49 mmol). (Yield 57%)

$^1$H-NMR (500 MHz, CHLOROFORM-D): δ 7.73 (s, 1H), 7.69 (s, 1H), 7.59 (s, 1H), 7.03-6.90 (m, 2H), 6.89-6.75 (m, 2H), 5.99 (s, 1H), 4.36-4.25 (m, 1H), 4.08 (dd, J=12.8, 3.1 Hz, 1H), 4.03-3.88 (m, 2H), 3.88-3.76 (m, 1H), 3.59-3.52 (m, 3H), 3.52-3.46 (m, 4H), 3.46-3.38 (m, 1H), 3.33 (d, J=6.1 Hz, 3H), 2.17-2.07 (m, 1H), 1.99 (td, J=6.6, 3.5 Hz, 1H), 1.90 (q, J=4.3 Hz, 1H), 1.62 (q, J=4.5 Hz, 1H), 1.36 (t, J=7.0 Hz, 3H), 1.29 (d, J=2.6 Hz, 6H)

Example 9: (R)—N-(6-(3-(2-ethoxyphenoxy)piperidin-1-yl)pyrazin-2-yl)-4-phenyloxazol-2-amine

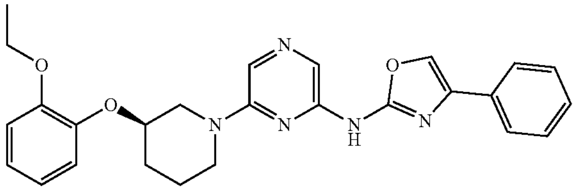 [SMILES: CCOc1ccccc1O[C@@H]1CCCN(c2cncc(Nc3nc(-c4ccccc4)co3)n2)C1]

The title compound was obtained in a similar manner to Example 1 by using (R)-2-chloro-6-(3-(2-ethoxyphenoxy)piperidin-1-yl)pyrazine (0.03 g, 0.09 mmol) prepared in Preparation Example 1 and 4-phenyloxazol-2-amine (0.016 g, 0.099 mmol) prepared in Preparation Example 25. (yield 4%)

$^1$H-NMR (500 MHz, CHLOROFORM-D) δ 7.92 (s, 1H), 7.87 (s, 1H), 7.72 (d, J=7.6 Hz, 1H), 7.66 (s, 1H), 7.41 (t, J=7.6 Hz, 1H), 7.34 (d, J=7.3 Hz, 1H), 7.28 (m, 2H), 7.01-6.84 (m, 3H), 6.84-6.74 (m, 1H), 4.29-4.18 (m, 1H), 4.06 (dd, J=13.4, 3.4 Hz, 1H), 4.01 (q, J=7.0 Hz, 2H), 3.75 (td, J=8.9, 4.3 Hz, 1H), 3.35 (dd, J=13.1, 8.2 Hz, 1H), 3.30-3.16 (m, 1H), 2.20-2.02 (m, 1H), 1.98-1.75 (m, 2H), 1.57-1.51 (m, 1H), 1.39 (t, J=6.9 Hz, 3H)

Example 10: (R)—N-(6-(3-(2-ethoxyphenoxy)piperidin-1-yl)pyrazin-2-yl)benzo[d]oxazol-2-amine

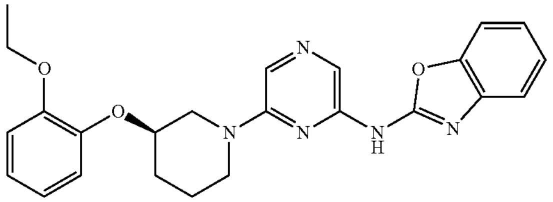

The title compound was obtained in a similar manner to Example 1 by using (R)-2-chloro-6-(3-(2-ethoxyphenoxy)piperidin-1-yl)pyrazine (0.1 g, 0.30 mmol) prepared in Preparation Example 1 and 2-aminobenzoxazole (0.05 g, 0.36 mmol). (Yield 19%)

$^1$H-NMR (500 MHz, CHLOROFORM-D) δ 8.77 (s, 1H), 7.87 (s, 1H), 7.55 (d, J=7.3 Hz, 1H), 7.44-7.34 (m, 1H), 7.17 (t, J=7.6 Hz, 1H), 7.06 (d, J=16.5 Hz, 1H), 6.97 (t, J=7.9 Hz, 2H), 6.88 (q, J=7.1 Hz, 2H), 4.32 (s, 1H), 4.10-3.90 (m, 3H), 3.78 (d, J=14.1 Hz, 1H), 3.62 (q, J=6.9 Hz, 1H), 3.43 (d, J=9.8 Hz, 1H), 2.21-1.87 (m, 4H), 1.61 (s, 1H), 1.37 (t, J=7.0 Hz, 3H)

Example 11: (R)-5-chloro-N-(6-(3-(2-ethoxyphenoxy)piperidin-1-yl)pyrazin-2-yl)benzo[d]oxazol-2-amine

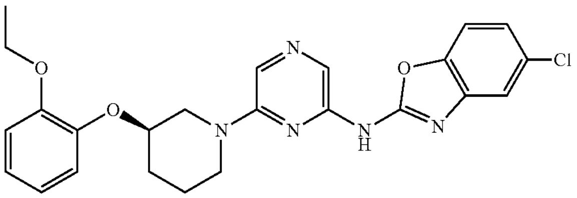 [SMILES: CCOc1ccccc1O[C@@H]1CCCN(c2cncc(Nc3nc4cc(Cl)ccc4o3)n2)C1]

The title compound was obtained in a similar manner to Example 1 by using (R)-2-chloro-6-(3-(2-ethoxyphenoxy) piperidin-1-yl)pyrazine (0.14 g, 0.42 mmol) prepared in Preparation Example 1 and 2-amino-(5-chloro)benzothiazole (0.071 g, 0.42 mmol). (Yield 51%)

$^1$H-NMR (400 MHz, CHLOROFORM-D): δ 8.73 (s, 1H), 7.89 (s, 1H), 7.52 (s, 1H), 7.16 (m, 1H), 7.13 (m, 2H), 6.99 (m, 2h), 6.86-6.91 (m, 2H), 4.34 (m, 1H), 3.93-4.03 (m, 3H), 3.75 (m, 1H), 3.67 (m, 1H), 3.49 (m, 1H), 2.11 (m, 1H), 2.02 (m, 1H), 1.93 (m, 1H), 1.63 (m, 1H), 1.37 (t, 3H)

Example 12: (R)-2-(2-((6-(3-(2-ethoxyphenoxy) piperidin-1-yl)pyrazin-2-yl)amino)benzo[d]oxazol-5-yl)acetic Acid

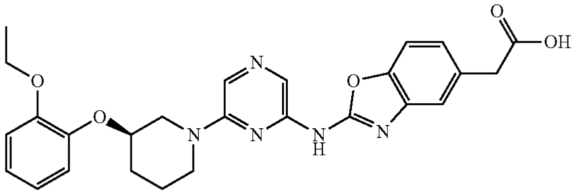 [SMILES: CCOc1ccccc1O[C@@H]1CCCN(c2cncc(Nc3nc4cc(CC(=O)O)ccc4o3)n2)C1]

(R)-2-chloro-6-(3-(2-ethoxyphenoxy)piperidin-1-yl) pyrazine (0.777 g, 2.328 mmol) obtained in Preparation Example 1 and methyl 2-(2-aminobenzo[d]oxazol-5-yl)acetate (0.4 g, 1.940 mmol) obtained in Preparation Example 16, tris(dibenzylideneacetone)dipalladium(0) (0.178 g, 0.194 mmol), 4,5-bis(diphenylphosphino)-9,9-dimethylxanthine (0.135 g, 0.233 mmol) and cesium carbonate (1.580 g, 4.85 mmol) were added to 20 ml of 1,4-dioxane and stirred under reflux for 4 hours. After the reaction was completed, the reaction mixture was cooled to room temperature, diluted with ethyl acetate, washed with an aqueous sodium hydrogen carbonate solution and brine, and dried over magnesium sulfate, and the organic solvent was removed under reduced pressure. The desired ester product was obtained by purification with silica gel column (ethyl acetate:hexane=4:1). (Yield 36%)

$^1$H-NMR (400 MHz, CHLOROFORM-D) δ 8.81-8.66 (m, 1H), 8.03 (d, J=50.8 Hz, 1H), 7.95-7.77 (m, 1H), 7.54-7.38 (m, 1H), 7.26 (q, J=7.8 Hz, 1H), 7.12-7.01 (m, 1H), 6.99-6.87 (m, 2H), 6.87-6.77 (m, 2H), 4.36-4.20 (m, 1H), 4.06-3.99 (m, 1H), 3.99-3.89 (m, 2H), 3.75 (td, J=9.6, 3.8 Hz, 1H), 3.69 (d, J=9.6 Hz, 5H), 3.61-3.46 (m, 1H), 3.46-3.30 (m, 1H), 2.18-2.03 (m, 1H), 2.01-1.74 (m, 2H), 1.68-1.44 (m, 1H), 1.44-1.28 (m, 3H)

The obtained ester compound (0.330 g, 0.655 mmol) was dissolved in 5 ml of THF, 2 ml of MeOH, and 2 ml of water. After adding sodium hydroxide (0.786 g, 19.66 mmol), the mixture was stirred at room temperature for 15 hours. After confirming the completion of the reaction by TLC, titration was adjusted to pH 4.5 using 1 N aqueous hydrogen chloride solution, diluted with ethyl acetate, and the water layer was removed. After drying the reaction product over magnesium sulfate, the organic solvent was removed under reduced pressure to obtain the title compound. (Yield 3%)

$^1$H-NMR (400 MHz, METHANOL-D4) δ 8.51 (s, 1H), 7.68 (s, 1H), 7.44-7.34 (1H), 7.25 (d, J=8.2 Hz, 1H), 7.11 (q, J=7.3 Hz, 1H), 6.96 (d, J=7.3 Hz, 1H), 6.86 (d, J=3.7 Hz, 2H), 6.84-6.71 (m, 2H), 4.40 (s, 1H), 3.89-3.83 (m, 2H), 3.82-3.74 (m, 2H), 3.62 (dd, J=16.9, 12.8 Hz, 1H), 3.55-3.50 (2H), 2.63 (s, 1H), 2.00 (dd, J=13.5, 3.4 Hz, 2H), 1.90 (d, J=8.2 Hz, 1H), 1.64-1.48 (m, 1H), 1.25 (t, J=6.9 Hz, 3H)

Example 13: (R)-2-(2-((6-(3-(2-ethoxyphenoxy) piperidin-1-yl)pyrazin-2-yl)amino)benzo[d]oxazol-5-yl)-2-methylpropanoic Acid

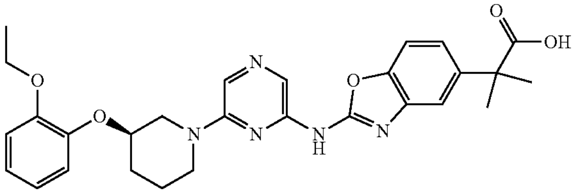 [SMILES: CCOc1ccccc1O[C@@H]1CCCN(c2cncc(Nc3nc4cc(C(C)(C)C(=O)O)ccc4o3)n2)C1]

The ester product was obtained in a similar manner to Example 12 by using (R)-2-chloro-6-(3-(2-ethoxyphenoxy) piperidin-1-yl)pyrazine (0.855 g, 2.56 mmol) obtained in Preparation Example 1 and methyl 2-(2-aminobenzo[d]oxazol-5-yl)-2-methylpropanoate (0.5 g, 2.134 mmol) obtained in Preparation Example 17. (Yield 66%)

$^1$H-NMR (400 MHz, CHLOROFORM-D) δ 8.82 (q, J=14.8 Hz, 1H), 8.62 (s, 1H), 7.86 (t, J=15.1 Hz, 1H), 7.56-7.46 (m, 1H), 7.34-7.20 (m, 1H), 7.21-7.03 (m, 1H), 7.03-6.83 (m, 2H), 6.83-6.69 (m, 2H), 4.33-4.15 (m, 1H), 4.16-3.97 (m, 1H), 3.90 (td, J=15.4, 8.1 Hz, 2H), 3.82-3.68 (m, 1H), 3.68-3.58 (m, 3H), 3.58-3.45 (m, 1H), 3.45-3.29 (m, 1H), 2.16-2.02 (m, 1H), 1.98-1.87 (m, 1H), 1.87-1.71 (m, 1H), 1.68-1.56 (m, 6H), 1.56-1.48 (m, 1H), 1.30 (t, J=6.9 Hz, 3H)

The title compound was obtained through a hydrolysis reaction of the obtained ester compound in a similar manner to Example 12. (Yield 56%)

m/z $(M+H)^+$ calculated for $C_{28}H_{32}N_5O_5$: 518. found 518.

Example 14: (R)-3-(2-((6-(3-(2-ethoxyphenoxy) piperidin-1-yl)pyrazin-2-yl)amino)benzo[d]oxazol-5-yl)-2,2-dimethylpropanoic Acid

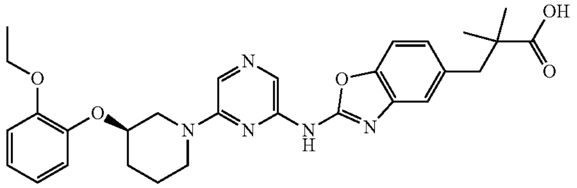 [SMILES: CCOc1ccccc1O[C@@H]1CCCN(c2cncc(Nc3nc4cc(CC(C)(C)C(=O)O)ccc4o3)n2)C1]

The title compound was obtained in a similar manner to Example 1 by using (R)-2-chloro-6-(3-(2-ethoxyphenoxy)

piperidin-1-yl)pyrazine (0.30 g, 0.90 mmol) prepared in Preparation Example 1 and methyl 3-(2-aminobenzo[d]oxazol-5-yl)-2,2-dimethylpropanoate (0.22 g, 0.90 mmol) synthesized in Preparation Example 21. (2 step yield 32%)

$^1$H-NMR (400 MHz, CHLOROFORM-D) δ 8.27 (s, 1H), 7.78 (s, 1H), 7.51 (s, 1H), 7.21 (d, J=8.2 Hz, 1H), 6.96 (d, J=8.2 Hz, 2H), 6.93-6.81 (m, 2H), 6.77 (t, J=7.5 Hz, 1H), 4.36-4.25 (m, 1H), 4.12 (d, J=16.5 Hz, 1H), 4.04-3.90 (m, 2H), 3.84 (d, J=13.3 Hz, 1H), 3.59 (dd, J=13.0, 7.5 Hz, 1H), 3.43 (t, J=9.6 Hz, 1H), 2.99 (s, 2H), 2.13 (t, J=5.9 Hz, 1H), 2.06-1.95 (m, 1H), 1.95-1.83 (m, 1H), 1.68-1.54 (m, 1H), 1.35 (t, J=6.9 Hz, 3H), 1.29 (s, 6H)

Example 15: (R,E)-3-(2-((6-(3-(2-ethoxyphenoxy) piperidin-1-yl)pyrazin-2-yl)amino)benzo[d]oxazol-5-yl)acrylic Acid

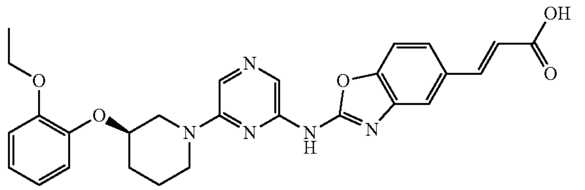 [SMILES: CCOc1ccccc1O[C@@H]1CCCN(c2cncc(Nc3nc4cc(/C=C/C(=O)O)ccc4o3)n2)C1]

The ester product was obtained in a similar manner to Example 12 by using (R)-2-chloro-6-(3-(2-ethoxyphenoxy) piperidin-1-yl)pyrazine (0.973 g, 2.91 mmol) obtained in Preparation Example 1 and methyl (E)-3-(2-aminobenzo[d] oxazol-5-yl)acrylate (0.53 g, 2.429 mmol) obtained in Preparation Example 22. (Yield 6%)

$^1$H-NMR (400 MHz, CHLOROFORM-D) δ 8.74 (s, 1H), 7.88 (s, 1H), 7.80-7.68 (m, 2H), 7.35 (dd, J=10.5, 8.7 Hz, 2H), 7.23-7.18 (1H), 6.99-6.91 (m, 2H), 6.91-6.84 (m, 2H), 6.42 (dd, J=16.7, 6.6 Hz, 1H), 4.41-4.24 (m, 1H), 4.06-3.87 (m, 3H), 3.85-3.79 (m, 3H), 3.79-3.70 (m, 1H), 3.69-3.54 (m, 1H), 3.54-3.35 (m, 1H), 2.21-2.07 (m, 1H), 2.02-1.86 (2H), 1.70-1.58 (1H), 1.36 (t, J=7.1 Hz, 3H)

The title compound was obtained through a hydrolysis reaction of the obtained ester compound in a similar manner to Example 12. (Yield 1%)

m/z $(M+H)^+$ calculated for $C_{27}H_{28}N_5O_5$: 502. found 502.

Example 16: (R)-3-(2-((6-(3-(2-ethoxyphenoxy) piperidin-1-yl)pyrazin-2-yl)amino)benzo[d]oxazol-5-yl)propanoic Acid

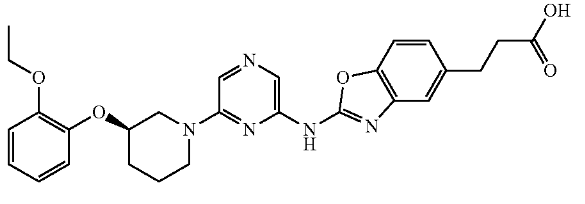 [SMILES: CCOc1ccccc1O[C@@H]1CCCN(c2cncc(Nc3nc4cc(CCC(=O)O)ccc4o3)n2)C1]

The ester product was obtained in a similar manner to Example 12 by using (R)-2-chloro-6-(3-(2-ethoxyphenoxy) piperidin-1-yl)pyrazine (1 g, 3.00 mmol) obtained in Preparation Example 1 and methyl 3-(2-aminophenzo[d]oxazol-5-yl)propanoate (0.550 g, 2.496 mmol) obtained in Preparation Example 23. (Yield 28%)

$^1$H-NMR (400 MHz, CHLOROFORM-D) δ 8.61 (d, J=4.1 Hz, 1H), 7.81 (s, 1H), 7.43-7.32 (m, 1H), 7.27 (d, J=8.2 Hz, 1H), 7.04-6.90 (m, 3H), 6.84 (t, J=7.1 Hz, 2H), 4.34-4.22 (m, 1H), 4.20-4.09 (m, 1H), 4.09-3.87 (m, 3H), 3.88-3.70 (m, 1H), 3.65-3.49 (m, 3H), 3.50-3.32 (m, 1H), 3.14-2.97 (m, 2H), 2.71 (t, J=7.8 Hz, 2H), 2.27-2.11 (m, 1H), 2.02-1.81 (m, 2H), 1.72-1.52 (m, 1H), 1.36 (t, J=6.9 Hz, 3H)

The title compound was obtained through a hydrolysis reaction of the obtained ester compound in a similar manner to Example 12. (Yield 5%)

m/z $(M+H)^+$ calculated for $C_{27}H_{30}N_5O_5$: 504. found 504.

Example 17: (R)-2-(2-((6-(3-(2-ethoxyphenoxy) piperidin-1-yl)pyrazin-2-yl)amino)benzo[d]oxazol-6-yl)-2-methylpropanoic Acid

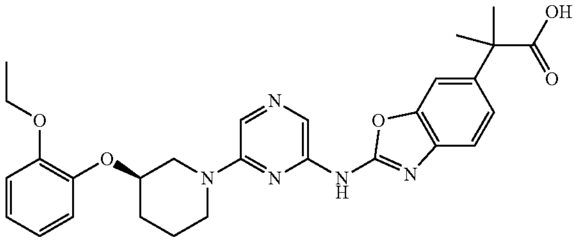 [SMILES: CCOc1ccccc1O[C@@H]1CCCN(c2cncc(Nc3nc4ccc(C(C)(C)C(=O)O)cc4o3)n2)C1]

The title compound was obtained in a similar manner to Example 12 by using (R)-2-chloro-6-(3-(2-ethoxyphenoxy) piperidin-1-yl)pyrazine (0.293 g, 0.878 mmol) obtained in Preparation Example 1 and methyl 2-(2-aminobenzo[d]oxazol-6-yl)-2-methylpropanoate (0.187 g, 0.798 mmol) obtained in Preparation Example 18. (2 step yield 7%)

$^1$H-NMR (400 MHz, CHLOROFORM-D) δ 8.55 (d, J=11.9 Hz, 1H), 7.82 (d, J=10.1 Hz, 1H), 7.55-7.44 (m, 1H), 7.44-7.36 (m, 1H), 7.31 (d, J=7.3 Hz, 1H), 7.02-6.87 (2H), 6.86-6.74 (m, 2H), 4.29 (t, J=3.4 Hz, 1H), 4.15-4.06 (m, 1H), 4.06-3.83 (m, 3H), 3.81-3.67 (m, 1H), 3.66-3.50 (1H), 3.50-3.35 (m, 1H), 2.15-2.04 (m, 1H), 2.03 (d, J=2.7 Hz, 1H), 2.01-1.82 (m, 2H), 1.62 (d, J=12.3 Hz, 6H), 1.37-1.28 (m, 3H)

Example 18: (R)-3-(2-((6-(3-(2-ethoxyphenoxy) piperidin-1-yl)pyrazin-2-yl)amino)benzo[d]oxazol-6-yl)propanoic Acid

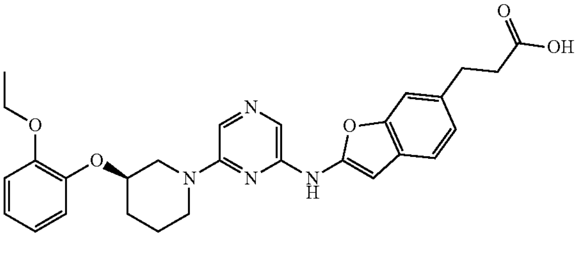 [SMILES: CCOc1ccccc1O[C@@H]1CCCN(c2cncc(Nc3cc4ccc(CCC(=O)O)cc4o3)n2)C1]

The product was obtained in a similar manner to Example 12 by using (R)-2-chloro-6-(3-(2-ethoxyphenoxy)piperidin-1-yl)pyrazine (0.8 g, 2.398 mmol) obtained in Preparation Example 1 and methyl 3-(2-aminobenzo[d]oxazol-6-yl)propanoate (0.44 g, 1.998 mmol) obtained in Preparation Example 24. (Yield 11%)

$^1$H-NMR (400 MHz, CHLOROFORM-D) δ 8.74 (s, 1H), 7.85 (s, 1H), 7.43 (d, J=8.2 Hz, 1H), 7.13-7.01 (m, 1H), 6.97 (t, J=7.1 Hz, 3H), 6.92-6.83 (m, 3H), 4.33 (d, J=4.1 Hz, 1H), 4.03-3.90 (3H), 3.79 (s, 1H), 3.66 (s, 3H), 3.60 (dd, J=13.0, 7.5 Hz, 2H), 3.03 (t, J=7.8 Hz, 2H), 2.71-2.60 (2H), 2.13-2.05 (1H), 1.98 (d, J=40.7 Hz, 2H), 1.75-1.63 (1H), 1.36 (t, J=7.1 Hz, 3H)

The title compound was obtained through a hydrolysis reaction of the obtained ester compound in a similar manner to Example 12. (Yield 3%)

m/z $(M+H)^+$ calculated for $C_{27}H_{30}N_5O_5$: 504. found 504.

Example 19: (R)-6-(3-(2-ethoxyphenoxy)piperidin-1-yl)-N-(1H-pyrazol-3-yl)pyrazin-2-amine

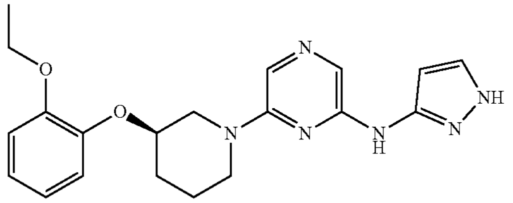 [SMILES: CCOc1ccccc1O[C@@H]1CCCN(c2cncc(Nc3cc[nH]n3)n2)C1]

Step 1: tert-butyl (R)-3-((6-(3-(2-ethoxyphenoxy)piperidin-1-yl)pyrazin-2-yl)amino-1H-pyrazole-1-carboxylate The desired product was obtained in a similar manner to Example 1 by using (R)-2-chloro-6-(3-(2-ethoxyphenoxy)piperidin-1-yl)pyrazine (1.540 g, 4.61 mmol) prepared in Preparation Example 1 and tert-butyl 3-amino-1H-pyrazole-1-carboxylate (0.930 g, 5.08 mmol) prepared in Preparation Example 64. (Yield 1%)

$^1$H-NMR (CHLOROFORM-D) δ 7.91 (d, J=2.7 Hz, 1H), 7.73-7.57 (m, 2H), 7.46-7.34 (1H), 7.07-6.95 (m, 2H), 6.95-6.80 (2H), 6.67-6.55 (1H), 4.30 (td, J=8.2, 3.9 Hz, 1H), 4.21 (dd, J=13.0, 3.5 Hz, 1H), 4.09-3.95 (m, 2H), 3.93-3.78 (1H), 3.41 (dd, J=13.0, 8.1 Hz, 1H), 3.36-3.23 (m, 1H), 2.20 (dd, J=12.7, 5.0 Hz, 1H), 2.00 (dd, J=9.3, 4.1 Hz, 1H), 1.95-1.81 (1H), 1.66 (s, 10H), 1.40 (t, J=7.0 Hz, 3H)

Step 2: (R)-6-(3-(2-ethoxyphenoxy)piperidin-1-yl)-N-(1H-pyrazol-3-yl)pyrazin-2-amine Tert-butyl (R)-3-((6-(3-(2-ethoxyphenoxy)piperidin-1-yl)pyrazin-2-yl)amino-1H-pyrazole-1-carboxylate (0.0124 g, 0.026 mmol) obtained in step 1 was dissolved in DCM (0.2 ml), then trifluoroacetic acid (0.026 ml) dissolved in DCM was added and stirred at room temperature for 1 hour 30 minutes. After removing the solvent under reduced pressure, it was dissolved in DCM and washed with water, and purified by silica gel column to obtain the title compound. (Yield 50%)

$^1$H-NMR (500 MHz, MeOD) δ 7.49 (s, 1H), 7.45 (s, 1H), 7.40 (s, 1H), 7.02 (d, J=7.6 Hz, 1H), 6.95 (d, J=3.7 Hz, 2H), 6.87 (d, J=11.9 Hz, 1H), 6.31 (s, 1H), 4.60 (s, 1H), 4.46-4.34 (1H), 4.13-3.90 (m, 2H), 3.75-3.66 (1H), 3.66-3.52 (m, 2H), 2.18-1.85 (3H), 1.75-1.56 (1H), 1.32 (t, J=6.7 Hz, 3H)

Example 20: (R)-2-(3-((6-(3-(2-ethoxyphenoxy)piperidin-1-yl)pyrazin-2-yl)amino)-1H-pyrazol-1-yl)acetic Acid

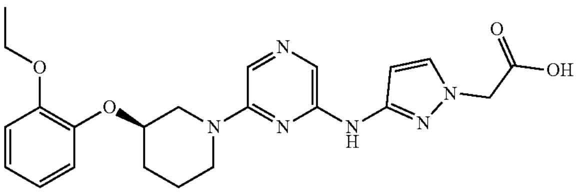 [SMILES: CCOc1ccccc1O[C@@H]1CCCN(c2cncc(Nc3ccn(CC(=O)O)n3)n2)C1]

Step 1: ethyl (R)-2-(3-((6-(3-(2-ethoxyphenoxy)piperidin-1-yl)pyrazin-2-yl)amino)-1H-pyrazol-1-yl)acetate (R)-6-(3-(2-ethoxyphenoxy)piperidin-1-yl)-N-(1H-pyrazol-3-yl)pyrazin-2-amine (0.200 g, 0.526 mmol) prepared in Example 19 and sodium hydride (0.025 g, 0.631 mmol) were dissolved in tetrahydrofuran (2.63 ml) and stirred for 30 minutes. Ethyl 2-bromoacetate (0.087 ml, 0.789 mmol) dissolved in tetrahydrofuran (2.63 ml) was added dropwise to the reaction solution, followed by stirring for 2 hours. Water was added dropwise to terminate the reaction, then dissolved in ethyl acetate and washed with brine. The organic solvent was dried over magnesium sulfate and the organic solvent was removed under reduced pressure. The desired product was obtained by purification with silica gel column. (Yield 3%)

$^1$H-NMR (500 MHz, CHLOROFORM-D) δ 7.69 (s, 1H), 7.59 (s, 1H), 7.32 (d, J=1.8 Hz, 1H), 7.09-6.81 (m, 4H), 6.66 (s, 1H), 6.36 (d, J=2.1 Hz, 1H), 4.83-4.70 (m, 2H), 4.37-4.18 (m, 4H), 4.05 (qd, J=6.8, 3.1 Hz, 2H), 3.99-3.83 (m, 1H), 3.35 (dd, J=13.0, 8.4 Hz, 1H), 3.31-3.18 (m, 1H), 2.29-2.12 (m, 1H), 1.98 (q, J=4.5 Hz, 1H), 1.93-1.78 (m, 1H), 1.79-1.55 (m, 2H), 1.42 (t, J=7.0 Hz, 3H), 1.31 (t, J=7.2 Hz, 3H), 1.28 (s, 1H)

Step 2: (R)-2-(3-((6-(3-(2-ethoxyphenoxy)piperidin-1-yl)pyrazin-2-yl)amino)-1H-pyrazol-1-yl)acetic Acid Ethyl (R)-2-(3-((6-(3-(2-ethoxyphenoxy)piperidin-1-yl)pyrazin-2-yl)amino)-1H-pyrazol-1-yl)acetate (0.0073 g, 0.016 mmol) obtained in step 1 was dissolved in 50% ethyl alcohol aqueous solution (0.156 ml), and lithium hydroxide (1.124 mg, 0.047 mmol) was added thereto, followed by stirring at 0° C. for 1 hour. After removing the solvent under reduced pressure, it was dissolved in ethyl acetate and washed with water. The title product was obtained by purification with silica gel column. (Yield 26%)

m/z $(M+H)^+$ calculated for $C_{22}H_{27}N_6O_4$: 439. found 439.

Example 21: (R)-3-(3-((6-(3-(2-ethoxyphenoxy)piperidin-1-yl)pyrazin-2-yl)amino)-1H-pyrazol-1-yl)-2,2-dimethylpropanoic Acid

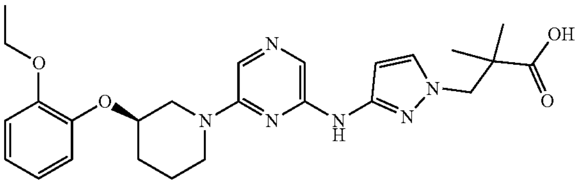 [SMILES: CCOc1ccccc1O[C@@H]1CCCN(c2cncc(Nc3ccn(CC(C)(C)C(=O)O)n3)n2)C1]

The title compound was obtained in a similar manner as in Example 1 by using (R)-2-chloro-6-(3-(2-ethoxyphenoxy)piperidin-1-yl)pyrazine (0.10 g, 0.30 mmol) prepared in Preparation Example 1 and methyl 3-(3-amino-1H-pyrazol-1-yl)-2,2-dimethylpropanoate (0.059 g, 0.30 mmol) obtained in Preparation Example 66. (Yield 45%)

$^1$H-NMR (400 MHz, CHLOROFORM-D): δ 9.32 (s, 1H), 7.45 (d, J=7.3 Hz, 2H), 7.13 (d, J=2.3 Hz, 1H), 7.06-6.77 (m, 5H), 6.47 (d, J=2.3 Hz, 1H), 4.35-4.14 (m, 4H), 4.06-3.89 (m, 2H), 3.89-3.78 (m, 1H), 3.37-3.08 (m, 2H), 2.17 (q, J=4.3 Hz, 1H), 1.99-1.71 (m, 2H), 1.71-1.53 (m, 1H), 1.36 (t, J=6.9 Hz, 3H), 1.22-1.09 (m, 6H)

Example 22: (R)-3-(3-(6-((4-(3-(2-ethoxyphenoxy)piperidin-1-yl)-5-fluoropyrimidin-2-yl)amino)pyridin-2-yl)phenyl)-2,2-dimethylpropanoic Acid

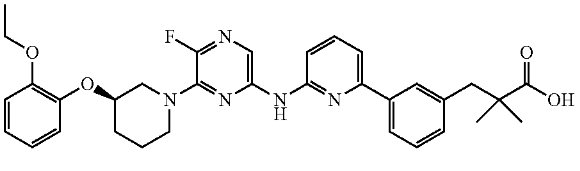

(R)-2-chloro-4-(3-(2-ethoxyphenoxy)piperidin-1-yl)-5-fluoropyrimidine (54 mg, 0.15 mmol) synthesized in Preparation Example 8 and tert-butyl 3-(3-(6-aminopyridin-2-yl)phenyl)-2,2-dimethylpropanoate (50 mg, 0.15 mmol) synthesized in Preparation Example 113 were dissolved in 1,4-dioxane, and the dissolved oxygen was removed, and filled with nitrogen to block exposure to outside air. Tris(dibenzylideneacetone)dipalladium(0) (8.4 mg, 9.19 μmol), 4,5-bis(diphenylphosphino)-9,9-dimethylxanthine (8.0 mg, 0.01 mmol), cesium carbonate (125 mg, 0.38 mmol) was added, a reflux cooling device was connected and heated for 12 hours. After the reaction was completed, the reaction mixture was cooled to room temperature, diluted with ethyl acetate, dried over magnesium sulfate, and the organic solvent was removed under reduced pressure. The desired product was obtained by purification with silica gel column (hexane:ethyl acetate). (Yield 15%)

The obtained ester compound (15 mg, 0.02 mmol) was dissolved in DCM, trifluoroacetic acid (36 μl, 0.47 mmol) was added, followed by stirring at room temperature for 2 hours. After completion of the reaction, the mixture was distilled under reduced pressure to remove excess trifluoroacetic acid, neutralized with 1 N sodium hydroxide, and extracted with ethyl acetate. The organic solvent was dried over magnesium sulfate and the organic solvent was removed under reduced pressure. The desired product was obtained by purification with silica gel column (hexane:ethyl acetate). (Yield 37%)

$^1$H-NMR (400 MHz, METHANOL-D4) δ 7.81 (s, 1H), 7.78 (d, J=7.8 Hz, 1H), 7.70 (t, J=7.8 Hz, 1H), 7.66-7.57 (1H), 7.54 (t, J=8.0 Hz, 1H), 7.45-7.23 (m, 5H), 7.23-7.11 (1H), 7.00-6.88 (m, 1H), 6.86 (d, J=4.1 Hz, 2H), 6.82-6.70 (m, 1H), 4.44 (d, J=2.7 Hz, 1H), 4.14-3.94 (m, 2H), 3.94-3.75 (m, 4H), 3.62 (d, J=8.7 Hz, 1H), 2.90 (s, 2H), 2.14-1.84 (m, 4H), 1.60 (d, J=7.3 Hz, 1H), 1.34-1.20 (m, 3H), 1.19-1.11 (m, 6H)

Example 23: (R)-6-(3-(2-ethoxyphenoxy)piperidin-1-yl)-N-(1-methyl-1H-tetrazol-5-yl)pyrazin-2-amine

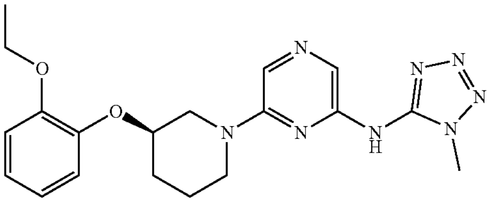 [SMILES: CCOc1ccccc1O[C@@H]1CCCN(c2cncc(Nc3nnnn3C)n2)C1]

The title compound was obtained in a similar manner to Example 1 by using (R)-2-chloro-6-(3-(2-ethoxyphenoxy)piperidin-1-yl)pyrazine (0.15 g, 0.45 mmol) prepared in Preparation Example land 1-methyl-1H-tetrazol-5-amine (0.049 g, 0.49 mmol). (Yield 44%)

$^1$H-NMR (500 MHz, CHLOROFORM-D): δ 8.18 (s, 1H), 7.79 (s, 1H), 7.41 (s, 1H), 7.01-6.89 (m, 2H), 6.88-6.75 (m, 2H), 4.34-4.23 (m, 1H), 4.06-3.91 (m, 2H), 3.88 (s, 3H), 3.86 (s, 1H), 3.70-3.56 (2H), 3.42 (q, J=4.5 Hz, 1H), 2.13-2.03 (m, 1H), 2.02-1.95 (m, 1H), 1.90 (q, J=4.1 Hz, 1H), 1.57 (q, J=4.5 Hz, 1H), 1.34 (t, J=7.0 Hz, 3H)

Example 24: (R)—N-6-(3-(2-ethoxyphenoxy)piperidin-1-yl)-N-phenylpyrazin-2-amine

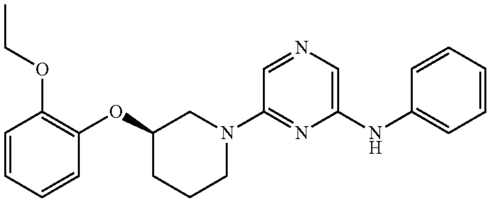 [SMILES: CCOc1ccccc1O[C@@H]1CCCN(c2cncc(Nc3ccccc3)n2)C1]

The title compound was obtained in a similar manner to Example 1 by using (R)-2-chloro-6-(3-(2-ethoxyphenoxy)piperidin-1-yl)pyrazine (0.09 g, 0.27 mmol) prepared in Preparation Example 1 and aniline (0.025 g, 0.27 mmol).

$^1$H-NMR (400 MHz, CHLOROFORM-D): δ 7.56 (s, 1H), 7.52 (s, 1H), 7.36 (d, J=8 Hz, 2H), 7.03 (d, J=8 Hz, 2H), 6.94-7.03 (m, 3H), 6.82-6.91 (m, 2H), 6.20 (s, 1H), 4.31 (m, 1H), 4.19 (m, 1H), 4.04 (m, 3H), 3.89 (m, 1H), 3.43 (m, 1H), 3.29 (m, 1H), 2.15 (m, 1H), 1.96 (m, 1H), 1.86 (m, 1H), 1.64 (m, 1H), 1.39 (t, 3H)

Example 25: (R)—N-(4-((6-(3-(2-ethoxyphenoxy)piperidin-1-yl)pyrazin-2-yl)amino)phenyl)methanesulfonamide

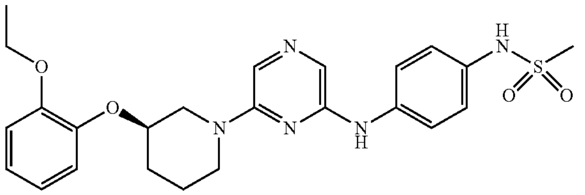

The title compound was obtained in a similar manner to Example 1 by using (R)-2-chloro-6-(3-(2-ethoxyphenoxy)piperidin-1-yl)pyrazine (0.15 g, 0.45 mmol) prepared in Preparation Example 1 and N-(4-aminophenyl)methanesulfonamide (0.092 g, 0.49 mmol). (Yield 69%)

$^1$H-NMR (500 MHz, CHLOROFORM-D): δ 7.57 (s, 1H), 7.45 (s, 1H), 7.42-7.33 (m, 2H), 7.13 (dd, J=9.6, 2.6 Hz, 2H), 7.03-6.93 (m, 2H), 6.89 (dd, J=7.9, 1.2 Hz, 1H), 6.82 (td, J=7.5, 1.4 Hz, 1H), 6.48 (s, 1H), 6.28 (s, 1H), 4.35-4.24 (m, 1H), 4.16 (dd, J=13.1, 3.4 Hz, 1H), 4.07-3.95 (m, 2H), 3.83 (td, J=8.9, 4.1 Hz, 1H), 3.43 (dd, J=13.4, 7.9 Hz, 1H), 3.37-3.24 (m, 1H), 2.96 (s, 3H), 2.23-2.09 (m, 1H), 1.98 (dd, J=9.8, 3.7 Hz, 1H), 1.93-1.80 (m, 1H), 1.69-1.61 (m, 1H), 1.38 (t, J=7.0 Hz, 3H)

Example 26: (R)-2-(4-((6-(3-(2-ethoxyphenoxy)piperidin-1-yl)pyrazin-2-yl)amino)phenyl)-N-(pyridin-4-ylmethyl)acetamide

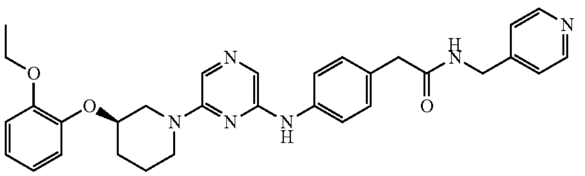

The title compound was obtained in a similar manner to Example 1 by using (R)-2-chloro-6-(3-(2-ethoxyphenoxy)piperidin-1-yl)pyrazine (0.15 g, 0.45 mmol) prepared in Preparation Example 1 and 2-(4-aminophenyl)-N-(pyridin-4-yl-methyl)acetamide (0.11 g, 0.49 mmol). (Yield 54%)

$^1$H-NMR (500 MHz, CHLOROFORM-D): δ 8.49 (d, J=5.5 Hz, 2H), 7.54 (s, 1H), 7.46 (s, 1H), 7.38 (d, J=8.6 Hz, 2H), 7.15 (d, J=7.9 Hz, 2H), 7.07 (d, J=5.5 Hz, 2H), 7.01-6.96 (1H), 6.95-6.91 (m, 1H), 6.90-6.85 (m, 1H), 6.80 (td, J=7.6, 1.4 Hz, 1H), 6.43 (s, 1H), 5.96 (s, 1H), 4.40 (d, J=6.1 Hz, 2H), 4.32-4.24 (m, 1H), 4.17 (dd, J=12.8, 3.1 Hz, 1H), 4.06-3.95 (m, 2H), 3.83 (td, J=8.6, 4.1 Hz, 1H), 3.60 (s, 2H), 3.40 (dd, J=12.8, 8.0 Hz, 1H), 3.34-3.24 (m, 1H), 2.21-2.11 (m, 1H), 1.97 (dd, J=9.7, 3.8 Hz, 1H), 1.87 (dd, J=9.2, 3.7 Hz, 1H), 1.67-1.55 (m, 1H), 1.37 (t, J=7.0 Hz, 3H)

Example 27: (R)-2-(4-((6-(3-(2-ethoxyphenoxy)piperidin-1-yl)pyrazin-2-yl)amino)phenyl)-2-methylpropanoic Acid

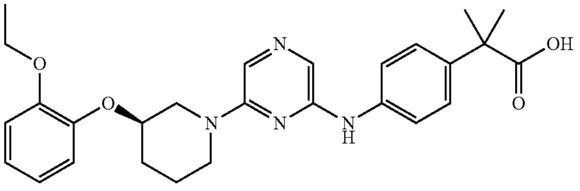 [SMILES: CCOc1ccccc1O[C@@H]1CCCN(c2cncc(Nc3ccc(C(C)(C)C(=O)O)cc3)n2)C1]

The desired product was obtained in a similar manner to Example 1 by using (R)-2-chloro-6-(3-(2-ethoxyphenoxy)piperidin-1-yl)pyrazine (0.30 g, 0.90 mmol) prepared in Preparation Example 1 and methyl 2-(4-aminophenyl)-2-methylpropanoate (0.19 g, 0.99 mmol) prepared in Preparation Example 14. (Yield 91%)

$^1$H-NMR (400 MHz, CHLOROFORM-D) δ 7.55 (s, 1H), 7.48 (s, 1H), 7.29-7.32 (m, 2H), 7.23 (dd, J=6.9, 1.8 Hz, 2H), 6.81-7.01 (m, 4H), 6.18 (s, 1H), 4.26-4.30 (m, 1H), 4.19 (dd, J=12.8, 3.7 Hz, 1H), 3.99-4.05 (m, 2H), 3.84-3.88 (m, 1H), 3.64 (s, 3H), 3.38 (dd, J=12.8, 8.2 Hz, 1H), 3.24-3.30 (m, 1H), 2.14-2.18 (m, 1H), 1.97 (q, J=4.6 Hz, 1H), 1.87 (dd, J=9.4, 3.4 Hz, 1H), 1.60-1.64 (m, 1H), 1.56 (s, 6H), 1.38 (t, J=6.9 Hz, 3H)

The title compound was obtained through a hydrolysis reaction of the obtained ester compound (0.40 g, 0.82 mmol) in a similar manner to Example 1. (Yield 23%)

$^1$H-NMR (400 MHz, CHLOROFORM-D) δ 7.51 (s, 1H), 7.42 (s, 1H), 7.27-7.31 (m, 4H), 6.85-6.99 (m, 4H), 6.34 (s, 1H), 4.25-4.29 (m, 1H), 4.16 (d, J=12.8 Hz, 1H), 3.97-4.03 (m, 2H), 3.79-3.82 (m, 1H), 3.39 (dd, J=13.0, 8.0 Hz, 1H), 3.26 (t, J=10.1 Hz, 1H), 2.12-2.15 (m, 1H), 1.93-1.97 (m, 1H), 1.81-1.89 (m, 1H), 1.58 (s, 7H), 1.36 (t, J=6.9 Hz, 3H)

Example 28: (R)-2-(4-((6-(3-(2-ethoxyphenoxy)pyridin-1-yl)pyrazin-2-yl)amino)phenyl)-2-methylpropanoic Acid

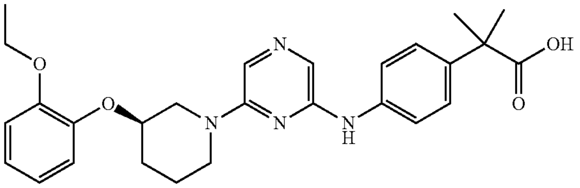 [SMILES: CCOc1ccccc1O[C@@H]1CCCN(c2cncc(Nc3ccc(C(C)(C)C(=O)O)cc3)n2)C1]

The desired product was obtained in a similar manner to Example 1 by using (R)-2-chloro-6-(3-(2-ethoxyphenoxy)piperidin-1-yl)pyridine (0.30 g, 0.90 mmol) prepared in Preparation Example 4 and methyl 2-(4-aminophenyl)-2-methylpropanoate (0.19 g, 0.99 mmol) prepared in Preparation Example 14. (Yield 88%)

$^1$H-NMR (400 MHz, CHLOROFORM-D) δ 7.30 (d, J=7.8 Hz, 2H), 7.24 (d, J=3.2 Hz, 1H), 7.20-7.22 (m, 2H), 7.04 (dd, J=8.0, 1.6 Hz, 1H), 6.82-6.96 (m, 3H), 6.19 (s, 1H), 6.11 (q, J=8.4 Hz, 2H), 4.24-4.36 (m, 2H), 3.96-4.06 (m, 3H), 3.64 (s, 3H), 3.47 (d, J=7.3 Hz, OH), 3.03-3.19 (m, 2H), 2.19 (dd, J=12.6, 4.3 Hz, 1H), 1.77-1.91 (m, 2H), 1.38-1.63 (m, 12H), 1.18-1.24 (m, 1H), −0.01 (t, J=3.2 Hz, 3H)

The title compound was obtained through a hydrolysis reaction of the obtained ester compound (0.40 g, 0.82 mmol) in a similar manner to Example 1.

$^1$H-NMR (400 MHz, CHLOROFORM-D) δ 7.22-7.30 (m, 5H), 7.03 (d, J=7.8 Hz, 1H), 6.89 (dq, J=28.9, 7.5 Hz, 3H), 6.14 (d, J=7.8 Hz, 1H), 6.08 (d, J=7.8 Hz, 1H), 4.24-4.32 (m, 2H), 4.03 (q, J=6.9 Hz, 2H), 3.95 (d, J=12.8 Hz, 1H), 3.17 (dd, J=11.9, 8.2 Hz, 1H), 3.07 (t, J=10.5 Hz, 1H), 2.19 (d, J=8.2 Hz, 1H), 1.89 (q, J=4.3 Hz, 1H), 1.78 (d, J=11.9 Hz, 1H), 1.57-1.65 (m, 7H), 1.39 (t, J=6.9 Hz, 3H)

Example 29: (R)-2-(3-((6-(3-(2-ethoxyphenoxy)piperidin-1-yl)pyrazin-2-yl)amino)phenyl)-2-methylpropanoic Acid

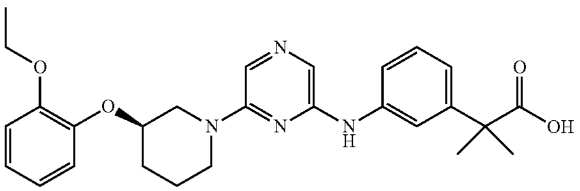 [SMILES: CCOc1ccccc1O[C@@H]1CCCN(c2cncc(Nc3cccc(C(C)(C)C(=O)O)c3)n2)C1]

The title compound was obtained in a similar manner as in Example 12 by using (R)-2-chloro-6-(3-(2-ethoxyphenoxy)piperidin-1-yl)pyrazine (1.036 g, 3.10 mmol) obtained in Preparation Example 1 and methyl 2-(3-aminophenyl)-2-methylpropanoate (0.5 g, 2.59 mmol) obtained in Preparation Example 15. (2 step yield 4%)

$^1$H-NMR (400 MHz, CHLOROFORM-D) δ 7.63 (s, 1H), 7.50 (s, 1H), 7.45 (s, 1H), 7.22 (d, J=7.8 Hz, 1H), 7.07 (t, J=9.8 Hz, 2H), 7.00-6.89 (m, 2H), 6.89-6.76 (m, 2H), 6.42 (s, 1H), 4.44-4.21 (m, 2H), 4.05-3.91 (m, 2H), 3.83 (q, J=4.4 Hz, 1H), 3.42-3.26 (1H), 3.26-3.05 (m, 1H), 2.25-2.06 (m, 1H), 1.93 (q, J=4.6 Hz, 1H), 1.83-1.67 (1H), 1.67-1.59 (m, 1H), 1.59-1.48 (m, 6H), 1.35 (t, J=6.9 Hz, 3H)

Example 30: (R)-3-(3'-((6-(3-(2-ethoxyphenoxy)piperidin-1-yl)pyrazin-2-yl)amino)-[1,1'-biphenyl]-4-yl)-2,2-dimethylpropanoic Acid

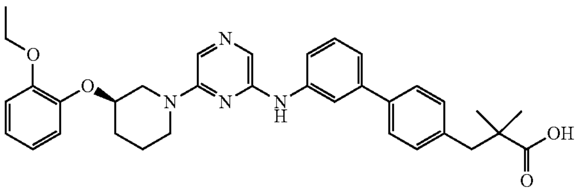 [SMILES: CCOc1ccccc1O[C@@H]1CCCN(c2cncc(Nc3cccc(-c4ccc(CC(C)(C)C(=O)O)cc4)c3)n2)C1]

The title compound was obtained in a similar manner to Example 22 by using (R)-2-chloro-6-(3-(2-ethoxyphenoxy)piperidin-1-yl)pyrazine (0.192 g, 0.575 mmol) obtained in Preparation Example 1 and tert-butyl 3-(3'-amino-[1,1'-biphenyl]-4-yl)-2,2-dimethylpropanoate (0.17 g, 0.522 mmol) obtained in Preparation Example 94. (2 step yield 12%)

$^1$H-NMR (400 MHz, CHLOROFORM-D) δ 7.58 (s, 1H), 7.55-7.48 (2H), 7.48-7.39 (m, 2H), 7.30-7.22 (2H), 7.18 (q, J=7.6 Hz, 3H), 6.93 (q, J=7.6 Hz, 2H), 6.88-6.83 (m, 1H), 6.83-6.73 (m, 1H), 6.53 (s, 1H), 4.37-4.18 (m, 1H), 4.18-4.06 (m, 1H), 4.05-3.89 (m, 2H), 3.83 (q, J=4.3 Hz, 1H), 3.53-3.36 (1H), 3.36-3.19 (m, 1H), 2.90 (s, 2H), 2.25-2.06 (1H), 1.99-1.74 (m, 2H), 1.70-1.48 (m, 1H), 1.34 (q, J=7.3 Hz, 3H), 1.23 (s, 6H)

Example 31: (R)-6-(3-(2-ethoxyphenoxy)piperidin-1-yl)-N-(pyridin-2-yl)pyrazin-2-amine

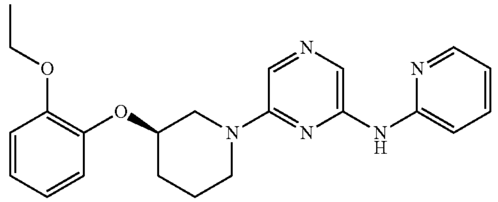

The title compound was obtained in a similar manner to Example 1 by using (R)-2-chloro-6-(3-(2-ethoxyphenoxy)piperidin-1-yl)pyrazine (0.20 g, 0.60 mmol) prepared in Preparation Example 1 and 2-aminopyridine (0.06 g, 0.66 mmol). (Yield 94%)

$^1$H-NMR (500 MHz, CHLOROFORM-D): δ 8.24 (d, J=4.9 Hz, 1H), 7.89 (s, 1H), 7.66 (s, 1H), 7.62 (d, J=8.6 Hz, 1H), 7.54-7.42 (m, 1H), 7.09 (s, 1H), 6.99 (d, J=7.9 Hz, 1H), 6.95 (t, J=7.0 Hz, 1H), 6.90-6.72 (m, 3H), 4.36-4.25 (m, 1H), 4.19 (dd, J=13.2, 3.3 Hz, 1H), 4.08-3.94 (m, 2H), 3.89-3.81 (m, 1H), 3.44 (dd, J=13.4, 7.9 Hz, 1H), 3.38-3.25 (m, 1H), 2.17 (t, J=5.8 Hz, 1H), 2.05-1.95 (1H), 1.93-1.79 (m, 1H), 1.67 (d, J=6.1 Hz, 1H), 1.37 (t, J=7.0 Hz, 3H)

Example 32: (R)-6-((6-(3-(2-ethoxyphenoxy)piperidin-1-yl)pyrazin-2-yl)amino)nicotinic Acid

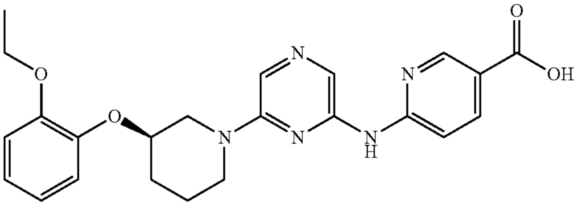 [SMILES: CCOc1ccccc1O[C@@H]1CCCN(c2cncc(Nc3ccc(C(=O)O)cn3)n2)C1]

The desired product was obtained in a similar manner to Example 1 by using (R)-2-chloro-6-(3-(2-ethoxyphenoxy)piperidin-1-yl)pyrazine (0.30 g, 0.90 mmol) prepared in Preparation Example 1 and methyl 6-aminonicotinate (0.15 g, 0.99 mmol). (Yield 72%)

$^1$H-NMR (500 MHz, CHLOROFORM-D): δ 8.87 (d, J=2.4 Hz, 1H), 8.08 (dd, J=8.9, 2.1 Hz, 1H), 7.90 (s, 1H), 7.73 (s, 1H), 7.65 (d, J=8.6 Hz, 1H), 7.36 (s, 1H), 7.04-6.92 (m, 2H), 6.90-6.68 (m, 2H), 4.32 (td, J=7.9, 3.7 Hz, 1H), 4.12 (dd, J=13.1, 3.4 Hz, 1H), 4.07-3.95 (m, 2H), 3.91 (s, 3H), 3.80 (td, J=9.2, 4.5 Hz, 1H), 3.53 (dd, J=13.1, 7.6 Hz, 1H), 3.46-3.31 (m, 1H), 2.27-2.11 (m, 1H), 2.09-1.99 (m, 1H), 1.97-1.84 (m, 1H), 1.66 (q, J=4.5 Hz, 1H), 1.36 (t, J=6.7 Hz, 3H)

The title compound was obtained through a hydrolysis reaction of the obtained ester compound (0.29 g, 0.65 mmol) in a similar manner to Example 1. (Yield 21%)

$^1$H-NMR (500 MHz, DMSO-D6): δ 12.99-12.26 (1H), 10.00 (s, 1H), 8.71 (s, 1H), 8.12 (s, 1H), 7.95 (d, J=7.9 Hz, 1H), 7.76 (s, 1H), 7.61 (d, J=8.6 Hz, 1H), 7.00 (d, J=7.9 Hz, 1H), 6.89 (d, J=6.7 Hz, 1H), 6.84 (d, J=7.3 Hz, 1H), 6.76 (t,

J=7.0 Hz, 1H), 4.40-4.24 (1H), 4.03 (d, J=11.6 Hz, 1H), 3.96-3.80 (m, 2H), 3.68 (d, J=13.4 Hz, 1H), 3.57-3.39 (m, 2H), 2.12-1.94 (1H), 1.86 (s, 1H), 1.72 (d, J=9.2 Hz, 1H), 1.54 (s, 1H), 1.18 (t, J=7.0 Hz, 3H)

Example 33: (R)-2-((6-(3-(2-ethoxyphenoxy)piperidin-1-yl)pyrazin-2-yl)amino)isonicotinic Acid

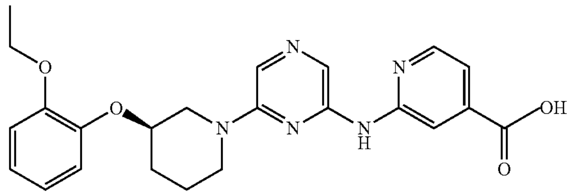

The desired product was obtained in a similar manner to Example 1 by using (R)-2-chloro-6-(3-(2-ethoxyphenoxy)piperidin-1-yl)pyrazine (0.20 g, 0.60 mmol) prepared in Preparation Example 1 and methyl 2-aminoisonicotinate (0.10 g, 0.66 mmol). (Yield 71%)

$^1$H-NMR (500 MHz, CHLOROFORM-D): δ 8.46 (s, 1H), 8.36 (d, J=4.9 Hz, 1H), 7.80 (s, 1H), 7.68 (s, 1H), 7.40 (d, J=5.5 Hz, 1H), 7.22 (s, 1H), 6.94 (d, J=7.9 Hz, 1H), 6.92-6.88 (1H), 6.86-6.82 (m, 1H), 6.80-6.67 (m, 1H), 4.38-4.28 (1H), 4.11 (dd, J=13.1, 3.4 Hz, 1H), 4.05-3.96 (m, 2H), 3.92 (dt, J=13.4, 3.8 Hz, 1H), 3.88 (s, 3H), 3.60 (dd, J=13.1, 7.6 Hz, 1H), 3.51-3.35 (m, 1H), 2.13 (s, 1H), 2.04 (td, J=6.6, 3.3 Hz, 1H), 1.93 (q, J=4.1 Hz, 1H), 1.66 (q, J=4.5 Hz, 1H), 1.36 (t, J=7.0 Hz, 3H)

The title compound was obtained through a hydrolysis reaction of the obtained ester compound (0.18 g, 0.40 mmol) in a similar manner to Example 1. (Yield 57%)

$^1$H-NMR (500 MHz, DMSO-D6): δ 9.76 (s, 1H), 8.31 (d, J=5.5 Hz, 2H), 8.04 (s, 1H), 7.66 (s, 1H), 7.24 (d, J=5.5 Hz, 1H), 6.96 (d, J=7.3 Hz, 1H), 6.87 (s, 1H), 6.81 (t, J=7.6 Hz, 1H), 6.72 (t, J=7.6 Hz, 1H), 4.29 (s, 1H), 3.93 (d, J=13.4 Hz, 1H), 3.89-3.76 (m, 2H), 3.70 (d, J=15.9 Hz, 1H), 3.64-3.51 (m, 2H), 1.97 (s, 1H), 1.84 (s, 1H), 1.73 (d, J=7.9 Hz, 1H), 1.53 (d, J=4.3 Hz, 1H), 1.18 (q, J=7.3 Hz, 3H)

Example 34: (R)-2-((6-(3-(2-ethoxyphenoxy)piperidin-1-yl)pyrazin-2-yl)amino)nicotinic Acid

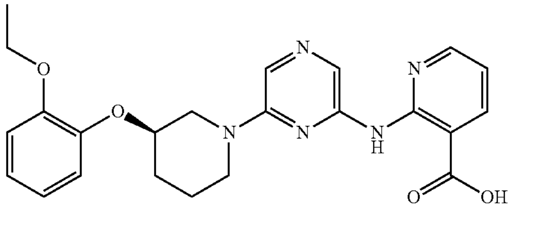 [SMILES: CCOc1ccccc1O[C@@H]1CCCN(c2cncc(Nc3ncccc3C(=O)O)n2)C1]

The desired product was obtained in a similar manner to Example 1 by using (R)-2-chloro-6-(3-(2-ethoxyphenoxy)piperidin-1-yl)pyrazine (0.20 g, 0.60 mmol) prepared in Preparation Example 1 and methyl 2-aminonicotinate (0.10 g, 0.66 mmol). (Yield 85%)

$^1$H-NMR (500 MHz, CHLOROFORM-D): δ 10.40 (s, 1H), 9.10 (s, 1H), 8.46 (q, J=2.2 Hz, 1H), 8.28 (dd, J=7.6, 2.1 Hz, 1H), 7.79 (s, 1H), 7.06 (q, J=3.1 Hz, 1H), 6.99-6.91 (m, 2H), 6.88 (q, J=3.3 Hz, 1H), 6.83 (q, J=4.3 Hz, 1H), 4.31-4.22 (m, 2H), 4.04 (qd, J=6.9, 2.3 Hz, 2H), 3.98 (t, J=4.6 Hz, 1H), 3.95 (s, 3H), 3.36 (dd, J=14.1, 9.2 Hz, 1H), 3.33-3.23 (m, 1H), 2.22-2.13 (m, 1H), 1.95 (q, J=4.5 Hz, 1H), 1.86 (d, J=10.4 Hz, 1H), 1.66-1.55 (m, 1H), 1.41 (t, J=7.0 Hz, 3H)

The title compound was obtained through a hydrolysis reaction of the obtained ester compound (0.21 g, 0.47 mmol) in a similar manner to Example 1. (Yield 74%)

$^1$H-NMR (500 MHz, DMSO-D6): δ 10.63 (s, 1H), 8.91 (s, 1H), 8.48 (q, J=2.2 Hz, 1H), 8.37-8.20 (1H), 7.90 (s, 1H), 7.11-6.97 (m, 2H), 6.87 (dt, J=12.2, 4.9 Hz, 3H), 4.43-4.20 (m, 1H), 4.04 (d, J=12.8 Hz, 1H), 3.95-3.79 (m, 2H), 3.76-3.62 (m, 1H), 3.59-3.42 (m, 2H), 2.08-1.94 (m, 1H), 1.83 (t, J=3.4 Hz, 1H), 1.75 (q, J=4.1 Hz, 1H), 1.51 (q, J=4.3 Hz, 1H), 1.20 (t, J=7.0 Hz, 3H)

Example 35: (R)-2-(2-((6-(3-(2-ethoxyphenoxy)piperidin-1-yl)pyrazin-2-yl)amino)pyridin-4-yl)-2-methylpropanoic Acid

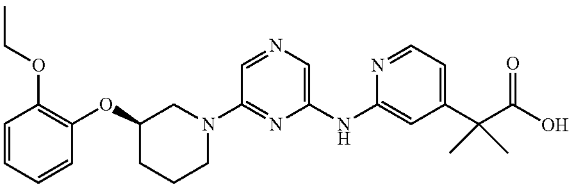 [SMILES: CCOc1ccccc1O[C@@H]1CCCN(c2cncc(Nc3cc(C(C)(C)C(=O)O)ccn3)n2)C1]

The title compound was obtained in a similar manner to Example 1 by using (R)-2-chloro-6-(3-(2-ethoxyphenoxy)piperidin-1-yl)pyrazine (1.12 g, 3.35 mmol) prepared in Preparation Example 1 and methyl 2-(2-aminopyridin-4-yl)-2-methylpropanoate (650 mg, 3.35 mmol) prepared in Preparation Example 60. (2 step yield 1%)

$^1$H-NMR (CHLOROFORM-D) δ 8.31 (s, 1H), 7.96 (d, J=4.6 Hz, 1H), 7.69 (s, 2H), 6.97-6.73 (5H), 4.36 (q, J=4.1 Hz, 1H), 4.06-3.92 (m, 3H), 3.89-3.75 (1H), 3.46 (t, J=10.2 Hz, 1H), 3.38-3.22 (m, 1H), 2.12 (d, J=5.5 Hz, 1H), 2.05 (d, J=15.3 Hz, 1H), 1.96 (s, 1H), 1.80-1.54 (7H), 1.33 (t, J=7.0 Hz, 3H)

Example 36: (R)-2-(6-((6-(3-(2-ethoxyphenoxy)piperidin-1-yl)pyrazin-2-yl)amino)pyridin-3-yl)acetic Acid

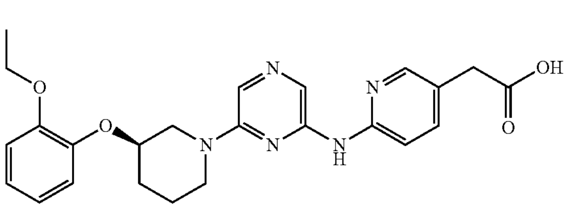 [SMILES: CCOc1ccccc1O[C@@H]1CCCN(c2cncc(Nc3ccc(CC(=O)O)cn3)n2)C1]

The desired product was obtained in a similar manner to Example 1 by using (R)-2-chloro-6-(3-(2-ethoxyphenoxy)piperidin-1-yl)pyrazine (0.14 g, 0.42 mmol) prepared in Preparation Example 1 and methyl 2-(6-aminopyridin-3-yl)acetate (0.08 g, 0.46 mmol) prepared in Preparation Example 12. (Yield 62%)

$^1$H-NMR (400 MHz, CHLOROFORM-D): δ 8.14 (s, 1H), 7.87 (s, 1H), 7.66 (s, 1H), 7.62 (d, J=8 Hz, 1H), 7.46 (d, J=8 Hz, 1H), 7.08 (s, 1H), 6.99 (m, 2H), 6.88 (m, 2H), 4.32 (m,

1H), 4.29 (m, 1H), 4.02 (m, 2H), 3.87 (m, 1H), 3.83 (s, 1H), 3.56 (s, 2H), 3.48 (m, 1H), 3.34 (m, 1H), 2.17 (m, 1H), 2.02 (m, 1H), 1.91 (m, 1H), 1.66 (m, 1H), 1.38 (t, 3H)

The title compound was obtained through a hydrolysis reaction of the obtained ester compound (0.11 g, 0.24 mmol) in a similar manner to Example 1. (Yield 19%)

$^1$H-NMR (400 MHz, DMSO-D6): (9.54 (s, 1H), 8.10 (s, 1H), 8.06 (s, 1H), 7.67 (s, 1H), 7.60 (d, J=8 Hz, 1H), 7.41 (d, J=6 Hz, 1H), 7.04 (d, J=8 Hz, 1H), 6.95 (m, 2H), 6.84 (m, 1H), 4.33 (m, 1H), 4.10 (m, 1H), 3.95 (m, 2H), 3.72 (m, 1H), 3.51 (s, 2H), 3.45 (m, 2H), 2.04 (m, 1H), 1.87 (m, 1H), 1.75 (m, 1H), 1.57 (m, 1H), 1.25 (t, 3H)

Example 37: (R,E)-3-(6-((6-(3-(2-ethoxyphenoxy) piperidin-1-yl)pyrazin-2-yl)amino)pyridin-3-yl) acrylic Acid

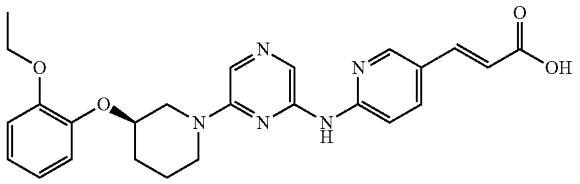 [SMILES: CCOc1ccccc1O[C@@H]1CCCN(c2cncc(Nc3ccc(/C=C/C(=O)O)cn3)n2)C1]

The desired product was obtained in a similar manner to Example 1 by using (R)-2-chloro-6-(3-(2-ethoxyphenoxy) piperidin-1-yl)pyrazine (0.50 g, 1.50 mmol) prepared in Preparation Example 1 and methyl (E)-3-(6-aminopyridin-3-yl)acrylate (0.29 g, 1.65 mmol) prepared in Preparation Example 13. (Yield 70%)

$^1$H-NMR (500 MHz, CHLOROFORM-D): δ 8.35 (s, 1H), 7.95-7.81 (1H), 7.71 (s, 1H), 7.64 (d, J=2.4 Hz, 2H), 7.62 (d, J=15.9 Hz, 1H), 7.23 (s, 1H), 7.01-6.92 (m, 2H), 6.91-6.79 (m, 2H), 6.34 (d, J=16.5 Hz, 1H), 4.33 (d, J=4.3 Hz, 1H), 4.19-4.13 (m, 1H), 4.05-3.96 (m, 2H), 3.82 (d, J=7.9 Hz, 4H), 3.50 (dd, J=12.8, 7.9 Hz, 1H), 3.36 (d, J=9.8 Hz, 1H), 2.21-2.13 (1H), 2.06-1.97 (1H), 1.97-1.87 (1H), 1.66 (s, 1H), 1.37 (t, J=7.0 Hz, 3H)

The title compound was obtained through a hydrolysis reaction of the obtained ester compound (0.15 g, 0.32 mmol) in a similar manner to Example 1. (Yield 82%)

$^1$H-NMR (500 MHz, DMSO-D6): δ 10.71 (s, 1H), 8.49 (s, 1H), 8.16 (s, 1H), 8.04 (d, J=6.7 Hz, 1H), 7.88 (s, 1H), 7.56-7.47 (m, 2H), 6.97 (d, J=6.1 Hz, 1H), 6.86-6.81 (1H), 6.80-6.70 (m, 2H), 6.47 (d, J=15.9 Hz, 1H), 4.45 (s, 1H), 3.92-3.72 (m, 5H), 3.61 (s, 1H), 1.96 (d, J=7.9 Hz, 1H), 1.84 (d, J=29.3 Hz, 2H), 1.55 (s, 1H), 1.13 (t, J=7.0 Hz, 3H)

Example 38: (R)-3-(6-((6-(3-(2-ethoxyphenoxy) piperidin-1-yl)pyrazin-2-yl)amino)pyridin-3-yl)propanoic Acid

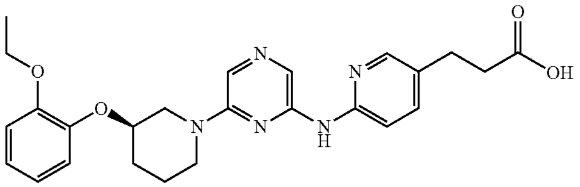 [SMILES: CCOc1ccccc1O[C@@H]1CCCN(c2cncc(Nc3ccc(CCC(=O)O)cn3)n2)C1]

(R,E)-3-(6-((6-(3-(2-ethoxyphenoxy)piperidin-1-yl) pyrazin-2-yl)amino)pyridin-3-yl)acrylic acid (0.3 g, 0.63 mmol) obtained in Example 37 and Pd/C (67 mg) were dissolved in 20 ml of methanol, and a reduction reaction was performed using a hydrogen balloon. After stirring at room temperature for 2 hours, it was filtered and the organic solvent was removed under reduced pressure to obtain the desired product. (Yield 63%)

$^1$H-NMR (500 MHz, CHLOROFORM-D): δ 8.09 (s, 1H), 7.83 (s, 1H), 7.63 (s, 1H), 7.58 (d, J=8.6 Hz, 1H), 7.37-7.32 (m, 1H), 7.12 (s, 1H), 7.01-6.92 (m, 2H), 6.90-6.79 (m, 2H), 4.35-4.27 (m, 1H), 4.19 (d, J=12.8 Hz, 1H), 4.05-3.97 (m, 2H), 3.82 (d, J=11.6 Hz, 1H), 3.67 (s, 3H), 3.42 (dd, J=12.8, 7.9 Hz, 1H), 3.32 (d, J=12.8 Hz, 1H), 2.87 (t, J=7.6 Hz, 2H), 2.60 (t, J=7.6 Hz, 2H), 2.18 (s, 1H), 2.03-1.95 (1H), 1.88 (d, J=9.8 Hz, 1H), 1.69 (s, 1H), 1.37 (t, J=7.0 Hz, 3H)

The title compound was obtained through a hydrolysis reaction of the obtained ester compound (0.15 g, 0.32 mmol) in a similar manner to Example 1. (Yield 57%)

$^1$H-NMR (500 MHz, DMSO-D6): δ 9.44 (s, 1H), 8.05 (d, J=1.8 Hz, 1H), 8.02 (s, 1H), 7.62 (s, 1H), 7.53 (d, J=8.6 Hz, 1H), 7.35 (dd, J=8.6, 2.4 Hz, 1H), 7.00 (dd, J=7.9, 1.8 Hz, 1H), 6.91 (dd, J=7.9, 1.2 Hz, 1H), 6.87 (td, J=7.6, 1.8 Hz, 1H), 6.78 (td, J=7.6, 1.6 Hz, 1H), 4.35-4.24 (m, 1H), 4.06 (d, J=12.8 Hz, 1H), 3.97-3.85 (m, 2H), 3.75-3.64 (m, 1H), 3.47-3.31 (m, 2H), 2.70 (t, J=7.6 Hz, 2H), 2.47 (t, J=1.5 Hz, 2H), 2.02 (s, 1H), 1.83 (s, 1H), 1.70 (d, J=9.2 Hz, 1H), 1.60-1.48 (m, 1H), 1.20 (t, J=7.0 Hz, 3H)

Example 39: (R)-3-(2-((6-(3-(2-ethoxyphenoxy) piperidin-1-yl)pyrazin-2-yl)amino)pyridin-4-yl)-2,2-dimethylpropanoic Acid

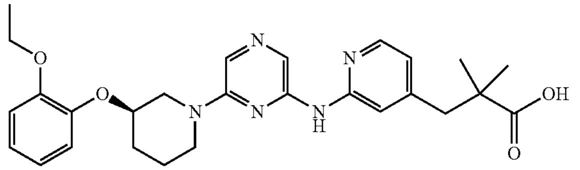 [SMILES: CCOc1ccccc1O[C@@H]1CCCN(c2cncc(Nc3cc(CC(C)(C)C(=O)O)ccn3)n2)C1]

The title compound was obtained in a similar manner to Example 22 by using (R)-2-chloro-6-(3-(2-ethoxyphenoxy) piperidin-1-yl)pyrazine (165 mg, 0.495 mmol) prepared in Preparation Example 1 and tert-butyl 3-(2-aminopyridin-4-yl)-2,2-dimethylpropanoate (124 mg, 0.495 mmol) prepared in Preparation 63. (2 step yield 41%)

$^1$H-NMR (400 MHz, CHLOROFORM-D) δ 9.06 (s, 1H), 8.01-7.82 (m, 2H), 7.60 (s, 1H), 7.55-7.45 (1H), 7.02-6.80 (m, 3H), 6.80-6.65 (m, 2H), 4.40-4.21 (m, 1H), 4.19-4.05 (m, 1H), 4.05-3.94 (m, 2H), 3.81-3.69 (m, 1H), 3.46 (dd, J=13.3, 7.8 Hz, 1H), 3.40-3.22 (m, 1H), 2.81-2.61 (2H), 2.15-2.03 (m, 1H), 1.97 (dd, J=9.8, 3.4 Hz, 1H), 1.91-1.75 (m, 1H), 1.72-1.49 (m, 1H), 1.34 (t, J=7.1 Hz, 3H), 1.22 (d, J=3.2 Hz, 6H)

Example 40: (R)-6-(3-(2-ethoxyphenoxy)piperidin-1-yl)-N-(5-phenylpyridin-2-yl)pyrazin-2-amine

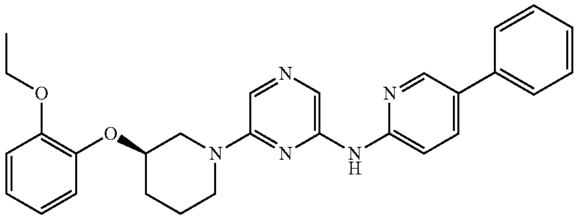 [SMILES: CCOc1ccccc1O[C@@H]1CCCN(c2cncc(Nc3ccc(-c4ccccc4)cn3)n2)C1]

The title compound was obtained in a similar manner to Example 1 by using (R)-2-chloro-6-(3-(2-ethoxyphenoxy)piperidin-1-yl)pyrazine (0.1 g, 0.30 mmol) prepared in Preparation Example 1 and 2-amino-(5-phenyl)pyridine (0.05 g, 0.30 mmol). (Yield 71%)

$^1$H-NMR (500 MHz, CHLOROFORM-D) δ 8.48 (d, J=2.4 Hz, 1H), 7.87 (s, 1H), 7.78-7.70 (2H), 7.67 (s, 1H), 7.61-7.52 (m, 2H), 7.51-7.42 (2H), 7.35 (t, J=7.3 Hz, 1H), 7.32 (s, 1H), 7.06-6.98 (1H), 6.93 (td, J=7.6, 1.2 Hz, 1H), 6.88 (dd, J=7.9, 1.8 Hz, 1H), 6.82 (td, J=7.5, 1.6 Hz, 1H), 4.41-4.29 (m, 1H), 4.22 (dd, J=12.8, 3.7 Hz, 1H), 4.10-3.94 (m, 2H), 3.86 (td, J=8.9, 4.1 Hz, 1H), 3.46 (dd, J=12.8, 7.9 Hz, 1H), 3.39-3.31 (m, 1H), 2.27-2.12 (m, 1H), 2.08-1.98 (m, 1H), 1.96-1.85 (m, 1H), 1.83-1.51 (m, 3H), 1.38 (t, J=7.0 Hz, 3H), 1.29 (d, J=39.7 Hz, 1H), 0.87 (dd, J=26.3, 19.6 Hz, OH)

Example 41: (R)-6-(3-(2-ethoxyphenoxy)piperidin-1-yl)-N-(4-phenylpyridin-2-yl)pyrazin-2-amine

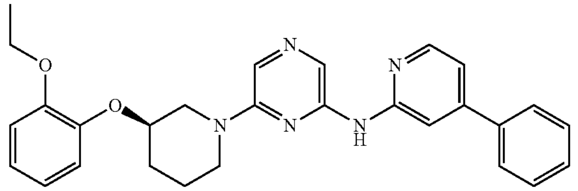 [SMILES: CCOc1ccccc1O[C@@H]1CCCN(c2cncc(Nc3cc(-c4ccccc4)ccn3)n2)C1]

The title compound was obtained in a similar manner to Example 1 by using (R)-2-chloro-6-(3-(2-ethoxyphenoxy)piperidin-1-yl)pyrazine (0.1 g, 0.30 mmol) prepared in Preparation Example 1 and 2-amino-(4-phenyl)pyridine (0.06 g, 0.36 mmol) prepared in Preparation Example 11. (Yield 45%)

$^1$H-NMR (500 MHz, CHLOROFORM-D) δ 8.35 (d, J=5.5 Hz, 1H), 7.92 (d, J=31.8 Hz, 1H), 7.86-7.82 (m, 3H), 7.65 (d, J=37.3 Hz, 1H), 7.50 (s, 1H), 7.35 (dt, J=19.0, 7.2 Hz, 3H), 7.29-7.26 (m, 1H), 6.92 (t, J=7.6 Hz, 2H), 6.84 (d, J=7.9 Hz, 1H), 6.78 (t, J=7.6 Hz, 1H), 5.53 (s, 1H), 4.41-4.26 (m, 1H), 4.11 (q, J=7.1 Hz, 1H), 4.06-3.88 (m, 3H), 3.85-3.70 (m, 1H), 3.61 (q, J=6.7 Hz, 1H), 3.54-3.39 (m, 1H), 2.18-2.06 (m, 2H), 2.05-1.98 (m, 2H), 1.97-1.85 (m, 1H), 1.63 (qd, J=8.8, 4.3 Hz, 1H), 1.44-1.30 (m, 3H), 1.29-1.14 (m, 2H)

Example 42: (R)-2-(3-(2-((6-(3-(2-ethoxyphenoxy)piperidin-1-yl)pyrazin-2-yl)amino)pyridin-4-yl)phenyl)-2-methylpropanoic Acid

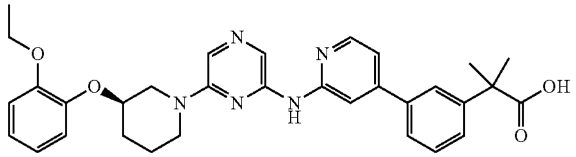 [SMILES: CCOc1ccccc1O[C@@H]1CCCN(c2cncc(Nc3cc(-c4cccc(C(C)(C)C(=O)O)c4)ccn3)n2)C1]

The title compound was obtained in a similar manner to Example 1 by using (R)-2-chloro-6-(3-(2-ethoxyphenoxy)piperidin-1-yl)pyrazine (0.237 g, 0.709 mmol) prepared in Preparation Example 1 and methyl 2-(3-(2-aminopyridin-4-yl)phenyl)-2-methylpropanoate (0.230 g, 0.851 mmol) prepared in Preparation Example 27. (yield 56%)

$^1$H-NMR (500 MHz, CHLOROFORM-D) δ 8.27 (s, 1H), 8.16-8.05 (1H), 7.81 (s, 1H), 7.66 (s, 2H), 7.50 (d, J=8.5 Hz, 2H), 7.40 (t, J=7.6 Hz, 1H), 7.05 (d, J=5.5 Hz, 1H), 6.93-6.84 (m, 2H), 6.81 (d, J=7.0 Hz, 1H), 6.77-6.65 (m, 1H), 4.29 (d, J=3.7 Hz, 1H), 4.10 (d, J=3.1 Hz, 1H), 3.94 (t, J=7.0 Hz, 2H), 3.90-3.79 (1H), 3.58 (dd, J=13.1, 7.6 Hz, 1H), 3.42 (s, 1H), 2.08 (m, 1H), 1.94-1.84 (m, 2H), 1.71 (d, J=8.2 Hz, 6H), 1.67-1.55 (1H), 1.33 (t, J=7.0 Hz, 3H)

Example 43: (R)-2-(4-(2-((6-(3-(2-ethoxyphenoxy)piperidin-1-yl)pyrazin-2-yl)amino)pyridin-4-yl)phenyl)-2-methylpropanoic Acid

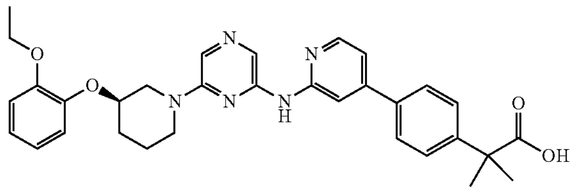 [SMILES: CCOc1ccccc1O[C@@H]1CCCN(c2cncc(Nc3cc(-c4ccc(C(C)(C)C(=O)O)cc4)ccn3)n2)C1]

The title compound was obtained in a similar manner to Example 1 by using (R)-2-chloro-6-(3-(2-ethoxyphenoxy)piperidin-1-yl)pyrazine (0.329 g, 0.986 mmol) prepared in Preparation Example 1 and methyl 2-(4-(2-aminopyridin-4-yl)phenyl)-2-methylpropanoate (0.32 g, 1.184 mmol) prepared in Preparation Example 26. (Yield 1%)

$^1$H-NMR (400 MHz, CHLOROFORM-D) δ 9.51 (s, 1H), 8.45 (d, J=8.7 Hz, 1H), 8.13-7.99 (m, 1H), 7.78 (d, J=10.1 Hz, 1H), 7.71-7.62 (m, 1H), 7.59 (d, J=8.7 Hz, 2H), 7.49 (t, J=9.1 Hz, 2H), 7.13-7.01 (m, 1H), 6.93-6.66 (m, 4H), 4.36-4.23 (m, 1H), 4.16-4.02 (m, 1H), 3.99-3.87 (m, 2H), 3.87-3.77 (m, 1H), 3.57 (dd, J=13.0, 7.5 Hz, 1H), 3.47-3.36 (m, 1H), 2.16-1.79 (m, 3H), 1.61 (s, 7H), 1.35-1.25 (m, 3H)

Example 44: (R)-3-(3-(2-((6-(3-(2-ethoxyphenoxy)piperidin-1-yl)pyrazin-2-yl)amino)pyridin-4-yl)phenyl)-2,2-dimethylpropanoic Acid

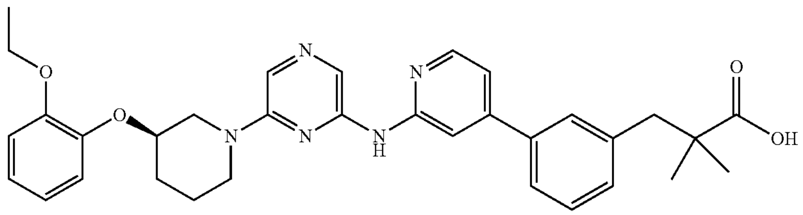 [SMILES: CCOc1ccccc1O[C@@H]1CCCN(c2cncc(Nc3cc(-c4cccc(CC(C)(C)C(=O)O)c4)ccn3)n2)C1]

The title compound was obtained in a similar manner to Example 1 by using (R)-2-chloro-6-(3-(2-ethoxyphenoxy)piperidin-1-yl)pyrazine (210 mg, 0.629 mmol) prepared in Preparation Example 1 and methyl 3-(3-(2-aminopyridin-4-yl)phenyl)-2,2-dimethylpropanoate (179 mg, 0.629 mmol) prepared in Preparation Example 58. (2 step yield 4%)

$^1$H-NMR (CHLOROFORM-D) δ 10.10 (s, 1H), 8.27 (s, 1H), 7.68 (d, J=5.5 Hz, 1H), 7.62 (s, 1H), 7.52 (s, 1H), 7.37 (d, J=7.9 Hz, 1H), 7.33 (t, J=7.5 Hz, 1H), 7.20 (d, J=7.3 Hz, 1H), 6.93 (s, 1H), 6.80 (dd, J=14.6, 7.9 Hz, 2H), 6.74 (d, J=7.9 Hz, 1H), 6.63 (t, J=7.6 Hz, 1H), 6.51 (d, J=4.9 Hz, 1H), 4.37-4.29 (m, 1H), 4.00 (dd, J=13.1, 2.7 Hz, 1H), 3.93-3.87 (m, 2H), 3.86-3.79 (m, 1H), 3.65 (dd, J=12.4, 7.8 Hz, 1H), 3.56-3.47 (m, 1H), 2.94 (dd, J=29.1, 13.0 Hz, 2H), 2.16-2.11 (m, 1H), 2.07-1.90 (m, 2H), 1.73-1.62 (m, 1H), 1.36-1.29 (m, 9H)

Example 45: (R)-3-(4-(2-((6-(3-(2-ethoxyphenoxy)piperidin-1-yl)pyrazin-2-yl)amino)pyridin-4-yl)phenyl)-2,2-dimethylpropanoic Acid

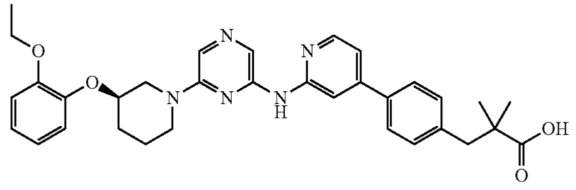 [SMILES: CCOc1ccccc1O[C@@H]1CCCN(c2cncc(Nc3cc(-c4ccc(CC(C)(C)C(=O)O)cc4)ccn3)n2)C1]

The title compound was obtained in a similar manner to Example 1 by using (R)-2-chloro-6-(3-(2-ethoxyphenoxy)piperidin-1-yl)pyrazine (175 mg, 0.524 mmol) prepared in Preparation Example 1 and tert-butyl 3-(4-(2-aminopyridin-4-yl)phenyl)-2,2-dimethylpropanoate (171 mg, 0.524 mmol) prepared in Preparation Example 71. (2 step yield 20%)

$^1$H-NMR (400 MHz, CHLOROFORM-D) δ 9.13 (s, 1H), 8.43-8.28 (1H), 8.08 (d, J=5.5 Hz, 1H), 7.70 (s, 1H), 7.59 (s, 1H), 7.46 (d, J=8.2 Hz, 2H), 7.23 (d, J=8.2 Hz, 2H), 7.02 (d, J=5.5 Hz, 1H), 6.96-6.64 (m, 4H), 4.34-4.18 (m, 1H), 4.01 (d, J=12.8 Hz, 1H), 3.93 (q, J=7.0 Hz, 2H), 3.79 (d, J=12.8 Hz, 1H), 3.50 (dd, J=12.8, 7.8 Hz, 1H), 3.43-3.25 (1H), 2.90 (s, 2H), 2.09-1.99 (m, 1H), 1.98-1.87 (m, 1H), 1.87-1.73 (m, 1H), 1.66-1.45 (m, 1H), 1.29 (q, J=6.9 Hz, 9H)

Example 46: (R)-3-(3-(2-((6-(3-(2-ethoxyphenoxy)piperidin-1-yl)pyrazin-2-yl)amino)pyridin-4-yl)phenyl)propanoic Acid

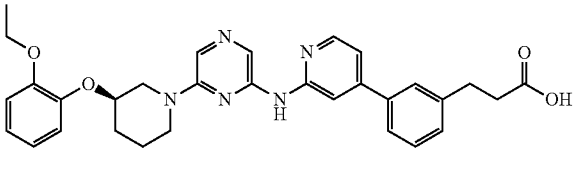 [SMILES: CCOc1ccccc1O[C@@H]1CCCN(c2cncc(Nc3cc(-c4cccc(CCC(=O)O)c4)ccn3)n2)C1]

Step 1: Methyl (R)-3-(3-(2-((6-(3-(2-ethoxyphenoxy)piperidin-1-yl)pyrazin-2-yl)amino)pyridin-4-yl)phenyl)propanoate The desired product was obtained in a similar manner to Example 1 by using (R)-2-chloro-6-(3-(2-ethoxyphenoxy)piperidin-1-yl)pyrazine (0.189 g, 0.568 mmol) prepared in Preparation Example 1 and methyl 3-(3-(2-aminopyridin-4-yl)phenyl)propanoate (0.160 g, 0.624 mmol) prepared in Preparation Example 56. (Yield 64%)

$^1$H-NMR (CHLOROFORM-D) δ 8.32 (d, J=5.2 Hz, 1H), 8.03 (s, 1H), 7.92 (s, 1H), 7.75-7.63 (1H), 7.56-7.45 (m, 2H), 7.37 (t, J=7.5 Hz, 1H), 7.28-7.24 (1H), 7.22 (s, 1H), 7.17-7.02 (m, 1H), 7.01-6.89 (m, 2H), 6.89-6.83 (m, 1H), 6.79 (td, J=7.6, 1.5 Hz, 1H), 4.40-4.25 (m, 1H), 4.22-4.09 (m, 1H), 4.04-3.95 (m, 2H), 3.93 (dt, J=13.1, 4.8 Hz, 1H), 3.70 (s, 3H), 3.58 (dd, J=13.1, 7.9 Hz, 1H), 3.51-3.37 (m, 1H), 3.03 (t, J=7.9 Hz, 2H), 2.69 (t, J=7.8 Hz, 2H), 2.24-2.11 (m, 1H), 2.05-1.97 (m, 1H), 1.97-1.84 (m, 1H), 1.76-1.66 (m, 1H), 1.37 (t, J=6.9 Hz, 3H)

Step 2: (R)-3-(3-(2-((6-(3-(2-ethoxyphenoxy)piperidin-1-yl)pyrazin-2-yl)amino)pyridin-4-yl)phenyl)propanoic Acid Methyl (R)-3-(3-(2-((6-(3-(2-ethoxyphenoxy)piperidin-1-yl)pyrazin-2-yl)amino)pyridin-4-yl)phenyl)propanoate (0.090 g, 0.163 mmol) obtained in step 1 was dissolved in methanol (0.813 ml) and THF (0.813 ml), and then 7 N aqueous sodium hydroxide solution (0.232 ml, 1.626 mmol) was added thereto and stirred at room temperature for 4 hours. After removing the solvent under reduced pressure, it was dissolved in ethyl acetate and washed with water. The title product was obtained by purification with silica gel column. (Yield 29%)

m/z $(M+H)^+$ calculated for $C_{31}H_{34}N_5O_4$: 540. found 540.

Example 47: (R)-3-(3-(5-((6-(3-(2-ethoxyphenoxy) piperidin-1-yl)pyrazin-2-yl)amino)pyridin-3-yl)phenyl)-2,2-dimethylpropanoic Acid

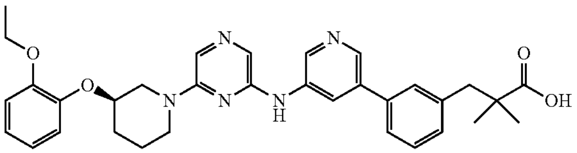 [SMILES: CCOc1ccccc1O[C@@H]1CCCN(c2cncc(Nc3cncc(-c4cccc(CC(C)(C)C(=O)O)c4)c3)n2)C1]

The title compound was obtained in a similar manner to Example 1 by using (R)-2-chloro-6-(3-(2-ethoxyphenoxy) piperidin-1-yl)pyrazine (20.3 mg, 0.0610 mmol) prepared in Preparation Example 1 and methyl 3-(3-(5-aminopyridin-3-yl)phenyl)-2,2-dimethylpropanoate (17.3 mg, 0.0610 mmol) prepared in Preparation Example 83. (2 step yield 29%)

$^1$H-NMR (400 MHz, CHLOROFORM-D) δ 8.50 (s, 1H), 8.24 (d, J=17.4 Hz, 2H), 7.81 (s, 1H), 7.47 (s, 1H), 7.43 (s, 1H), 7.32 (t, J=7.5 Hz, 2H), 7.24 (s, 1H), 7.14 (d, J=7.3 Hz, 1H), 6.90 (d, J=7.8 Hz, 1H), 6.84 (t, J=7.8 Hz, 1H), 6.77 (d, J=6.9 Hz, 1H), 6.74-6.61 (1H), 4.40 (s, 1H), 4.04-3.70 (m, 4H), 3.59 (d, J=12.8 Hz, 1H), 3.48 (d, J=6.9 Hz, 1H), 3.06-2.80 (m, 2H), 2.15-1.81 (m, 3H), 1.56 (d, J=4.6 Hz, 1H), 1.32-1.30 (3H), 1.29 (d, J=3.7 Hz, 6H)

Example 48: (R)-3-(3-(5-((6-(3-(2-ethoxyphenoxy) piperidin-1-yl)pyrazin-2-yl)amino)pyridin-2-yl)phenyl)-2,2-dimethylpropanoic Acid

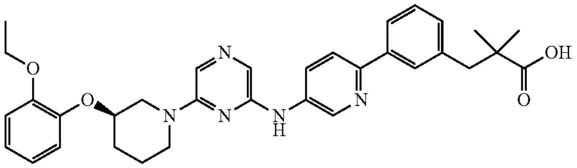 [SMILES: CCOc1ccccc1O[C@@H]1CCCN(c2cncc(Nc3ccc(-c4cccc(CC(C)(C)C(=O)O)c4)nc3)n2)C1]

The title compound was obtained in a similar manner as in Example 1 by using (R)-2-chloro-6-(3-(2-ethoxyphenoxy)piperidin-1-yl)pyrazine (51.9 mg, 0.155 mmol) prepared in Preparation Example 1 and methyl 3-(3-(5-aminopyridin-2-yl)phenyl)-2,2-dimethylpropanoate (44.2 mg, 0.155 mmol) prepared in Preparation Example 102. (2 step yield 60%)

$^1$H-NMR (400 MHz, CHLOROFORM-D) δ 8.54 (d, J=2.7 Hz, 1H), 7.87-7.70 (m, 3H), 7.41 (s, 1H), 7.40-7.31 (m, 2H), 7.20 (d, J=7.3 Hz, 1H), 7.14 (s, 1H), 6.98-6.84 (m, 3H), 6.84-6.74 (m, 1H), 6.70 (s, 1H), 4.37-4.19 (1H), 4.11-3.94 (m, 2H), 3.94-3.84 (m, 1H), 3.62-3.53 (m, 1H), 3.49 (dd, J=12.6, 7.5 Hz, 1H), 3.31-3.15 (m, 1H), 2.99 (dd, J=19.7, 13.3 Hz, 2H), 2.05 (d, J=4.6 Hz, 1H), 2.00-1.90 (m, 1H), 1.90-1.77 (m, 1H), 1.64-1.48 (m, 1H), 1.35 (t, J=7.1 Hz, 3H), 1.30 (d, J=4.6 Hz, 6H)

Example 49: (R)-2-(6-((6-(3-(2-ethoxyphenoxy) piperidin-1-yl)pyrazin-2-yl)amino)pyridin-3-yl)phenyl)-2-methylpropanoic Acid

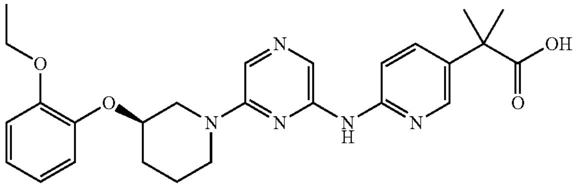

The title compound was obtained in a similar manner as in Example 1 by using (R)-2-chloro-6-(3-(2-ethoxyphenoxy)piperidin-1-yl)pyrazine (137 mg, 0.409 mmol) prepared in Preparation Example 1 and methyl 2-(6-aminopyridin-3-yl)-2-methylpropanoate (79.5 mg, 0.409 mmol) prepared in Preparation Example 19. (2 step yield 30%)

$^1$H-NMR (400 MHz, CHLOROFORM-D) δ 10.36 (s, 1H), 8.21 (s, 1H), 8.07 (d, J=9.1 Hz, 1H), 7.71 (s, 1H), 7.67-7.51 (2H), 7.06-6.70 (m, 4H), 4.42-4.25 (m, 1H), 4.19 (dd, J=13.0, 3.4 Hz, 1H), 4.09-3.89 (m, 2H), 3.81 (td, J=8.8, 4.1 Hz, 1H), 3.42 (dd, J=12.8, 8.2 Hz, 1H), 3.36-3.21 (m, 1H), 2.17 (t, J=6.2 Hz, 1H), 2.01 (dd, J=9.6, 3.7 Hz, 1H), 1.95-1.78 (m, 1H), 1.77-1.46 (m, 7H), 1.44-1.19 (m, 3H)

Example 50: (R)-2-(6-((6-(3-(2-ethoxyphenoxy) piperidin-1-yl)pyrazin-2-yl)amino)pyridin-2-yl)-2-methylpropanoic Acid

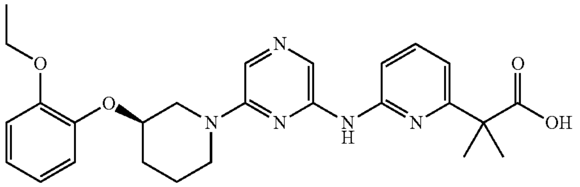 [SMILES: CCOc1ccccc1O[C@@H]1CCCN(c2cncc(Nc3cccc(C(C)(C)C(=O)O)n3)n2)C1]

The title compound was obtained in the same manner as in Example 1 by using (R)-2-chloro-6-(3-(2-ethoxyphenoxy)piperidin-1-yl)pyrazine (56.1 mg, 0.168 mmol) prepared in Preparation Example 1 and ethyl 2-(6-aminopyridin-2-yl)-2-methylpropanoate (35.0 mg, 0.168 mmol) prepared in Preparation Example 61. (2 step yield 39%)

$^1$H-NMR (400 MHz, CHLOROFORM-D) δ 8.05 (s, 1H), 7.65 (s, 1H), 7.62-7.49 (m, 2H), 7.45 (d, J=8.7 Hz, 1H), 7.06-6.73 (m, 5H), 4.41-4.22 (m, 1H), 4.11 (dd, J=13.0, 3.4 Hz, 1H), 4.06-3.87 (m, 2H), 3.77 (td, J=8.9, 4.1 Hz, 1H), 3.51 (dd, J=13.3, 7.8 Hz, 1H), 3.44-3.26 (m, 1H), 2.24-2.10 (m, 1H), 2.04-1.94 (m, 1H), 1.94-1.79 (m, 1H), 1.65 (d, J=2.7 Hz, 6H), 1.63-1.44 (m, 1H), 1.40-1.30 (m, 3H)

Example 51: (R)-3-(6-((6-(3-(2-ethoxyphenoxy)piperidin-1-yl)pyrazin-2-yl)amino)pyridin-2-yl)-2,2-dimethylpropanoic Acid

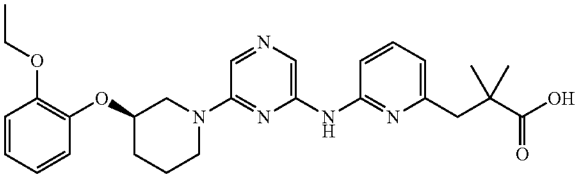 [SMILES: CCOc1ccccc1O[C@@H]1CCCN(c2cncc(Nc3cccc(CC(C)(C)C(=O)O)n3)n2)C1]

The title compound was obtained in a similar manner to Example 22 by using (R)-2-chloro-6-(3-(2-ethoxyphenoxy)piperidin-1-yl)pyrazine (151 mg, 0.451 mmol) prepared in Preparation Example 1 and tert-butyl 3-(6-aminopyridin-2-yl)-2,2-dimethylpropanoate (113 mg, 0.451 mmol) prepared in Preparation Example 62. (2 step yield 27%)

$^1$H-NMR (CHLOROFORM-D) δ 9.67 (s, 1H), 7.91 (d, J=8.2 Hz, 1H), 7.61 (s, 1H), 7.56 (s, 1H), 7.42 (t, J=7.9 Hz, 1H), 7.04-6.90 (m, 2H), 6.87 (d, J=7.6 Hz, 1H), 6.80 (t, J=7.6 Hz, 1H), 6.69 (d, J=7.3 Hz, 1H), 4.28 (td, J=8.1, 4.0 Hz, 1H), 4.23-4.14 (m, 1H), 4.05-3.90 (m, 2H), 3.81 (q, J=4.4 Hz, 1H), 3.37 (dd, J=13.0, 8.1 Hz, 1H), 3.26 (t, J=9.9 Hz, 1H), 2.99 (t, J=14.5 Hz, 2H), 2.18-2.11 (m, 1H), 1.97 (dd, J=9.2, 4.0 Hz, 1H), 1.92-1.78 (m, 1H), 1.72-1.54 (m, 1H), 1.36 (t, J=6.9 Hz, 3H), 1.26 (d, J=4.0 Hz, 6H)

Example 52: 1-(6-((6-((R)-3-(2-ethoxyphenoxy)piperidin-1-yl)pyrazin-2-yl)amino)pyridin-2-yl)pyrrolidine-3-carboxylic Acid

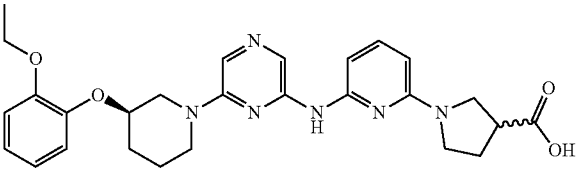 [SMILES: CCOc1ccccc1O[C@@H]1CCCN(c2cncc(Nc3cccc(N4CCC(C(=O)O)C4)n3)n2)C1]

The title compound was obtained in a similar manner to Example 1 by using (R)-2-chloro-6-(3-(2-ethoxyphenoxy)piperidin-1-yl)pyrazine (0.093 g, 0.280 mmol) prepared in Preparation Example 1 and methyl 1-(6-aminopyridin-2-yl)pyrrolidine-3-carboxylate (0.065 g, 0.294 mmol) prepared in Preparation Example 38. (Yield 22%)

$^1$H-NMR (500 MHz, CHLOROFORM-D) δ 8.58 (s, 1H), 7.65 (s, 1H), 7.33 (t, J=7.9 Hz, 1H), 7.09-6.92 (m, 2H), 6.92-6.81 (m, 2H), 6.42 (d, J=6.4 Hz, 1H), 5.94 (d, J=8.2 Hz, 1H), 4.40-4.25 (1H), 4.16 (d, J=12.8 Hz, 1H), 4.10-3.97 (2H), 3.92 (t, J=9.0 Hz, 1H), 3.88-3.77 (m, 2H), 3.68-3.55 (m, 1H), 3.52-3.42 (m, 2H), 3.42-3.29 (m, 1H), 3.23 (t, J=7.0 Hz, 1H), 2.40 (dt, J=20.0, 7.6 Hz, 1H), 2.30 (td, J=12.2, 7.0 Hz, 1H), 2.23-2.13 (m, 1H), 2.05-1.95 (m, 1H), 1.95-1.81 (m, 1H), 1.76-1.50 (m, 1H), 1.39 (t, J=7.0 Hz, 3H)

Example 53: 1-(6-((6-((R)-3-(2-ethoxyphenoxy)piperidin-1-yl)pyrazin-2-yl)amino)pyridin-2-yl)-3-methylpyrrolidine-3-carboxylic Acid

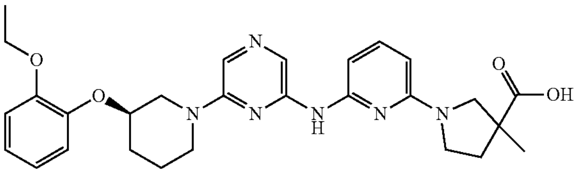

The title compound was obtained in a similar manner to Example 1 by using (R)-2-chloro-6-(3-(2-ethoxyphenoxy)piperidin-1-yl)pyrazine (0.068 g, 0.202 mmol) prepared in Preparation Example 1 and methyl 1-(6-aminopyridin-2-yl)-3-methylpyrrolidine-3-carboxylate (0.050 g, 0.213 mmol) prepared in Preparation Example 49. (Yield 40%)

$^1$H-NMR (500 MHz, CHLOROFORM-D) δ 11.21-9.78 (1H), 8.62 (d, J=16.5 Hz, 1H), 7.75-7.62 (m, 1H), 7.33 (t, J=7.9 Hz, 1H), 7.04-6.99 (m, 1H), 6.99-6.93 (m, 1H), 6.93-6.83 (2H), 6.48-6.32 (m, 1H), 6.02-5.86 (m, 1H), 4.40-4.24 (m, 1H), 4.17 (dd, J=13.1, 3.1 Hz, 1H), 4.12-3.91 (m, 3H), 3.82 (td, J=8.8, 4.1 Hz, 1H), 3.66-3.53 (m, 2H), 3.50 (s, 1H), 3.48 (t, J=6.7 Hz, 1H), 3.43-3.25 (m, 1H), 2.70-2.53 (m, 1H), 2.16 (dd, J=12.4, 5.6 Hz, 1H), 2.03-1.80 (m, 3H), 1.75-1.57 (m, 1H), 1.47 (s, 3H), 1.39 (t, J=6.9 Hz, 3H)

Example 54: 1-(6-((6-((R)-3-(2-ethoxyphenoxy)piperidin-1-yl)pyrazin-2-yl)amino)pyridin-2-yl)piperidine-3-carboxylic Acid

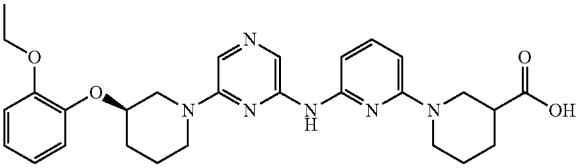 [SMILES: CCOc1ccccc1O[C@@H]1CCCN(c2cncc(Nc3cccc(N4CCCC(C(=O)O)C4)n3)n2)C1]

Step 1: Ethyl 1-(6-((6-((R)-3-(2-ethoxyphenoxy)piperidin-1-yl)pyrazin-2-yl)amino)pyridin-2-yl)piperidine-3-carboxylate The desired product was obtained in a similar manner to Example 1 by using (R)-2-chloro-6-(3-(2-ethoxyphenoxy)piperidin-1-yl)pyrazine (0.224 g, 0.670 mmol) prepared in Preparation Example 1 and ethyl 1-(6-aminopyridin-2-yl)piperidine-3-carboxylate (0.192 g, 0.770 mmol) prepared in Preparation 65. (Yield 38%)

$^1$H-NMR (CHLOROFORM-D) δ 8.14 (d, J=23.8 Hz, 1H), 7.73-7.57 (1H), 7.42-7.32 (1H), 7.03 (d, J=7.9 Hz, 1H), 6.97 (t, J=7.6 Hz, 1H), 6.94-6.77 (m, 3H), 6.70 (d, J=7.9 Hz, 1H), 6.27 (d, J=8.2 Hz, 1H), 4.32 (d, J=10.4 Hz, 2H), 4.26-4.09 (m, 4H), 4.09-3.93 (m, 2H), 3.88 (d, J=12.8 Hz, 1H), 3.42 (dd, J=13.0, 8.1 Hz, 1H), 3.36-3.23 (m, 1H), 3.23-3.08 (m, 1H), 3.00 (t, J=11.9 Hz, 1H), 2.68-2.50 (1H), 2.19 (d, J=7.3 Hz, 1H), 2.09 (d, J=13.1 Hz, 1H), 1.99 (d, J=9.8 Hz, 1H), 1.94-1.84 (m, 1H), 1.84-1.70 (m, 2H), 1.70-1.48 (m, 2H), 1.40 (t, J=6.9 Hz, 3H), 1.34-1.12 (m, 3H)

Step 2: 1-(6-((6-((R)-3-(2-ethoxyphenoxy)piperidin-1-yl)pyrazin-2-yl)amino)pyridin-2-yl)piperidine-3-carboxylic Acid Ethyl 1-(6-((6-((R)-3-(2-ethoxyphenoxy)piperidin-1-yl) pyrazin-2-yl)amino)pyridin-2-yl)piperidine-3-carboxylate (0.140 g, 0.256 mmol) obtained in step 1 was dissolved in ethanol (1.280 ml) and THF (1.280 ml), and then 6N aqueous sodium hydroxide solution (0.427 ml, 2.56 mmol) was added thereto and stirred at room temperature for 6 hours. After removing the solvent under reduced pressure, it was dissolved in ethyl acetate and washed with water. The title product was obtained by purification with silica gel column. (Yield 52%)

m/z $(M+H)^+$ calculated for $C_{28}H_{35}N_6O_4$: 519. found 519.

Example 55: (R)-1-(6-((6-((R)-3-(2-ethoxyphenoxy) piperidin-1-yl)pyrazin-2-yl)amino)pyridin-2-yl)piperidine-3-carboxylic Acid

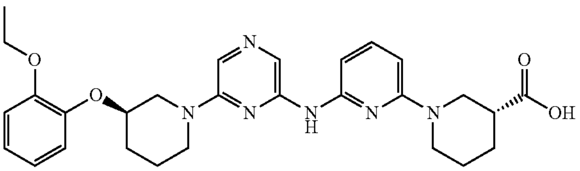

Step 1: Ethyl (R)-1-(6-((6-((R)-3-(2-ethoxyphenoxy)piperidin-1-yl)pyrazin-2-yl)amino)pyridin-2-yl)piperidine-3-carboxylate The desired product was obtained in a similar manner to Example 1 by using (R)-2-chloro-6-(3-(2-ethoxyphenoxy) piperidin-1-yl)pyrazine (0.370 g, 1.108 mmol) prepared in Preparation Example 1 and ethyl (R)-1-(6-aminopyridin-2-yl)piperidine-3-carboxylate (0.290 g, 1.163 mmol) prepared in Preparation Example 31. (Yield 33%)

$^1$H-NMR (500 MHz, CHLOROFORM-D) δ 8.13 (s, 1H), 7.65 (s, 1H), 7.37 (t, J=7.9 Hz, 1H), 7.08-6.84 (m, 4H), 6.78-6.64 (m, 2H), 6.28 (d, J=8.2 Hz, 1H), 4.42-4.27 (m, 2H), 4.27-4.09 (m, 4H), 4.04 (t, J=6.0 Hz, 2H), 3.91 (s, 1H), 3.43 (dd, J=13.0, 8.1 Hz, 1H), 3.31 (s, 1H), 3.24-3.09 (m, 1H), 3.01 (s, 1H), 2.60 (s, 1H), 2.19 (s, 1H), 2.10 (d, J=27.2 Hz, 1H), 2.05-1.95 (1H), 1.95-1.85 (1H), 1.81 (d, J=13.4 Hz, 2H), 1.66 (s, 2H), 1.46-1.38 (3H), 1.30 (t, J=7.2 Hz, 3H)

Step 2: (R)-1-(6-((6-((R)-3-(2-ethoxyphenoxy)piperidin-1-yl)pyrazin-2-yl)amino)pyridin-2-yl)piperidine-3-carboxylic Acid The title compound was obtained in a similar manner to Step 2 of Example 54 by using ethyl (R)-1-(6-((6-((R)-3-(2-ethoxyphenoxy)piperidin-1-yl)pyrazin-2-yl)amino)pyridin-2-yl)piperidine-3-carboxylate (0.200 g, 0.366 mmol) obtained in step 1. (Yield 30%)

m/z $(M+H)^+$ calculated for $C_{28}H_{35}N_6O_4$: 519. found 519.

Example 56: (R)-1-(6-((6-(3-(2-ethoxyphenoxy) piperidin-1-yl)pyrazin-2-yl)amino)pyridin-2-yl)piperidine-4-carboxylic Acid

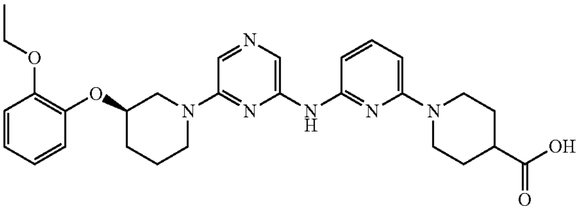 [SMILES: CCOc1ccccc1O[C@@H]1CCCN(c2cncc(Nc3cccc(N4CCC(C(=O)O)CC4)n3)n2)C1]

The title compound was obtained in a similar manner to Example 1 by using (R)-2-chloro-6-(3-(2-ethoxyphenoxy) piperidin-1-yl) pyrazine (0.306 g, 0.917 mmol) prepared in Preparation Example 1 and ethyl 1-(6-aminopyridin-2-yl) piperidin-4-carboxylate (0.240 g, 0.963 mmol) prepared in Preparation Example 29. (Yield 38%)

$^1$H-NMR (500 MHz, CHLOROFORM-D) δ 8.66 (s, 1H), 7.70-7.62 (1H), 7.39 (t, J=7.9 Hz, 1H), 7.05-6.87 (m, 4H), 6.73 (s, 1H), 6.25 (q, J=4.1 Hz, 2H), 4.43-4.28 (m, 1H), 4.24 (dd, J=12.8, 4.3 Hz, 2H), 4.15 (q, J=7.2 Hz, 2H), 3.82 (d, J=18.3 Hz, 1H), 3.54 (dd, J=12.8, 7.6 Hz, 1H), 3.46-3.30 (m, 1H), 3.04 (t, J=11.4 Hz, 2H), 2.60 (d, J=10.7 Hz, 1H), 2.16 (d, J=12.2 Hz, 3H), 2.02 (s, 1H), 1.96-1.79 (m, 3H), 1.65 (s, 1H), 1.40 (t, J=7.0 Hz, 3H)

Example 57: (R)-2-(1-(6-((6-(3-(2-ethoxyphenoxy) piperidin-1-yl)pyrazin-2-yl)amino)pyridin-2-yl)piperidin-4-yl)acetic Acid

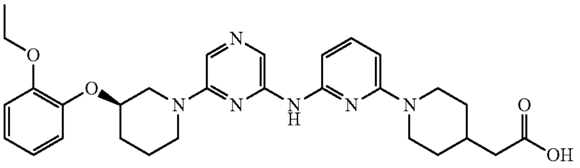 [SMILES: CCOc1ccccc1O[C@@H]1CCCN(c2cncc(Nc3cccc(N4CCC(CC(=O)O)CC4)n3)n2)C1]

The title compound was obtained in a similar manner to Example 12 by using (R)-2-chloro-6-(3-(2-ethoxyphenoxy) piperidin-1-yl)pyrazine (0.237 g, 0.710 mmol) obtained in Preparation Example 1 and ethyl 2-(1-(6-aminopyridin-2-yl)piperidin-4-yl)acetate (0.17 g, 0.646 mmol) obtained in Preparation Example 36. (2 step yield 11%)

$^1$H-NMR (400 MHz, CHLOROFORM-D) δ 8.25 (d, J=15.6 Hz, 1H), 7.63-7.54 (m, 1H), 7.33 (t, J=8.2 Hz, 1H), 7.05-6.90 (m, 2H), 6.90-6.78 (m, 2H), 6.58 (d, J=7.8 Hz, 1H), 6.24-6.16 (m, 1H), 5.28 (s, 1H), 4.39-4.25 (m, 1H), 4.24-4.10 (m, 3H), 4.07-3.91 (m, 2H), 3.88-3.75 (m, 1H), 3.53-3.36 (1H), 3.36-3.24 (m, 1H), 2.86 (t, J=11.7 Hz, 2H), 2.37-2.20 (m, 2H), 2.20-2.10 (m, 1H), 2.07-2.01 (m, 1H), 2.01-1.92 (1H), 1.92-1.77 (m, 3H), 1.73-1.53 (m, 1H), 1.44-1.29 (m, 5H)

Example 58: (R)-2-(1-(6-((6-(3-(2-ethoxyphenoxy)piperidin-1-yl)pyrazin-2-yl)amino)pyridin-2-yl)piperidin-4-yl)-2-methylpropanoic Acid

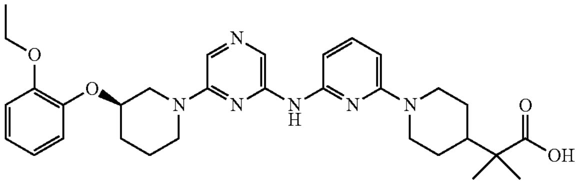 [SMILES: CCOc1ccccc1O[C@@H]1CCCN(c2cncc(Nc3cccc(N4CCC(C(C)(C)C(=O)O)CC4)n3)n2)C1]

The title compound was obtained in a similar manner to Example 12 by using (R)-2-chloro-6-(3-(2-ethoxyphenoxy)piperidin-1-yl)pyrazine (0.093 g, 0.278 mmol) obtained in Preparation Example 1 and methyl 2-(1-(6-aminopyridin-2-yl)piperidin-4-yl)-2-methylpropanoate (0.07 g, 0.252 mmol) obtained in Preparation Example 34. (2 step yield 49%)

$^1$H-NMR (400 MHz, CHLOROFORM-D) δ 8.20 (s, 1H), 7.59 (s, 1H), 7.38 (s, 1H), 7.32 (q, J=8.1 Hz, 1H), 7.04-6.90 (m, 2H), 6.90-6.79 (2H), 6.64 (d, J=7.8 Hz, 1H), 6.20 (d, J=8.2 Hz, 1H), 4.29 (q, J=4.1 Hz, 3H), 4.22-4.13 (m, 1H), 4.06-3.91 (m, 2H), 3.82 (q, J=4.4 Hz, 1H), 3.42 (dd, J=13.0, 8.0 Hz, 1H), 3.36-3.23 (1H), 2.86-2.69 (m, 2H), 2.23-2.10 (m, 1H), 1.96 (dd, J=9.6, 3.7 Hz, 1H), 1.91-1.77 (m, 2H), 1.72 (d, J=11.9 Hz, 2H), 1.67-1.52 (m, 1H), 1.52-1.40 (m, 1H), 1.40-1.29 (m, 3H), 1.24 (q, J=7.3 Hz, 1H), 1.15 (d, J=16.9 Hz, 6H)

Example 59: 2-(((S)-1-(6-((6-((R)-3-(2-ethoxyphenoxy)piperidin-1-yl)pyrazin-2-yl)amino)pyridin-2-yl)piperidin-3-yl)acetic Acid

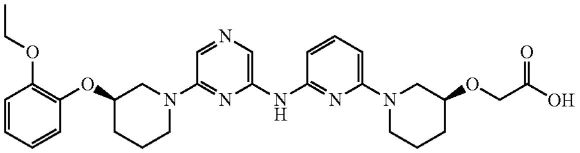 [SMILES: CCOc1ccccc1O[C@@H]1CCCN(c2cncc(Nc3cccc(N4CCC[C@H](OCC(=O)O)C4)n3)n2)C1]

The desired title compound was obtained in a similar manner to Example 19 by using (R)-2-chloro-6-(3-(2-ethoxyphenoxy)piperidin-1-yl)pyrazine (0.047 g, 0.139 mmol) prepared in Preparation Example 1 and tert-butyl (S)-2-((1-(6-aminopyridin-2-yl)piperidin-3-yl)oxy)acetate (0.045 g, 0.146 mmol) prepared in Preparation Example 45. (Yield 11.4%)

$^1$H-NMR (500 MHz, CHLOROFORM-D) δ 8.66 (s, 1H), 7.68 (s, 1H), 7.36 (t, J=7.9 Hz, 1H), 7.07-6.93 (2H), 6.89 (t, J=7.3 Hz, 2H), 6.34 (s, 1H), 6.25-6.15 (1H), 4.78-4.44 (1H), 4.31 (s, 2H), 4.19-4.06 (2H), 4.06-3.93 (2H), 3.77 (s, 1H), 3.64 (s, 1H), 3.59-3.44 (m, 2H), 3.44-3.28 (1H), 3.15 (s, 1H), 3.00 (s, 1H), 2.13 (s, 1H), 2.08 (d, J=13.1 Hz, 1H), 2.02-1.93 (1H), 1.93-1.80 (2H), 1.60 (s, 3H), 1.39 (t, J=7.0 Hz, 3H)

Example 60: (R)-2-(3-(6-((6-(3-(2-ethoxyphenoxy)piperidin-1-yl)pyrazin-2-yl)amino)pyridin-2-yl)phenyl)-2-methylpropanoic Acid

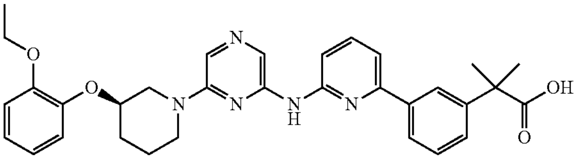 [SMILES: CCOc1ccccc1O[C@@H]1CCCN(c2cncc(Nc3cccc(-c4cccc(C(C)(C)C(=O)O)c4)n3)n2)C1]

The desired title compound was obtained in a similar manner to Example 1 by using (R)-2-chloro-6-(3-(2-ethoxyphenoxy)piperidin-1-yl)pyrazine (74.1 mg, 0.222 mmol) prepared in Preparation Example 1 and methyl 2-(3-(6-aminopyridin-2-yl)phenyl)-2-methylpropanoate (60.0 mg, 0.222 mmol) prepared in Preparation Example 52. (2 step yield 66%)

$^1$H-NMR (400 MHz, CHLOROFORM-D) δ 8.84 (s, 1H), 8.23 (s, 1H), 7.68 (d, J=9.1 Hz, 2H), 7.59 (t, J=8.0 Hz, 1H), 7.51-7.36 (m, 2H), 7.33 (s, 1H), 7.28 (s, 1H), 7.05-6.92 (m, 3H), 6.88 (dq, J=9.7, 1.9 Hz, 2H), 4.33 (td, J=7.8, 3.8 Hz, 1H), 4.14 (dd, J=12.8, 3.2 Hz, 1H), 4.08-3.90 (2H), 3.82 (q, J=4.4 Hz, 1H), 3.52 (dd, J=12.8, 7.8 Hz, 1H), 3.46-3.28 (m, 1H), 2.00 (d, J=9.6 Hz, 2H), 1.95-1.80 (m, 1H), 1.74-1.53 (m, 7H), 1.38 (t, J=7.1 Hz, 3H)

Example 61: (R)-2-(4-(6-((6-(3-(2-ethoxyphenoxy)piperidin-1-yl)pyrazin-2-yl)amino)pyridin-2-yl)phenyl)-2-methylpropanoic Acid

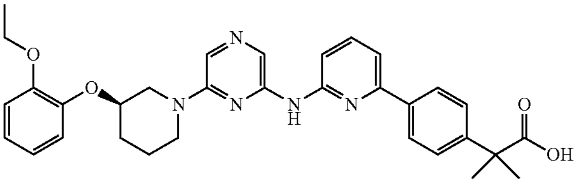 [SMILES: CCOc1ccccc1O[C@@H]1CCCN(c2cncc(Nc3cccc(-c4ccc(C(C)(C)C(=O)O)cc4)n3)n2)C1]

The title compound was obtained in a similar manner to Example 1 by using (R)-2-chloro-6-(3-(2-ethoxyphenoxy)piperidin-1-yl)pyrazine (61.7 mg, 0.185 mmol) prepared in Preparation Example 1 and methyl 2-(4-(6-aminopyridin-2-yl)phenyl)-2-methylpropanoate (50.0 mg, 0.185 mmol) prepared in Preparation Example 54. (2 step yield 16%)

$^1$H-NMR (400 MHz, CHLOROFORM-D) δ 9.10 (s, 1H), 8.01 (s, 1H), 7.86-7.71 (m, 3H), 7.68 (s, 1H), 7.56 (t, J=8.0 Hz, 1H), 7.47 (d, J=8.2 Hz, 2H), 7.16 (d, J=7.3 Hz, 1H), 7.08-6.74 (m, 4H), 4.43-4.26 (m, 1H), 4.20 (dd, J=13.3, 3.2 Hz, 1H), 4.11-3.93 (m, 2H), 3.85 (q, J=4.4 Hz, 1H), 3.49 (dd, J=13.0, 8.0 Hz, 1H), 3.43-3.26 (m, 1H), 2.28-2.09 (m, 1H), 2.09-1.97 (m, 1H), 1.96-1.80 (m, 1H), 1.78-1.65 (m, 1H), 1.63 (s, 6H), 1.38 (t, J=6.9 Hz, 3H)

Example 62: (R)-2-(4-(6-((6-(3-((3-ethoxypyridin-2-yl)oxy)piperidin-1-yl)pyrazin-2-yl)amino)pyridin-2-yl)phenyl)-2-methylpropanoic Acid

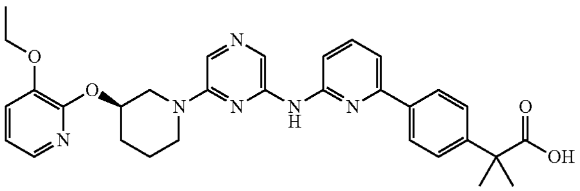 [SMILES: CCOc1cccnc1O[C@@H]1CCCN(c2cncc(Nc3cccc(-c4ccc(C(C)(C)C(=O)O)cc4)n3)n2)C1]

The title compound was obtained in a similar manner to Example 12 by using (R)-2-chloro-6-(3-((3-ethoxypyridin-2-yl)oxy)piperidin-1-yl)pyrazine (0.272 g, 0.814 mmol) obtained in Preparation Example 3 and methyl 2-(4-(6-aminopyridin-2-yl)phenyl)-2-methylpropanoate (0.2 g, 0.740 mmol) obtained in Preparation Example 54. (2 step yield 43%)

$^1$H-NMR (400 MHz, METHANOL-D4) δ 8.30-8.19 (m, 1H), 7.97 (td, J=4.3, 2.3 Hz, 2H), 7.65-7.49 (m, 3H), 7.46 (dd, J=8.7, 2.3 Hz, 2H), 7.29 (ddd, J=19.4, 7.8, 2.5 Hz, 2H), 7.07-6.94 (m, 1H), 6.82-6.64 (m, 1H), 5.18 (d, J=2.7 Hz, 1H), 4.12-4.02 (m, 2H), 3.90-3.79 (m, 2H), 3.79-3.69 (m, 2H), 3.66-3.48 (1H), 2.20-2.00 (m, 2H), 1.96 (d, J=4.6 Hz, 1H), 1.70-1.60 (1H), 1.57 (d, J=2.3 Hz, 6H), 1.22-1.19 (m, 3H)

Example 63: (R)-3-(3-(6-((6-(3-(2-ethoxyphenoxy)piperidin-1-yl)pyrazin-2-yl)amino)pyridin-2-yl)phenyl)-2,2-dimethylpropanoic Acid

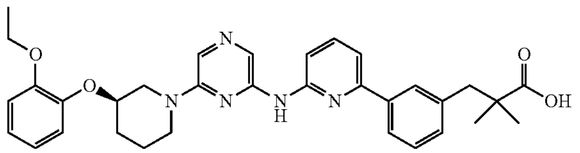 [SMILES: CCOc1ccccc1O[C@@H]1CCCN(c2cncc(Nc3cccc(-c4cccc(CC(C)(C)C(=O)O)c4)n3)n2)C1]

The title compound was obtained in a similar manner to Example 22 by using (R)-2-chloro-6-(3-(2-ethoxyphenoxy)piperidin-1-yl)pyrazine (81.0 mg, 0.242 mmol) prepared in Preparation Example 1 and tert-butyl 3-(3-(6-aminopyridin-2-yl)phenyl)-2,2-dimethylpropanoate (79.0 mg, 0.242 mmol) prepared in Preparation Example 113. (2 step yield 77%)

$^1$H-NMR (400 MHz, CHLOROFORM-D) δ 9.57 (s, 1H), 8.22 (s, 1H), 7.68 (d, J=7.8 Hz, 1H), 7.65 (s, 1H), 7.60 (t, J=7.8 Hz, 1H), 7.33 (t, J=7.5 Hz, 2H), 7.15 (d, J=7.8 Hz, 1H), 7.08-6.82 (4H), 6.78 (s, 1H), 6.58 (d, J=8.2 Hz, 1H), 4.42-4.23 (m, 1H), 4.17-4.04 (m, 1H), 4.04-3.88 (m, 2H), 3.80 (dt, J=13.3, 4.9 Hz, 1H), 3.56 (dd, J=13.0, 7.5 Hz, 1H), 3.44-3.28 (m, 1H), 3.01 (s, 2H), 2.21-2.08 (m, 1H), 2.08-1.94 (m, 1H), 1.94-1.80 (m, 1H), 1.72-1.50 (m, 1H), 1.38 (t, J=7.1 Hz, 3H), 1.25 (s, 6H)

Example 64: (R)-3-(3-(6-((6-(3-((3-ethoxypyridin-2-yl)oxy)piperidin-1-yl)pyrazin-2-yl)amino)pyridin-2-yl)phenyl)-2,2-dimethylpropanoic Acid

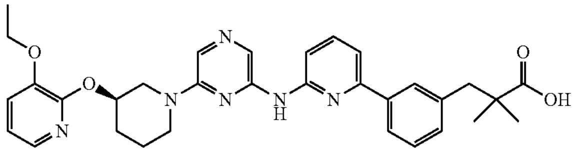 [SMILES: CCOc1cccnc1O[C@@H]1CCCN(c2cncc(Nc3cccc(-c4cccc(CC(C)(C)C(=O)O)c4)n3)n2)C1]

The title compound was obtained in a similar manner to Example 22 by using (R)-2-chloro-6-(3-((3-ethoxypyridin-2-yl)oxy)piperidin-1-yl)pyrazine (205 mg, 0.613 mmol) prepared in Preparation Example 3 and tert-butyl 3-(3-(6-aminopyridin-2-yl)phenyl)-2,2-dimethylpropanoate (200 mg, 0.613 mmol) prepared in Preparation Example 113. (2 step yield 39%)

$^1$H-NMR (CHLOROFORM-D) δ 9.54 (s, 1H), 8.24 (s, 1H), 7.77 (d, J=5.2 Hz, 1H), 7.70 (d, J=4.6 Hz, 2H), 7.62 (t, J=7.9 Hz, 1H), 7.36 (d, J=7.6 Hz, 2H), 7.18 (d, J=7.6 Hz, 1H), 6.93 (d, J=7.6 Hz, 1H), 6.83 (dd, J=7.6, 5.2 Hz, 1H), 6.61 (s, 1H), 6.55 (d, J=7.9 Hz, 1H), 5.30-5.14 (1H), 4.05-3.80 (4H), 3.80-3.68 (1H), 3.68-3.54 (1H), 3.12-2.90 (2H), 2.28-2.12 (1H), 2.12-1.93 (2H), 1.78-1.63 (1H), 1.33-1.29 (3H), 1.29-1.27 (3H), 1.27-1.24 (3H)

Example 65: (R)-3-(3-(6-((6-(3-(2-ethoxyphenoxy)piperidin-1-yl)pyridin-2-yl)amino)pyridin-2-yl)phenyl)-2,2-dimethylpropanoic Acid

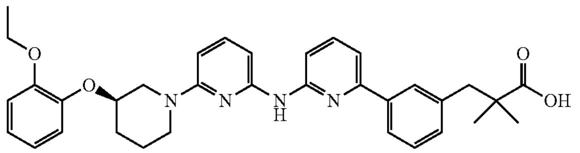 [SMILES: CCOc1ccccc1O[C@@H]1CCCN(c2cccc(Nc3cccc(-c4cccc(CC(C)(C)C(=O)O)c4)n3)n2)C1]

The title compound was obtained in a similar manner to Example 22 by using (R)-2-chloro-6-(3-(2-ethoxyphenoxy)piperidin-1-yl)pyridine (204 mg, 0.613 mmol) prepared in Preparation Example 4 and tert-butyl 3-(3-(6-aminopyridin-2-yl)phenyl)-2,2-dimethylpropanoate (200 mg, 0.613 mmol) prepared in Preparation Example 113. (2 step yield 12%)

$^1$H-NMR (400 MHz, METHANOL-D4) δ 7.80 (d, J=8.7 Hz, 2H), 7.63-7.47 (m, 2H), 7.44 (t, J=8.0 Hz, 1H), 7.35 (t, J=7.8 Hz, 1H), 7.24 (d, J=7.8 Hz, 2H), 7.04-6.70 (m, 5H), 6.28 (d, J=8.2 Hz, 1H), 4.41-4.22 (m, 1H), 4.12 (d, J=11.4 Hz, 1H), 4.04-3.87 (m, 2H), 3.76 (d, J=12.8 Hz, 1H), 3.47-3.32 (m, 2H), 2.96 (s, 2H), 2.15-2.03 (m, 1H), 1.94 (td, J=6.6, 3.2 Hz, 1H), 1.88-1.72 (m, 1H), 1.71-1.53 (m, 1H), 1.31 (t, J=6.9 Hz, 3H), 1.21 (s, 6H)

Example 66: (R)-3-(3-(6-((2-(3-(2-ethoxyphenoxy)piperidin-1-yl)pyrimidin-4-yl)amino)pyridin-2-yl)phenyl)-2,2-dimethylpropanoic Acid

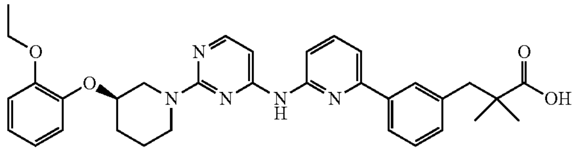 [SMILES: CCOc1ccccc1O[C@@H]1CCCN(c2nccc(Nc3cccc(-c4cccc(CC(C)(C)C(=O)O)c4)n3)n2)C1]

The title compound was obtained in a similar manner to Example 22 by using (R)-4-chloro-2-(3-(2-ethoxyphenoxy)piperidin-1-yl)pyrimidine (205 mg, 0.613 mmol) prepared in Preparation Example 5 and tert-butyl 3-(3-(6-aminopyridin-2-yl)phenyl)-2,2-dimethylpropanoate (200 mg, 0.613 mmol) prepared in Preparation Example 113. (2 step yield 49%)

$^1$H-NMR (CHLOROFORM-D) δ 8.28 (s, 1H), 7.98 (d, J=5.8 Hz, 1H), 7.76 (s, 1H), 7.67 (d, J=7.6 Hz, 1H), 7.45 (t, J=7.3 Hz, 2H), 7.33 (t, J=7.6 Hz, 1H), 7.20 (d, J=7.6 Hz, 1H), 7.12 (d, J=7.3 Hz, 1H), 7.04 (d, J=7.9 Hz, 1H), 6.96-6.86 (m, 2H), 6.83 (d, J=7.6 Hz, 1H), 6.46 (s, 1H), 4.51 (d, J=12.8 Hz, 1H), 4.39-4.24 (m, 1H), 4.19 (q, J=4.5 Hz, 1H), 4.08-3.86 (m, 2H), 3.48 (d, J=21.4 Hz, 1H), 3.37 (d, J=12.8 Hz, 1H), 2.96 (s, 2H), 2.20 (dd, J=15.4, 4.1 Hz, 1H), 1.94 (dt, J=9.2, 3.8 Hz, 1H), 1.88 (dd, J=9.9, 3.5 Hz, 1H), 1.70-1.56 (m, 1H), 1.37 (t, J=6.9 Hz, 3H), 1.24 (s, 6H)

Example 67: (R)-3-(3-(6-((4-(3-(2-ethoxyphenoxy)piperidin-1-yl)pyrimidin-2-yl)amino)pyridin-2-yl)phenyl)-2,2-dimethylpropanoic Acid

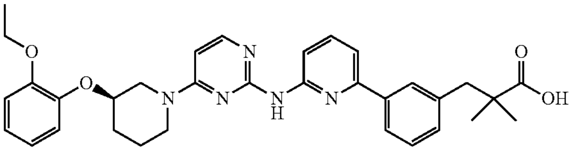

The title compound was obtained in a similar manner to Example 22 by using (R)-2-chloro-4-(3-(2-ethoxyphenoxy)piperidin-1-yl)pyrimidine (205 mg, 0.613 mmol) prepared in Preparation Example 6 and tert-butyl 3-(3-(6-aminopyridin-2-yl)phenyl)-2,2-dimethylpropanoate (200 mg, 0.613 mmol) prepared in Preparation Example 113. (2 step yield 46%)

$^1$H-NMR (400 MHz, METHANOL-D4) δ 8.23 (d, J=6.4 Hz, 1H), 7.84 (s, 1H), 7.76 (t, J=7.1 Hz, 2H), 7.48 (t, J=7.3 Hz, 2H), 7.38 (t, J=7.5 Hz, 1H), 7.28 (d, J=7.8 Hz, 1H), 7.00 (d, J=7.3 Hz, 1H), 6.96-6.76 (m, 3H), 6.45 (d, J=5.9 Hz, 1H), 4.55 (s, 1H), 4.28-4.01 (m, 2H), 4.01-3.73 (m, 3H), 3.59 (d, J=9.1 Hz, 1H), 2.95 (s, 2H), 2.15-1.98 (m, 3H), 1.76-1.58 (m, 1H), 1.30 (t, J=6.9 Hz, 3H), 1.21 (s, 6H)

Example 68: (R)-3-(3-(6-((4-(3-((3-ethoxypyridin-2-yl)oxy)piperidin-1-yl)pyrimidin-2-yl)amino)pyridin-2-yl)phenyl)-2,2-dimethylpropanoic Acid

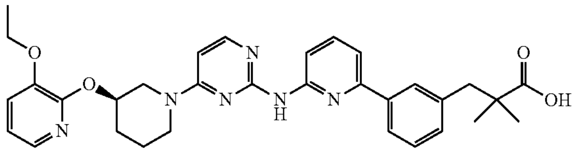 [SMILES: CCOc1cccnc1O[C@@H]1CCCN(c2ccnc(Nc3cccc(-c4cccc(CC(C)(C)C(=O)O)c4)n3)n2)C1]

The title compound was obtained in a similar manner to Example 22 by using (R)-2-chloro-4-(3-((3-ethoxypyridin-2-yl)oxy)piperidin-1-yl)pyrimidine (205 mg, 0.613 mmol) prepared in Preparation Example 7 and tert-butyl 3-(3-(6-aminopyridin-2-yl)phenyl)-2,2-dimethylpropanoate (200 mg, 0.613 mmol) prepared in Preparation Example 113. (2 step yield 29%)

$^1$H-NMR (400 MHz, CHLOROFORM-D) δ 9.40 (s, 1H), 8.16 (s, 1H), 7.82 (s, 2H), 7.70 (d, J=7.8 Hz, 1H), 7.60 (s, 1H), 7.49 (d, J=20.1 Hz, 1H), 7.36-7.27 (m, 2H), 7.21 (d, J=7.3 Hz, 1H), 6.98 (d, J=7.3 Hz, 1H), 6.69 (s, 1H), 6.05 (s, 1H), 5.28 (t, J=2.7 Hz, 1H), 4.09-3.82 (m, 4H), 3.70 (s, 2H), 3.02 (d, J=13.3 Hz, 2H), 2.16-1.94 (m, 3H), 1.69 (s, 1H), 1.30 (t, J=7.1 Hz, 3H), 1.26 (d, J=1.4 Hz, 6H)

Example 69: (R)-3-(3-(3-((6-(3-(2-ethoxyphenoxy)piperidin-1-yl)pyrazin-2-yl)amino)-1H-pyrazol-1-yl)phenyl)-2,2-dimethylpropanoic Acid

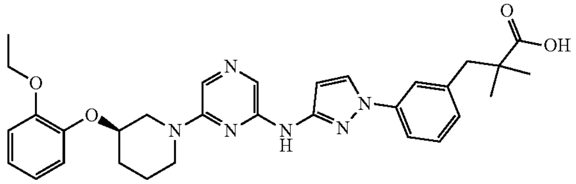 [SMILES: CCOc1ccccc1O[C@@H]1CCCN(c2cncc(Nc3ccn(-c4cccc(CC(C)(C)C(=O)O)c4)n3)n2)C1]

The title compound was obtained in a similar manner to Example 22 by using (R)-2-chloro-6-(3-(2-ethoxyphenoxy)piperidin-1-yl)pyrazine (0.10 g, 0.30 mmol) prepared in Preparation Example 1 and methyl 3-(3-(3-amino-1H-pyrazol-1-yl)phenyl)-2,2-dimethylpropanoate (0.094 g, 0.30 mmol) obtained in Preparation Example 67. (Yield 40%)

$^1$H-NMR (400 MHz, CHLOROFORM-D): δ 8.53 (s, 1H), 7.61 (s, 2H), 7.57 (s, 1H), 7.50 (s, 1H), 7.35-7.27 (m, 2H), 7.06 (t, J=2.5 Hz, 1H), 7.00-6.88 (m, 2H), 6.88-6.72 (m, 2H), 6.51 (d, J=2.3 Hz, 1H), 4.25 (t, J=3.9 Hz, 1H), 4.21-4.14 (m, 1H), 3.98 (qd, J=6.9, 1.5 Hz, 2H), 3.79 (q, J=4.4 Hz, 1H), 3.42-3.17 (m, 2H), 2.99 (s, 2H), 2.20-2.08 (m, 1H), 1.99-1.77 (m, 2H), 1.64-1.54 (m, 1H), 1.35 (t, J=7.1 Hz, 3H), 1.26 (s, 6H)

Example 70: (R)-3-(3-(6-((2-(3-(2-ethoxyphenoxy)piperidin-1-yl)-5-(trifluoromethyl)pyrimidin-4-yl)amino)pyridin-2-yl)phenyl)-2,2-dimethylpropanoic Acid

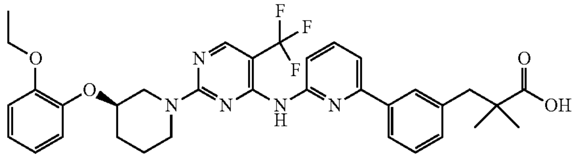 [SMILES: CCOc1ccccc1O[C@@H]1CCCN(c2ncc(C(F)(F)F)c(Nc3cccc(-c4cccc(CC(C)(C)C(=O)O)c4)n3)n2)C1]

The title compound was obtained in a similar manner to Example 22 by using (R)-4-chloro-2-(3-(2-ethoxyphenoxy)piperidin-1-yl)-5-(trifluoromethyl)pyrimidine (79 mg, 0.20 mmol) of Preparation Example 9 and tert-butyl 3-(3-(6-aminopyridin-2-yl)phenyl)-2,2-dimethylpropanoate (64 mg, 0.20 mmol) synthesized in Preparation Example 113. (2 step yield 65%)

$^1$H-NMR (400 MHz, METHANOL-D4) δ 8.25 (s, 1H), 7.80 (d, J=7.8 Hz, 1H), 7.75 (s, 1H), 7.68 (s, OH), 7.44 (d, J=4.1 Hz, 1H), 7.38-7.28 (1H), 7.24 (d, J=7.8 Hz, 1H), 7.06-6.43 (m, 5H), 4.46 (s, 1H), 4.07 (q, J=7.2 Hz, 2H), 3.98-3.56 (m, 4H), 2.94 (s, 2H), 2.13-1.88 (m, 4H), 1.59 (d, J=3.7 Hz, 1H), 1.21 (t, J=7.1 Hz, 3H), 1.18 (s, 6H)

Example 71: (R)-3-(3-(6-((4-(3-(2-ethoxyphenoxy)piperidin-1-yl)-5-(trifluoromethyl)pyrimidin-2-yl)amino)pyridin-2-yl)phenyl)-2,2-dimethylpropanoic Acid

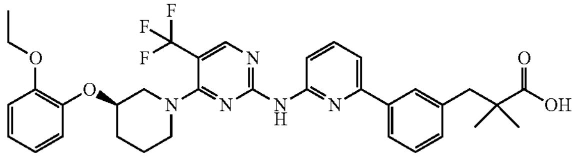 [SMILES: CCOc1ccccc1O[C@@H]1CCCN(c2nc(Nc3cccc(-c4cccc(CC(C)(C)C(=O)O)c4)n3)ncc2C(F)(F)F)C1]

The title compound was obtained in a similar manner to Example 22 by using (R)-2-chloro-4-(3-(2-ethoxyphenoxy)piperidin-1-yl)-5-(trifluoromethyl)pyrimidine (135 mg, 0.38 mmol) synthesized in Preparation Example 10 and tert-butyl 3-(3-(6-aminopyridin-2-yl)phenyl)-2,2-dimethylpropanoate (110 mg, 0.238 mmol) synthesized in Preparation Example 113. (2 step yield 18%)

$^1$H-NMR (400 MHz, METHANOL-D4) δ 9.34 (s, 1H), 8.89 (s, 1H), 8.85-8.74 (m, 1H), 8.23 (d, J=2.7 Hz, 1H), 7.91 (q, J=1.4 Hz, 1H), 7.33-7.19 (m, 3H), 7.19-7.06 (m, 4H), 7.01 (t, J=7.5 Hz, 1H), 3.99 (q, J=7.0 Hz, 2H), 3.72 (s, 2H), 2.82 (s, 2H), 1.18-1.01 (m, 9H)

Example 72: (R)-3-(4-(6-((6-(3-(2-ethoxyphenoxy)piperidin-1-yl)pyrazin-2-yl)amino)pyridin-2-yl)phenyl)-2,2-dimethylpropanoic Acid

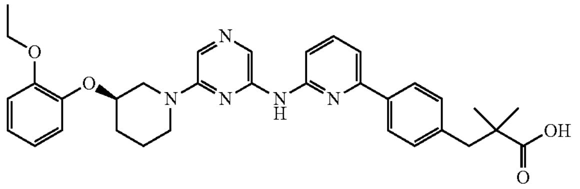 [SMILES: CCOc1ccccc1O[C@@H]1CCCN(c2cncc(Nc3cccc(-c4ccc(CC(C)(C)C(=O)O)cc4)n3)n2)C1]

The title compound was obtained in a similar manner to Example 22 by using (R)-2-chloro-6-(3-(2-ethoxyphenoxy)piperidin-1-yl)pyrazine (146 mg, 0.438 mmol) prepared in Preparation Example 1 and tert-butyl 3-(4-(6-aminopyridin-2-yl)phenyl)-2,2-dimethylpropanoate (143 mg, 0.438 mmol) prepared in Preparation Example 77. (2 step yield 71%)

$^1$H-NMR (400 MHz, CHLOROFORM-D) δ 8.16 (s, 1H), 8.02 (s, 1H), 7.85 (d, J=8.2 Hz, 2H), 7.67 (s, 1H), 7.55 (q, J=8.1 Hz, 1H), 7.48 (d, J=8.2 Hz, 1H), 7.40-7.29 (m, 2H), 7.24-7.15 (m, 1H), 7.08-6.76 (m, 4H), 4.32 (td, J=7.9, 4.0 Hz, 1H), 4.18 (dd, J=13.5, 3.4 Hz, 1H), 4.07-3.91 (m, 2H), 3.83 (td, J=9.0, 4.1 Hz, 1H), 3.48 (dd, J=13.0, 8.0 Hz, 1H), 3.42-3.25 (m, 1H), 2.94 (s, 2H), 2.27-2.11 (m, 1H), 2.04-1.95 (m, 1H), 1.95-1.79 (m, 1H), 1.76-1.53 (m, 1H), 1.37 (t, J=7.1 Hz, 3H), 1.24 (s, 6H)

Example 73: (R)-(4-(6-((6-(3-(2-ethoxyphenoxy)piperidin-1-yl)pyrazin-2-yl)amino)pyridin-2-yl)phenyl)glycine

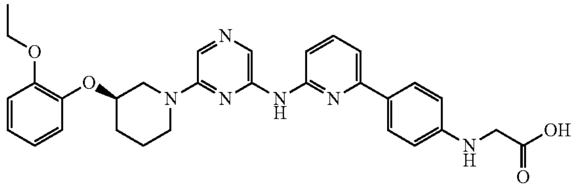 [SMILES: CCOc1ccccc1O[C@@H]1CCCN(c2cncc(Nc3cccc(-c4ccc(NCC(=O)O)cc4)n3)n2)C1]

The title compound was obtained in a similar manner to Example 22 by using (R)-2-chloro-6-(3-(2-ethoxyphenoxy)piperidin-1-yl)pyrazine (70 mg, 0.21 mmol) synthesized in Preparation Example 1 and ethyl (4-(6-aminopyridin-2-yl)phenyl)glycinate (57 mg, 0.21 mmol) synthesized in Preparation Example 100. (2 step yield 25%)

$^1$H-NMR (400 MHz, METHANOL-D4) δ 8.20 (s, 1H), 7.90-7.75 (2H), 7.49 (s, 1H), 7.47 (d, J=8.5 Hz, 1H), 7.26 (d, J=8.2 Hz, 1H), 7.21 (d, J=7.8 Hz, 1H), 6.98 (d, J=7.8 Hz, 2H), 6.88 (d, J=4.1 Hz, 3H), 6.81 (dt, J=8.7, 3.9 Hz, 1H), 6.65 (d, J=8.7 Hz, 2H), 4.40 (t, J=3.4 Hz, 1H), 4.14-3.81 (m, 4H), 3.71 (d, J=6.9 Hz, 1H), 3.68 (s, 2H), 3.67-3.55 (m, 2H), 2.22-1.90 (m, 3H), 1.70-1.50 (m, 1H), 1.34-1.22 (m, 3H)

Example 74: (R)-(4-(6-((6-(3-((3-ethoxypyridin-2-yl)oxy)piperidin-1-yl)pyrazin-2-yl)amino)pyridin-2-yl)phenyl)glycine

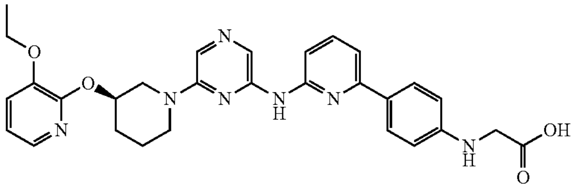 [SMILES: CCOc1cccnc1O[C@@H]1CCCN(c2cncc(Nc3cccc(-c4ccc(NCC(=O)O)cc4)n3)n2)C1]

The title compound was obtained in a similar manner to Example 1 by using (R)-2-chloro-6-(3-((3-ethoxypyridin-2-yl)oxy)piperidin-1-yl)pyrazine (58 mg, 0.17 mmol) synthesized in Preparation Example 3 and ethyl (4-(6-aminopyridin-2-yl)phenyl)glycinate (47 mg, 0.17 mmol) synthesized in Preparation Example 100. (2 step yield 21%)

$^1$H-NMR (400 MHz, METHANOL-D4) δ 8.19 (s, 1H), 7.82 (d, J=8.7 Hz, 2H), 7.58 (q, J=2.3 Hz, 1H), 7.51 (s, 1H), 7.48 (t, J=8.0 Hz, 1H), 7.18 (q, J=7.9 Hz, 2H), 7.02 (dd, J=7.8, 1.4 Hz, 1H), 6.72 (dd, J=7.8, 5.0 Hz, 1H), 6.65 (d, J=8.7 Hz, 2H), 5.18 (q, J=2.9 Hz, 1H), 4.07 (dd, J=13.7, 5.5 Hz, 1H), 3.93-3.76 (m, 5H), 3.73 (d, J=7.3 Hz, 2H), 3.69-3.51 (m, 1H), 2.19-1.95 (m, 4H), 1.63 (dd, J=9.5, 6.5 Hz, 1H), 1.21 (t, J=7.1 Hz, 3H)

Example 75: (R)-(4-(6-((2-(3-(2-ethoxyphenoxy)piperidin-1-yl)pyrimidin-4-yl)amino)pyridin-2-yl)phenyl)glycine

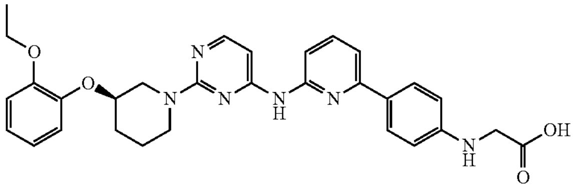 [SMILES: CCOc1ccccc1O[C@@H]1CCCN(c2nccc(Nc3cccc(-c4ccc(NCC(=O)O)cc4)n3)n2)C1]

The title compound was obtained in a similar manner to Example 1 by using (R)-4-chloro-2-(3-(2-ethoxyphenoxy)piperidin-1-yl)pyrimidine (58 mg, 0.17 mmol) synthesized in Preparation Example 5 and ethyl (4-(6-aminopyridin-2-yl)phenyl)glycinate (47 mg, 0.17 mmol) synthesized in Preparation Example 100. (2 step yield 18%)

$^1$H-NMR (400 MHz, METHANOL-D4) δ 7.98-7.85 (m, 2H), 7.81 (d, J=9.1 Hz, 2H), 7.53 (t, J=8.0 Hz, 1H), 7.39 (d, J=8.2 Hz, 1H), 7.31 (d, J=7.3 Hz, 1H), 6.95 (d, J=6.9 Hz, 1H), 6.92-6.80 (m, 3H), 6.80-6.68 (m, 2H), 6.66 (d, J=8.7 Hz, 2H), 4.41 (q, J=3.2 Hz, 1H), 4.06-3.98 (1H), 3.97-3.84 (4H), 3.83 (s, 2H), 3.79 (d, J=13.7 Hz, 2H), 2.12-1.84 (m, 4H), 1.67-1.51 (m, 1H), 1.26 (t, J=6.9 Hz, 3H)

Example 76: (R)-(4-(6-((4-(3-(2-ethoxyphenoxy)piperidin-1-yl)pyrazin-2-yl)amino)pyridin-2-yl)phenyl)glycine

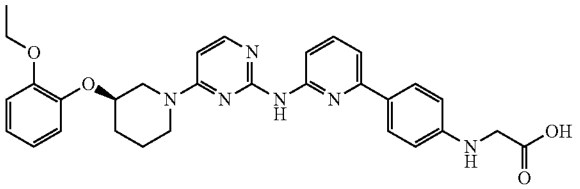 [SMILES: CCOc1ccccc1O[C@@H]1CCCN(c2ccnc(Nc3cccc(-c4ccc(NCC(=O)O)cc4)n3)n2)C1]

The title compound was obtained in a similar manner to Example 1 by using (R)-2-chloro-4-(3-(2-ethoxyphenoxy)piperidin-1-yl)pyrimidine (58 mg, 0.17 mmol) synthesized in Preparation Example 6 and ethyl (4-(6-aminopyridin-2-yl)phenyl)glycinate (47 mg, 0.17 mmol) synthesized in Preparation Example 100. (2 step yield 11%)

$^1$H-NMR (400 MHz, METHANOL-D4) δ 7.89 (d, J=6.4 Hz, 1H), 7.65 (d, J=8.2 Hz, 3H), 7.31 (d, J=8.2 Hz, 1H), 7.18 (s, 1H), 6.96 (d, J=8.2 Hz, 1H), 6.92-6.73 (m, 3H), 6.74-6.56 (2H), 6.39 (s, 1H), 4.51 (s, 1H), 4.30-3.98 (m, 1H), 3.97-3.81 (m, 2H), 3.79 (s, 1H), 3.67 (d, J=7.8 Hz, 2H), 3.50 (dd, J=11.4, 6.9 Hz, 1H), 2.00 (s, 3H), 1.59 (q, J=7.5 Hz, 1H), 1.29-1.18 (m, 3H)

Example 77: (R)-2-((4-(6-((6-(3-(2-ethoxyphenoxy)piperidin-1-yl)pyrazin-2-yl)amino)pyridin-2-yl)phenyl)amino)-2-methylpropanoic Acid

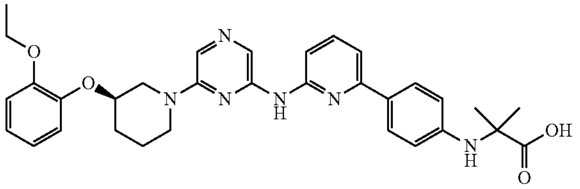 [SMILES: CCOc1ccccc1O[C@@H]1CCCN(c2cncc(Nc3cccc(-c4ccc(NC(C)(C)C(=O)O)cc4)n3)n2)C1]

The title compound was obtained in a similar manner to Example 1 by using (R)-2-chloro-6-(3-(2-ethoxyphenoxy)piperidin-1-yl)pyrazine (0.15 g, 0.45 mmol) synthesized in Preparation Example 1 and ethyl 2-((4-(6-aminopyridin-2-yl)phenyl)amino)-2-methylpropanoate (146 mg, 0.49 mmol) synthesized in Preparation Example 98. (2 step yield 74%)

$^1$H-NMR (400 MHz, METHANOL-D4) δ 8.29 (s, 1H), 7.80 (d, J=8.2 Hz, 2H), 7.52-7.39 (2H), 7.24-7.12 (m, 2H), 6.97 (d, J=8.2 Hz, 1H), 6.87 (d, J=4.1 Hz, 2H), 6.84-6.72 (m, 1H), 6.59 (d, J=8.2 Hz, 2H), 4.38 (t, J=3.2 Hz, 1H), 4.14 (q, J=7.0 Hz, 2H), 4.02-3.79 (m, 3H), 3.68 (q, J=6.7 Hz, 1H), 3.62 (s, 2H), 2.05 (d, J=12.3 Hz, 2H), 1.88 (d, J=10.5 Hz, 1H), 1.60 (s, 1H), 1.52 (d, J=4.1 Hz, 7H), 1.34-1.23 (m, 3H), 1.19-1.15 (m, 3H)

Example 78: (R)-3-(3-(6-((6-(3-(2-ethoxyphenoxy)piperidin-1-yl)pyrazin-2-yl)amino)pyridin-2-yl)-4-fluorophenyl)-2,2-dimethylpropanoic Acid

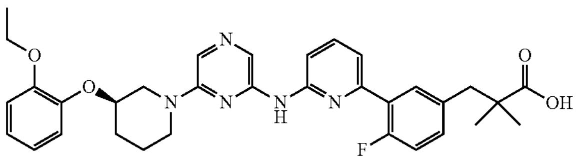 [SMILES: CCOc1ccccc1O[C@@H]1CCCN(c2cncc(Nc3cccc(-c4cc(CC(C)(C)C(=O)O)ccc4F)n3)n2)C1]

The title compound was obtained in a similar manner to Example 22 by using (R)-2-chloro-6-(3-(2-ethoxyphenoxy)piperidin-1-yl)pyrazine (73 mg, 0.22 mmol) synthesized in Preparation Example 1 and tert-butyl 3-(3-(6-aminopyridin-2-yl)-4-fluorophenyl)-2,2-dimethylpropanoate (69 mg, 0.20 mmol) synthesized in Preparation Example 89. (2 step yield 81%)

$^1$H-NMR (400 MHz, METHANOL-D4) δ 8.48 (s, 1H), 7.84 (dd, J=7.5, 2.5 Hz, 1H), 7.57 (t, J=8.0 Hz, 1H), 7.53 (s, 1H), 7.38-7.24 (m, 2H), 7.24-7.15 (m, 1H), 7.06 (dd, J=11.2, 8.5 Hz, 1H), 6.98 (d, J=7.3 Hz, 1H), 6.93-6.86 (m, 2H), 6.86-6.74 (m, 1H), 4.48-4.33 (m, 1H), 4.00-3.78 (m, 3H), 3.72 (q, J=6.6 Hz, 1H), 3.64 (t, J=5.5 Hz, 2H), 2.91 (s, 2H), 2.14-1.99 (m, 2H), 1.89 (d, J=8.2 Hz, 1H), 1.61 (d, J=5.9 Hz, 1H), 1.26 (t, J=7.1 Hz, 4H), 1.18 (s, 6H)

Example 79: (R)-3-(3-(6-((6-(3-((3-ethoxypyridin-2-yl)oxy)piperidin-1-yl)pyrazin-2-yl)amino)pyridin-2-yl)-4-fluorophenyl)-2,2-dimethylpropanoic Acid

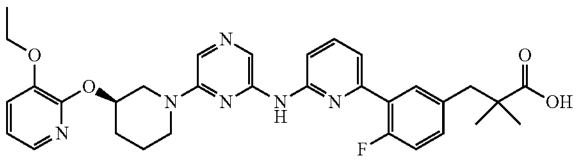 [SMILES: CCOc1cccnc1O[C@@H]1CCCN(c2cncc(Nc3cccc(-c4cc(CC(C)(C)C(=O)O)ccc4F)n3)n2)C1]

The title compound was obtained in a similar manner to Example 22 by using (R)-2-chloro-6-(3-((3-ethoxypyridin-2-yl)oxy)piperidin-1-yl)pyrazine (73 mg, 0.22 mmol) synthesized in Preparation Example 3 and tert-butyl 3-(3-(6-aminopyridin-2-yl)-4-fluorophenyl)-2,2-dimethylpropanoate (69 mg, 0.20 mmol) synthesized in Preparation Example 89. (2 step yield 98%)

$^1$H-NMR (400 MHz, METHANOL-D4) δ 8.35 (s, 1H), 7.83-7.68 (2H), 7.65 (s, 1H), 7.59-7.44 (1H), 7.41-7.31 (m, 1H), 7.26 (s, 1H), 7.19 (d, J=8.2 Hz, 1H), 7.13 (dd, J=11.2, 8.5 Hz, 1H), 7.01 (dd, J=7.8, 1.4 Hz, 1H), 6.78-6.62 (1H), 5.15 (s, 1H), 4.19-4.09 (m, 1H), 3.97-3.85 (m, 1H), 3.85-3.72 (m, 2H), 3.69 (d, J=12.8 Hz, 1H), 3.57 (d, J=9.6 Hz, 1H), 2.93 (s, 2H), 2.15-1.99 (m, 3H), 1.62 (d, J=6.4 Hz, 1H), 1.25-1.15 (m, 9H)

Example 80: (R)-2-(3-(6-((6-(3-(2-ethoxyphenoxy)piperidin-1-yl)pyrazin-2-yl)amino)pyridin-2-yl)phenoxy)-2-methylpropanoic Acid

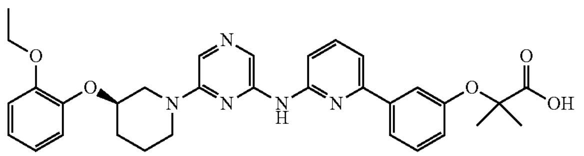

The title compound was obtained in a similar manner to Example 1 by using (R)-2-chloro-6-(3-(2-ethoxyphenoxy)piperidin-1-yl)pyrazine (111 mg, 0.333 mmol) prepared in Preparation Example 1 and ethyl 2-(3-(6-aminopyridin-2-yl)phenoxy)-2-methylpropanoate (100 mg, 0.333 mmol) prepared in Preparation Example 88. (2 step yield 61%)

$^1$H-NMR (400 MHz, CHLOROFORM-D) δ 9.42 (s, 1H), 7.99 (t, J=2.1 Hz, 1H), 7.62 (t, J=8.5 Hz, 2H), 7.51 (d, J=8.2 Hz, 1H), 7.44-7.28 (m, 2H), 7.09-6.93 (m, 3H), 6.89 (qd, J=7.5, 1.6 Hz, 2H), 6.79 (s, 1H), 6.61 (d, J=7.8 Hz, 1H), 4.42-4.24 (m, 1H), 4.07 (dd, J=13.3, 3.7 Hz, 1H), 4.04-3.88 (m, 2H), 3.87-3.70 (m, 1H), 3.58 (dd, J=13.0, 7.5 Hz, 1H), 3.48-3.30 (m, 1H), 2.25-2.08 (1H), 2.08-1.95 (m, 1H), 1.95-1.81 (m, 1H), 1.72-1.48 (m, 7H), 1.37 (t, J=7.1 Hz, 3H)

Example 81: (R)-2-(3-(6-((6-(3-((3-ethoxypyridin-2-yl)oxy)piperidin-1-yl)pyrazin-2-yl)amino)pyridin-2-yl)phenoxy)-2-methylpropanoic Acid

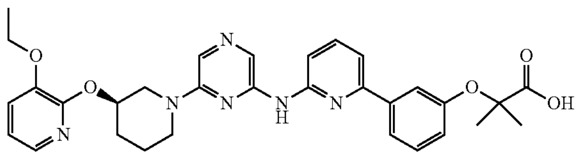

The title compound was obtained in a similar manner to Example 1 by using (R)-2-chloro-6-(3-((3-ethoxypyridin-2-yl)oxy)piperidin-1-yl)pyrazine (111 mg, 0.333 mmol) prepared in Preparation Example 3 and ethyl 2-(3-(6-amino-pyridin-2-yl)phenoxy)-2-methylpropanoate (100 mg, 0.333 mmol) prepared in Preparation Example 88. (2 step yield 76%)

$^1$H-NMR (400 MHz, CHLOROFORM-D) δ 9.36 (s, 1H), 7.99 (t, J=2.1 Hz, 1H), 7.74 (dd, J=5.0, 1.4 Hz, 1H), 7.65 (s, 1H), 7.60 (t, J=7.8 Hz, 1H), 7.51 (d, J=7.8 Hz, 1H), 7.43-7.29 (m, 2H), 7.03 (dd, J=7.8, 2.3 Hz, 1H), 6.94 (dd, J=7.8, 1.4 Hz, 1H), 6.81 (dd, J=7.8, 5.0 Hz, 1H), 6.64 (s, 1H), 6.57 (d, J=7.8 Hz, 1H), 5.23 (q, J=3.5 Hz, 1H), 3.91 (d, J=5.0 Hz, 2H), 3.90-3.79 (m, 2H), 3.72 (q, J=3.7 Hz, 1H), 3.59 (t, J=3.9 Hz, 1H), 2.16 (t, J=4.3 Hz, 1H), 2.10-1.94 (m, 2H), 1.73-1.55 (m, 7H), 1.27 (t, J=6.9 Hz, 3H)

Example 82: (R)-2-(4-(6-((6-(3-(2-ethoxyphenoxy)piperidin-1-yl)pyrazin-2-yl)amino)pyridin-2-yl)phenoxy)-2-methylpropanoic Acid

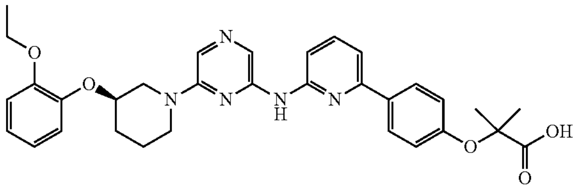

The title compound was obtained in a similar manner to Example 1 by using (R)-2-chloro-6-(3-(2-ethoxyphenoxy)piperidin-1-yl)pyrazine (111 mg, 0.333 mmol) prepared in Preparation Example 1 and ethyl 2-(4-(6-aminopyridin-2-yl)phenoxy)-2-methylpropanoate (100 mg, 0.333 mmol) prepared in Preparation Example 97. (2 step yield 69%)

$^1$H-NMR (400 MHz, CHLOROFORM-D) δ 8.07 (s, 1H), 7.74 (d, J=8.7 Hz, 2H), 7.67 (d, J=6.4 Hz, 2H), 7.62-7.48 (1H), 7.13 (d, J=7.3 Hz, 1H), 7.09-7.01 (2H), 7.01-6.96 (1H), 6.93 (td, J=7.7, 1.4 Hz, 1H), 6.89-6.74 (m, 2H), 4.42-4.24 (m, 1H), 4.14 (dd, J=12.8, 3.2 Hz, 1H), 4.07-3.89 (m, 2H), 3.89-3.69 (m, 1H), 3.52 (dd, J=12.8, 7.8 Hz, 1H), 3.44-3.27 (m, 1H), 2.26-2.09 (m, 1H), 2.09-1.96 (m, 1H), 1.96-1.81 (m, 1H), 1.64 (t, J=16.0 Hz, 7H), 1.36 (t, J=6.9 Hz, 3H)

Example 83: (R)-2-(4-(6-((6-(3-((3-ethoxypyridin-2-yl)oxy)piperidin-1-yl)pyrazin-2-yl)amino)pyridin-2-yl)phenoxy)-2-methylpropanoic Acid

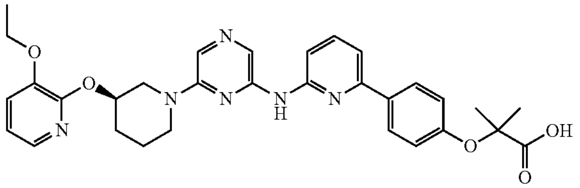 [SMILES: CCOc1cccnc1O[C@@H]1CCCN(c2cncc(Nc3cccc(-c4ccc(OC(C)(C)C(=O)O)cc4)n3)n2)C1]

The title compound was obtained in a similar manner to Example 1 by using (R)-2-chloro-6-(3-((3-ethoxypyridin-2-yl)oxy)piperidin-1-yl)pyrazine (111 mg, 0.333 mmol) prepared in Preparation Example 3 and ethyl 2-(4-(6-aminopyridin-2-yl)phenoxy)-2-methylpropanoate (100 mg, 0.333 mmol) prepared in Preparation Example 97. (2 step yield 71%)

$^1$H-NMR (400 MHz, CHLOROFORM-D) δ 8.05 (s, 1H), 7.75 (d, J=9.1 Hz, 2H), 7.71 (s, 1H), 7.66-7.46 (m, 3H), 7.12 (d, J=7.3 Hz, 1H), 7.05 (d, J=8.7 Hz, 2H), 6.95 (dd, J=7.8, 1.4 Hz, 1H), 6.70 (dd, J=7.8, 5.0 Hz, 1H), 5.26 (t, J=3.2 Hz, 1H), 3.99 (dd, J=13.5, 3.0 Hz, 1H), 3.94-3.81 (m, 3H), 3.75 (d, J=13.7 Hz, 1H), 3.65-3.46 (m, 1H), 2.27-2.11 (m, 1H), 2.11-1.89 (2H), 1.79-1.67 (m, 1H), 1.65 (d, J=1.8 Hz, 6H), 1.38-1.19 (m, 3H)

Example 84: (R)-2-(3-(6-((6-(3-(2-ethoxyphenoxy)piperidin-1-yl)pyrazin-2-yl)amino)pyridin-2-yl)-4-fluorophenoxy)-2-methylpropanoic Acid

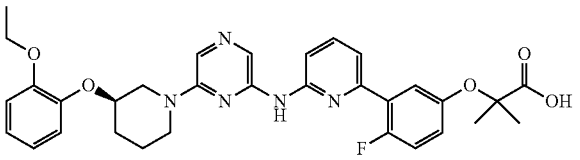 [SMILES: CCOc1ccccc1O[C@@H]1CCCN(c2cncc(Nc3cccc(-c4cc(OC(C)(C)C(=O)O)ccc4F)n3)n2)C1]

The title compound was obtained in a similar manner to Example 1 by using (R)-2-chloro-6-(3-(2-ethoxyphenoxy)piperidin-1-yl)pyrazine (115 mg, 0.35 mmol) synthesized in Preparation Example 1 and ethyl 2-(3-(6-aminopyridin-2-yl)-4-fluorophenoxy)-2-methylpropanoate (100 mg, 0.31 mmol) synthesized in Preparation Example 92. (2 step yield 45%)

$^1$H-NMR (400 MHz, METHANOL-D4) δ 8.30 (s, 1H), 7.67-7.47 (m, 3H), 7.35 (d, J=8.2 Hz, 1H), 7.31 (dd, J=7.5, 2.1 Hz, 1H), 7.08 (dd, J=11.0, 9.1 Hz, 1H), 7.02-6.92 (m, 2H), 6.87 (d, J=4.1 Hz, 2H), 6.81 (q, J=4.0 Hz, 1H), 4.42 (s, 1H), 4.01-3.82 (m, 3H), 3.76 (q, J=6.7 Hz, 1H), 3.72-3.56 (m, 2H), 2.14-2.00 (2H), 1.91 (d, J=8.7 Hz, 1H), 1.70-1.58 (m, 1H), 1.56 (s, 6H), 1.26 (t, J=7.1 Hz, 3H)

Example 85: (R)-2-(3-(6-((6-(3-((3-ethoxypyridin-2-yl)oxy)piperidin-1-yl)pyrazin-2-yl)amino)pyridin-2-yl)-4-fluorophenoxy)-2-methylpropanoic Acid

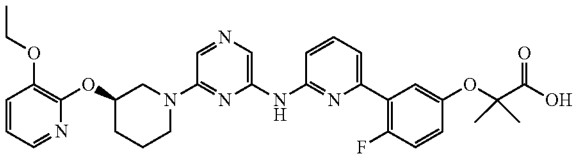 [SMILES: CCOc1cccnc1O[C@@H]1CCCN(c2cncc(Nc3cccc(-c4cc(OC(C)(C)C(=O)O)ccc4F)n3)n2)C1]

The title compound was obtained in a similar manner to Example 1 by using (R)-2-chloro-6-(3-((3-ethoxypyridin-2-yl)oxy)piperidin-1-yl)pyrazine (116 mg, 0.35 mmol) synthesized in Preparation Example 3 and ethyl 2-(3-(6-aminopyridin-2-yl)-4-fluorophenoxy)-2-methylpropanoate (100 mg, 0.31 mmol) synthesized in Preparation Example 92. (2 step yield 42%)

$^1$H-NMR (400 MHz, METHANOL-D4) δ 8.26 (s, 1H), 7.66-7.47 (m, 4H), 7.30 (dd, J=8.2, 2.7 Hz, 2H), 7.17-6.99 (m, 2H), 6.95 (dt, J=9.0, 3.5 Hz, 1H), 6.72 (dd, J=7.8, 5.0 Hz, 1H), 5.19 (q, J=2.9 Hz, 1H), 4.17-3.98 (m, 2H), 3.93-3.70 (m, 4H), 3.67-3.51 (m, 1H), 2.17-2.00 (m, 2H), 1.96 (s, 1H), 1.64 (t, J=3.0 Hz, 1H), 1.56 (s, 6H), 1.21 (t, J=7.1 Hz, 3H)

Example 86: (R)-3-(4-(6-((6-(3-(2-ethoxyphenoxy)piperidin-1-yl)pyrazin-2-yl)amino)pyridin-2-yl)-1H-pyrazol-1-yl)-2,2-dimethylpropanoic Acid

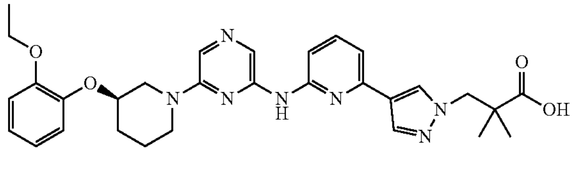 [SMILES: CCOc1ccccc1O[C@@H]1CCCN(c2cncc(Nc3cccc(-c4cnn(CC(C)(C)C(=O)O)c4)n3)n2)C1]

The title compound was obtained in a similar manner to Example 1 by using (R)-2-chloro-6-(3-(2-ethoxyphenoxy) piperidin-1-yl)pyrazine (0.050 g, 0.15 mmol) prepared in Preparation Example 1 and methyl 3-(4-(6-aminopyridin-2-yl)-1H-pyrazol-1-yl)-2,2-dimethylpropanoate (0.041 g, 0.15 mmol) obtained in Preparation Example 116. (Yield 14%)

$^1$H-NMR (400 MHz, METHANOL-D4): (8.18 (s, 1H), 8.11 (s, 1H), 7.95 (s, 1H), 7.63-7.50 (m, 2H), 7.21-7.07 (m, 2H), 6.99-6.86 (m, 1H), 6.86-6.70 (m, 3H), 4.41 (d, J=9.1 Hz, 1H), 4.35 (s, 2H), 3.94-3.68 (m, 5H), 3.64-3.54 (m, 1H), 2.12-2.00 (m, 2H), 1.98-1.88 (m, 1H), 1.68-1.53 (m, 1H), 1.28-1.18 (m, 9H)

Example 87: (R)-3-((6-((6-(3-(2-ethoxyphenoxy) piperidin-1-yl)pyrazin-2-yl)amino)pyridin-2-yl)oxy) benzoic Acid

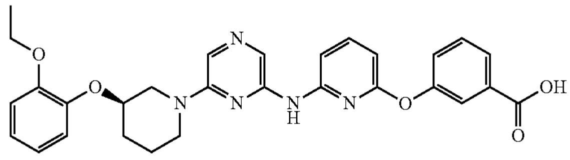 [SMILES: CCOc1ccccc1O[C@@H]1CCCN(c2cncc(Nc3cccc(Oc4cccc(C(=O)O)c4)n3)n2)C1]

The title compound was obtained in a similar manner to Example 12 by using (R)-2-chloro-6-(3-(2-ethoxyphenoxy) piperidin-1-yl)pyrazine (0.098 g, 0.293 mmol) obtained in Preparation Example 1 and methyl 3-((6-aminopyridin-2-yl) oxy)benzoate (0.065 g, 0.266 mmol) obtained in Preparation Example 107. (2 step yield 50%)

$^1$H-NMR (400 MHz, METHANOL-D4) δ 7.84 (d, J=7.8 Hz, 1H), 7.70 (t, J=2.1 Hz, 1H), 7.65 (s, 1H), 7.54 (t, J=8.0 Hz, 1H), 7.48 (t, J=8.0 Hz, 1H), 7.42 (s, 1H), 7.36-7.28 (m, 1H), 7.19 (d, J=7.8 Hz, 1H), 7.02-6.93 (m, 1H), 6.93-6.84 (m, 2H), 6.80 (dq, J=8.6, 2.6 Hz, 1H), 6.45 (d, J=7.8 Hz, 1H), 4.40 (td, J=6.6, 3.5 Hz, 1H), 3.98-3.76 (m, 3H), 3.71 (q, J=6.7 Hz, 1H), 3.66-3.52 (m, 2H), 2.14-1.97 (m, 2H), 1.94-1.80 (m, 1H), 1.67-1.50 (m, 1H), 1.23 (t, J=6.9 Hz, 3H)

Example 88: (R)-3-((6-((6-(3-((3-ethoxypyridin-2-yl)oxy)piperidin-1-yl)pyrazin-2-yl)amino)pyridin-2-yl)oxy)benzoic Acid

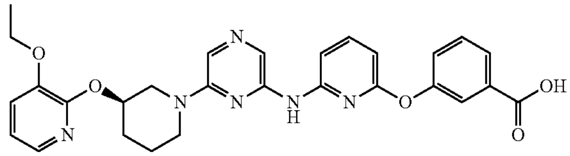 [SMILES: CCOc1cccnc1O[C@@H]1CCCN(c2cncc(Nc3cccc(Oc4cccc(C(=O)O)c4)n3)n2)C1]

The title compound was obtained in a similar manner to Example 12 by using (R)-2-chloro-6-(3-((3-ethoxypyridin-2-yl)oxy)piperidin-1-yl)pyrazine (0.098 g, 0.293 mmol) obtained in Preparation Example 3 and methyl 3-((6-aminopyridin-2-yl)oxy)benzoate (0.065 g, 0.266 mmol) obtained in Preparation Example 107. (2 step yield 21%)

$^1$H-NMR (400 MHz, METHANOL-D4) δ 7.84 (dd, J=7.8, 1.4 Hz, 1H), 7.71 (t, J=2.1 Hz, 1H), 7.61 (s, 1H), 7.59-7.45 (m, 3H), 7.42 (s, 1H), 7.36-7.27 (m, 1H), 7.12 (d, J=8.2 Hz, 1H), 7.02 (dd, J=8.0, 1.6 Hz, 1H), 6.73 (dd, J=7.8, 5.0 Hz, 1H), 6.45 (d, J=7.8 Hz, 1H), 5.17 (q, J=2.7 Hz, 1H), 4.15-4.01 (1H), 3.87-3.62 (4H), 3.61-3.47 (m, 1H), 2.12-1.91 (m, 3H), 1.65-1.53 (m, 1H), 1.15 (t, J=7.1 Hz, 3H)

Example 89: (R)-4-((6-((6-(3-(2-ethoxyphenoxy) piperidin-1-yl)pyrazin-2-yl)amino)pyridin-2-yl)oxy) benzoic Acid

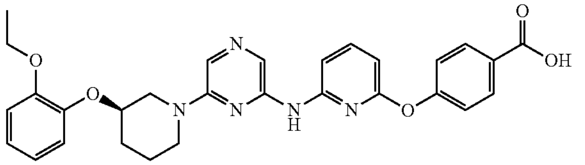 [SMILES: CCOc1ccccc1O[C@@H]1CCCN(c2cncc(Nc3cccc(Oc4ccc(C(=O)O)cc4)n3)n2)C1]

The title compound was obtained in a similar manner to Example 12 by using (R)-2-chloro-6-(3-(2-ethoxyphenoxy) piperidin-1-yl)pyrazine (0.15 g, 0.45 mmol) obtained in Preparation Example 1 and methyl 4-((6-aminopyridin-2-yl) oxy)benzoate (0.1 g, 0.409 mmol) obtained in Preparation Example 104. (2 step yield 70%)

$^1$H-NMR (400 MHz, CHLOROFORM-D) δ 8.32-8.20 (m, 2H), 7.98 (s, 1H), 7.80 (d, J=8.2 Hz, 1H), 7.59 (q, J=7.6 Hz, 1H), 7.27 (t, J=2.3 Hz, 1H), 7.04-6.78 (m, 5H), 6.62 (d, J=8.2 Hz, 1H), 6.60-6.47 (m, 1H), 4.37-4.22 (m, 1H), 4.05 (dd, J=13.3, 3.2 Hz, 1H), 4.01-3.83 (m, 2H), 3.72 (td, J=9.3, 4.1 Hz, 1H), 3.54 (dd, J=13.3, 7.8 Hz, 1H), 3.42-3.33 (m, 1H), 2.19-2.05 (m, 1H), 2.01-1.81 (m, 2H), 1.57 (qd, J=8.8, 4.6 Hz, 1H), 1.37-1.28 (m, 3H)

Example 90: (R)-4-((6-((6-(3-((3-ethoxypyridin-2-yl)oxy)piperidin-1-yl)pyrazin-2-yl)amino)pyridin-2-yl)oxy)benzoic Acid

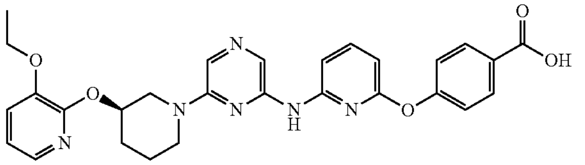 [SMILES: CCOc1cccnc1O[C@@H]1CCCN(c2cncc(Nc3cccc(Oc4ccc(C(=O)O)cc4)n3)n2)C1]

The title compound was obtained in a similar manner to Example 12 by using (R)-2-chloro-6-(3-((3-ethoxypyridin-2-yl)oxy)piperidin-1-yl)pyrazine (0.151 g, 0.450 mmol) obtained in Preparation Example 3 and methyl 4-((6-aminopyridin-2-yl)oxy)benzoate (0.1 g, 0.409 mmol) obtained in Preparation Example 104. (2 step yield 71%)

$^1$H-NMR (400 MHz, CHLOROFORM-D) δ 8.19 (t, J=8.9 Hz, 2H), 7.92 (d, J=17.8 Hz, 1H), 7.75-7.66 (m, 2H), 7.58 (t, J=7.8 Hz, 1H), 7.44-7.26 (m, 1H), 7.24-7.16 (m, 2H), 6.97-6.89 (m, 1H), 6.83-6.68 (m, 2H), 6.55 (t, J=8.5 Hz, 1H), 5.20 (s, 1H), 3.96-3.82 (m, 3H), 3.82-3.72 (m, 1H), 3.72-3.52 (m, 2H), 2.10 (q, J=4.1 Hz, 1H), 2.01 (q, J=5.3 Hz, 2H), 1.65 (s, 1H), 1.26-1.20 (3H)

Example 91: (R)-2-(3-((6-((6-(3-(2-ethoxyphenoxy)piperidin-1-yl)pyrazin-2-yl)amino)pyridin-2-yl)oxy)phenyl)-2-methylpropanoic Acid

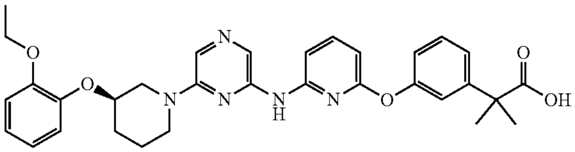 [SMILES: CCOc1ccccc1O[C@@H]1CCCN(c2cncc(Nc3cccc(Oc4cccc(C(C)(C)C(=O)O)c4)n3)n2)C1]

The title compound was obtained in a similar manner to Example 1 by using (R)-2-chloro-6-(3-(2-ethoxyphenoxy)piperidin-1-yl)pyrazine (117 mg, 0.349 mmol) prepared in Preparation Example 1 and methyl 2-(3-((6-aminopyridin-2-yl)oxy)phenyl)-2-methylpropanoate (100 mg, 0.349 mmol) prepared in Preparation Example 109. (2 step yield 47%)

$^1$H-NMR (400 MHz, METHANOL-D4) δ 7.72 (d, J=4.1 Hz, 1H), 7.62-7.50 (1H), 7.47 (s, 1H), 7.44-7.31 (1H), 7.25 (d, J=8.7 Hz, 1H), 7.22-7.16 (1H), 7.14 (t, J=2.1 Hz, 1H), 7.07-6.96 (m, 2H), 6.96-6.87 (2H), 6.87-6.75 (m, 1H), 6.41 (d, J=7.8 Hz, 1H), 4.41 (td, J=6.7, 3.4 Hz, 1H), 4.02-3.80 (m, 3H), 3.71 (q, J=6.6 Hz, 1H), 3.63 (t, J=5.3 Hz, 2H), 2.18-1.99 (m, 2H), 1.91 (qd, J=7.9, 3.9 Hz, 1H), 1.71-1.56 (m, 1H), 1.54 (s, 6H), 1.27 (t, J=6.9 Hz, 3H)

Example 92: (R)-2-(3-((6-((6-(3-((3-ethoxypyridin-2-yl)oxy)piperidin-1-yl)pyrazin-2-yl)amino)pyridin-2-yl)oxy)phenyl)-2-methylpropanoic Acid

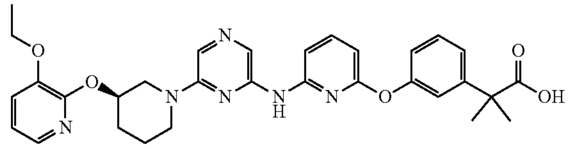 [SMILES: CCOc1cccnc1O[C@@H]1CCCN(c2cncc(Nc3cccc(Oc4cccc(C(C)(C)C(=O)O)c4)n3)n2)C1]

The title compound was obtained in a similar manner to Example 1 by using (R)-2-chloro-6-(3-((3-ethoxypyridin-2-yl)oxy)piperidin-1-yl)pyrazine (117 mg, 0.349 mmol) prepared in Preparation Example 3 and methyl 2-(3-((6-aminopyridin-2-yl)oxy)phenyl)-2-methylpropanoate (100 mg, 0.349 mmol) prepared in Preparation Example 109. (2 step yield 56%)

$^1$H-NMR (400 MHz, METHANOL-D4) δ 7.68 (s, 1H), 7.61 (q, J=2.3 Hz, 1H), 7.52 (t, J=8.0 Hz, 1H), 7.48 (s, 1H), 7.43-7.31 (m, 1H), 7.31-7.22 (m, 1H), 7.22-7.10 (m, 2H), 7.06 (dd, J=7.8, 1.4 Hz, 1H), 7.03-6.92 (m, 1H), 6.77 (dd, J=7.8, 5.0 Hz, 1H), 6.40 (d, J=7.3 Hz, 1H), 5.20 (q, J=2.9 Hz, 1H), 4.04 (dd, J=13.7, 5.9 Hz, 1H), 3.96-3.69 (m, 4H), 3.69-3.53 (m, 1H), 2.22-1.89 (3H), 1.77-1.58 (m, 1H), 1.55 (s, 6H), 1.20 (t, J=7.1 Hz, 3H)

Example 93: (R)-2-(4-((6-((6-(3-(2-ethoxyphenoxy)piperidin-1-yl)pyrazin-2-yl)amino)pyridin-2-yl)oxy)phenyl)-2-methylpropanoic Acid

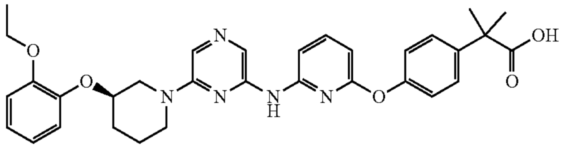 [SMILES: CCOc1ccccc1O[C@@H]1CCCN(c2cncc(Nc3cccc(Oc4ccc(C(C)(C)C(=O)O)cc4)n3)n2)C1]

The title compound was obtained in a similar manner to Example 1 by using (R)-2-chloro-6-(3-(2-ethoxyphenoxy)piperidin-1-yl)pyrazine (117 mg, 0.349 mmol) prepared in Preparation Example 1 and methyl 2-(4-((6-aminopyridin-2-yl)oxy)phenyl)-2-methylpropanoate (100 mg, 0.349 mmol) prepared in Preparation Example 106. (2 step yield 58%)

$^1$H-NMR (400 MHz, METHANOL-D4) δ 7.66 (d, J=8.7 Hz, 1H), 7.52 (t, J=8.0 Hz, 1H), 7.49-7.41 (m, 3H), 7.29 (d, J=7.8 Hz, 1H), 7.07 (dt, J=9.5, 2.5 Hz, 2H), 6.99 (d, J=7.8 Hz, 1H), 6.94-6.87 (m, 2H), 6.87-6.74 (m, 1H), 6.40 (d, J=7.8 Hz, 1H), 4.51-4.33 (m, 1H), 4.05-3.81 (m, 3H), 3.73 (q, J=6.6 Hz, 1H), 3.68-3.54 (2H), 2.22-1.98 (m, 2H), 1.97-1.82 (m, 1H), 1.73-1.53 (7H), 1.27 (t, J=7.1 Hz, 3H)

Example 94: (R)-2-(4-((6-((6-(3-((3-ethoxypyridin-2-yl)oxy)piperidin-1-yl)pyrazin-2-yl)amino)pyridin-2-yl)oxy)phenyl)-2-methylpropanoic Acid

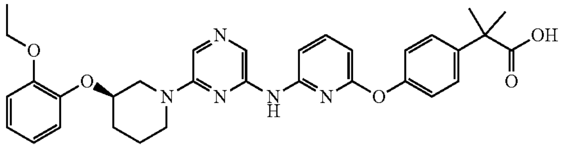 [SMILES: CCOc1ccccc1O[C@@H]1CCCN(c2cncc(Nc3cccc(Oc4ccc(C(C)(C)C(=O)O)cc4)n3)n2)C1]

The title compound was obtained in a similar manner to Example 1 by using (R)-2-chloro-6-(3-((3-ethoxypyridin-2-yl)oxy)piperidin-1-yl)pyrazine (117 mg, 0.349 mmol) prepared in Preparation Example 3 and methyl 2-(4-((6-aminopyridin-2-yl)oxy)phenyl)-2-methylpropanoate (100 mg, 0.349 mmol) prepared in Preparation Example 106. (2 step yield 71%)

$^1$H-NMR (400 MHz, METHANOL-D4) δ 7.68-7.55 (m, 2H), 7.55-7.35 (m, 4H), 7.21 (d, J=7.8 Hz, 1H), 7.13-6.98 (m, 3H), 6.76 (dd, J=7.8, 5.0 Hz, 1H), 6.39 (d, J=7.8 Hz, 1H), 5.29-5.12 (m, 1H), 4.04 (dd, J=13.7, 5.9 Hz, 1H), 3.96-3.67 (m, 4H), 3.67-3.50 (m, 1H), 2.20-1.89 (m, 3H), 1.73-1.59 (m, 1H), 1.57 (d, J=7.8 Hz, 6H), 1.20 (t, J=6.9 Hz, 3H)

Example 95: (R)-2-(3-((6-((6-(3-(2-ethoxyphenoxy)piperidin-1-yl)pyrazin-2-yl)amino)pyridin-2-yl)oxy)phenyl)acetic Acid

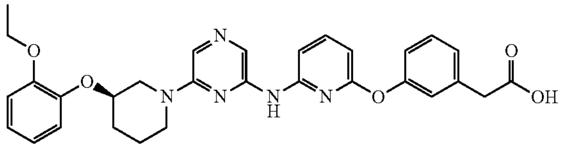 [SMILES: CCOc1ccccc1O[C@@H]1CCCN(c2cncc(Nc3cccc(Oc4cccc(CC(=O)O)c4)n3)n2)C1]

The title compound was obtained in a similar manner to Example 1 by using (R)-2-chloro-6-(3-(2-ethoxyphenoxy) piperidin-1-yl)pyrazine (90.0 mg, 0.271 mmol) prepared in Preparation Example 1 and methyl 2-(3-((6-aminopyridin-2yl)oxy)phenyl)acetate (70.0 mg, 0.271 mmol) prepared in Preparation Example 108. (2 step yield 27%)

$^1$H-NMR (400 MHz, CHLOROFORM-D) δ 8.04 (s, 1H), 7.66-7.46 (m, 2H), 7.37 (t, J=7.8 Hz, 1H), 7.30 (d, J=16.0 Hz, 1H), 7.23 (s, 1H), 7.08-6.90 (m, 4H), 6.90-6.76 (m, 2H), 6.69-6.45 (m, 2H), 4.30 (t, J=3.4 Hz, 1H), 4.06-3.84 (m, 3H), 3.74 (s, 2H), 3.65 (s, 2H), 3.42 (d, J=11.0 Hz, 1H), 2.08 (d, J=6.4 Hz, 1H), 2.04-1.81 (m, 2H), 1.58 (qd, J=8.5, 4.2 Hz, 1H), 1.33 (t, J=7.1 Hz, 3H)

Example 96: (R)-2-(3-((6-((6-(3-((3-ethoxypyridin-2-yl)oxy)piperidin-1-yl)pyrazin-2-yl)amino)pyridin-2-yl)oxy)phenyl)acetic Acid

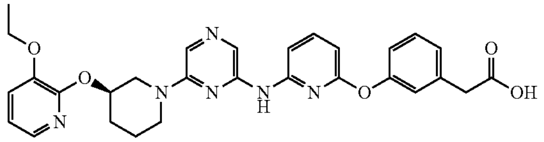 [SMILES: CCOc1cccnc1O[C@@H]1CCCN(c2cncc(Nc3cccc(Oc4cccc(CC(=O)O)c4)n3)n2)C1]

The title compound was obtained in a similar manner to Example 1 by using (R)-2-chloro-6-(3-((3-ethoxypyridin-2-yl)oxy)piperidin-1-yl)pyrazine (91.0 mg, 0.271 mmol) prepared in Preparation Example 3 and methyl 2-(3-((6-aminopyridin-2yl)oxy)phenyl)acetate (70.0 mg, 0.271 mmol) prepared in Preparation Example 108. (2 step yield 13%)

$^1$H-NMR (400 MHz, METHANOL-D4) δ 7.69 (s, 1H), 7.61 (dd, J=5.0, 1.4 Hz, 1H), 7.52 (t, J=7.8 Hz, 1H), 7.47 (s, 1H), 7.40-7.28 (1H), 7.23-6.94 (m, 5H), 6.77 (dd, J=7.8, 5.0 Hz, 1H), 6.41 (d, J=7.8 Hz, 1H), 5.28-5.11 (m, 1H), 4.04 (dd, J=13.7, 5.9 Hz, 1H), 3.93-3.68 (m, 4H), 3.64 (s, 2H), 3.63-3.50 (m, 1H), 2.14-1.91 (m, 3H), 1.73-1.54 (m, 1H), 1.20 (t, J=7.1 Hz, 3H)

Example 97: (R)-2-(4-((6-((6-(3-(2-ethoxyphenoxy) piperidin-1-yl)pyrazin-2-yl)amino)pyridin-2-yl)oxy) phenyl)acetic Acid

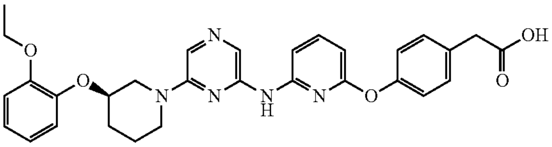 [SMILES: CCOc1ccccc1O[C@@H]1CCCN(c2cncc(Nc3cccc(Oc4ccc(CC(=O)O)cc4)n3)n2)C1]

The title compound was obtained in a similar manner to Example 1 by using (R)-2-chloro-6-(3-(2-ethoxyphenoxy) piperidin-1-yl)pyrazine (90.0 mg, 0.271 mmol) prepared in Preparation Example 1 and methyl 2-(4-((6-aminopyridin-2-yl)oxy)phenyl)acetate (70.0 mg, 0.271 mmol) prepared in Preparation Example 105. (2 step yield 17%)

$^1$H-NMR (400 MHz, CHLOROFORM-D) δ 7.57 (s, 1H), 7.52 (t, J=7.8 Hz, 1H), 7.49-7.42 (m, 1H), 7.37 (d, J=8.2 Hz, 2H), 7.10 (dt, J=9.3, 2.3 Hz, 2H), 7.08-6.98 (m, 1H), 6.94 (td, J=8.5, 1.5 Hz, 2H), 6.90-6.81 (m, 2H), 6.78 (d, J=7.8 Hz, 1H), 6.50 (d, J=7.8 Hz, 1H), 4.30 (td, J=7.5, 3.7 Hz, 1H), 4.07-3.88 (m, 3H), 3.76 (d, J=7.3 Hz, 2H), 3.69 (dd, J=8.5, 4.8 Hz, 1H), 3.59-3.45 (m, 1H), 3.44-3.26 (m, 1H), 2.21-2.05 (m, 1H), 2.03-1.92 (m, 1H), 1.91-1.77 (m, 1H), 1.58 (tt, J=13.0, 4.4 Hz, 1H), 1.34 (t, J=6.9 Hz, 3H)

Example 98: (R)-2-(4-((6-((6-(3-((3-ethoxypyridin-2-yl)oxy)piperidin-1-yl)pyrazin-2-yl)amino)pyridin-2-yl)oxy)phenyl)acetic Acid

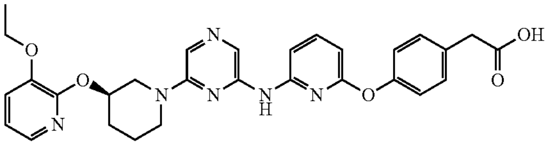 [SMILES: CCOc1cccnc1O[C@@H]1CCCN(c2cncc(Nc3cccc(Oc4ccc(CC(=O)O)cc4)n3)n2)C1]

The title compound was obtained in a similar manner to Example 1 by using (R)-2-chloro-6-(3-((3-ethoxypyridin-2-yl)oxy)piperidin-1-yl)pyrazine (91.0 mg, 0.271 mmol) prepared in Preparation Example 3 and methyl 2-(4-((6-aminopyridin-2-yl)oxy)phenyl)acetate (70.0 mg, 0.271 mmol) prepared in Preparation Example 105. (2 step yield 25%)

$^1$H-NMR (400 MHz, CHLOROFORM-D) δ 7.70 (td, J=3.0, 1.5 Hz, 1H), 7.62 (d, J=8.2 Hz, 1H), 7.52 (td, J=7.9, 1.7 Hz, 1H), 7.44-7.33 (m, 3H), 7.09 (dd, J=8.9, 2.1 Hz, 2H), 6.94 (dd, J=7.8, 1.8 Hz, 1H), 6.90 (s, 1H), 6.78 (ddd, J=7.7, 4.9, 1.0 Hz, 1H), 6.68 (d, J=7.8 Hz, 1H), 6.51 (dd, J=7.8, 2.3 Hz, 1H), 5.25-5.09 (m, 1H), 3.96-3.86 (m, 2H), 3.86-3.75 (m, 4H), 3.75-3.61 (m, 1H), 3.59-3.36 (1H), 2.23-2.06 (m, 1H), 2.06-1.87 (m, 2H), 1.75-1.55 (m, 1H), 1.27 (t, J=7.1 Hz, 3H)

Example 99: (R)-4-(((6-((6-(3-(2-ethoxyphenoxy) piperidin-1-yl)pyrazin-2-yl)amino)pyridin-2-yl)oxy) methyl)benzoic Acid

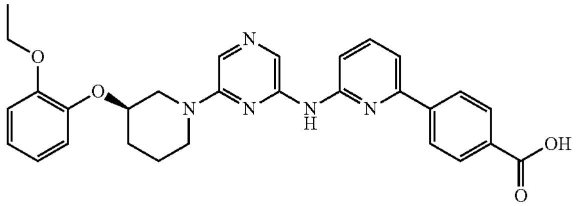 [SMILES: CCOc1ccccc1O[C@@H]1CCCN(c2cncc(Nc3cccc(-c4ccc(C(=O)O)cc4)n3)n2)C1]

The title compound was obtained in a similar manner to Example 12 by using (R)-2-chloro-6-(3-(2-ethoxyphenoxy) piperidin-1-yl)pyrazine (0.095 g, 0.285 mmol) obtained in Preparation Example 1 and methyl 4-(((6-aminopyridin-2-yl)oxy)methyl)benzoate (0.067 g, 0.259 mmol) obtained in Preparation Example 110. (2 step yield 21%)

$^1$H-NMR (400 MHz, METHANOL-D4) δ 8.03 (s, 1H), 7.99 (d, J=8.2 Hz, 2H), 7.54 (dd, J=17.8, 8.2 Hz, 2H), 7.47 (s, 1H), 7.43 (t, J=8.0 Hz, 1H), 7.03 (d, J=8.2 Hz, 1H), 6.97 (d, J=7.3 Hz, 1H), 6.90-6.83 (m, 2H), 6.83-6.76 (m, 1H), 6.40-6.31 (m, 1H), 5.43 (s, 2H), 4.48-4.29 (m, 1H), 3.96-3.75 (m, 3H), 3.75-3.66 (m, 1H), 3.60 (dd, J=19.4, 4.8 Hz, 2H), 2.11-1.99 (m, 2H), 1.94-1.82 (m, 1H), 1.66-1.52 (m, 1H), 1.23 (t, J=7.1 Hz, 3H)

Example 100: (R)-3-(3-(6-((6-(3-(2-ethoxyphenoxy)piperidin-1-yl)pyrazin-2-yl)amino)-5-fluoropyridin-2-yl)phenyl)-2,2-dimethylpropanoic Acid

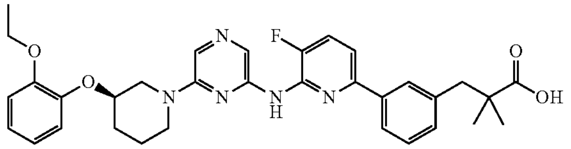

The title compound was obtained in a similar manner to Example 22 by using (R)-6-(3-(2-ethoxyphenoxy)piperidin-1-yl)pyrazin-2-amine (44 mg, 0.14 mmol) synthesized in Preparation Example 2 and tert-butyl 3-(3-(6-chloro-5-fluoropyridin-2-yl)phenyl)-2,2-dimethylpropanoate (51 mg, 0.14 mmol) synthesized in Step 1 of Preparation Example 85. (2 step yield 12%)

$^1$H-NMR (400 MHz, METHANOL-D4) δ 8.91 (s, 1H), 7.83 (s, 1H), 7.79 (d, J=8.2 Hz, 1H), 7.68 (s, 1H), 7.56 (dd, J=10.5, 8.7 Hz, 1H), 7.43 (dd, J=8.5, 3.0 Hz, 1H), 7.35 (t, J=7.8 Hz, 1H), 7.22 (d, J=7.3 Hz, 1H), 6.97 (q, J=3.2 Hz, 1H), 6.91-6.74 (m, 3H), 4.49 (d, J=2.5 Hz, 1H), 4.15-4.01 (m, 1H), 3.96 (d, J=8.2 Hz, 1H), 3.85 (tdd, J=16.8, 6.9, 2.7 Hz, 2H), 3.75 (d, J=14.2 Hz, 1H), 3.61-3.47 (m, 1H), 2.95 (s, 2H), 2.13-1.90 (m, 3H), 1.60 (d, J=5.9 Hz, 1H), 1.23 (t, J=6.9 Hz, 3H), 1.20-1.09 (6H)

Example 101: (R)-3-(3-(6-((6-(3-((3-ethoxypyridin-2-yl)oxy)piperidin-1-yl)pyrazin-2-yl)amino)-5-fluoropyridin-2-yl)phenyl)-2,2-dimethylpropanoic Acid

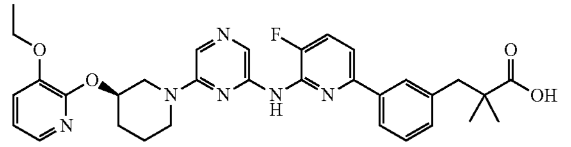 [SMILES: CCOc1cccnc1O[C@@H]1CCCN(c2cncc(Nc3nc(-c4cccc(CC(C)(C)C(=O)O)c4)ccc3F)n2)C1]

The title compound was obtained in a similar manner to Example 22 by using (R)-2-chloro-6-(3-((3-ethoxypyridin-2-yl)oxy)piperidin-1-yl)pyrazine (45 mg, 0.13 mmol) synthesized in Preparation Example 3 and tert-butyl 3-(3-(6-amino-5-fluoropyridin-2-yl)phenyl)-2,2-dimethylpropanoate (46 mg, 0.13 mmol) synthesized in Preparation Example 85. (2 step yield 24%)

$^1$H-NMR (400 MHz, METHANOL-D4) δ 8.99 (s, 1H), 7.86 (s, 1H), 7.79 (d, J=7.8 Hz, 1H), 7.71-7.58 (m, 2H), 7.48 (dd, J=10.5, 8.2 Hz, 1H), 7.41-7.34 (m, 1H), 7.31 (d, J=7.8 Hz, 1H), 7.19 (d, J=7.3 Hz, 1H), 6.96 (dd, J=7.8, 1.8 Hz, 1H), 6.78 (dd, J=7.8, 5.0 Hz, 1H), 5.16 (q, J=2.6 Hz, 1H), 4.20 (dd, J=14.0, 5.3 Hz, 1H), 3.94-3.82 (m, 1H), 3.81-3.70 (m, 2H), 3.70-3.63 (m, 1H), 3.63-3.47 (m, 1H), 2.94 (dd, J=15.6, 13.3 Hz, 2H), 2.16-1.89 (m, 4H), 1.70-1.53 (m, 1H), 1.19 (d, J=5.9 Hz, 6H), 1.15 (d, J=6.9 Hz, 3H)

Example 102: (R)-3-(3-(6-((6-(3-(2-ethoxyphenoxy)piperidin-1-yl)pyrazin-2-yl)amino)-3-fluoropyridin-2-yl)phenyl)-2,2-dimethylpropanoic Acid

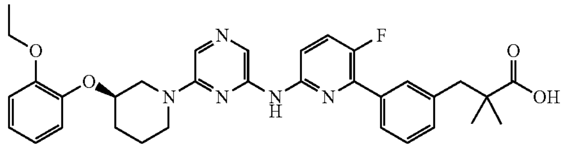 [SMILES: CCOc1ccccc1O[C@@H]1CCCN(c2cncc(Nc3ccc(F)c(-c4cccc(CC(C)(C)C(=O)O)c4)n3)n2)C1]

The title compound was obtained in a similar manner to Example 22 by using (R)-6-(3-(2-ethoxyphenoxy)piperidin-1-yl)pyrazin-2-amine (43 mg, 0.14 mmol) synthesized in Preparation Example 2 and tert-butyl 3-(3-(6-chloro-3-fluoropyridin-2-yl)phenyl)-2,2-dimethylpropanoate (50 mg, 0.14 mmol) synthesized in Step 1 of Preparation Example 87. (2 step yield 55%)

$^1$H-NMR (400 MHz, METHANOL-D4) δ 8.40 (s, 1H), 7.78 (d, J=6.4 Hz, 2H), 7.55 (s, 1H), 7.49 (dd, J=10.5, 8.7 Hz, 1H), 7.42-7.33 (m, 1H), 7.33-7.17 (m, 2H), 6.95 (d, J=6.9 Hz, 1H), 6.90-6.73 (m, 3H), 4.51 (t, J=2.7 Hz, 1H), 4.04-3.93 (m, 2H), 3.93-3.80 (2H), 3.76 (d, J=14.2 Hz, 1H), 3.49 (td, J=8.9, 4.1 Hz, 1H), 2.95 (s, 2H), 2.13-1.99 (m, 3H), 1.70-1.53 (m, 1H), 1.23 (t, J=6.9 Hz, 4H), 1.19 (s, 6H)

Example 103: (R)-3-(3-(6-((6-(3-((3-ethoxypyridin-2-yl)oxy)piperidin-1-yl)pyrazin-2-yl)amino)-3-fluoropyridin-2-yl)phenyl)-2,2-dimethylpropanoic Acid

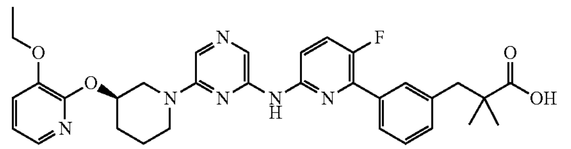 [SMILES: CCOc1cccnc1O[C@@H]1CCCN(c2cncc(Nc3ccc(F)c(-c4cccc(CC(C)(C)C(=O)O)c4)n3)n2)C1]

The title compound was obtained in a similar manner to Example 22 by using (R)-2-chloro-6-(3-((3-ethoxypyridin-2-yl)oxy)piperidin-1-yl)pyrazine (113 mg, 0.34 mmol) synthesized in Preparation Example 3 and tert-butyl 3-(3-(6-amino-3-fluoropyridin-2-yl)phenyl)-2,2-dimethylpropanoate (68 mg, 0.23 mmol) synthesized in Preparation Example 87. (2 step yield 54%)

$^1$H-NMR (400 MHz, METHANOL-D4) δ 8.24 (s, 1H), 7.90-7.73 (m, 2H), 7.59 (dd, J=5.0, 1.4 Hz, 1H), 7.52 (s, 1H), 7.46-7.26 (m, 3H), 7.23 (d, J=7.3 Hz, 1H), 7.03 (dd, J=8.0, 1.6 Hz, 1H), 6.73 (dd, J=7.8, 5.0 Hz, 1H), 5.28-5.12 (m, 1H), 4.16-3.98 (m, 2H), 3.95-3.69 (m, 4H), 3.69-3.51 (m, 1H), 2.94 (s, 2H), 2.18-2.00 (m, 2H), 1.96 (d, J=9.1 Hz, 1H), 1.72-1.55 (m, 1H), 1.25-1.16 (m, 9H)

Example 104: (R)-2-(3-(6-((6-(3-((3-ethoxypyridin-2-yl)oxy)piperidin-1-yl)pyrazin-2-yl)amino)-5-fluoropyridin-2-yl)phenoxy)-2-methylpropanoic Acid

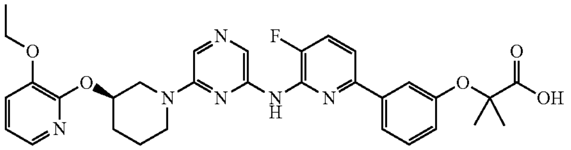 [SMILES: CCOc1cccnc1O[C@@H]1CCCN(c2cncc(Nc3nc(-c4cccc(OC(C)(C)C(=O)O)c4)ccc3F)n2)C1]

Step 1: (R)-6-(3-((3-ethoxypyridin-2-yl)oxy)piperidin-1-yl)pyrazin-2-amine

The desired product was obtained in a similar manner to Preparation Example 19 (Step 3, Step 4) by using (R)-2-chloro-6-(3-((3-ethoxypyridin-2-yl)oxy)piperidin-1-yl) pyrazine (5 g, 14.93 mmol) synthesized in Preparation Example 3. (2 step yield 90%)

$^1$H-NMR (400 MHz, CHLOROFORM-D) δ 7.72 (dd, J=4.8, 1.6 Hz, 1H), 7.31 (s, 1H), 7.28 (s, 1H), 7.02 (dd, J=7.8, 1.4 Hz, 1H), 6.82 (dd, J=7.8, 5.0 Hz, 1H), 5.27-5.09 (m, 1H), 4.03-3.77 (m, 4H), 3.77-3.66 (1H), 3.66-3.52 (1H), 2.20-1.89 (m, 4H), 1.74-1.56 (m, 1H), 1.39-1.27 (m, 3H)

Step 2: (R)—N-(6-chloro-3-fluoropyridin-2-yl)-6-(3-((3-ethoxypyridin-2-yl)oxy)piperidine-1-yl) pyrazin-2-amine (R)-6-(3-((3-ethoxypyridin-2-yl)oxy)piperidin-1-yl) pyrazin-2-amine (2.91 g, 9.23 mmol) synthesized in step 1 and 2,6-dichloro-3-fluoropyridine (1.84 g, 11.07 mmol), tris(dibenzylideneacetone)dipalladium(0) (507 mg, 0.55 mmol), 4,5-bis(diphenylphosphino)-9,9-dimethylxanthine (481 mg, 0.83 mmol) and cesium carbonate (7.52 g, 23.07 mmol) were dissolved in 1,4-dioxane and stirred under reflux for 4 hours. After the reaction was completed, the reaction mixture was cooled to room temperature, diluted with ethyl acetate, washed with aqueous sodium hydrogen carbonate solution and brine, and the organic solvent was dried over magnesium sulfate, and then removed under reduced pressure. The desired product was obtained by purification with silica gel column (hexane:ethyl acetate). (Yield 39%)

$^1$H-NMR (400 MHz, CHLOROFORM-D) δ 8.84 (s, 1H), 7.90-7.78 (1H), 7.73 (q, J=2.3 Hz, 1H), 7.36-7.26 (m, 1H), 6.95 (dd, J=7.8, 1.8 Hz, 1H), 6.87 (s, 1H), 6.84-6.71 (m, 2H), 5.28-5.12 (m, 1H), 4.04-3.81 (m, 4H), 3.77 (qd, J=6.8, 3.4 Hz, 1H), 3.63-3.44 (m, 1H), 2.16 (td, J=8.8, 4.6 Hz, 1H), 2.02-1.89 (m, 2H), 1.67 (td, J=8.3, 4.1 Hz, 1H), 1.30 (t, J=6.9 Hz, 3H)

Step 3: (R)-2-(3-(6-((6-(3-((3-ethoxypyridin-2-yl) oxy)piperidin-1-yl)pyrazin-2-yl) amino)-5-fluoropyridin-2-yl)phenoxy)-2-methylpropanoic Acid (R)—N-(6-chloro-3-fluoropyridin-2-yl)-6-(3-((3-ethoxypyridin-2-yl)oxy)piperidin-1-yl)pyrazin-2-amine (157 mg, 0.35 mmol) synthesized in step 2 and ethyl 2-methyl-2-(3-(4,4,5,5-tetramethyl-1,3,2-dioxaborolan-2-yl)phenoxy)propanoate (142 mg, 0.423 mmol) synthesized in step 2 of Preparation Example 88 were dissolved in 1,4-dioxane, and potassium phosphate tribasic (225 mg, 1.059 mmol) was added. After removing the dissolved oxygen from the reaction mixture, it was filled with nitrogen and the inflow of outside air was blocked. Palladium acetate (4.75 mg, 0.021 mmol) was added, followed by connecting a reflux cooling device and heated for 14 hours at 140° C. After completion of the reaction, the mixture was filtered through Celite and concentrated under reduced pressure, and the mixture was purified by column chromatography (hexane:ethyl acetate) to synthesize the desired compound. (Yield 12%)

The obtained ester compound (27 mg, 0.04 mmol) was dissolved in THF:methanol:water=1:1:1, and lithium hydroxide (10 mg, 0.44 mmol) was added, followed by stirring at room temperature for 12 hours. After completion of the reaction, it was diluted with water, neutralized with 1 N hydrochloric acid solution, extracted with ethyl acetate, and the organic solvent was dried over magnesium sulfate, and the organic solvent was removed under reduced pressure. The title compound was obtained by purification with silica gel column (ethyl acetate:methanol). (Yield 36%)

$^1$H-NMR (400 MHz, METHANOL-D4) δ 8.85 (s, 1H), 7.72-7.54 (m, 4H), 7.48 (dd, J=10.5, 8.7 Hz, 1H), 7.38-7.23 (m, 2H), 7.04-6.94 (1H), 6.94-6.89 (m, 1H), 6.78 (dd, J=7.8, 5.0 Hz, 1H), 5.16 (t, J=2.5 Hz, 1H), 4.18 (dd, J=13.7, 5.5 Hz, 1H), 3.92-3.63 (m, 4H), 3.57 (t, J=4.8 Hz, 1H), 2.15-2.00 (m, 2H), 1.97 (d, J=3.7 Hz, 1H), 1.62 (s, 1H), 1.59 (s, 6H), 1.16 (t, J=6.9 Hz, 3H)

Example 105: (R)-2-(3-(6-((6-(3-((3-ethoxypyridin-2-yl)oxy)piperidin-1-yl)pyrazin-2-yl)amino)-3-fluoropyridin-2-yl)phenoxy)-2-methylpropanoic Acid

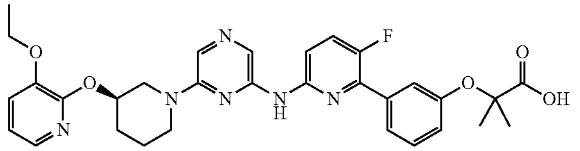 [SMILES: CCOc1cccnc1O[C@@H]1CCCN(c2cncc(Nc3ccc(F)c(-c4cccc(OC(C)(C)C(=O)O)c4)n3)n2)C1]

Step 1: (R)—N-(6-chloro-5-fluoropyridin-2-yl)-6-(3-((3-ethoxypyridin-2-yl)oxy)piperidine-1-yl) pyrazin-2-amine The title compound was synthesized in a similar manner to Step 2 of Example 104 by using (R)-6-(3-((3-ethoxypyridin-2-yl)oxy)piperidin-1-yl)pyrazin-2-amine (2.91 g, 9.23 mmol) synthesized in step 1 of Example 104 and 2,6-dichloro-3-fluoropyridine (1.84 g, 11.07 mmol). (Yield 8%)

1H-NMR (400 MHz, CHLOROFORM-D) δ 7.69 (s, 1H), 7.68 (s, 1H), 7.66-7.61 (1H), 7.59 (dd, J=8.7, 2.7 Hz, 1H), 7.34-7.19 (m, 2H), 7.08 (d, J=21.5 Hz, 1H), 6.97 (dd, J=7.8, 1.4 Hz, 1H), 6.74 (dd, J=7.8, 5.0 Hz, 1H), 5.33-5.15 (1H), 4.07-4.01 (m, 1H), 4.01-3.83 (m, 2H), 3.83-3.65 (m, 2H), 3.61-3.41 (m, 1H), 2.16 (td, J=8.6, 4.4 Hz, 1H), 2.11-1.95 (m, 4H), 1.81-1.59 (m, 1H), 1.31 (t, J=7.1 Hz, 3H)

Step 2: (R)-2-(3-(6-((6-(3-((3-ethoxypyridin-2-yl) oxy)piperidin-1-yl)pyrazin-2-yl)amino)-3-fluoropyridin-2-yl)phenoxy)-2-methylpropanoic Acid The title compound was synthesized in a similar manner to Step 3 of Example 104 by using (R)—N-(6-chloro-5-fluoropyridin-2-yl)-6-(3-((3-ethoxypyridin-2-yl)oxy)piperidin-1-yl)pyrazin-2-amine (170 mg, 0.38 mmol) synthesized in step 1 and ethyl 2-methyl-2-(3-(4,4,5,5-tetramethyl-1,3,2-dioxaborolan-2-yl)phenoxy)propanoate (153 mg, 0.46 mmol) synthesized in step 2 of Preparation Example 88. (2 step yield 4%)

$^1$H-NMR (400 MHz, METHANOL-D4) δ 8.08 (s, 1H), 7.68-7.45 (m, 5H), 7.44-7.25 (m, 3H), 7.03 (dd, J=7.8, 1.4 Hz, 1H), 6.96 (dd, J=8.2, 1.8 Hz, 1H), 6.78-6.63 (1H), 5.20 (s, 1H), 4.08 (t, J=7.1 Hz, 1H), 3.91-3.68 (m, 4H), 3.68-3.49 (1H), 2.17-2.02 (3H), 1.97 (d, J=8.7 Hz, 2H), 1.67-1.61 (1H), 1.58 (d, J=8.7 Hz, 6H), 1.20 (t, J=7.1 Hz, 3H)

Example 106: (R)-3-(3-(6-((6-(3-((3-ethoxypyridin-2-yl)oxy)piperidin-1-yl)pyrazin-2-yl)amino)-3-fluoropyridin-2-yl)-4-fluorophenyl)-2,2-dimethylpropanoic Acid

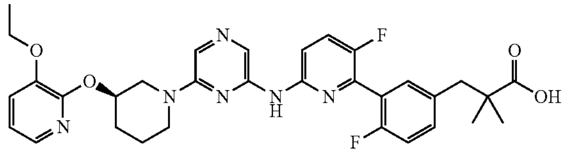 [SMILES: CCOc1cccnc1O[C@@H]1CCCN(c2cncc(Nc3ccc(F)c(-c4cc(CC(C)(C)C(=O)O)ccc4F)n3)n2)C1]

The title compound was obtained in a similar manner to Example 22 by using (R)-2-chloro-6-(3-((3-ethoxypyridin-2-yl)oxy)piperidin-1-yl)pyrazine (46 mg, 0.14 mmol) synthesized in Preparation Example 3 and tert-butyl 3-(3-(6-amino-3-fluoropyridin-2-yl)-4-fluorophenyl)-2,2-dimethylpropanoate (45 mg, 0.12 mmol) synthesized in Preparation Example 114. (2 step yield 57%)

$^1$H-NMR (400 MHz, METHANOL-D4) δ 8.96 (s, 1H), 7.80 (dd, J=7.8, 1.8 Hz, 1H), 7.65 (dd, J=5.0, 1.4 Hz, 1H), 7.63 (s, 1H), 7.48 (dd, J=10.7, 8.5 Hz, 1H), 7.41-7.28 (m, 1H), 7.27-7.12 (m, 1H), 7.07 (dd, J=11.4, 8.2 Hz, 1H), 6.97 (dd, J=7.8, 1.4 Hz, 1H), 6.78 (dd, J=7.8, 5.0 Hz, 1H), 5.15 (q, J=2.7 Hz, 1H), 4.25-4.12 (1H), 3.92-3.62 (4H), 3.62-3.46 (m, 1H), 2.91 (s, 2H), 2.15-1.89 (m, 4H), 1.69-1.52 (1H), 1.20-1.17 (m, 6H), 1.15 (t, J=6.9 Hz, 3H)

Example 107: (R)-3-(3-(6-((6-(3-(2-ethoxyphenoxy)piperidin-1-yl)pyrazin-2-yl)amino)-5-fluoropyridin-2-yl)-4-fluorophenyl)-2,2-dimethylpropanoic Acid

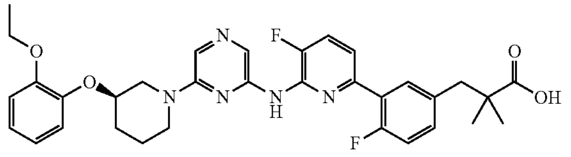 [SMILES: CCOc1ccccc1O[C@@H]1CCCN(c2cncc(Nc3nc(-c4cc(CC(C)(C)C(=O)O)ccc4F)ccc3F)n2)C1]

The title compound was obtained in a similar manner to Example 22 by using (R)-2-chloro-6-(3-(2-ethoxyphenoxy)piperidin-1-yl)pyrazine (132 mg, 0.40 mmol) synthesized in Preparation Example 1 and tert-butyl 3-(3-(6-amino-5-fluoropyridin-2-yl)-4-fluorophenyl)-2,2-dimethylpropanoate (130 mg, 0.36 mmol) synthesized in Preparation Example 115. (2 step yield 37%)

$^1$H-NMR (400 MHz, METHANOL-D4) δ 8.15 (s, 1H), 7.51 (s, 1H), 7.49-7.41 (m, 2H), 7.37 (t, J=8.9 Hz, 1H), 7.32-7.19 (m, 1H), 7.08 (dd, J=10.1, 8.2 Hz, 1H), 6.97 (d, J=7.8 Hz, 1H), 6.92-6.85 (2H), 6.84-6.72 (m, 1H), 4.49-4.33 (m, 1H), 4.00-3.80 (m, 3H), 3.73 (q, J=6.7 Hz, 1H), 3.63 (t, J=5.5 Hz, 2H), 2.90 (s, 2H), 2.16-2.00 (m, 2H), 1.95-1.81 (m, 1H), 1.61 (dd, J=9.6, 3.2 Hz, 1H), 1.35-1.23 (3H), 1.18 (s, 6H)

Example 108: (R)-3-(3-(6-((6-(3-((3-ethoxypyridin-2-yl)oxy)piperidin-1-yl)pyrazin-2-yl)amino)-5-fluoropyridin-2-yl)-4-fluorophenyl)-2,2-dimethylpropanoic Acid

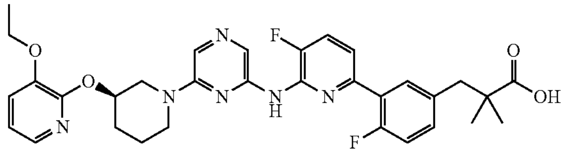 [SMILES: CCOc1cccnc1O[C@@H]1CCCN(c2cncc(Nc3nc(-c4cc(CC(C)(C)C(=O)O)ccc4F)ccc3F)n2)C1]

The title compound was obtained in a similar manner to Example 22 by using (R)-2-chloro-6-(3-((3-ethoxypyridin-2-yl)oxy)piperidin-1-yl)pyrazine (132 mg, 0.40 mmol) synthesized in Preparation Example 3 and tert-butyl 3-(3-(6-amino-5-fluoropyridin-2-yl)-4-fluorophenyl)-2,2-dimethylpropanoate (130 mg, 0.36 mmol) synthesized in Preparation Example 115. (2 step yield 41%)

$^1$H-NMR (400 MHz, METHANOL-D4) δ 8.30 (s, 1H), 7.59 (dd, J=5.0, 1.4 Hz, 2H), 7.50 (t, J=9.1 Hz, 1H), 7.43 (dd, J=7.1, 2.1 Hz, 1H), 7.38-7.21 (2H), 7.11 (dd, J=10.1, 8.2 Hz, 1H), 7.03 (dd, J=7.8, 1.4 Hz, 1H), 6.75 (dd, J=7.8, 5.0 Hz, 1H), 5.25 (t, J=2.5 Hz, 1H), 4.21 (dd, J=14.2, 5.0 Hz, 1H), 3.94 (d, J=13.3 Hz, 1H), 3.89-3.66 (3H), 3.66-3.47 (m, 1H), 2.91 (s, 2H), 2.17-2.00 (m, 3H), 1.72-1.56 (m, 1H), 1.24-1.18 (m, 9H)

Example 109: (R)-2-(4-(6-((6-(3-(2-ethoxyphenoxy)piperidin-1-yl)pyrazin-2-yl)amino)-3-(trifluoromethyl)pyridin-2-yl)phenyl)-2-methylpropanoic Acid

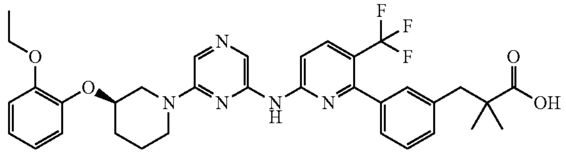 [SMILES: CCOc1ccccc1O[C@@H]1CCCN(c2cncc(Nc3ccc(C(F)(F)F)c(-c4cccc(CC(C)(C)C(=O)O)c4)n3)n2)C1]

The title compound was obtained in a similar manner to Example 12 by using (R)-2-chloro-6-(3-(2-ethoxyphenoxy)piperidin-1-yl)pyrazine (0.2 g, 0.598 mmol) obtained in Preparation Example 1 and methyl 2-(4-(6-amino-3-(trifluoromethyl)pyridin-2-yl)phenyl)-2-methylpropanoate (0.184 g, 0.544 mmol) obtained in Preparation Example 75. (2 step yield 40%)

$^1$H-NMR (CHLOROFORM-D) δ 9.19 (s, 1H), 8.13 (d, J=8.5 Hz, 2H), 7.91 (d, J=8.2 Hz, 1H), 7.78 (s, 1H), 7.70 (d, J=8.5 Hz, 2H), 7.41 (d, J=8.2 Hz, 1H), 7.24 (s, 1H), 7.06-6.82 (m, 4H), 4.38-4.23 (m, 1H), 4.23-4.09 (m, 1H), 4.09-3.87 (2H), 3.81 (d, J=13.7 Hz, 1H), 3.56 (dd, J=13.1, 7.6 Hz, 1H), 3.50-3.31 (m, 1H), 2.17 (d, J=28.7 Hz, 1H), 2.05-1.98 (m, 1H), 1.98-1.88 (m, 2H), 1.64 (td, J=9.0, 4.5 Hz, 6H), 1.39 (t, J=7.0 Hz, 3H)

Example 110: (R)-3-(3-(6-((6-(3-(2-ethoxyphenoxy)piperidin-1-yl)pyrazin-2-yl)amino)-4-(trifluoromethyl)pyridin-2-yl)phenyl)-2,2-dimethylpropanoic Acid

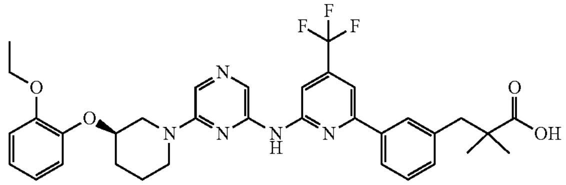 [SMILES: CCOc1ccccc1O[C@@H]1CCCN(c2cncc(Nc3cc(C(F)(F)F)cc(-c4cccc(CC(C)(C)C(=O)O)c4)n3)n2)C1]

The title compound was obtained in a similar manner to Example 22 by using (R)-2-chloro-6-(3-(2-ethoxyphenoxy)piperidin-1-yl)pyrazine (110 mg, 0.330 mmol) prepared in Preparation Example 1 and tert-butyl 3-(3-(6-amino-4-(trifluoromethyl)pyridin-2-yl)phenyl)-2,2-dimethylpropanoate (130 mg, 0.330 mmol) prepared in Preparation Example 84. (2 step yield 80%)

$^1$H-NMR (400 MHz, CHLOROFORM-D) δ 9.44 (s, 1H), 8.19 (s, 1H), 7.79-7.62 (m, 2H), 7.55-7.43 (1H), 7.36 (t, J=7.8 Hz, 1H), 7.21 (d, J=7.8 Hz, 1H), 7.02-6.82 (m, 5H), 6.80 (s, 1H), 4.42-4.26 (m, 1H), 4.09-3.85 (m, 3H), 3.85-3.70 (m, 1H), 3.66 (q, J=6.9 Hz, 1H), 3.53-3.34 (1H), 3.09-2.97 (2H), 2.16-2.08 (m, 1H), 2.08-1.96 (m, 1H), 1.96-1.84 (1H), 1.61 (qd, J=8.7, 4.5 Hz, 1H), 1.36 (t, J=7.1 Hz, 3H), 1.25 (d, J=1.4 Hz, 6H)

Example 111: (R)-3-(3-(6-((6-(3-(2-ethoxyphenoxy)piperidin-1-yl)pyrazin-2-yl)amino)-3-methylpyridin-2-yl)phenyl)-2,2-dimethylpropanoic Acid

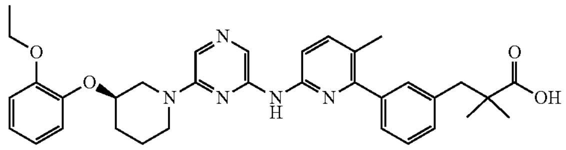 [SMILES: CCOc1ccccc1O[C@@H]1CCCN(c2cncc(Nc3ccc(C)c(-c4cccc(CC(C)(C)C(=O)O)c4)n3)n2)C1]

The title compound was obtained in a similar manner to Example 22 by using (R)-2-chloro-6-(3-(2-ethoxyphenoxy)piperidin-1-yl)pyrazine (26 mg, 0.08 mmol) synthesized in Preparation Example 1 and tert-butyl 3-(3-(6-amino-3-methylpyridin-2-yl)phenyl)-2,2-dimethylpropanoate (24 mg, 0.07 mmol) synthesized in Preparation Example 91. (2 step yield 44%)

$^1$H-NMR (400 MHz, METHANOL-D4) δ 8.07 (s, 1H), 7.48 (s, 1H), 7.45-7.26 (m, 6H), 7.20 (d, J=7.3 Hz, 1H), 6.97 (d, J=7.8 Hz, 1H), 6.88 (d, J=3.7 Hz, 2H), 6.85-6.72 (m, 1H), 4.47-4.31 (m, 1H), 4.02-3.80 (m, 3H), 3.76-3.53 (m, 4H), 2.92 (s, 2H), 2.24 (d, J=9.1 Hz, 3H), 2.16-1.96 (m, 4H), 1.96-1.82 (m, 1H), 1.69-1.53 (m, 1H), 1.26 (t, J=7.1 Hz, 3H), 1.18 (s, 6H)

Example 112: (R)-3-(3-(6-((6-(3-(2-ethoxyphenoxy)piperidin-1-yl)pyrazin-2-yl)amino)pyrazin-2-yl)phenyl)-2,2-dimethylpropanoic Acid

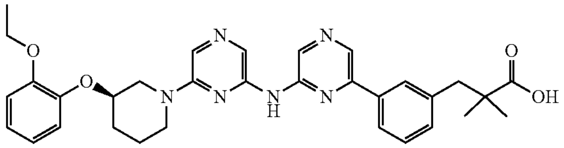 [SMILES: CCOc1ccccc1O[C@@H]1CCCN(c2cncc(Nc3cncc(-c4cccc(CC(C)(C)C(=O)O)c4)n3)n2)C1]

The title compound was obtained in a similar manner to Example 22 by using (R)-2-chloro-6-(3-(2-ethoxyphenoxy)piperidin-1-yl)pyrazine (99.0 mg, 0.296 mmol) prepared in Preparation Example 1 and tert-butyl 3-(3-(6-aminopyrazin-2-yl)phenyl)-2,2-dimethylpropanoate (97.0 mg, 0.296 mmol) prepared in Preparation Example 82. (2 step yield 88%)

$^1$H-NMR (400 MHz, CHLOROFORM-D) δ 9.37 (s, 1H), 8.60 (s, 1H), 8.21 (s, 1H), 8.07 (s, 1H), 7.89-7.78 (1H), 7.74 (d, J=6.9 Hz, 1H), 7.37 (t, J=7.8 Hz, 1H), 7.22 (d, J=7.3 Hz, 1H), 7.06-6.76 (m, 5H), 4.36 (d, J=4.1 Hz, 1H), 3.95 (ddd, J=30.9, 16.2, 7.5 Hz, 3H), 3.84-3.61 (2H), 3.62-3.42 (m, 1H), 3.01 (s, 2H), 2.21-1.85 (m, 3H), 1.61 (dd, J=21.5, 8.2 Hz, 1H), 1.36 (t, J=7.1 Hz, 3H), 1.26 (s, 6H)

Example 113: (R)—N-(6-(3-(2-ethoxyphenoxy)piperidin-1-yl)pyrazin-2-yl)pyrimidin-2-amine

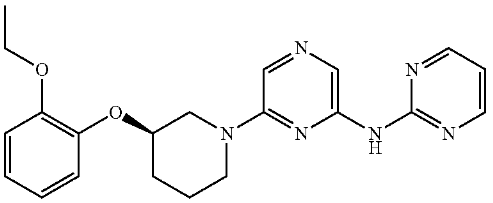 [SMILES: CCOc1ccccc1O[C@@H]1CCCN(c2cncc(Nc3ncccn3)n2)C1]

The title compound was obtained in a similar manner to Example 1 by using (R)-2-chloro-6-(3-(2-ethoxyphenoxy)piperidin-1-yl)pyrazine (0.10 g, 0.30 mmol) prepared in Preparation Example 1 and 2-aminopyrimidine (0.03 g, 0.33 mmol). (Yield 72%)

$^1$H-NMR (500 MHz, CHLOROFORM-D): δ 8.93 (s, 1H), 8.49 (d, J=4.9 Hz, 2H), 7.79 (s, 1H), 7.61 (s, 1H), 7.05-6.99 (1H), 6.97-6.93 (m, 1H), 6.88 (t, J=7.3 Hz, 2H), 6.79 (t, J=4.9 Hz, 1H), 4.27 (td, J=8.1, 3.9 Hz, 1H), 4.15 (dd, J=13.1, 3.4 Hz, 1H), 4.07-3.93 (m, 2H), 3.85 (td, J=8.9, 4.1 Hz, 1H), 3.53-3.38 (m, 1H), 3.36-3.21 (m, 1H), 2.15 (dd, J=11.3, 3.4 Hz, 1H), 2.04-1.93 (m, 1H), 1.91-1.80 (m, 1H), 1.61 (td, J=9.3, 4.3 Hz, 1H), 1.44-1.32 (m, 3H)

Example 114: (R)-2-((6-(3-(2-ethoxyphenoxy)piperidin-1-yl)pyrazin-2-yl)amino)pyrimidine-5-carboxylic Acid

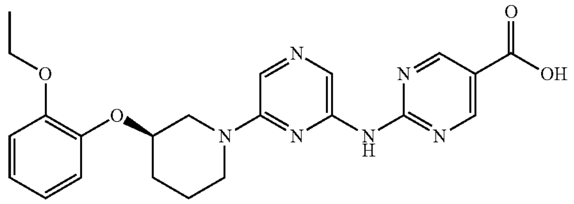 [SMILES: CCOc1ccccc1O[C@@H]1CCCN(c2cncc(Nc3ncc(C(=O)O)cn3)n2)C1]

The title compound was obtained in a similar manner to Example 1 by using (R)-2-chloro-6-(3-(2-ethoxyphenoxy) piperidin-1-yl)pyrazine (0.15 g, 0.45 mmol) prepared in Preparation Example 1 and methyl 2-aminopyrimidine-5-carboxylate (0.076 g, 0.49 mmol). (Yield 54%)

$^1$H-NMR (500 MHz, CHLOROFORM-D): δ 9.03 (s, 2H), 8.98-8.88 (1H), 7.85 (s, 1H), 7.71 (s, 1H), 6.97 (q, J=8.4 Hz, 2H), 6.91-6.78 (m, 2H), 4.42-4.22 (m, 1H), 4.19-4.06 (m, 1H), 4.04-3.97 (m, 2H), 3.93 (d, J=1.2 Hz, 3H), 3.81 (q, J=4.5 Hz, 1H), 3.63-3.51 (m, 1H), 3.43-3.32 (m, 1H), 2.13 (t, J=5.8 Hz, 1H), 2.07-1.96 (m, 1H), 1.91 (q, J=4.3 Hz, 1H), 1.62 (d, J=4.3 Hz, 1H), 1.38 (t, J=6.4 Hz, 3H)

The title compound was obtained through a hydrolysis reaction of the obtained ester compound (0.11 g, 0.24 mmol) in a similar manner to Example 1. (Yield 75%)

$^1$H-NMR (500 MHz, DMSO-D6): (13.39-12.85 (1H), 10.16 (s, 1H), 8.93 (d, J=17.7 Hz, 2H), 8.61 (s, 1H), 7.98-7.78 (1H), 7.01 (d, J=6.7 Hz, 1H), 6.94-6.85 (m, 2H), 6.80 (t, J=6.7 Hz, 1H), 4.29 (t, J=3.7 Hz, 1H), 4.08 (d, J=13.4 Hz, 1H), 3.99-3.80 (m, 2H), 3.72 (d, J=14.7 Hz, 1H), 3.47 (q, J=6.7 Hz, 2H), 1.99 (d, J=9.2 Hz, 1H), 1.80 (s, 1H), 1.69 (t, J=4.3 Hz, 1H), 1.59-1.41 (m, 1H), 1.33-1.04 (m, 3H)

Example 115: (R)-2-(2-((6-(3-(2-ethoxyphenoxy) piperidin-1-yl)pyrazin-2-yl)pyrimidin-4-yl)-2-methylpropanoic Acid

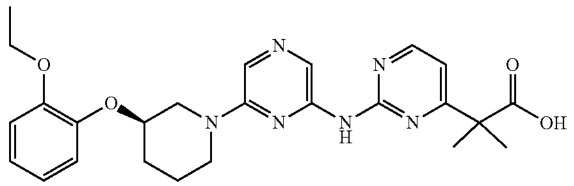 [SMILES: CCOc1ccccc1O[C@@H]1CCCN(c2cncc(Nc3nccc(C(C)(C)C(=O)O)n3)n2)C1]

The title compound was obtained in a similar manner to Example 1 by using (R)-2-chloro-6-(3-(2-ethoxyphenoxy) piperidin-1-yl)pyrazine (1.62 g, 4.85 mmol) prepared in Preparation Example 1 and ethyl 2-(2-aminopyrimidin-4-yl)-2-methylpropanoate (1.02 g, 4.85 mmol) synthesized in Preparation Example 20. (2 step yield 17%)

$^1$H-NMR (400 MHz, DMSO-D6) (8.97 (s, 1H), 8.85 (s, 1H), 8.31 (d, 1H), 7.80 (s, 1H), 7.06 (d, 1H), 6.94-6.87 (m, 4H), 4.33 (m, 1H), 4.11 (d, 1H), 3.94 (m, 2H), 3.79 (m, 1H), 3.45 (m, 2H), 2.02 (m, 1H), 1.85 (m, 1H), 1.71 (m, 1H), 1.55 (m, 1H), 1.25 (t, 3H)

Example 116: (R)-2-(2-((4-(3-((3-ethoxypyridin-2-yl)oxy)piperidin-1-yl)pyrimidin-2-yl)pyrimidin-4-yl)-2-methylpropanoic Acid

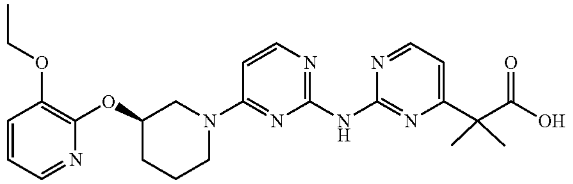 [SMILES: CCOc1cccnc1O[C@@H]1CCCN(c2ccnc(Nc3nccc(C(C)(C)C(=O)O)n3)n2)C1]

The title compound was obtained in a similar manner to Example 1 by using (R)-2-chloro-6-(3-((3-ethoxypyridin-2-yl)oxy)piperidin-1-yl)pyrazine (0.15 g, 0.49 mmol) obtained in Preparation Example 3 and ethyl 2-(2-aminopyrimidin-4-yl)-2-methylpropanoate (94 mg, 0.49 mmol) synthesized in Preparation Example 20. (2 step yield 54%)

$^1$H-NMR (400 MHz, DMSO-D6) (8.93 (s, 1H), 8.22 (d, J=4.6 Hz, 1H), 7.96 (d, J=5.9 Hz, 1H), 7.65 (d, J=4.6 Hz, 1H), 7.22 (d, J=7.3 Hz, 1H), 6.99-6.80 (m, 2H), 6.30 (d, J=5.0 Hz, 1H), 5.06 (s, 1H), 4.12 (s, 1H), 4.04-3.75 (m, 3H), 3.55 (dd, J=12.6, 7.5 Hz, 2H), 2.09 (s, 1H), 1.77 (d, J=13.7 Hz, 2H), 1.52 (d, J=5.0 Hz, 1H), 1.30 (d, J=5.9 Hz, 6H), 1.23 (t, J=7.1 Hz, 3H)

Example 117: (2-((6-((R)-3-(2-ethoxyphenoxy)piperidin-1-yl)pyrazin-2-yl)amino)pyrimidin-4-yl)-L-proline

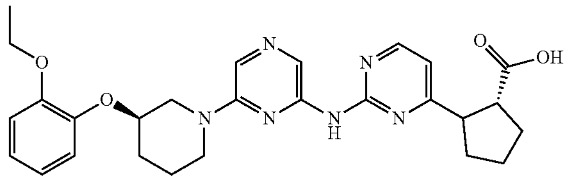 [SMILES: CCOc1ccccc1O[C@@H]1CCCN(c2cncc(Nc3nccc(C4CCC[C@H]4C(=O)O)n3)n2)C1]

Step 1: Methyl (2-((6-((R)-3-(2-ethoxyphenoxy) piperidin-1-yl)pyrazin-2-yl)amino)pyrimidin-4-yl)-L-Prolinate The title compound was obtained in a similar manner to Example 1 by using (R)-2-chloro-6-(3-(2-ethoxyphenoxy) piperidin-1-yl)pyrazine (0.172 g, 0.514 mmol) prepared in Preparation Example 1 and methyl (2-aminopyrimidin-4-yl)-L-prolinate (0.120 g, 0.540 mmol) prepared in Preparation Example 37. (Yield 72%)

$^1$H-NMR (500 MHz, CHLOROFORM-D) δ 9.24-8.69 (1H), 8.07 (s, 1H), 8.02-7.79 (1H), 7.73 (d, J=6.4 Hz, 1H), 7.11-6.66 (m, 4H), 5.95 (s, 1H), 4.78 (s, 1H), 4.27 (d, J=7.6 Hz, 1H), 4.19 (d, J=13.1 Hz, 1H), 4.12 (dd, J=12.2, 7.0 Hz, 1H), 4.07-3.96 (m, 2H), 3.88 (s, 1H), 3.72 (d, J=7.9 Hz, 3H), 3.65-3.49 (1H), 3.35 (d, J=28.4 Hz, 2H), 3.21 (s, 1H), 2.34-2.21 (1H), 2.16 (d, J=5.8 Hz, 2H), 2.03-1.98 (1H), 1.91 (s, 1H), 1.90-1.72 (1H), 1.61 (s, 1H), 1.42-1.30 (m, 3H)

Step 2: (2-((6-((R)-3-(2-ethoxyphenoxy)piperidin-1-yl)pyrazin-2-yl)amino)pyrimidin-4-yl)-L-proline Methyl (2-((6-((R)-3-(2-ethoxyphenoxy)piperidin-1-yl) pyrazin-2-yl)amino)pyrimidin-4-yl-L-prolinate (0.191 g, 0.368 mmol) obtained in step 1 was dissolved in methanol (1.8 ml) and THF (1.8 ml), and then 6 N aqueous sodium hydroxide solution (0.306 ml, 1.838 mmol) was added and stirred at room temperature for 4 hours. After removing the solvent under reduced pressure, it was dissolved in ethyl acetate and washed with water. The title compound was obtained by purification with silica gel column. (Yield 47%)

m/z $(M+H)^+$ calculated for $C_{26}H_{32}N_7O_4$: 506. found 506.

Example 118: 1-(2-((6-((R)-3-(2-ethoxyphenoxy)piperidin-1-yl)pyrazin-2-yl)amino)pyrimidin-4-yl)pyrrolidine-3-carboxylic Acid

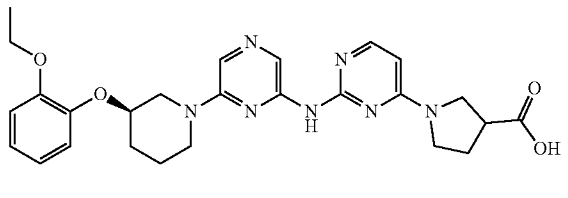 [SMILES: CCOc1ccccc1O[C@@H]1CCCN(c2cncc(Nc3nccc(N4CCC(C(=O)O)C4)n3)n2)C1]

The title compound was obtained in a similar manner to Example 1 by using (R)-2-chloro-6-(3-(2-ethoxyphenoxy)piperidin-1-yl)pyrazine (0.140 g, 0.446 mmol) prepared in Preparation Example 1 and methyl 1-(2-aminopyrimidin-4-yl)pyrrolidine-3-carboxylate (0.104 g, 0.468 mmol) prepared in Preparation Example 39. (Yield 53%)

$^1$H-NMR (500 MHz, CHLOROFORM-D) δ 8.94 (s, 1H), 8.90-8.36 (1H), 7.86 (s, 1H), 7.72 (s, 1H), 7.01 (d, J=7.9 Hz, 1H), 7.00-6.94 (1H), 6.89 (t, J=7.8 Hz, 2H), 5.89 (d, J=6.1 Hz, 1H), 4.36-4.24 (m, 1H), 4.18 (d, J=13.1 Hz, 1H), 4.12-3.94 (m, 3H), 3.87 (d, J=13.1 Hz, 2H), 3.84-3.70 (1H), 3.69-3.51 (1H), 3.51-3.40 (1H), 3.36 (d, J=9.8 Hz, 1H), 3.30-3.11 (1H), 2.58-2.37 (1H), 2.27 (s, 1H), 2.12 (s, 1H), 1.97 (d, J=13.7 Hz, 1H), 1.88 (s, 1H), 1.68-1.53 (m, 1H), 1.40 (t, J=7.0 Hz, 3H)

Example 119: 1-(2-((6-((R)-3-(2-ethoxyphenoxy)piperidin-1-yl)pyrazin-2-yl)amino)pyrimidin-4-yl)-3-methylpyrrolidine-3-carboxylic Acid

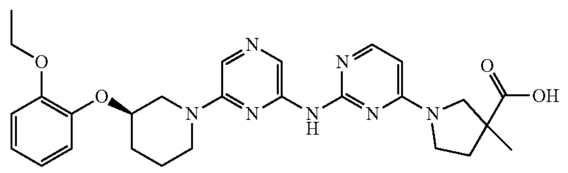 [SMILES: CCOc1ccccc1O[C@@H]1CCCN(c2cncc(Nc3nccc(N4CCC(C)(C(=O)O)C4)n3)n2)C1]

The title compound was obtained in a similar manner to Example 1 by using (R)-2-chloro-6-(3-(2-ethoxyphenoxy)piperidin-1-yl)pyrazine (0.226 g, 0.677 mmol) prepared in Preparation Example 1 and methyl 1-(2-aminopyrimidin-4-yl)-3-methylpyrrolidine-3-carboxylate (0.168 g, 0.711 mmol) prepared in Preparation Example 48. (Yield 23%)

$^1$H-NMR (400 MHz, CHLOROFORM-D) δ 8.94 (s, 1H), 8.28-7.95 (1H), 7.85 (s, 1H), 7.67 (s, 1H), 7.02-6.82 (4H), 5.84 (d, J=6.4 Hz, 1H), 4.26 (d, J=4.1 Hz, 1H), 4.19-4.07 (m, 1H), 3.99 (qd, J=6.9, 3.3 Hz, 2H), 3.85 (s, 1H), 3.78-3.50 (2H), 3.49-3.35 (m, 2H), 3.30 (s, 1H), 3.22-3.04 (1H), 2.68-2.53 (1H), 2.10 (s, 1H), 1.92 (t, J=15.1 Hz, 3H), 1.57 (d, J=14.2 Hz, 1H), 1.46 (s, 3H), 1.37 (t, J=6.9 Hz, 3H)

Example 120: 1-(2-((6-((R)-3-(2-ethoxyphenoxy)piperidin-1-yl)pyrazin-2-yl)amino)pyrimidin-4-yl)piperidine-3-carboxylic Acid

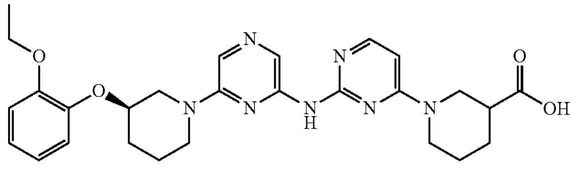 [SMILES: CCOc1ccccc1O[C@@H]1CCCN(c2cncc(Nc3nccc(N4CCCC(C(=O)O)C4)n3)n2)C1]

The title compound was obtained in a similar manner to Example 46 by using (R)-2-chloro-6-(3-(2-ethoxyphenoxy)piperidin-1-yl)pyrazine (0.145 g, 0.436 mmol) prepared in Preparation Example 1 and ethyl 1-(2-aminopyrimidin-4-yl)piperidine-3-carboxylate (0.120 g, 0.479 mmol) prepared in Preparation Example 43. (Yield 31%)

$^1$H-NMR (400 MHz, CHLOROFORM-D) δ 8.74 (s, 1H), 7.90-7.55 (m, 2H), 7.02-6.78 (m, 4H), 6.20-6.00 (1H), 4.28-4.06 (m, 2H), 4.06-3.87 (m, 3H), 3.78 (s, 1H), 3.55-3.19 (m, 3H), 3.15 (s, 1H), 2.47 (s, 1H), 2.04 (d, J=11.9 Hz, 2H), 1.96-1.67 (m, 4H), 1.62-1.39 (m, 2H), 1.34 (t, J=6.9 Hz, 3H), 1.29-1.11 (m, 1H)

Example 121: (R)-1-(2-((6-((R)-3-(2-ethoxyphenoxy)piperidin-1-yl)pyrazin-2-yl)amino)pyrimidin-4-yl)piperidine-3-carboxylic Acid

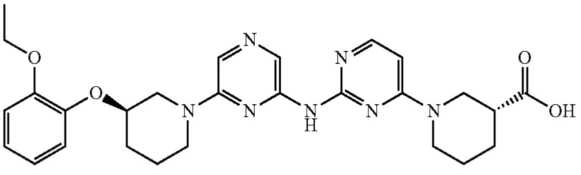 [SMILES: CCOc1ccccc1O[C@@H]1CCCN(c2cncc(Nc3nccc(N4CCC[C@@H](C(=O)O)C4)n3)n2)C1]

Step 1: Ethyl (R)-1-(2-((6-((R)-3-(2-ethoxyphenoxy)piperidin-1-yl)pyrazin-2-yl)amino)pyrimidine-4-yl)piperidine-3-carboxylate The title compound was obtained in a similar manner to Example 1 by using (R)-2-chloro-6-(3-(2-ethoxyphenoxy)piperidin-1-yl)pyrazine (0.061 g, 0.182 mmol) prepared in Preparation Example 1 and ethyl (R)-1-(2-aminopyrimidin-4-yl)piperidine-3-carboxylate (0.050 g, 0.200 mmol) prepared in Preparation Example 30. (Yield 42%)

$^1$H-NMR (500 MHz, CHLOROFORM-D) δ 8.83 (s, 1H), 8.02 (d, J=6.4 Hz, 1H), 7.73 (s, 1H), 7.36 (s, 1H), 7.08-6.99 (1H), 6.99-6.93 (1H), 6.93-6.82 (m, 2H), 6.13 (d, J=6.4 Hz, 1H), 4.34-4.22 (m, 2H), 4.22-4.07 (m, 4H), 4.07-3.94 (m, 2H), 3.87 (dt, J=12.9, 4.6 Hz, 1H), 3.46-3.32 (m, 2H), 3.32-3.23 (m, 1H), 3.23-3.11 (m, 1H), 2.63-2.47 (m, 1H), 2.16 (dd, J=12.8, 4.6 Hz, 1H), 2.08 (td, J=8.7, 4.3 Hz, 1H), 2.01-1.91 (m, 1H), 1.91-1.73 (m, 3H), 1.69-1.48 (m, 2H), 1.47-1.33 (m, 3H), 1.26 (t, J=7.2 Hz, 3H)

Step 2: (R)-1-(2-((6-((R)-3-(2-ethoxyphenoxy)piperidin-1-yl)pyrazin-2-yl)amino)pyrimidin-4-yl)piperidine-3-carboxylic Acid Ethyl (R)-1-(2-((6-((R)-3-(2-ethoxyphenoxy)piperidin-1-yl)pyrazin-2-yl)amino)pyrimidin-4-yl)piperidine-3-carboxylate (0.042 g, 0.077 mmol) obtained in step 1 was dissolved in ethanol (0.4 ml) and THF (0.4 ml), and then 7 N aqueous sodium hydroxide solution (0.110 ml, 0.767 mmol) was added and stirred at room temperature for 4 hours. After removing the solvent under reduced pressure, it was dissolved in ethyl acetate and washed with water. The title compound was obtained by purification with silica gel column. (Yield 37%)

m/z $(M+H)^+$ calculated for $C_{27}H_{34}N_7O_4$: 520. found 520.

Example 122: 1-(2-((6-((R)-3-(2-ethoxyphenoxy) piperidin-1-yl)pyrazin-2-yl)amino)pyrimidin-4-yl)-3-methylpiperidine-3-carboxylic Acid

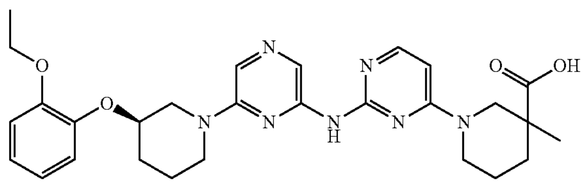 [SMILES: CCOc1ccccc1O[C@@H]1CCCN(c2cncc(Nc3nccc(N4CCCC(C)(C(=O)O)C4)n3)n2)C1]

Step 1: Ethyl 1-(2-((6-((R)-3-(2-ethoxyphenoxy) piperidin-1-yl)pyrazin-2-yl)amino)pyrimidin-4-yl)-3-methylpiperidine-3-carboxylate The desired product was obtained in a similar manner to Example 1 by using (R)-2-chloro-6-(3-(2-ethoxyphenoxy) piperidin-1-yl)pyrazine (0.111 g, 0.331 mmol) prepared in Preparation Example 1 and ethyl 1-(2-aminopyrimidin-4-yl)-3-methylpiperidine-3-carboxylate (0.092 g, 0.348 mmol) prepared in Preparation Example 40. (Yield 63%)

$^1$H-NMR (500 MHz, CHLOROFORM-D) δ 8.88 (s, 1H), 8.01 (d, J=6.1 Hz, 1H), 7.84-7.72 (1H), 7.13 (s, 1H), 7.06 (t, J=8.4 Hz, 1H), 7.02-6.96 (1H), 6.96-6.87 (m, 2H), 6.30-6.14 (1H), 4.48-4.25 (2H), 4.25-4.18 (m, 1H), 4.18-4.08 (m, 2H), 4.08-3.96 (2H), 3.96-3.79 (1H), 3.52-3.34 (1H), 3.34-3.25 (m, 1H), 3.25-3.15 (m, 1H), 3.15-2.99 (m, 1H), 2.45-2.23 (m, 1H), 2.19-2.14 (m, 1H), 2.02-1.93 (m, 1H), 1.93-1.82 (1H), 1.82-1.60 (m, 3H), 1.55-1.46 (m, 2H), 1.43 (t, J=6.9 Hz, 3H), 1.24 (s, 3H), 1.20 (t, J=7.2 Hz, 3H)

Step 2: 1-(2-((6-((R)-3-(2-ethoxyphenoxy)piperidin-1-yl)pyrazin-2-yl)amino)pyrimidin-4-yl)-3-methylpiperidine-3-carboxylic Acid Ethyl 1-(2-((6-((R)-3-(2-ethoxyphenoxy)piperidin-1-yl) pyrazin-2-yl)amino)pyrimidin-4-yl)-3-methylpiperidine-3-carboxylate (0.117 g, 0.208 mmol) obtained in step 1 was dissolved in ethanol (1 ml) and THF (1 ml), and then 6N aqueous sodium hydroxide solution (0.174 ml, 1.042 mmol) was added and stirred at room temperature for 7 hours. After removing the solvent under reduced pressure, it was dissolved in ethyl acetate and washed with water. The title compound was obtained by purification with silica gel column. (Yield 56%)

m/z $(M+H)^+$ calculated for $C_{27}H_{35}N_7O_4$: 520.62. found 520.

Example 123: (R)-1-(2-((6-(3-(2-ethoxyphenoxy) piperidin-1-yl)pyrazin-2-yl)amino)pyrimidin-4-yl) piperidine-4-carboxylic Acid

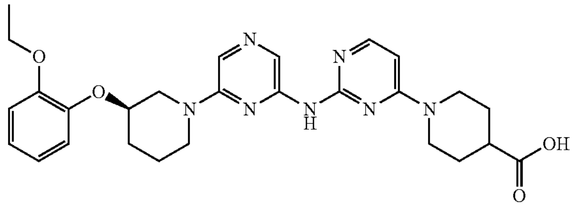 [SMILES: CCOc1ccccc1O[C@@H]1CCCN(c2cncc(Nc3nccc(N4CCC(C(=O)O)CC4)n3)n2)C1]

Step 1: Ethyl (R)-1-(2-((6-(3-(2-ethoxyphenoxy) piperidin-1-yl)pyrazin-2-yl)amino)pyrimidin-4-yl) piperidine-4-carboxylate The desired product was obtained in a similar manner to Example 1 by using (R)-2-chloro-6-(3-(2-ethoxyphenoxy) piperidin-1-yl)pyrazine (0.242 g, 0.726 mmol) prepared in Preparation Example 1 and ethyl 1-(2-aminopyrimidin-4-yl) piperidine-4-carboxylate (0.200 g, 0.799 mmol) prepared in Preparation Example 28. (Yield 73%)

$^1$H-NMR (500 MHz, CHLOROFORM-D) δ 8.83 (s, 1H), 8.03 (d, J=6.1 Hz, 1H), 7.81-7.70 (1H), 7.16 (s, 1H), 7.13-7.02 (m, 1H), 7.02-6.96 (m, 1H), 6.96-6.85 (m, 2H), 6.13 (d, J=6.1 Hz, 1H), 4.38-4.25 (m, 3H), 4.24-4.10 (m, 4H), 3.97-3.82 (m, 1H), 3.41 (dd, J=13.0, 8.1 Hz, 1H), 3.36-3.23 (m, 1H), 3.20-3.04 (m, 2H), 2.70-2.55 (m, 1H), 2.25-2.12 (m, 1H), 2.06-1.95 (m, 3H), 1.95-1.83 (m, 1H), 1.83-1.71 (m, 2H), 1.71-1.61 (m, 2H), 1.43 (t, J=7.0 Hz, 3H), 1.29 (td, J=7.2, 4.0 Hz, 3H)

Step 2: (R)-1-(2-((6-(3-(2-ethoxyphenoxy)piperidin-1-yl)pyrazin-2-yl)amino)pyrimidin-4-yl)piperidine-4-carboxylic Acid The title compound was obtained in a similar manner to Step 2 of Example 122 by using ethyl 1-(2-((6-((R)-3-(2-ethoxyphenoxy)piperidin-1-yl)pyrazin-2-yl)amino)pyrimidin-4-yl)-3-methylpiperidine-3-carboxylate (0.290 g, 0.530 mmol) obtained in step 1. (Yield 51%)

m/z $(M+H)^+$ calculated for $C_{28}H_{36}N_7O_4$: 534. found 534.

Example 124: 5-(2-((6-((R)-3-(2-ethoxyphenoxy) piperidin-1-yl)pyrazin-2-yl)amino)pyrimidin-4-yl) bicyclo[2.2.1]heptane-2-carboxylic Acid

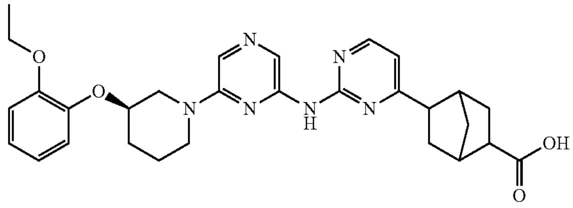 [SMILES: CCOc1ccccc1O[C@@H]1CCCN(c2cncc(Nc3nccc(C4CC5CC4CC5C(=O)O)n3)n2)C1]

The title compound was obtained in a similar manner to Example 46 by using (R)-2-chloro-6-(3-(2-ethoxyphenoxy) piperidin-1-yl)pyrazine (0.063 g, 0.187 mmol) prepared in Preparation Example 1 and methyl 5-(2-aminopyrimidin-4- yl)bicyclo[2.2.1]heptane-2-carboxylate (0.051 g, 0.206 mmol) prepared in Preparation Example 101. (Yield 9%)

$^1$H-NMR (500 MHz, CHLOROFORM-D) δ 9.07-8.88 (m, 1H), 8.41-8.26 (m, 1H), 7.87-7.68 (m, 2H), 7.12-7.00 (1H), 6.97 (t, J=7.6 Hz, 1H), 6.90 (t, J=9.2 Hz, 2H), 6.79-6.64 (m, 1H), 4.38-4.25 (m, 1H), 4.25-4.10 (2H), 4.10-3.96 (m, 1H), 3.94-3.78 (m, 1H), 3.59-3.43 (m, 1H), 3.43-3.26 (m, 1H), 3.02-2.78 (m, 2H), 2.55-2.41 (m, 1H), 2.24-2.12 (m, 1H), 2.06-1.94 (m, 2H), 1.94-1.85 (m, 2H), 1.85-1.73 (m, 2H), 1.73-1.57 (m, 2H), 1.46-1.37 (m, 4H), 1.37-1.30 (1H)

Example 125: (R)-2-(1-(2-((6-(3-(2-ethoxyphenoxy) piperidin-1-yl)pyrazin-2-yl)amino)pyrimidin-4-yl) piperidin-4-yl)acetic Acid

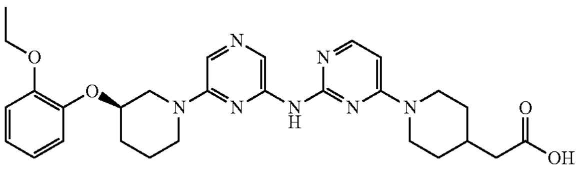

The title compound was obtained in a similar manner to Example 12 by using (R)-2-chloro-6-(3-(2-ethoxyphenoxy) piperidin-1-yl)pyrazine (0.354 g, 1.061 mmol) obtained in Preparation Example 1 and ethyl 2-(1-(2-aminopyrimidin-4-yl)piperidin-4-yl)acetate (0.255 g, 0.965 mmol) obtained in Preparation Example 32. (2 step yield 39%)

$^1$H-NMR (400 MHz, CHLOROFORM-D) δ 8.77 (d, J=6.4 Hz, 1H), 7.88 (d, J=6.4 Hz, 1H), 7.64 (d, J=14.2 Hz, 1H), 7.03-6.79 (m, 4H), 6.01 (d, J=6.4 Hz, 1H), 5.29 (s, 1H), 4.54-4.06 (m, 4H), 4.05-3.94 (m, 2H), 3.81 (d, J=12.8 Hz, 1H), 3.47-3.15 (m, 2H), 3.02-2.77 (2H), 2.22 (d, J=6.4 Hz, 2H), 2.16-1.97 (2H), 1.84 (dd, J=30.9, 21.3 Hz, 4H), 1.64-1.46 (m, 1H), 1.39-1.30 (m, 3H), 1.30-1.12 (2H)

Example 126: (R)-2-(1-(2-((6-(3-(2-ethoxyphenoxy) piperidin-1-yl)pyrazin-2-yl)amino)pyrimidin-4-yl) piperidin-4-yl)-2-methylpropanoic Acid

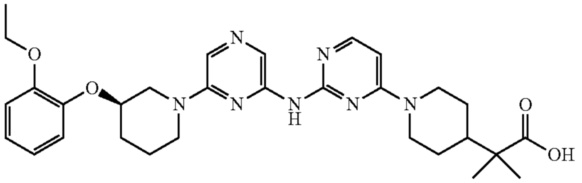 [SMILES: CCOc1ccccc1O[C@@H]1CCCN(c2cncc(Nc3nccc(N4CCC(C(C)(C)C(=O)O)CC4)n3)n2)C1]

The title compound was obtained in a similar manner to Example 12 by using (R)-2-chloro-6-(3-(2-ethoxyphenoxy) piperidin-1-yl)pyrazine (0.264 g, 0.79 mmol) obtained in Preparation Example 1 and methyl 2-(1-(2-aminopyrimidin-4-yl)piperidin-4-yl)-2-methylpropanoate (0.2 g, 0.719 mmol) obtained in Preparation Example 33. (2 step yield 20%)

$^1$H-NMR (400 MHz, CHLOROFORM-D) δ 8.68 (s, 1H), 7.87-7.79 (m, 1H), 7.70 (d, J=10.5 Hz, 1H), 7.00-6.91 (m, 2H), 6.90-6.83 (m, 3H), 6.10 (d, J=6.9 Hz, 1H), 4.51 (s, 1H), 4.33-4.18 (m, 1H), 4.15-3.93 (m, 4H), 3.92-3.78 (m, 1H), 3.53-3.29 (m, 2H), 2.92 (t, J=12.1 Hz, 2H), 2.09 (d, J=15.1 Hz, 1H), 2.00-1.71 (m, 5H), 1.57 (td, J=8.9, 4.9 Hz, 1H), 1.39-1.34 (m, 5H), 1.20-1.14 (6H)

Example 127: (R)-2-(4-(2-((6-(3-(2-ethoxyphenoxy) piperidin-1-yl)pyrazin-2-yl)amino)pyrimidin-4-yl) piperazin-1-yl)acetic Acid

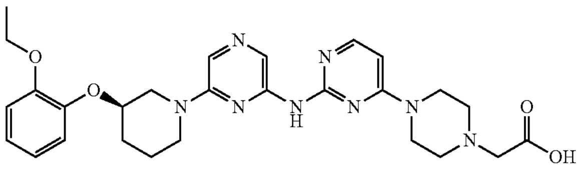 [SMILES: CCOc1ccccc1O[C@@H]1CCCN(c2cncc(Nc3nccc(N4CCN(CC(=O)O)CC4)n3)n2)C1]

Step 1: Ethyl (R)-2-(4-(2-((6-(3-(2-ethoxyphenoxy) piperidin-1-yl)pyrazin-2-yl)amino)pyrimidin-4-yl) piperazin-1-yl)acetate The desired product was obtained in a similar manner to Example 1 by using (R)-2-chloro-6-(3-(2-ethoxyphenoxy) piperidin-1-yl)pyrazine (0.021 g, 0.063 mmol) prepared in Preparation Example 1 and ethyl 2-(4-(2-aminopyrimidin-4-yl)piperazin-1-yl)acetate (0.0175 g, 0.066 mmol) prepared in Preparation Example 35. (Yield 93%)

$^1$H-NMR (400 MHz, CHLOROFORM-D) δ 8.78 (s, 1H), 8.01 (d, J=5.9 Hz, 1H), 7.71 (s, 1H), 7.15 (t, J=7.1 Hz, 1H), 7.09-6.83 (m, 4H), 6.06 (d, J=6.4 Hz, 1H), 4.53-4.11 (m, 4H), 4.11-3.94 (m, 2H), 3.94-3.80 (m, 1H), 3.71 (d, J=11.0 Hz, 4H), 3.51-3.33 (m, 1H), 3.27 (s, 2H), 2.66 (t, J=4.6 Hz, 4H), 2.14 (d, J=8.2 Hz, 1H), 2.06-1.84 (m, 2H), 1.82 (s, 1H), 1.69-1.50 (m, 1H), 1.50-1.33 (m, 3H), 1.27 (q, J=6.9 Hz, 3H)

Step 2: (R)-2-(4-(2-((6-(3-(2-ethoxyphenoxy)piperidin-1-yl)pyrazin-2-yl)amino)pyrimidin-4-yl)piperazin-1-yl)acetic Acid Ethyl (R)-2-(4-(2-((6-(3-(2-ethoxyphenoxy)piperidin-1-yl)pyrazin-2-yl)amino)pyrimidin-4-yl)piperazin-1-yl)acetate (0.033 g, 0.059 mmol) obtained in step 1 was dissolved in ethanol (0.3 ml) and THF (0.3 ml), and then 6 N aqueous sodium hydroxide solution (0.049 ml, 0.293 mmol) was added and stirred at room temperature for 2 hours. After removing the solvent under reduced pressure, it was dissolved in ethyl acetate and washed with water. The title compound was obtained by purification with Prep. TLC. (Yield 3%)

m/z $(M+H)^+$ calculated for $C_2H_{35}N_8O_4$: 535. found 535.

Example 128: 2-((S)-1-(2-((6-((R)-3-(2-ethoxyphenoxy)piperidin-1-yl)pyrazin-2-yl)amino)pyrimidin-4-yl)piperidin-3-yl)acetic Acid

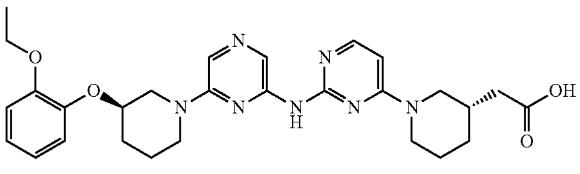 [SMILES: CCOc1ccccc1O[C@@H]1CCCN(c2cncc(Nc3nccc(N4CCC[C@@H](CC(=O)O)C4)n3)n2)C1]

Step 1: Benzyl 2-((S)-1-(2-((6-((R)-3-(2-ethoxyphenoxy)piperidin-1-yl)pyrazin-2-yl)amino)pyrimidin-4-yl)piperidin-3-yl)acetate The desired product was obtained in a similar manner to Example 1 by using (R)-2-chloro-6-(3-(2-ethoxyphenoxy)piperidin-1-yl)pyrazine (0.056 g, 0.166 mmol) prepared in Preparation Example 1 and benzyl (S)-2-(1-(2-aminopyrimidin-4-yl)piperidin-3-yl)acetate (0.057 g, 0.175 mmol) prepared in Preparation Example 41. (Yield 74%)

$^1$H-NMR (500 MHz, CHLOROFORM-D) δ 8.85 (s, 1H), 7.98 (d, J=6.1 Hz, 1H), 7.79-7.70 (1H), 7.51-7.31 (m, 6H), 7.14-6.82 (4H), 6.12-5.96 (1H), 5.24-5.06 (2H), 4.45-4.24 (m, 2H), 4.24-4.18 (m, 1H), 4.14 (q, J=7.1 Hz, 1H), 4.10-3.94 (m, 2H), 3.89 (td, J=8.7, 4.2 Hz, 1H), 3.46-3.34 (1H), 3.34-3.20 (m, 1H), 3.14-3.01 (1H), 2.87 (dd, J=13.1, 10.1 Hz, 1H), 2.52-2.31 (2H), 2.23-2.08 (m, 2H), 2.02-1.82 (m, 3H), 1.76 (dt, J=13.4, 3.9 Hz, 1H), 1.71-1.52 (m, 2H), 1.42 (t, J=6.9 Hz, 3H), 1.39-1.30 (m, 1H)

Step 2: 2-((S)-1-(2-((6-((R)-3-(2-ethoxyphenoxy)piperidin-1-yl)pyrazin-2-yl)amino)pyrimidin-4-yl)piperidin-3-yl)acetic Acid Benzyl 2-((S)-1-(2-((6-((R)-3-(2-ethoxyphenoxy)piperidin-1-yl)pyrazin-2-yl)amino)pyrimidin-4-yl)piperidin-3-yl)acetate (0.077 g, 0.123 mmol) obtained in step 1 was dissolved in methanol (0.6 ml), and then Pd/C (0.008 g, 0.075 mmol) was added and stirred at room temperature for 2 hours by using a hydrogen balloon. After filtering through a Celite pad and removing the solvent under reduced pressure, the desired title compound was obtained by purification by Prep. TLC. (Yield 22%)

m/z $(M+H)^+$ calculated for $C_{28}H_{36}N_7O_4$: 534. found 534.

Example 129: (E)-3-((S)-1-(2-((6-((R)-3-(2-ethoxyphenoxy)piperidin-1-yl)pyrazin-2-yl)amino)pyrimidin-4-yl)piperidin-3-yl)acrylic Acid

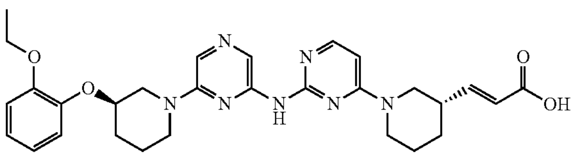 [SMILES: CCOc1ccccc1O[C@@H]1CCCN(c2cncc(Nc3nccc(N4CCC[C@@H](/C=C/C(=O)O)C4)n3)n2)C1]

The title compound was obtained in a similar manner to Example 46 by using (R)-2-chloro-6-(3-(2-ethoxyphenoxy)piperidin-1-yl)pyrazine (0.167 g, 0.500 mmol) prepared in Preparation Example 1 and ethyl (S,E)-3-(1-(2-aminopyrimidin-4-yl)piperidin-3-yl)acrylate (0.145 g, 0.525 mmol) prepared in Preparation Example 42. (Yield 37%)

$^1$H-NMR (400 MHz, CHLOROFORM-D) δ 8.77 (s, 1H), 7.95 (d, J=5.9 Hz, 1H), 7.70 (s, 1H), 7.06-6.77 (m, 5H), 6.09 (d, J=6.4 Hz, 1H), 6.05-5.92 (1H), 4.65-4.39 (1H), 4.31-4.21 (m, 1H), 4.22-4.08 (m, 2H), 4.05-3.91 (m, 3H), 3.84 (d, J=12.8 Hz, 1H), 3.50-3.26 (m, 2H), 3.01 (t, J=11.7 Hz, 1H), 2.94-2.80 (m, 1H), 2.43 (s, 1H), 2.21-2.05 (m, 1H), 1.96 (s, 2H), 1.90-1.73 (m, 2H), 1.64-1.41 (m, 3H), 1.37 (t, J=7.1 Hz, 3H)

Example 130: 3-((S)-1-(2-((6-((R)-3-(2-ethoxyphenoxy)piperidin-1-yl)pyrazin-2-yl)amino)pyrimidin-4-yl)piperidin-3-yl)propanoic Acid

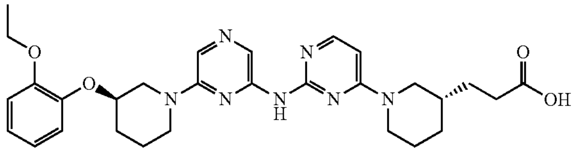 [SMILES: CCOc1ccccc1O[C@@H]1CCCN(c2cncc(Nc3nccc(N4CCC[C@@H](CCC(=O)O)C4)n3)n2)C1]

Step 1: Ethyl 3-((S)-1-(2-((6-((R)-3-(2-ethoxyphenoxy)piperidin-1-yl)pyrazin-2-yl)amino)pyrimidin-4-yl)piperidin-3-yl)propanoate Ethyl (E)-3-((S)-1-(2-((6-((R)-3-(2-ethoxyphenoxy)piperidin-1-yl)pyrazin-2-yl)amino)pyrimidin-4-yl)piperidin-3-yl)acrylate (0.120 g, 0.209 mmol), ester intermediate prepared in Example 129 was dissolved in ethanol (1 ml) and then Pd/C (0.012 g, 0.113 mmol) was added and the reduction reaction was performed by using a hydrogen balloon. After filtration through a Celite pad, the solvent was removed under reduced pressure, and purified by silica gel column to obtain the desired product. (Yield 80%)

$^1$H-NMR (400 MHz, CHLOROFORM-D) δ 8.81 (q, J=7.0 Hz, 1H), 7.98 (t, J=6.2 Hz, 1H), 7.71 (d, J=7.3 Hz, 1H), 7.58 (s, 1H), 7.24-7.03 (m, 1H), 7.03-6.89 (m, 2H), 6.89-6.78 (m, 2H), 6.12-5.98 (m, 1H), 4.32-4.20 (m, 2H), 4.17 (d, J=13.7 Hz, 2H), 4.13-4.04 (m, 2H), 4.04-3.92 (m, 2H), 3.92-3.76 (m, 1H), 3.35 (dd, J=13.0, 8.0 Hz, 1H), 3.30-3.17 (m, 1H), 3.03-2.84 (m, 1H), 2.74-2.58 (m, 1H), 2.45-2.27 (m, 2H), 2.13 (dd, J=12.3, 4.6 Hz, 1H), 1.98-1.78 (m, 3H), 1.78-1.68 (m, 1H), 1.68-1.41 (m, 5H), 1.41-1.31 (m, 3H), 1.31-1.09 (m, 4H)

Step 2: 3-((S)-1-(2-((6-((R)-3-(2-ethoxyphenoxy)piperidin-1-yl)pyrazin-2-yl)amino)pyrimidin-4-yl)piperidin-3-yl)propanoic Acid The title compound was obtained in a similar hydrolysis method to Example 46 by using ethyl 3-((S)-1-(2-((6-((R)-3-(2-ethoxyphenoxy)piperidin-1-yl)pyrazin-2-yl)amino)pyrimidin-4-yl)piperidin-3-yl)propanoate (0.096 g, 0.167 mmol) obtained in step 1. (Yield 49%)

$^1$H-NMR (CHLOROFORM-D) δ 8.79 (s, 1H), 7.88 (t, J=3.1 Hz, 1H), 7.66 (d, J=8.5 Hz, 1H), 7.06-6.97 (1H), 6.95 (t, J=7.8 Hz, 1H), 6.91-6.80 (2H), 6.15-6.02 (1H), 4.62 (s, 1H), 4.34-4.20 (m, 1H), 4.13 (d, J=12.8 Hz, 1H), 4.07-3.92 (3H), 3.92-3.76 (m, 1H), 3.48 (s, 1H), 3.44 (dd, J=13.1, 7.9 Hz, 1H), 3.34 (dd, J=12.8, 9.8 Hz, 1H), 2.92 (t, J=11.6 Hz, 1H), 2.56 (t, J=11.9 Hz, 1H), 2.49 (t, J=6.6 Hz, 2H), 2.11 (s, 1H), 2.01-1.80 (3H), 1.76 (d, J=13.1 Hz, 1H), 1.72-1.43 (m, 5H), 1.38 (t, J=7.0 Hz, 3H), 1.32-1.17 (m, 1H)

Example 131: 2-(((S)-1-(2-((6-((R)-3-(2-ethoxyphenoxy)piperidin-1-yl)pyrazin-2-yl)amino)pyrimidin-4-yl)piperidin-3-yl)oxy)acetic Acid

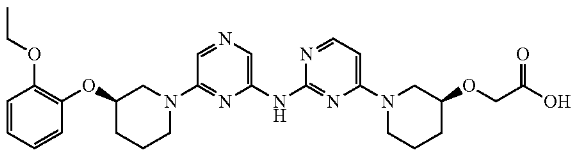 [SMILES: CCOc1ccccc1O[C@@H]1CCCN(c2cncc(Nc3nccc(N4CCC[C@H](OCC(=O)O)C4)n3)n2)C1]

The title compound was obtained in a similar manner to Example 19 by using (R)-2-chloro-6-(3-(2-ethoxyphenoxy) piperidin-1-yl)pyrazine (0.275 g, 0.825 mmol) prepared in Preparation Example 1 and tert-butyl (S)-2-((1-(2-aminopyrimidin-4-yl)piperidin-3-yl)oxy)acetate (0.267 g, 0.866 mmol) prepared in Preparation Example 44. (Yield 31%)

$^1$H-NMR (CHLOROFORM-D) δ 8.97-8.80 (m, 1H), 7.94 (t, J=6.3 Hz, 1H), 7.85-7.56 (m, 2H), 7.10-6.75 (m, 4H), 6.15-6.01 (m, 1H), 5.24-4.77 (m, 1H), 4.45-4.27 (m, 1H), 4.27-4.16 (m, 1H), 4.16-3.86 (m, 4H), 3.80-3.51 (m, 2H), 3.51-3.43 (m, 2H), 3.43-3.31 (1H), 3.30-3.10 (m, 1H), 3.10-2.89 (m, 1H), 2.22-1.96 (m, 3H), 1.95-1.76 (2H), 1.65-1.41 (m, 3H), 1.40-1.29 (m, 3H)

Example 132: 2-(((R)-1-(2-((6-((R)-3-(2-ethoxyphenoxy)piperidin-1-yl)pyrazin-2-yl)amino)pyrimidin-4-yl)piperidin-3-yl)oxy)acetic Acid

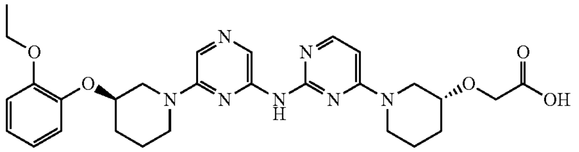 [SMILES: CCOc1ccccc1O[C@@H]1CCCN(c2cncc(Nc3nccc(N4CCC[C@@H](OCC(=O)O)C4)n3)n2)C1]

The title compound was obtained in a similar manner to Example 19 by using (R)-2-chloro-6-(3-(2-ethoxyphenoxy) piperidin-1-yl)pyrazine (0.235 g, 0.704 mmol) prepared in Preparation Example 1 and tert-butyl (R)-2-((1-(2-aminopyrimidin-4-yl)piperidin-3-yl)oxy)acetate (0.228 g, 0.739 mmol) prepared in Preparation Example 46. (Yield 75%)

$^1$H-NMR (400 MHz, CHLOROFORM-D) δ 8.71-8.49 (1H), 7.74 (d, J=14.6 Hz, 2H), 7.03-6.80 (m, 5H), 6.19 (s, 1H), 4.41-4.18 (m, 2H), 4.12 (s, 1H), 4.04-3.89 (m, 3H), 3.74 (d, J=5.5 Hz, 2H), 3.64-3.38 (m, 4H), 3.33 (s, 2H), 2.06 (d, J=5.0 Hz, 2H), 2.02-1.81 (m, 3H), 1.73 (s, 1H), 1.64-1.41 (m, 2H), 1.35 (t, J=6.9 Hz, 3H)

Example 133: 2-(((R)-1-(2-((6-((R)-3-(2-ethoxyphenoxy)piperidin-1-yl)pyrazin-2-yl)amino)pyrimidin-4-yl)piperidin-3-yl)oxy)-2-methylpropanoic Acid

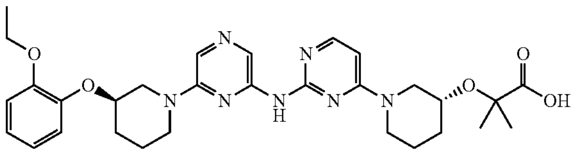 [SMILES: CCOc1ccccc1O[C@@H]1CCCN(c2cncc(Nc3nccc(N4CCC[C@@H](OC(C)(C)C(=O)O)C4)n3)n2)C1]

The title compound was obtained in a similar manner to Example 19 by using (R)-2-chloro-6-(3-(2-ethoxyphenoxy) piperidin-1-yl)pyrazine (0.077 g, 0.232 mmol) prepared in Preparation Example 1 and tert-butyl (R)-2-((1-(2-aminopyrimidin-4-yl)piperidin-3-yl)oxy)-2-methylpropanoate (0.082 g, 0.244 mmol) prepared in Preparation Example 47. (Yield 19%)

$^1$H-NMR (400 MHz, CHLOROFORM-D) δ 8.79 (s, 1H), 7.79 (s, 1H), 7.66 (s, 1H), 7.03-6.88 (m, 2H), 6.85 (dd, J=7.1, 2.5 Hz, 2H), 6.22 (d, J=46.7 Hz, 1H), 5.28 (s, 1H), 4.24 (q, J=3.8 Hz, 1H), 4.10 (q, J=7.2 Hz, 1H), 4.04-3.92 (m, 2H), 3.83 (d, J=12.3 Hz, 1H), 3.57 (s, 1H), 3.45 (dd, J=12.6, 8.0 Hz, 1H), 3.32 (t, J=9.8 Hz, 1H), 2.94 (s, 2H), 2.10 (s, 1H), 2.02-1.99 (OH), 1.94 (dd, J=9.6, 3.7 Hz, 1H), 1.89-1.72 (m, 2H), 1.64-1.47 (m, 3H), 1.43 (d, J=12.8 Hz, 6H), 1.39-1.30 (m, 4H)

Example 134: (R)-4-(2-((6-(3-(2-ethoxyphenoxy)piperidin-1-yl)pyrazin-2-yl)amino)pyrimidin-4-yl)oxy)cyclohexane-1-carboxylic Acid

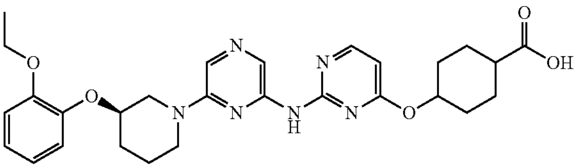 [SMILES: CCOc1ccccc1O[C@@H]1CCCN(c2cncc(Nc3nccc(OC4CCC(C(=O)O)CC4)n3)n2)C1]

The title compound was obtained in a similar manner to Example 46 by using (R)-2-chloro-6-(3-(2-ethoxyphenoxy) piperidin-1-yl)pyrazine (0.172 g, 0.514 mmol) prepared in Preparation Example 1 and ethyl 4-((2-aminopyrimidin-4-yl)oxy)cyclohexane-1-carboxylate (0.150 g, 0.565 mmol) prepared in Preparation Example 117. (Yield 38%)

$^1$H-NMR (400 MHz, CHLOROFORM-D) δ 8.79 (d, J=5.5 Hz, 1H), 8.15 (t, J=5.7 Hz, 1H), 7.74 (d, J=12.3 Hz, 1H), 7.57-7.38 (m, 1H), 7.04-6.81 (m, 4H), 6.23 (dd, J=9.8, 5.7 Hz, 1H), 5.21 (d, J=70.0 Hz, 1H), 4.35-4.20 (m, 1H), 4.19-4.06 (m, 1H), 4.06-3.90 (m, 2H), 3.90-3.72 (m, 1H), 3.60-3.24 (m, 2H), 2.59-2.24 (m, 2H), 2.15 (d, J=11.0 Hz, 2H), 2.10-1.93 (m, 3H), 1.92-1.83 (m, 1H), 1.78 (t, J=12.6 Hz, 2H), 1.68-1.46 (3H), 1.38 (td, J=7.1, 5.0 Hz, 3H)

Example 135: (1R,4r)-4-((2-((6-((R)-3-(2-ethoxyphenoxy)piperidin-1-yl)pyrazin-2-yl)amino)pyrimidin-4-yl)oxy)cyclohexane-1-carboxylic Acid

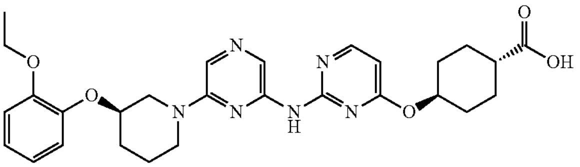 [SMILES: CCOc1ccccc1O[C@@H]1CCCN(c2cncc(Nc3nccc(O[C@H]4CC[C@H](C(=O)O)CC4)n3)n2)C1]

Step 1: Methyl (1R,4r)-4-((2-((6-((R)-3-(2-ethoxyphenoxy)piperidin-1-yl)pyrazin-2-yl)amino)pyrimidin-4-yl)oxy)cyclohexane-1-carboxylate The desired product was obtained in a similar manner to Example 1 by using (R)-2-chloro-6-(3-(2-ethoxyphenoxy) piperidin-1-yl)pyrazine (0.080 g, 0.239 mmol) prepared in Preparation Example 1 and methyl (1r,4r)-4-((2-aminopyrimidin-4-yl)oxy)cyclohexane-1-carboxylate (0.066 g, 0.263 mmol) prepared in Preparation Example 50. (Yield 49%) $^1$H-NMR (400 MHz, CHLOROFORM-D) δ 8.80 (s, 1H), 8.16 (d, J=5.9 Hz, 1H), 7.77 (s, 1H), 7.07-6.83 (m, 4H), 6.20 (d, J=5.9 Hz, 1H), 5.05 (s, 1H), 4.26 (t, J=4.1 Hz, 1H), 4.14 (d, J=15.6 Hz, 1H), 4.08-3.91 (m, 2H), 3.84 (d, J=13.7 Hz, 1H), 3.67 (d, J=10.1 Hz, 3H), 3.43 (dd, J=13.3, 8.2 Hz, 1H), 3.32 (s, 1H), 2.36 (s, 1H), 2.24 (d, J=16.9 Hz, 2H), 2.19-2.04 (m, 3H), 2.03 (s, 1H), 1.92-1.79 (1H), 1.64 (dd, J=32.7, 13.0 Hz, 4H), 1.39 (t, J=6.9 Hz, 3H), 1.25 (d, J=6.4 Hz, 1H)

Step 2: 2-((S)-1-(2-((6-((R)-3-(2-ethoxyphenoxy)piperidin-1-yl)pyrazin-2-yl)amino)pyrimidin-4-yl)piperidin-3-yl)acetic Acid The title compound was obtained in a similar hydrolysis method to Example 46 by using methyl (1R,4r)-4-((2-((6-((R)-3-(2-ethoxyphenoxy)piperidin-1-yl)pyrazin-2-yl)amino)pyrimidin-4-yl)oxy)cyclohexane-1-carboxylate (0.064 g, 0.117 mmol) obtained in step 1. (Yield 19%)

m/z $(M+H)^+$ calculated for $C_{28}H_{35}N_6O_5$: 535. found 535.

Example 136: (1R,4r)-4-((2-((6-((R)-3-((3-ethoxypyridin-2-yl)oxy)piperidin-1-yl)pyrazin-2-yl)amino)pyrimidin-4-yl)oxy)cyclohexane-1-carboxylic Acid

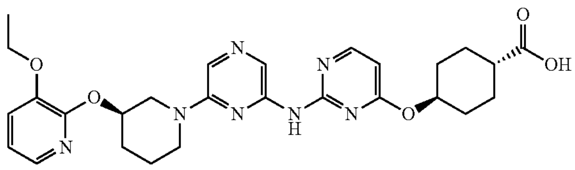 [SMILES: CCOc1cccnc1O[C@@H]1CCCN(c2cncc(Nc3nccc(O[C@H]4CC[C@H](C(=O)O)CC4)n3)n2)C1]

The title compound was obtained in a similar manner to Example 46 by using (R)-2-chloro-6-(3-((3-ethoxypyridin-2-yl)oxy)piperidin-1-yl)pyrazine (0.080 g, 0.239 mmol) prepared in Preparation Example 3 and methyl (1r,4r)-4-((2-aminopyrimidin-4-yl)oxy)cyclohexane-1-carboxylate (0.066 g, 0.263 mmol) prepared in Preparation Example 50. (Yield 16%)

$^1$H-NMR (400 MHz, CHLOROFORM-D) δ 8.77 (s, 1H), 8.17-8.09 (1H), 7.73 (t, J=2.5 Hz, 2H), 7.35 (s, 1H), 6.97 (d, J=7.8 Hz, 1H), 6.80 (dd, J=7.8, 5.0 Hz, 1H), 6.21 (d, J=5.5 Hz, 1H), 5.25-5.06 (2H), 4.09-3.97 (m, 1H), 3.97-3.84 (m, 2H), 3.80 (d, J=13.3 Hz, 1H), 3.73 (q, J=6.7 Hz, 1H), 3.47 (t, J=9.4 Hz, 1H), 2.41-2.24 (m, 4H), 2.15 (d, J=8.2 Hz, 2H), 2.04-1.89 (2H), 1.84-1.72 (3H), 1.51 (q, J=12.3 Hz, 2H), 1.30 (t, J=6.9 Hz, 3H)

Example 137: (1S,4s)-4-((2-((6-((R)-3-(2-ethoxyphenoxy)piperidin-1-yl)pyrazin-2-yl)amino)pyrimidin-4-yl)oxy)cyclohexane-1-carboxylic Acid

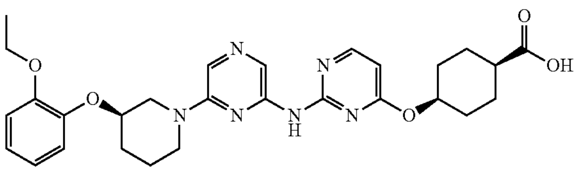

The title compound was obtained in a similar manner to Example 46 by using (R)-2-chloro-6-(3-(2-ethoxyphenoxy)piperidin-1-yl)pyrazine (0.184 g, 0.551 mmol) prepared in Preparation Example 1 and methyl (1s,4s)-4-((2-aminopyrimidin-4-yl)oxy)cyclohexane-1-carboxylate (0.180 g, 0.716 mmol) prepared in Preparation Example 51. (Yield 62%)

$^1$H-NMR (400 MHz, DMSO-D6) (9.20 (s, 1H), 8.59 (s, 1H), 8.21 (d, J=5.5 Hz, 1H), 7.78 (s, 1H), 7.01 (dd, J=7.5, 1.6 Hz, 1H), 6.95-6.77 (m, 3H), 6.32 (d, J=5.5 Hz, 1H), 5.17 (s, 1H), 4.28 (q, J=3.7 Hz, 1H), 4.13-3.99 (m, 1H), 3.98-3.82 (m, 2H), 3.71 (d, J=14.6 Hz, 1H), 3.45 (q, J=6.6 Hz, 3H), 2.35 (s, 1H), 1.98 (s, 1H), 1.89-1.60 (m, 9H), 1.58-1.40 (m, 1H), 1.20 (t, J=6.9 Hz, 3H)

Example 138: (1S,4s)-4-((2-((6-((R)-3-((3-ethoxypyridin-2-yl)oxy)piperidin-1-yl)pyrazin-2-yl)amino)pyrimidin-4-yl)oxy)cyclohexane-1-carboxylic Acid

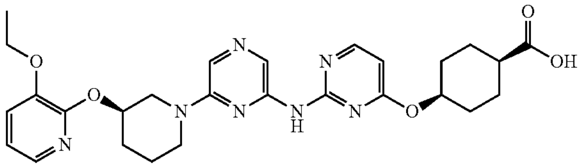 [SMILES: CCOc1cccnc1O[C@@H]1CCCN(c2cncc(Nc3nccc(O[C@H]4CC[C@@H](C(=O)O)CC4)n3)n2)C1]

The title compound was obtained in a similar manner to Example 46 by using (R)-2-chloro-6-(3-((3-ethoxypyridin-2-yl)oxy)piperidin-1-yl)pyrazine (0.137 g, 0.410 mmol) prepared in Preparation Example 3 and methyl (1s,4s)-4-((2-aminopyrimidin-4-yl)oxy)cyclohexane-1-carboxylate (0.134 g, 0.533 mmol) prepared in Preparation Example 51. (Yield 62%)

$^1$H-NMR (400 MHz, DMSO-D6) (9.13 (s, 1H), 8.60 (s, 1H), 8.20 (d, J=5.5 Hz, 1H), 7.86-7.75 (1H), 7.65 (dd, J=4.8, 1.6 Hz, 1H), 7.18 (dd, J=7.8, 1.4 Hz, 1H), 6.85 (dd, J=7.8, 5.0 Hz, 1H), 6.32 (d, J=5.9 Hz, 1H), 5.17 (s, 1H), 5.13-5.00 (m, 1H), 4.07 (dd, J=13.5, 3.0 Hz, 1H), 3.95-3.83 (m, 2H), 3.78 (d, J=11.4 Hz, 1H), 3.50 (dd, J=13.3, 7.8 Hz, 1H), 3.46-3.38 (m, 2H), 2.36 (s, 1H), 2.06 (d, J=11.0 Hz, 1H), 1.88-1.59 (m, 9H), 1.53 (q, J=4.1 Hz, 1H), 1.27-1.15 (m, 3H)

Example 139: (R)-6-(2-((6-(3-(2-ethoxyphenoxy)piperidin-1-yl)pyrazin-2-yl)amino)pyrimidin-4-yl)picolinic Acid

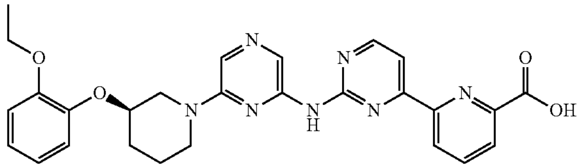 [SMILES: CCOc1ccccc1O[C@@H]1CCCN(c2cncc(Nc3nccc(-c4cccc(C(=O)O)n4)n3)n2)C1]

(R)-2-chloro-6-(3-(2-ethoxyphenoxy)piperidin-1-yl)pyrazine (23.2 mg, 0.07 mmol) prepared in Preparation Example 1 and ethyl 6-(2-aminopyrimidin-4-yl)picolinate (17 mg, 0.07 mmol) prepared in Preparation Example 72, tris(dibenzylideneacetone)dipalladium(0) (3.8 mg, 4.18 μmol), 4,5-bis(diphenylphosphino)-9,9-dimethylxanthine (3.62 mg, 6.26 μmol) and cesium carbonate (56.7 mg, 0.17 mmol) were dissolved in 1,4-dioxane and stirred under reflux for 4 hours. After the reaction was completed, the reaction mixture was cooled to room temperature, diluted with ethyl acetate, washed with an aqueous sodium hydrogen carbonate solution and brine, and dried over magnesium sulfate, and the organic solvent was removed under reduced pressure. The title compound was obtained by purification with silica gel column (hexane:ethyl acetate). (Yield 21%)

The obtained ester compound (7.8 mg, 0.014 mmol) was dissolved in THF:methanol:water=1:1:1, and lithium hydroxide (1.0 mg, 0.04 mmol) was added, followed by stirring at room temperature for 12 hours. After completion of the reaction, it was diluted with water, neutralized with 1

N hydrochloric acid solution, extracted with ethyl acetate, and dried over magnesium sulfate, and the organic solvent was removed under reduced pressure. The title compound was obtained by purification with silica gel column (ethyl acetate:methanol). (Yield 27%)

$^1$H-NMR (400 MHz, METHANOL-D4) δ 8.89-8.80 (1H), 8.66-8.61 (1H), 8.52-8.45 (1H), 8.24-8.20 (1H), 8.14-8.08 (1H), 8.04-7.96 (1H), 7.71-7.63 (1H), 7.06-6.96 (1H), 6.95-6.79 (4H), 4.47-4.33 (1H), 4.07-3.81 (5H), 3.80-3.51 (3H), 2.20-1.89 (3H), 1.70-1.50 (1H), 1.37-1.28 (1H), 1.28-1.23 (3H)

Example 140: (R)-2-(3-(2-((6-(3-(2-ethoxyphenoxy) piperidin-1-yl)pyrazin-2-yl)amino)pyrimidin-4-yl) phenyl)acetic Acid

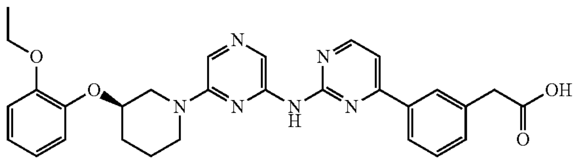 [SMILES: CCOc1ccccc1O[C@@H]1CCCN(c2cncc(Nc3nccc(-c4cccc(CC(=O)O)c4)n3)n2)C1]

The title compound was obtained in a similar manner to Example 12 by using (R)-2-chloro-6-(3-(2-ethoxyphenoxy) piperidin-1-yl)pyrazine (0.574 g, 1.718 mmol) obtained in Preparation Example 1 and methyl 2-(3-(2-aminopyrimidin-4-yl)phenyl)acetate (0.38 g, 1.562 mmol) obtained in Preparation Example 70. (2 step yield 8%)

$^1$H-NMR (400 MHz, METHANOL-D4) δ 8.87 (t, J=15.1 Hz, 1H), 8.55-8.46 (m, 1H), 8.16-8.02 (m, 1H), 8.02-7.92 (m, 1H), 7.73-7.55 (m, 1H), 7.55-7.43 (m, 1H), 7.43-7.31 (m, 2H), 7.07-6.93 (m, 1H), 6.93-6.76 (m, 3H), 5.43 (d, J=14.6 Hz, 1H), 4.36 (td, J=6.4, 3.2 Hz, 1H), 3.90-3.83 (m, 2H), 3.73 (q, J=6.7 Hz, 1H), 3.69-3.59 (m, 2H), 3.56 (d, J=8.7 Hz, 2H), 2.13-1.91 (m, 2H), 1.92-1.79 (m, 1H), 1.68-1.44 (m, 1H), 1.24 (t, J=6.9 Hz, 3H)

Example 141: (R)-2-(3-(2-((6-(3-(2-ethoxyphenoxy) piperidin-1-yl)pyrazin-2-yl)amino)pyrimidin-4-yl) phenyl)-2-methylpropanoic Acid

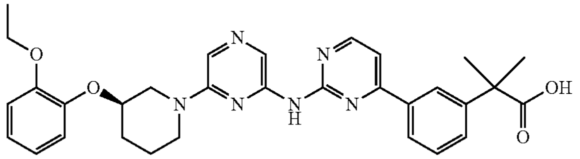 [SMILES: CCOc1ccccc1O[C@@H]1CCCN(c2cncc(Nc3nccc(-c4cccc(C(C)(C)C(=O)O)c4)n3)n2)C1]

The title compound was obtained in a similar manner to Example 46 by using (R)-2-chloro-6-(3-(2-ethoxyphenoxy) piperidin-1-yl)pyrazine (0.097 g, 0.292 mmol) prepared in Preparation Example 1 and methyl 2-(3-(2-aminopyrimidin-4-yl)phenyl)-2-methylpropanoate (0.087 g, 0.321 mmol) prepared in Preparation Example 53. (Yield 53%)

$^1$H-NMR (500 MHz, CHLOROFORM-D) δ 9.10 (s, 1H), 8.53 (d, J=5.2 Hz, 1H), 8.40 (s, 1H), 7.79 (d, J=7.9 Hz, 1H), 7.74 (s, 1H), 7.59 (d, J=7.9 Hz, 1H), 7.55-7.43 (m, 2H), 7.09-6.86 (m, 4H), 4.33 (td, J=7.9, 3.7 Hz, 1H), 4.19-4.10 (m, 1H), 4.10-3.96 (m, 2H), 3.84 (dt, J=12.9, 4.8 Hz, 1H), 3.55 (dd, J=13.1, 7.9 Hz, 1H), 3.51-3.37 (m, 1H), 2.18 (d, J=18.9 Hz, 1H), 2.06-1.98 (m, 1H), 1.98-1.91 (m, 1H), 1.73-1.60 (m, 7H), 1.41 (t, J=7.0 Hz, 3H)

Example 142: (R)-2-(3-(2-((6-(3-((3-ethoxypyridin-2-yl)oxy)piperidin-1-yl)pyrazin-2-yl)amino)pyrimidin-4-yl)phenyl)-2-methylpropanoic Acid

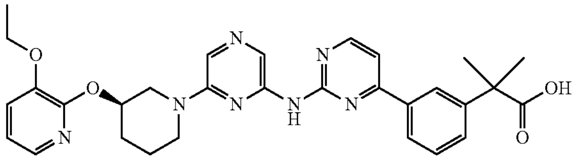 [SMILES: CCOc1cccnc1O[C@@H]1CCCN(c2cncc(Nc3nccc(-c4cccc(C(C)(C)C(=O)O)c4)n3)n2)C1]

The title compound was obtained in a similar manner to Example 12 by using (R)-2-chloro-6-(3-((3-ethoxypyridin-2-yl)oxy)piperidin-1-yl)pyrazine (0.081 g, 0.243 mmol) obtained in Preparation Example 3 and methyl 2-(3-(2-aminopyrimidin-4-yl)phenyl)-2-methylpropanoate (0.06 g, 0.221 mmol) obtained in Preparation Example 53. (2 step yield 52%)

$^1$H-NMR (400 MHz, CHLOROFORM-D) δ 8.97 (s, 1H), 8.51-8.42 (m, 1H), 8.28 (s, 1H), 8.01-7.81 (m, 1H), 7.81-7.75 (m, 2H), 7.75-7.67 (m, 1H), 7.60-7.49 (m, 1H), 7.48-7.37 (m, 1H), 7.20 (dd, J=5.5, 1.8 Hz, 1H), 7.00-6.92 (m, 1H), 6.82-6.74 (m, 1H), 5.24-5.11 (m, 1H), 4.02 (dd, J=13.3, 2.7 Hz, 1H), 3.98-3.83 (m, 2H), 3.83-3.67 (m, 2H), 3.49 (t, J=9.4 Hz, 1H), 2.27-2.09 (m, 1H), 2.02-1.83 (m, 2H), 1.66 (d, J=5.0 Hz, 1H), 1.63 (s, 6H), 1.35-1.25 (m, 3H)

Example 143: (R)-2-(4-(2-((6-(3-(2-ethoxyphenoxy) piperidin-1-yl)pyrazin-2-yl)amino)pyrimidin-4-yl) phenyl)-2-methylpropanoic Acid

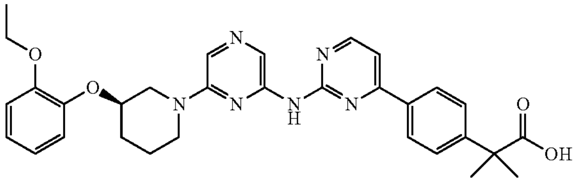 [SMILES: CCOc1ccccc1O[C@@H]1CCCN(c2cncc(Nc3nccc(-c4ccc(C(C)(C)C(=O)O)cc4)n3)n2)C1]

The title compound was obtained in a similar manner to Example 12 by using (R)-2-chloro-6-(3-(2-ethoxyphenoxy) piperidin-1-yl)pyrazine (0.271 g, 0.811 mmol) obtained in Preparation Example 1 and methyl 2-(4-(2-aminopyrimidin-4-yl)phenyl)-2-methylpropanoate (0.2 g, 0.737 mmol) obtained in Preparation Example 55. (2 step yield 27%)

$^1$H-NMR (400 MHz, CHLOROFORM-D) δ 9.12 (s, 1H), 8.48 (t, J=4.3 Hz, 1H), 8.12 (d, J=8.2 Hz, 2H), 7.89 (d, J=13.7 Hz, 1H), 7.71 (s, 1H), 7.66 (d, J=8.2 Hz, 2H), 6.95 (ddd, J=13.4, 7.7, 1.7 Hz, 2H), 6.90-6.79 (m, 2H), 4.42-4.23 (m, 1H), 4.11-3.88 (m, 3H), 3.84-3.69 (m, 1H), 3.69-3.54 (m, 1H), 3.44 (t, J=9.8 Hz, 1H), 2.18-2.05 (1H), 2.05-1.79 (m, 2H), 1.71 (d, J=14.6 Hz, 6H), 1.65-1.47 (m, 1H), 1.41-1.30 (m, 3H)

Example 144: (R)-2-(4-(2-((6-(3-((3-ethoxypyridin-2-yl)oxy)piperidin-1-yl)pyrazin-2-yl)amino)pyrimidin-4-yl)phenyl)-2-methylpropanoic Acid

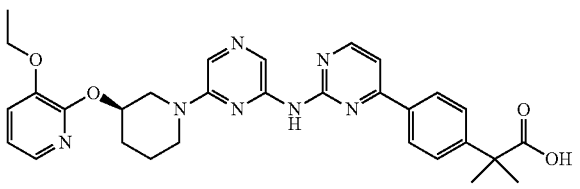 [SMILES: CCOc1cccnc1O[C@@H]1CCCN(c2cncc(Nc3nccc(-c4ccc(C(C)(C)C(=O)O)cc4)n3)n2)C1]

The title compound was obtained in a similar manner to Example 12 by using (R)-2-chloro-6-(3-((3-ethoxypyridin-2-yl)oxy)piperidin-1-yl)pyrazine (0.271 g, 0.811 mmol) obtained in Preparation Example 3 and methyl 2-(4-(2-aminopyrimidin-4-yl)phenyl)-2-methylpropanoate (0.2 g, 0.737 mmol) obtained in Preparation Example 55. (2 step yield 42%)

$^1$H-NMR (400 MHz, CHLOROFORM-D) δ 9.08 (s, 1H), 8.47 (d, J=5.0 Hz, 1H), 8.11 (d, J=8.7 Hz, 2H), 7.79 (s, 1H), 7.74 (d, J=5.0 Hz, 2H), 7.65 (d, J=8.7 Hz, 2H), 7.24 (s, 1H), 6.93 (d, J=7.8 Hz, 1H), 6.86-6.72 (m, 1H), 5.19 (s, 1H), 3.97 (d, J=13.3 Hz, 1H), 3.93-3.71 (m, 4H), 3.62-3.42 (m, 1H), 2.23-2.08 (m, 1H), 2.08-1.88 (m, 2H), 1.71 (d, J=17.4 Hz, 6H), 1.64 (d, J=6.9 Hz, 1H), 1.31-1.22 (m, 3H)

Example 145: (R)-3-(3-(2-((6-(3-(2-ethoxyphenoxy)piperidin-1-yl)pyrazin-2-yl)amino)pyrimidin-4-yl)phenyl)propanoic Acid

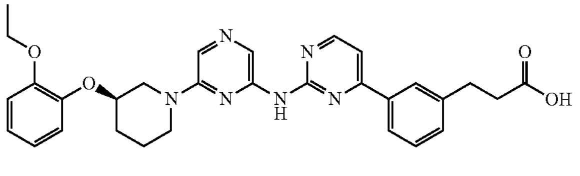 [SMILES: CCOc1ccccc1O[C@@H]1CCCN(c2cncc(Nc3nccc(-c4cccc(CCC(=O)O)c4)n3)n2)C1]

The title compound was obtained in a similar manner to Example 46 by using (R)-2-chloro-6-(3-(2-ethoxyphenoxy)piperidin-1-yl)pyrazine (0.090 g, 0.269 mmol) prepared in Preparation Example 1 and methyl 3-(3-(2-aminopyrimidin-4-yl)phenyl)propanoate (0.076 g, 0.295 mmol) prepared in Preparation Example 57. (Yield 37%)

$^1$H-NMR (500 MHz, CHLOROFORM-D) δ 9.38 (s, 1H), 8.53 (d, J=5.2 Hz, 1H), 8.37 (s, 1H), 7.73 (d, J=5.8 Hz, 2H), 7.50 (d, J=7.3 Hz, 1H), 7.42 (t, J=7.6 Hz, 1H), 7.35 (d, J=7.6 Hz, 1H), 7.01 (q, J=8.1 Hz, 2H), 6.92 (dd, J=13.9, 7.5 Hz, 2H), 4.34 (q, J=3.9 Hz, 1H), 4.14 (dd, J=13.3, 3.5 Hz, 1H), 4.08-3.97 (m, 2H), 3.85 (d, J=17.4 Hz, 1H), 3.55 (dd, J=13.3, 7.8 Hz, 1H), 3.43 (d, J=9.5 Hz, 1H), 3.16 (t, J=6.1 Hz, 2H), 2.71 (t, J=6.3 Hz, 2H), 2.19 (s, 1H), 2.04 (m, 1H), 1.94 (m, J=1H), 1.67-1.62 (1H), 1.49-1.35 (3H)

Example 146: (R)-3-(3-(2-((6-(3-(2-ethoxyphenoxy)piperidin-1-yl)pyrazin-2-yl)amino)pyrimidin-4-yl)phenyl)-2,2-dimethylpropanoic Acid

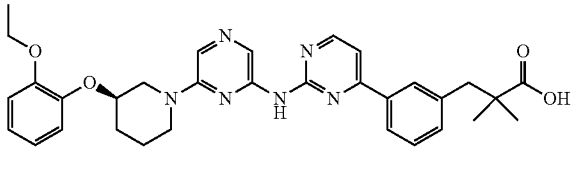

The title compound was obtained in a similar manner to Example 1 by using (R)-2-chloro-6-(3-(2-ethoxyphenoxy)piperidin-1-yl)pyrazine (329 mg, 0.985 mmol) prepared in Preparation Example 1 and methyl 3-(3-(2-aminopyrimidin-4-yl)phenyl)-2,2-dimethylpropanoate (281 mg, 0.985 mmol) prepared in Preparation Example 59. (2 step yield 27%)

$^1$H-NMR (400 MHz, CHLOROFORM-D) δ 9.43 (d, J=1.4 Hz, 1H), 8.51 (d, J=5.0 Hz, 1H), 8.32 (s, 1H), 7.71 (d, J=8.7 Hz, 2H), 7.36 (t, J=7.5 Hz, 1H), 7.23 (q, J=2.9 Hz, 2H), 7.08-6.79 (m, 4H), 4.40-4.21 (m, 1H), 4.20-4.07 (m, 1H), 4.07-3.90 (m, 2H), 3.90-3.72 (1H), 3.52 (dd, J=12.8, 7.8 Hz, 1H), 3.37 (t, J=10.7 Hz, 1H), 3.02 (s, 2H), 2.15 (q, J=5.5 Hz, 1H), 2.04-1.79 (m, 2H), 1.73-1.50 (m, 1H), 1.39 (t, J=7.1 Hz, 3H), 1.24 (s, 6H)

Example 147: (R)-3-(3-(2-((6-(3-((3-ethoxypyridin-2-yl)oxy)piperidin-1-yl)pyrazin-2-yl)amino)pyrimidin-4-yl)phenyl)-2,2-dimethylpropanoic Acid

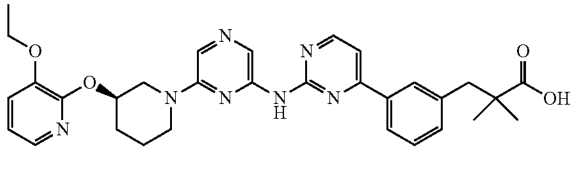

The title compound was obtained in a similar manner to Example 22 by using (R)-2-chloro-6-(3-((3-ethoxypyridin-2-yl)oxy)piperidin-1-yl)pyrazine (123 mg, 0.366 mmol) prepared in Preparation Example 3 and tert-butyl 3-(3-(2-aminopyrimidin-4-yl)phenyl)-2,2-dimethylpropanoate (120 mg, 0.366 mmol) prepared in Preparation Example 80. (2 step yield 85%)

$^1$H-NMR (400 MHz, CHLOROFORM-D) δ 9.39 (s, 1H), 8.49 (d, J=5.0 Hz, 1H), 8.33 (s, 1H), 7.82-7.64 (m, 3H), 7.37 (t, J=7.8 Hz, 2H), 7.25 (s, 2H), 6.95 (dd, J=7.8, 1.4 Hz, 1H), 6.82 (dd, J=7.8, 5.0 Hz, 1H), 5.21 (td, J=6.7, 3.4 Hz, 1H), 4.06-3.69 (5H), 3.64-3.50 (m, 1H), 3.02 (dd, J=16.9, 13.3 Hz, 2H), 2.26-2.12 (m, 1H), 2.09-1.92 (m, 2H), 1.77-1.59 (m, 1H), 1.39-1.27 (m, 3H), 1.24 (d, J=5.9 Hz, 6H)

Example 148: (R)-3-(3-(2-((6-(3-(2-ethoxyphenoxy)piperidin-1-yl)pyridin-2-yl)amino)pyrimidin-4-yl)phenyl)-2,2-dimethylpropanoic Acid

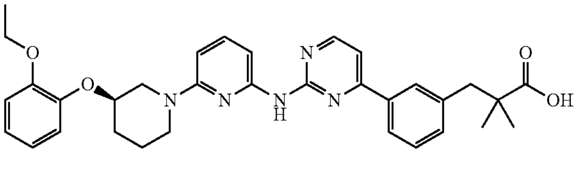 [SMILES: CCOc1ccccc1O[C@@H]1CCCN(c2cccc(Nc3nccc(-c4cccc(CC(C)(C)C(=O)O)c4)n3)n2)C1]

The title compound was obtained in a similar manner to Example 22 by using (R)-2-chloro-6-(3-(2-ethoxyphenoxy) piperidin-1-yl)pyridine (122 mg, 0.366 mmol) prepared in Preparation Example 4 and tert-butyl 3-(3-(2-aminopyrimidin-4-yl)phenyl)-2,2-dimethylpropanoate (120 mg, 0.366 mmol) prepared in Preparation Example 80. (2 step yield 12%)

$^1$H-NMR (400 MHz, CHLOROFORM-D) δ 8.49 (s, 1H), 8.23 (d, J=5.5 Hz, 1H), 7.69-7.46 (m, 2H), 7.42-7.26 (m, 3H), 7.10 (d, J=9.1 Hz, 1H), 7.06-6.93 (m, 1H), 6.89-6.78 (m, 1H), 6.78-6.62 (m, 3H), 6.15 (d, J=8.7 Hz, 1H), 4.56 (s, 1H), 3.91-3.63 (m, 3H), 3.54 (d, J=13.7 Hz, 1H), 3.45 (d, J=11.9 Hz, 1H), 3.29 (s, 1H), 3.00 (dd, J=24.5, 13.0 Hz, 2H), 2.15-1.89 (m, 3H), 1.62 (d, J=15.6 Hz, 1H), 1.26 (d, J=8.2 Hz, 6H), 1.16 (t, J=7.1 Hz, 3H)

Example 149: (R)-3-(3-(2-((2-(3-(2-ethoxyphenoxy) piperidin-1-yl)pyrimidin-4-yl)amino)pyrimidin-4-yl) phenyl)-2,2-dimethylpropanoic Acid

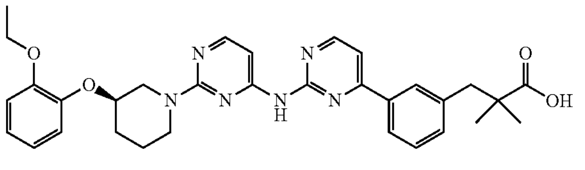 [SMILES: CCOc1ccccc1O[C@@H]1CCCN(c2nccc(Nc3nccc(-c4cccc(CC(C)(C)C(=O)O)c4)n3)n2)C1]

The title compound was obtained in a similar manner to Example 22 by using (R)-4-chloro-2-(3-(2-ethoxyphenoxy) piperidin-1-yl)pyrimidine (122 mg, 0.366 mmol) prepared in Preparation Example 5 and tert-butyl 3-(3-(2-aminopyrimidin-4-yl)phenyl)-2,2-dimethylpropanoate (120 mg, 0.366 mmol) prepared in Preparation Example 80. (2 step yield 74%)

$^1$H-NMR (400 MHz, METHANOL-D4) δ 8.68 (d, J=5.5 Hz, 1H), 8.13-7.95 (m, 4H), 7.65 (d, J=5.5 Hz, 1H), 7.55-7.33 (m, 2H), 7.00 (d, J=7.8 Hz, 1H), 6.94-6.79 (3H), 4.68 (s, 1H), 4.35 (d, J=11.9 Hz, 1H), 4.02-3.84 (m, 2H), 3.78 (d, J=12.3 Hz, 1H), 3.61-3.42 (m, 1H), 3.40-3.32 (m, 1H), 3.00 (s, 2H), 2.19-1.92 (m, 3H), 1.67 (q, J=4.6 Hz, 1H), 1.27 (t, J=6.9 Hz, 3H), 1.24-1.15 (6H)

Example 150: (R)-3-(3-(2-((4-(3-(2-ethoxyphenoxy) piperidin-1-yl)pyrimidin-2-yl)amino)pyrimidin-4-yl) phenyl)-2,2-dimethylpropanoic Acid

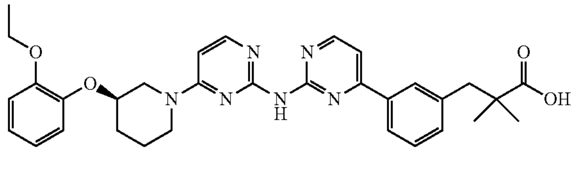 [SMILES: CCOc1ccccc1O[C@@H]1CCCN(c2ccnc(Nc3nccc(-c4cccc(CC(C)(C)C(=O)O)c4)n3)n2)C1]

The title compound was obtained in a similar manner to Example 22 by using (R)-2-chloro-4-(3-(2-ethoxyphenoxy) piperidin-1-yl)pyrimidine (122 mg, 0.366 mmol) prepared in Preparation Example 6 and tert-butyl 3-(3-(2-aminopyrimidin-4-yl)phenyl)-2,2-dimethylpropanoate (120 mg, 0.366 mmol) prepared in Preparation Example 80. (2 step yield 70%)

$^1$H-NMR (400 MHz, CHLOROFORM-D) δ 8.52 (s, 1H), 8.33 (s, 1H), 7.66 (d, J=7.8 Hz, 1H), 7.35 (t, J=7.3 Hz, 2H), 7.27 (d, J=7.3 Hz, 2H), 7.05-6.71 (m, 5H), 6.31 (s, 1H), 4.40 (d, J=4.1 Hz, 1H), 4.06-3.81 (m, 3H), 3.69 (d, J=21.0 Hz, 1H), 2.95 (s, 2H), 2.04 (s, 5H), 1.68 (d, J=9.1 Hz, 1H), 1.36 (t, J=6.9 Hz, 3H), 1.25 (s, 6H)

Example 151: (R)-2-(4-(2-((6-(3-(2-ethoxyphenoxy) piperidin-1-yl)pyrazin-2-yl)amino)pyrimidin-4-yl) phenyl)acetic Acid

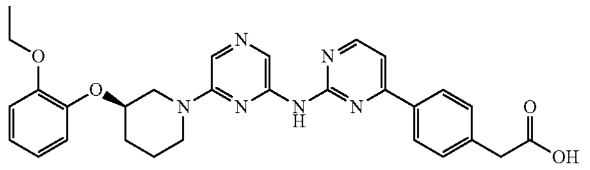 [SMILES: CCOc1ccccc1O[C@@H]1CCCN(c2cncc(Nc3nccc(-c4ccc(CC(=O)O)cc4)n3)n2)C1]

The title compound was obtained in a similar manner to Example 12 by using (R)-2-chloro-6-(3-(2-ethoxyphenoxy) piperidin-1-yl)pyrazine (0.106 g, 0.317 mmol) obtained in Preparation Example 1 and methyl 2-(4-(2-aminopyrimidin-4-yl)phenyl)acetate (0.07 g, 0.288 mmol) obtained in Preparation Example 74. (2 step yield 4%)

$^1$H-NMR (400 MHz, METHANOL-D4) δ 8.86 (s, 1H), 8.54-8.46 (m, 1H), 8.07 (d, J=8.7 Hz, 2H), 7.65 (s, 1H), 7.51-7.43 (2H), 7.40 (d, J=5.5 Hz, 1H), 7.05-6.96 (1H), 6.96-6.80 (m, 3H), 4.41 (q, J=3.2 Hz, 1H), 3.99-3.77 (m, 4H), 3.74 (dt, J=13.6, 3.9 Hz, 1H), 3.69-3.57 (m, 1H), 3.54 (s, 2H), 2.19-2.05 (m, 1H), 2.05-1.96 (m, 2H), 1.96-1.88 (m, 1H), 1.26 (t, 3H)

Example 152: (R)-2-(4-(2-((6-(3-((3-ethoxypyridin-2-yl)oxy)piperidin-1-yl)pyrazin-2-yl)amino)pyrimidin-4-yl)phenyl)acetic Acid

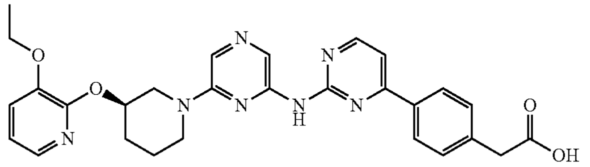 [SMILES: CCOc1cccnc1O[C@@H]1CCCN(c2cncc(Nc3nccc(-c4ccc(CC(=O)O)cc4)n3)n2)C1]

The title compound was obtained in a similar manner to Example 12 by using (R)-2-chloro-6-(3-((3-ethoxypyridin-2-yl)oxy)piperidin-1-yl)pyrazine (0.143 g, 0.428 mmol) obtained in Preparation Example 3 and methyl 2-(4-(2-aminopyrimidin-4-yl)phenyl)acetate (0.1 g, 0.389 mmol) obtained in Preparation Example 74. (2 step yield 1%)

$^1$H-NMR (400 MHz, CHLOROFORM-D) δ 9.07 (s, 1H), 8.53-8.41 (1H), 8.11 (d, J=8.2 Hz, 2H), 7.80-7.70 (m, 2H), 7.51 (d, J=8.2 Hz, 2H), 7.46 (s, 1H), 7.22 (d, J=5.0 Hz, 1H), 6.99-6.91 (m, 1H), 6.85-6.75 (m, 1H), 5.20 (t, J=3.4 Hz, 1H), 4.03-3.97 (m, 1H), 3.94-3.83 (m, 2H), 3.79 (q, J=7.0 Hz, 2H), 3.74 (s, 2H), 3.56-3.42 (m, 1H), 2.17 (d, J=10.1 Hz, 1H), 2.06-1.93 (m, 2H), 1.66 (s, 1H), 1.27 (t, J=6.9 Hz, 3H)

Example 153: (R)-3-(4-(2-((6-(3-(2-ethoxyphenoxy)piperidin-1-yl)pyrazin-2-yl)amino)pyrimidin-4-yl)phenyl)-2,2-dimethylpropanoic Acid

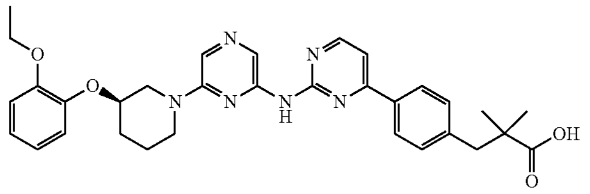 [SMILES: CCOc1ccccc1O[C@@H]1CCCN(c2cncc(Nc3nccc(-c4ccc(CC(C)(C)C(=O)O)cc4)n3)n2)C1]

The title compound was obtained in a similar manner to Example 22 by using (R)-2-chloro-6-(3-(2-ethoxyphenoxy)piperidin-1-yl)pyrazine (73.9 mg, 0.221 mmol) prepared in Preparation Example 1 and tert-butyl 3-(4-(2-aminopyrimidin-4-yl)phenyl)-2,2-dimethylpropanoate (72.5 mg, 0.221 mmol) prepared in Preparation Example 81. (2 step yield 61%)

$^1$H-NMR (CHLOROFORM-D) δ 9.07 (s, 1H), 8.49 (d, J=5.2 Hz, 1H), 7.98 (d, J=7.9 Hz, 2H), 7.83 (s, 1H), 7.81-7.73 (1H), 7.34 (d, J=7.9 Hz, 2H), 7.24 (d, J=5.2 Hz, 1H), 7.04-6.79 (m, 4H), 4.33 (d, J=7.6 Hz, 1H), 4.11-4.02 (m, 1H), 4.02-3.89 (m, 2H), 3.82-3.69 (m, 1H), 3.64 (dd, J=13.4, 7.3 Hz, 1H), 3.56-3.42 (1H), 2.97 (d, J=15.0 Hz, 2H), 2.16-2.06 (m, 1H), 2.01 (d, J=14.0 Hz, 1H), 1.93 (d, J=11.9 Hz, 1H), 1.67-1.51 (m, 1H), 1.37 (t, J=6.9 Hz, 3H), 1.26 (d, J=5.2 Hz, 6H)

Example 154: (R)-3-(4-(2-((6-(3-((3-ethoxypyridin-2-yl)oxy)piperidin-1-yl)pyrazin-2-yl)amino)pyrimidin-4-yl)phenyl)-2,2-dimethylpropanoic Acid

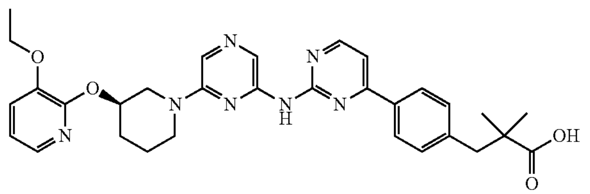 [SMILES: CCOc1cccnc1O[C@@H]1CCCN(c2cncc(Nc3nccc(-c4ccc(CC(C)(C)C(=O)O)cc4)n3)n2)C1]

The title compound was obtained in a similar manner to Example 1 by using (R)-2-chloro-6-(3-((3-ethoxypyridin-2-yl)oxy)piperidin-1-yl)pyrazine (70.4 mg, 0.210 mmol) prepared in Preparation Example 3 and methyl 3-(4-(2-aminopyrimidin-4-yl)phenyl)-2,2-dimethylpropanoate (60.0 mg, 0.210 mmol) prepared in Preparation Example 76. (2 step yield 63%)

$^1$H-NMR (400 MHz, METHANOL-D4) δ 8.87 (s, 1H), 8.60-8.43 (m, 1H), 8.08 (d, J=8.2 Hz, 2H), 7.70 (q, J=2.3 Hz, 2H), 7.49-7.26 (m, 3H), 7.04 (dd, J=7.8, 1.4 Hz, 1H), 6.84 (dd, J=7.8, 5.0 Hz, 1H), 5.29-5.12 (1H), 4.14 (dd, J=13.7, 5.5 Hz, 1H), 3.97-3.69 (m, 4H), 3.64 (t, J=9.4 Hz, 1H), 3.03-2.94 (2H), 2.20-1.95 (m, 3H), 1.75-1.56 (m, 1H), 1.25-1.14 (m, 9H)

Example 155: (R)-3-(4-(2-((2-(3-(2-ethoxyphenoxy)piperidin-1-yl)pyrimidin-4-yl)amino)pyrimidin-4-yl)phenyl)-2,2-dimethylpropanoic Acid

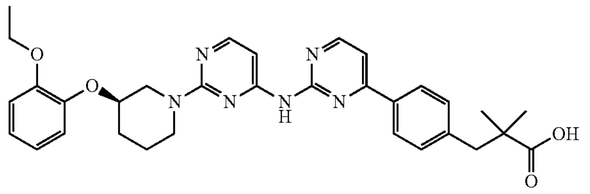 [SMILES: CCOc1ccccc1O[C@@H]1CCCN(c2nccc(Nc3nccc(-c4ccc(CC(C)(C)C(=O)O)cc4)n3)n2)C1]

The title compound was obtained in a similar manner to Example 1 by using (R)-4-chloro-2-(3-(2-ethoxyphenoxy)piperidin-1-yl)pyrimidine (70.2 mg, 0.210 mmol) prepared in Preparation Example 5 and methyl 3-(4-(2-aminopyrimidin-4-yl)phenyl)-2,2-dimethylpropanoate (60.0 mg, 0.210 mmol) prepared in Preparation Example 76. (2 step yield 64%)

$^1$H-NMR (400 MHz, METHANOL-D4) δ 8.55 (d, J=5.5 Hz, 1H), 8.15 (d, J=5.9 Hz, 1H), 8.11-8.02 (2H), 7.70 (d, J=5.9 Hz, 1H), 7.46 (d, J=5.5 Hz, 1H), 7.37 (d, J=8.7 Hz, 2H), 7.13-6.98 (m, 1H), 6.98-6.80 (m, 3H), 4.35 (td, J=7.2, 3.5 Hz, 1H), 4.24 (dd, J=13.3, 3.2 Hz, 1H), 4.05-3.89 (m, 3H), 3.86-3.72 (1H), 3.66 (td, J=8.7, 4.0 Hz, 1H), 2.96 (s, 2H), 2.20-2.04 (m, 1H), 2.01-1.92 (m, 1H), 1.92-1.78 (m, 1H), 1.67-1.48 (m, 1H), 1.32 (t, J=7.1 Hz, 3H), 1.20 (s, 6H)

Example 156: (R)-3-(4-(2-((4-(3-(2-ethoxyphenoxy)piperidin-1-yl)pyrimidin-2-yl)amino)pyrimidin-4-yl)phenyl)-2,2-dimethylpropanoic Acid

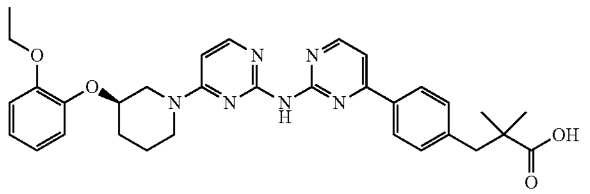 [SMILES: CCOc1ccccc1O[C@@H]1CCCN(c2ccnc(Nc3nccc(-c4ccc(CC(C)(C)C(=O)O)cc4)n3)n2)C1]

The title compound was obtained in a similar manner to Example 1 by using (R)-2-chloro-4-(3-(2-ethoxyphenoxy)piperidin-1-yl)pyrimidine (70.2 mg, 0.210 mmol) prepared in Preparation Example 6 and methyl 3-(4-(2-aminopyrimidin-4-yl)phenyl)-2,2-dimethylpropanoate (60.0 mg, 0.210 mmol prepared in Preparation Example 76. (2 step yield 36%)

$^1$H-NMR (400 MHz, METHANOL-D4) δ 8.59 (d, J=5.5 Hz, 1H), 8.08 (d, J=8.2 Hz, 2H), 7.95 (d, J=6.9 Hz, 1H), 7.61 (d, J=5.5 Hz, 1H), 7.39 (d, J=8.2 Hz, 2H), 7.06-6.96 (m, 1H), 6.96-6.76 (m, 3H), 6.54 (d, J=6.4 Hz, 1H), 4.56 (s, 1H), 4.37-4.17 (1H), 4.06-3.86 (m, 2H), 3.86-3.73 (m, 1H), 3.66-3.51 (m, 1H), 3.34 (d, J=5.5 Hz, 1H), 2.93 (s, 2H), 2.17-1.96 (m, 3H), 1.76-1.57 (m, 1H), 1.29 (t, J=6.9 Hz, 3H), 1.15 (s, 6H)

Example 157: (R)-3-(4-(2-((4-(3-((3-ethoxypyridin-2-yl)oxy)piperidin-1-yl)pyrimidin-2-yl)amino)pyrimidin-4-yl)phenyl)-2,2-dimethylpropanoic Acid

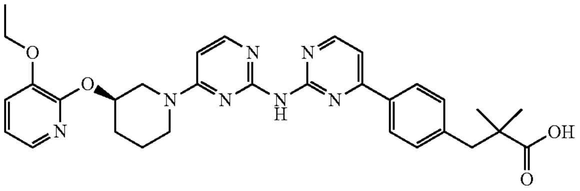 [SMILES: CCOc1cccnc1O[C@@H]1CCCN(c2ccnc(Nc3nccc(-c4ccc(CC(C)(C)C(=O)O)cc4)n3)n2)C1]

The title compound was obtained in a similar manner to Example 1 by using (R)-2-chloro-4-(3-((3-ethoxypyridin-2-yl)oxy)piperidin-1-yl)pyrimidine (70.4 mg, 0.210 mmol) prepared in Preparation Example 7 and methyl 3-(4-(2-aminopyrimidin-4-yl)phenyl)-2,2-dimethylpropanoate (60.0 mg, 0.210 mmol) prepared in Preparation Example 76. (2 step yield 60%)

$^1$H-NMR (400 MHz, METHANOL-D4) δ 8.61 (d, J=5.5 Hz, 1H), 8.17-8.01 (2H), 7.94 (d, J=6.9 Hz, 1H), 7.68 (d, J=3.7 Hz, 1H), 7.63 (d, J=5.5 Hz, 1H), 7.38 (d, J=8.2 Hz, 2H), 7.21-7.04 (1H), 6.93-6.76 (m, 1H), 6.57 (d, J=4.6 Hz, 1H), 5.32 (s, 1H), 4.62-4.04 (1H), 4.02-3.74 (3H), 3.73-3.54 (m, 1H), 2.94 (s, 2H), 2.19-1.96 (m, 3H), 1.82-1.63 (m, 1H), 1.30 (q, J=6.9 Hz, −1H), 1.27-1.20 (m, 3H), 1.17 (s, 6H)

Example 158: (R)-2-(3-(2-((6-(3-(2-ethoxyphenoxy)piperidin-1-yl)pyrazin-2-yl)amino)pyrimidin-4-yl)phenoxy)-2-methylpropanoic Acid

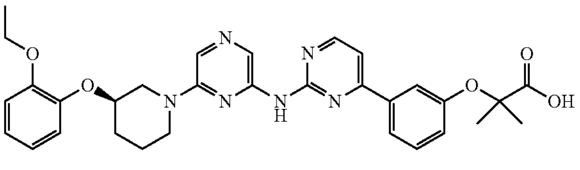 [SMILES: CCOc1ccccc1O[C@@H]1CCCN(c2cncc(Nc3nccc(-c4cccc(OC(C)(C)C(=O)O)c4)n3)n2)C1]

The title compound was obtained in a similar manner to Example 12 by using (R)-2-chloro-6-(3-(2-ethoxyphenoxy)piperidin-1-yl)pyrazine (0.175 g, 0.525 mmol) obtained in Preparation Example 1 and ethyl 2-(3-(2-aminopyrimidin-4-yl)phenoxy)-2-methylpropanoate (0.19 g, 0.631 mmol) obtained in Preparation Example 68. (2 step yield 62%)

$^1$H-NMR (400 MHz, METHANOL-D4) δ 8.85 (s, 1H), 8.49 (d, J=5.0 Hz, 1H), 7.76-7.55 (m, 3H), 7.40-7.26 (m, 2H), 7.05 (d, J=7.3 Hz, 2H), 6.99 (d, J=5.9 Hz, 1H), 6.87 (s, 3H), 4.74-4.49 (1H), 4.49-4.32 (1H), 3.90 (d, J=14.2 Hz, 2H), 3.83-3.69 (m, 2H), 3.65 (s, 1H), 2.08-1.97 (2H), 1.92 (s, 1H), 1.63-1.59 (1H), 1.56 (s, 6H), 1.26 (s, 3H)

Example 159: (R)-2-(3-(2-((6-(3-((3-ethoxypyridin-2-yl)oxy)piperidin-1-yl)pyrazin-2-yl)amino)pyrimidin-4-yl)phenoxy)-2-methylpropanoic Acid

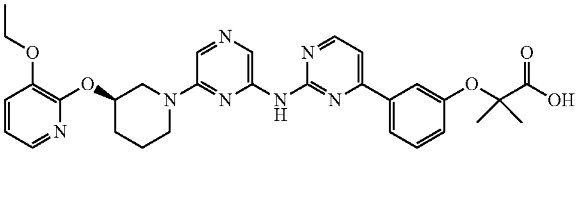 [SMILES: CCOc1cccnc1O[C@@H]1CCCN(c2cncc(Nc3nccc(-c4cccc(OC(C)(C)C(=O)O)c4)n3)n2)C1]

The title compound was obtained in a similar manner to Example 1 by using (R)-2-chloro-6-(3-((3-ethoxypyridin-2-yl)oxy)piperidin-1-yl)pyrazine (78.0 mg, 0.232 mmol) prepared in Preparation Example 3 and ethyl 2-(3-(2-aminopyrimidin-4-yl)phenoxy)-2-methylpropanoate (70.0 mg, 0.232 mmol) prepared in Preparation Example 68. (2 step yield 64%)

$^1$H-NMR (CHLOROFORM-D) δ 9.24 (s, 1H), 8.51 (d, J=5.2 Hz, 1H), 8.09 (s, 1H), 7.79-7.74 (1H), 7.71 (s, 1H), 7.55 (d, J=7.6 Hz, 1H), 7.37 (t, J=7.8 Hz, 1H), 7.33-7.27 (1H), 7.16-7.07 (1H), 6.97 (d, J=7.6 Hz, 1H), 6.88-6.76 (1H), 5.22 (q, J=3.4 Hz, 1H), 3.99 (d, J=13.4 Hz, 1H), 3.96-3.83 (m, 3H), 3.83-3.71 (m, 1H), 3.66-3.50 (m, 1H), 2.25-2.12 (m, 1H), 2.09-1.95 (m, 2H), 1.78-1.67 (m, 1H), 1.67-1.58 (6H), 1.29 (t, J=6.9 Hz, 3H)

Example 160: (R)-2-(4-(2-((6-(3-(2-ethoxyphenoxy)piperidin-1-yl)pyrazin-2-yl)amino)pyrimidin-4-yl)phenoxy)-2-methylpropanoic Acid

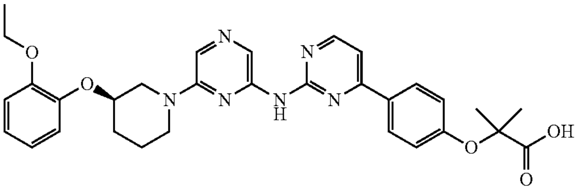 [SMILES: CCOc1ccccc1O[C@@H]1CCCN(c2cncc(Nc3nccc(-c4ccc(OC(C)(C)C(=O)O)cc4)n3)n2)C1]

The title compound was obtained in a similar manner to Example 12 by using (R)-2-chloro-6-(3-(2-ethoxyphenoxy)piperidin-1-yl)pyrazine (0.277 g, 0.83 mmol) obtained in Preparation Example 1 and ethyl 2-(4-(2-aminopyrimidin-4-yl)phenoxy)-2-methylpropanoate (0.3 g, 0.996 mmol) obtained in Preparation Example 69. (2 step yield 33%)

$^1$H-NMR (MeOD) δ 8.89 (s, 1H), 8.43 (d, J=4.9 Hz, 1H), 7.97 (d, J=8.2 Hz, 2H), 7.61 (s, 1H), 7.19 (d, J=5.2 Hz, 1H), 7.00 (d, J=7.0 Hz, 2H), 6.93 (d, J=7.6 Hz, 1H), 6.89-6.68 (m, 3H), 4.33 (t, J=3.2 Hz, 1H), 3.95-3.77 (m, 3H), 3.64 (q, J=6.7 Hz, 1H), 3.59-3.49 (m, 2H), 2.06-1.98 (m, 2H), 1.94 (d, J=4.6 Hz, 1H), 1.89-1.74 (m, 1H), 1.61 (d, J=13.7 Hz, 6H), 1.24 (t, J=7.0 Hz, 3H)

Example 161: (R)-2-((4-(2-((6-(3-(2-ethoxyphenoxy)piperidin-1-yl)pyrazin-2-yl)amino)pyrimidin-4-yl)phenyl)amino)-2-methylpropanoic Acid

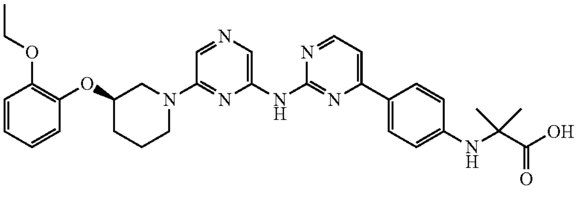 [SMILES: CCOc1ccccc1O[C@@H]1CCCN(c2cncc(Nc3nccc(-c4ccc(NC(C)(C)C(=O)O)cc4)n3)n2)C1]

The desired title compound was obtained in a similar manner to Example 1 by using (R)-2-chloro-6-(3-(2-ethoxyphenoxy)piperidin-1-yl)pyrazine (0.15 g, 0.45 mmol) synthesized in Preparation Example 1 and ethyl 2-((4-(2-aminopyrimidin-4-yl)phenyl)amino)-2-methylpropanoate (45 mg, 0.75 mmol) synthesized in Preparation Example 99. (61% yield)

$^1$H-NMR (MeOD) δ 8.92 (s, 1H), 8.39 (d, J=5.5 Hz, 1H), 7.99 (d, J=8.8 Hz, 2H), 7.68 (s, 1H), 7.30 (d, J=5.5 Hz, 1H), 7.04 (d, J=7.6 Hz, 1H), 6.99-6.84 (m, 3H), 6.70 (d, J=8.8 Hz, 2H), 4.46 (s, 1H), 4.03-3.83 (m, 4H), 3.83-3.71 (1H), 3.71-3.55 (1H), 2.06 (d, J=24.4 Hz, 2H), 1.99-1.88 (1H), 1.65 (s, 1H), 1.59 (s, 6H), 1.37-1.28 (m, 3H)

Example 162: (R)-2-(4-((2-((6-(3-(2-ethoxyphenoxy)piperidin-1-yl)pyrazin-2-yl)amino)pyrimidin-4-yl)oxy)phenyl)acetic Acid

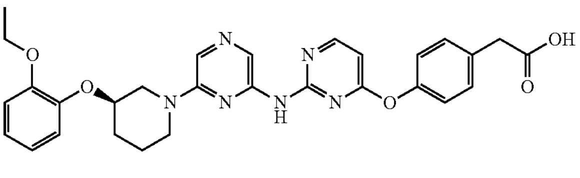 [SMILES: CCOc1ccccc1O[C@@H]1CCCN(c2cncc(Nc3nccc(Oc4ccc(CC(=O)O)cc4)n3)n2)C1]

The title compound was obtained in a similar manner to Example 12 by using (R)-2-chloro-6-(3-(2-ethoxyphenoxy)piperidin-1-yl)pyrazine (0.142 g, 0.424 mmol) obtained in Preparation Example 1 and methyl 2-(4-((2-aminopyrimidin-4-yl)oxy)phenyl)acetate (0.1 g, 0.386 mmol) obtained in Preparation Example 103. (2 step yield 29%)

$^1$H-NMR (400 MHz, CHLOROFORM-D) δ 8.31 (d, J=5.5 Hz, 1H), 7.70-7.61 (1H), 7.55 (s, 1H), 7.45 (d, J=8.2 Hz, 2H), 7.42-7.37 (1H), 7.13-7.07 (2H), 6.92 (dd, J=7.1, 1.6 Hz, 2H), 6.89-6.79 (m, 2H), 6.53 (d, J=5.5 Hz, 1H), 4.33-4.18 (m, 1H), 4.04-3.87 (m, 3H), 3.80 (s, 2H), 3.71-3.52 (2H), 3.48-3.35 (m, 1H), 2.09-2.00 (m, 1H), 2.00-1.84 (m, 2H), 1.61-1.49 (m, 1H), 1.39-1.30 (3H)

Example 163: (R)-2-(4-((2-((6-(3-((3-ethoxypyridin-2-yl)oxy)piperidin-1-yl)pyrazin-2-yl)amino)pyrimidin-4-yl)phenyl)acetic Acid

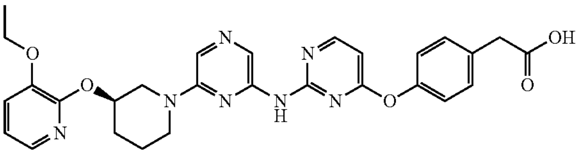 [SMILES: CCOc1cccnc1O[C@@H]1CCCN(c2cncc(Nc3nccc(Oc4ccc(CC(=O)O)cc4)n3)n2)C1]

The title compound was obtained in a similar manner to Example 12 by using (R)-2-chloro-6-(3-((3-ethoxypyridin-2-yl)oxy)piperidin-1-yl)pyrazine (0.142 g, 0.424 mmol) obtained in Preparation Example 3 and methyl 2-(4-((2-aminopyrimidin-4-yl)oxy)phenyl)acetate (0.1 g, 0.386 mmol) obtained in Preparation Example 103. (2 step yield 14%)

$^1$H-NMR (400 MHz, CHLOROFORM-D) δ 8.31 (d, J=5.5 Hz, 1H), 7.77-7.69 (m, 2H), 7.50-7.42 (m, 3H), 7.32 (s, 1H), 7.09 (dd, J=6.4, 1.8 Hz, 2H), 6.95 (dd, J=7.8, 1.4 Hz, 1H), 6.80 (dd, J=7.8, 5.0 Hz, 1H), 6.55 (d, J=5.9 Hz, 1H), 5.14 (q, J=3.5 Hz, 1H), 3.96-3.79 (m, 5H), 3.74 (q, J=7.0 Hz, 2H), 3.52 (s, 1H), 2.11 (dd, J=15.8, 8.9 Hz, 1H), 2.01-1.90 (m, 2H), 1.68-1.57 (m, 1H), 1.26 (d, J=6.9 Hz, 3H)

Example 164: (R)-3-(3-(2-((6-(3-(2-ethoxyphenoxy)piperidin-1-yl)pyrazin-2-yl)amino)-5-fluoropyrimidin-4-yl)phenyl)-2,2-dimethylpropanoic Acid

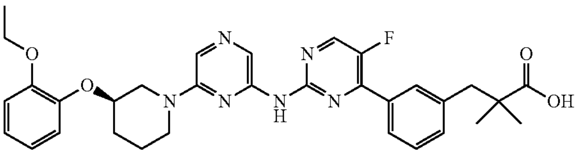 [SMILES: CCOc1ccccc1O[C@@H]1CCCN(c2cncc(Nc3ncc(F)c(-c4cccc(CC(C)(C)C(=O)O)c4)n3)n2)C1]

The title compound was obtained in a similar manner to Example 22 by using (R)-2-chloro-6-(3-(2-ethoxyphenoxy)piperidin-1-yl)pyrazine (129 mg, 0.41 mmol) synthesized in Preparation Example 1 and tert-butyl 3-(3-(2-chloro-5-fluoropyrimidin-4-yl)phenyl)-2,2-dimethylpropanoate (150 mg, 0.41 mmol) synthesized in Preparation Example 79. (2 step yield 32%)

$^1$H-NMR (400 MHz, METHANOL-D4) δ 8.79 (s, 1H), 8.49 (d, J=3.0 Hz, 1H), 7.94 (d, J=11.4 Hz, 2H), 7.65 (s, 1H), 7.42 (t, J=7.5 Hz, 1H), 7.36 (d, J=7.8 Hz, 1H), 7.04-6.93 (m, 1H), 6.92-6.76 (m, 3H), 4.48 (s, 1H), 3.95 (d, J=5.9 Hz, 2H), 3.87 (tdd, J=16.9, 6.9, 2.7 Hz, 2H), 3.78 (d, J=13.7 Hz, 1H), 3.60-3.42 (m, 1H), 2.96 (s, 2H), 2.11-1.88 (m, 3H), 1.59 (s, 1H), 1.33-1.20 (m, 3H), 1.19 (s, 6H)

Example 165: (R)-3-(3-(2-((6-(3-((3-ethoxypyridin-2-yl)oxy)piperidin-1-yl)pyrazin-2-yl)amino)-5-(trifluoromethyl)pyrimidin-4-yl)phenyl)-2,2-dimethylpropanoic Acid

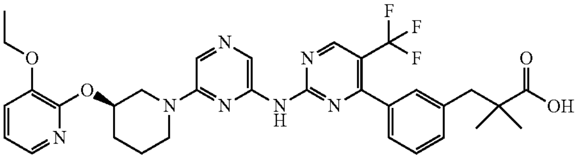 [SMILES: CCOc1cccnc1O[C@@H]1CCCN(c2cncc(Nc3ncc(C(F)(F)F)c(-c4cccc(CC(C)(C)C(=O)O)c4)n3)n2)C1]

The title compound was obtained in a similar manner to Example 22 by using (R)-2-chloro-6-(3-((3-ethoxypyridin-2-yl)oxy)piperidin-1-yl)pyrazine (36 mg, 0.11 mmol) synthesized in Preparation Example 3 and tert-butyl 3-(3-(2-amino-5-(trifluoromethyl)pyrimidin-4-yl)phenyl)-2,2-dimethylpropanoate (42 mg, 0.11 mmol) synthesized in Preparation Example 86. (2 step yield 15%)

$^1$H-NMR (400 MHz, METHANOL-D4) δ 8.81 (s, 1H), 8.45 (d, J=4.1 Hz, 1H), 7.98 (s, 1H), 7.94 (d, J=7.8 Hz, 1H), 7.73-7.63 (m, 2H), 7.41 (t, J=7.5 Hz, 1H), 7.35 (d, J=7.8 Hz, 1H), 7.03 (dd, J=7.8, 1.4 Hz, 1H), 6.80 (dd, J=7.8, 5.0 Hz, 1H), 5.15 (q, J=2.9 Hz, 1H), 4.06-3.94 (m, 1H), 3.94-3.70 (m, 5H), 3.62 (d, J=8.2 Hz, 1H), 2.96 (s, 2H), 2.16-1.88 (m, 4H), 1.69-1.54 (m, 1H), 1.21-1.10 (m, 9H)

Example 166: (R)-3-(3-(2-((6-(3-((3-ethoxypyridin-2-yl)oxy)piperidin-1-yl)pyrazin-2-yl)amino)-6-(trifluoromethyl)pyrimidin-4-yl)phenyl)-2,2-dimethylpropanoic Acid

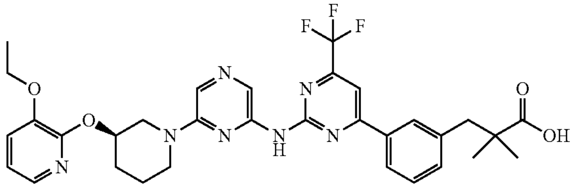 [SMILES: CCOc1cccnc1O[C@@H]1CCCN(c2cncc(Nc3nc(-c4cccc(CC(C)(C)C(=O)O)c4)cc(C(F)(F)F)n3)n2)C1]

The title compound was obtained in a similar manner to Example 1 by using (R)-2-chloro-6-(3-((3-ethoxypyridin-2-yl)oxy)piperidin-1-yl)pyrazine (104 mg, 0.31 mmol) synthesized in Preparation Example 3 and methyl 3-(3-(2-amino-6-(trifluoromethyl)pyrimidin-4-yl)phenyl)-2,2-dimethylpropanoate (100 mg, 0.28 mmol) synthesized in Preparation Example 93. (2 step yield 65%)

$^1$H-NMR (400 MHz, METHANOL-D4) δ 8.81 (s, 1H), 8.07 (s, 1H), 8.04 (d, J=7.3 Hz, 1H), 7.70 (s, 1H), 7.69 (s, 1H), 7.67 (dd, J=5.0, 1.4 Hz, 1H), 7.48-7.34 (m, 2H), 7.00 (dd, J=7.8, 1.4 Hz, 1H), 6.79 (dd, J=7.8, 5.0 Hz, 1H), 5.17 (q, J=2.7 Hz, 1H), 4.12 (dd, J=13.0, 4.8 Hz, 1H), 3.96-3.68 (m, 4H), 3.60 (td, J=9.0, 4.1 Hz, 1H), 2.98 (s, 2H), 2.17-1.99 (m, 2H), 1.95 (s, 1H), 1.71-1.54 (m, 1H), 1.24-1.15 (m, 9H)

Example 167: (R)-3-(3-(2-((6-(3-(2-ethoxyphenoxy)piperidin-1-yl)pyrazin-2-yl)amino)-6-(trifluoromethyl)pyrimidin-4-yl)phenyl)-2,2-dimethylpropanoic Acid

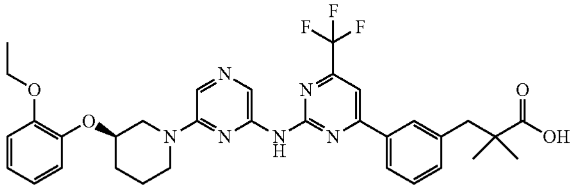 [SMILES: CCOc1ccccc1O[C@@H]1CCCN(c2cncc(Nc3nc(-c4cccc(CC(C)(C)C(=O)O)c4)cc(C(F)(F)F)n3)n2)C1]

The title compound was obtained in a similar manner to Example 1 by using (R)-2-chloro-6-(3-(2-ethoxyphenoxy)piperidin-1-yl)pyrazine (104 mg, 0.31 mmol) synthesized in Preparation Example 1 and methyl 3-(3-(2-amino-6-(trifluoromethyl)pyrimidin-4-yl)phenyl)-2,2-dimethylpropanoate (100 mg, 0.28 mmol) synthesized in Preparation Example 93. (2 step yield 49%)

$^1$H-NMR (400 MHz, METHANOL-D4) δ 8.85 (s, 1H), 8.07 (s, 1H), 8.06-7.96 (m, 1H), 7.70 (s, 1H), 7.69 (s, 1H), 7.49-7.31 (m, 2H), 6.99 (dd, J=7.5, 2.1 Hz, 1H), 6.93-6.77 (m, 3H), 4.42 (t, J=3.4 Hz, 1H), 3.99-3.82 (4H), 3.82-3.69 (m, 1H), 3.69-3.52 (1H), 2.98 (s, 2H), 2.12-2.00 (2H), 1.93 (t, J=8.9 Hz, 1H), 1.60 (d, J=3.7 Hz, 1H), 1.23 (t, J=7.1 Hz, 3H), 1.19 (s, 6H)

Example 168: (R)-2-(3-(4-((6-(3-(2-ethoxyphenoxy)piperidin-1-yl)pyrazin-2-yl)amino)pyrimidin-2-yl)phenyl)-2-methylpropanoic Acid

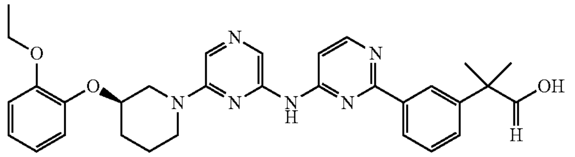

The title compound was obtained in a similar manner to Example 12 by using (R)-2-chloro-6-(3-(2-ethoxyphenoxy)piperidin-1-yl)pyrazine (0.108 g, 0.324 mmol) obtained in Preparation Example 1 and methyl 2-(3-(4-aminopyrimidin-2-yl)phenyl)-2-methylpropanoate (0.08 g, 0.295 mmol) obtained in Preparation Example 111. (2 step yield 94%)

$^1$H-NMR (400 MHz, METHANOL-D4) δ 8.40 (d, J=1.8 Hz, 1H), 8.27 (t, J=6.4 Hz, 1H), 8.22-8.11 (m, 2H), 7.62 (d, J=8.7 Hz, 1H), 7.51 (d, J=7.8 Hz, 1H), 7.46-7.37 (m, 1H), 7.32 (s, 1H), 6.96 (t, J=6.9 Hz, 1H), 6.84 (d, J=4.6 Hz, 2H), 6.82-6.75 (m, 1H), 4.43 (s, 1H), 3.94-3.77 (m, 4H), 3.77-3.63 (1H), 3.56 (d, J=9.1 Hz, 1H), 2.10-2.00 (2H), 1.92 (d, J=8.7 Hz, 1H), 1.61 (s, 6H), 1.60-1.55 (1H), 1.24 (dd, J=6.2, 2.1 Hz, 3H)

Example 169: (R)-2-(4-(4-((6-(3-(2-ethoxyphenoxy)piperidin-1-yl)pyrazin-2-yl)amino)pyrimidin-2-yl)phenyl)-2-methylpropanoic Acid

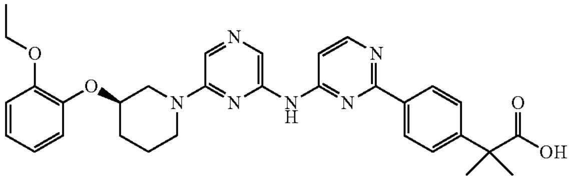 [SMILES: CCOc1ccccc1O[C@@H]1CCCN(c2cncc(Nc3ccnc(-c4ccc(C(C)(C)C(=O)O)cc4)n3)n2)C1]

The title compound was obtained in a similar manner to Example 12 by using (R)-2-chloro-6-(3-(2-ethoxyphenoxy)piperidin-1-yl)pyrazine (0.095 g, 0.284 mmol) obtained in Preparation Example 1 and methyl 2-(4-(4-aminopyrimidin-2-yl)phenyl)-2-methylpropanoate (0.07 g, 0.258 mmol) obtained in Preparation Example 112. (2 step yield 87%)

$^1$H-NMR (400 MHz, METHANOL-D4) δ 8.31-8.21 (m, 3H), 8.16 (s, 1H), 7.61 (d, J=2.3 Hz, 1H), 7.52-7.44 (2H), 7.29 (d, J=3.7 Hz, 1H), 6.95 (d, J=7.8 Hz, 1H), 6.86-6.81 (m, 2H), 6.81-6.75 (m, 1H), 4.41 (d, J=2.3 Hz, 1H), 3.96-3.74 (4H), 3.67 (d, J=13.7 Hz, 1H), 3.60-3.45 (m, 1H), 2.10-1.99 (m, 2H), 1.95-1.84 (m, 1H), 1.63 (d, J=15.1 Hz, 1H), 1.57 (s, 6H), 1.25 (t, J=7.8 Hz, 3H)

Example 170: (R)-3-(3-(4-((6-(3-(2-ethoxyphenoxy)piperidin-1-yl)pyrazin-2-yl)amino)pyrimidin-2-yl)phenyl)-2,2-dimethylpropanoic Acid

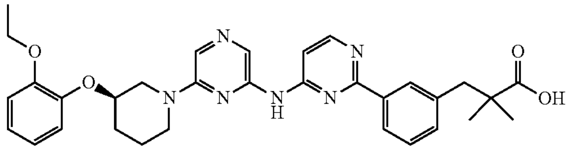

The title compound was obtained in a similar manner to Example 1 by using (R)-2-chloro-6-(3-(2-ethoxyphenoxy) piperidin-1-yl)pyrazine (82.0 mg, 0.245 mmol) prepared in Preparation Example 1 and methyl 3-(3-(4-aminopyrimidin-2-yl)phenyl)-2,2-dimethylpropanoate (70.0 mg, 0.245 mmol) prepared in Preparation Example 90. (2 step yield 65%)

$^{1}$H-NMR (400 MHz, METHANOL-D4) δ 8.36 (s, 1H), 8.34-8.26 (m, 1H), 8.26-8.13 (m, 2H), 7.70 (s, 1H), 7.39 (t, J=7.5 Hz, 1H), 7.36-7.22 (m, 2H), 7.01 (d, J=7.8 Hz, 1H), 6.94-6.75 (m, 3H), 4.47 (t, J=3.4 Hz, 1H), 4.02-3.84 (m, 4H), 3.84-3.72 (m, 1H), 3.71-3.55 (m, 1H), 2.99 (s, 2H), 2.22-2.02 (m, 2H), 2.00-1.81 (m, 1H), 1.75-1.54 (m, 1H), 1.27 (t, J=6.9 Hz, 3H), 1.21 (s, 6H)

Example 171: (R)-3-(3-(4-((6-(3-((3-ethoxypyridin-2-yl)oxy)piperidin-1-yl)pyrazin-2-yl)amino)pyrimidin-2-yl)phenyl)-2,2-dimethylpropanoic Acid

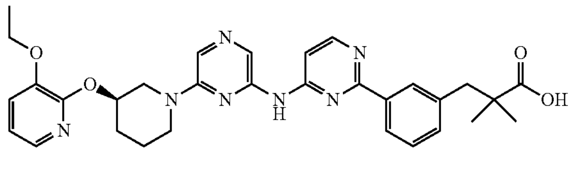 [SMILES: CCOc1cccnc1O[C@@H]1CCCN(c2cncc(Nc3ccnc(-c4cccc(CC(C)(C)C(=O)O)c4)n3)n2)C1]

The title compound was obtained in a similar manner to Example 1 by using (R)-2-chloro-6-(3-((3-ethoxypyridin-2-yl)oxy)piperidin-1-yl)pyrazine (71.6 mg, 0.214 mmol) prepared in Preparation Example 3 and methyl 3-(3-(4-amino-pyrimidin-2-yl)phenyl)-2,2-dimethylpropanoate (61.0 mg, 0.214 mmol) prepared in Preparation Example 90. (2 step yield 45%)

$^{1}$H-NMR (400 MHz, CHLOROFORM-D) δ 9.30 (s, 1H), 8.40 (d, J=5.9 Hz, 1H), 8.35-8.18 (m, 2H), 7.80-7.62 (m, 2H), 7.47-7.31 (1H), 7.24 (d, J=7.3 Hz, 1H), 7.09 (s, 1H), 6.91 (dd, J=7.8, 1.8 Hz, 1H), 6.79 (dd, J=7.8, 5.0 Hz, 1H), 6.50 (d, J=5.5 Hz, 1H), 5.21 (q, J=3.2 Hz, 1H), 4.02-3.72 (m, 4H), 3.63 (s, 1H), 3.57 (s, 1H), 3.01 (dd, J=23.3, 13.7 Hz, 2H), 2.22-2.07 (m, 1H), 2.02 (q, J=5.0 Hz, 2H), 1.75-1.53 (m, 1H), 1.29-1.22 (m, 9H)

Example 172: (R)-3-(4-(4-((6-(3-(2-ethoxyphenoxy) piperidin-1-yl)pyrazin-2-yl)amino)pyrimidin-2-yl) phenyl)-2,2-dimethylpropanoic Acid

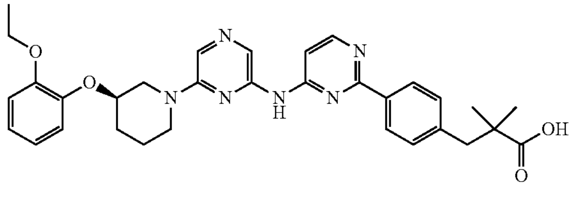 [SMILES: CCOc1ccccc1O[C@@H]1CCCN(c2cncc(Nc3ccnc(-c4ccc(CC(C)(C)C(=O)O)cc4)n3)n2)C1]

The title compound was obtained in a similar manner to Example 1 by using (R)-2-chloro-6-(3-(2-ethoxyphenoxy) piperidin-1-yl)pyrazine (82.0 mg, 0.245 mmol) prepared in Preparation Example 1 and methyl 3-(4-(4-aminopyrimidin-2-yl)phenyl)-2,2-dimethylpropanoate (70.0 mg, 0.245 mmol) prepared in Preparation Example 96. (2 step yield 59%)

$^{1}$H-NMR (400 MHz, METHANOL-D4) δ 8.30 (d, J=5.9 Hz, 1H), 8.24 (d, J=8.2 Hz, 3H), 7.69 (s, 1H), 7.42-7.24 (m, 3H), 7.00 (d, J=7.3 Hz, 1H), 6.94-6.74 (m, 3H), 4.48 (t, J=3.4 Hz, 1H), 4.02-3.82 (m, 4H), 3.82-3.70 (m, 1H), 3.70-3.53 (m, 1H), 2.95 (s, 2H), 2.22-1.87 (m, 3H), 1.74-1.55 (m, 1H), 1.36-1.23 (3H), 1.20 (s, 6H)

Example 173: (R)-3-(4-(4-((6-(3-((3-ethoxypyridin-2-yl)oxy)piperidin-1-yl)pyrazin-2-yl)amino)pyrimidin-2-yl)phenyl)-2,2-dimethylpropanoic Acid

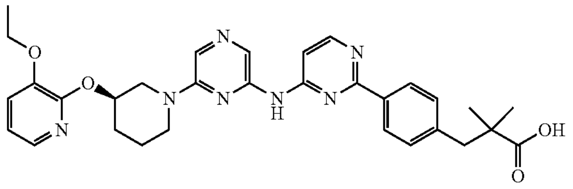 [SMILES: CCOc1cccnc1O[C@@H]1CCCN(c2cncc(Nc3ccnc(-c4ccc(CC(C)(C)C(=O)O)cc4)n3)n2)C1]

The title compound was obtained in a similar manner to Example 1 by using (R)-2-chloro-6-(3-((3-ethoxypyridin-2-yl)oxy)piperidin-1-yl)pyrazine (82.0 mg, 0.245 mmol) prepared in Preparation Example 3 and methyl 3-(4-(4-amino-pyrimidin-2-yl)phenyl)-2,2-dimethylpropanoate (70.0 mg, 0.245 mmol) prepared in Preparation Example 96. (2 step yield 52%)

$^{1}$H-NMR (400 MHz, METHANOL-D4) δ 8.31 (d, J=5.5 Hz, 1H), 8.28-8.22 (2H), 8.20 (s, 1H), 7.70 (s, 1H), 7.60 (dd, J=5.0, 1.4 Hz, 1H), 7.40-7.20 (3H), 7.02 (dd, J=7.8, 1.4 Hz, 1H), 6.71 (dd, J=7.8, 5.0 Hz, 1H), 5.26 (t, J=2.7 Hz, 1H), 4.23 (dd, J=13.7, 5.5 Hz, 1H), 4.00-3.68 (m, 4H), 3.70-3.51 (m, 1H), 2.95 (s, 2H), 2.23-1.91 (m, 3H), 1.67 (dd, J=9.1, 3.2 Hz, 1H), 1.23-1.12 (m, 9H)

Example 174: (R)-2-(3-(4-((6-(3-(2-ethoxyphenoxy) piperidin-1-yl)pyrazin-2-yl)amino)pyrimidin-2-yl) phenoxy)-2-methylpropanoic Acid

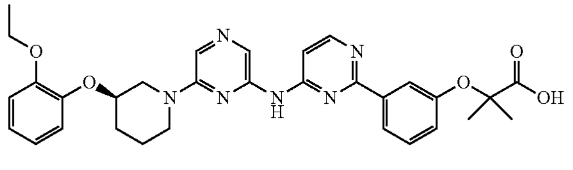 [SMILES: CCOc1ccccc1O[C@@H]1CCCN(c2cncc(Nc3ccnc(-c4cccc(OC(C)(C)C(=O)O)c4)n3)n2)C1]

The title compound was obtained in a similar manner to Example 1 by using (R)-2-chloro-6-(3-(2-ethoxyphenoxy) piperidin-1-yl)pyrazine (53.2 mg, 0.159 mmol) prepared in Preparation Example 1 and ethyl 2-(3-(4-aminopyrimidin-2-yl)phenoxy)-2-methylpropanoate (48.0 mg, 0.159 mmol) prepared in Preparation Example 95. (2 step yield 47%)

$^{1}$H-NMR (CHLOROFORM-D) δ 59.25 (s, 1H), 8.54-8.41 (1H), 8.11 (d, J=7.9 Hz, 2H), 7.71 (d, J=5.8 Hz, 1H), 7.45-7.34 (1H), 7.17-7.04 (1H), 7.04-6.93 (m, 3H), 6.93-6.79 (m, 2H), 6.57 (d, J=5.5 Hz, 1H), 4.36 (t, J=3.4 Hz, 1H), 4.06-3.84 (m, 3H), 3.80-3.61 (2H), 3.51 (t, J=8.8 Hz, 1H), 2.18-2.06 (m, 1H), 2.06-1.98 (m, 1H), 1.95 (dd, J=12.2, 4.3 Hz, 1H), 1.68-1.64 (1H), 1.64 (s, 6H), 1.35 (t, J=7.0 Hz, 3H)

Example 175: (R)-2-(3-(4-((6-(3-((3-ethoxypyridin-2-yl)oxy)piperidin-1-yl)pyrazin-2-yl)amino)pyrimidin-2-yl)phenoxy)-2-methylpropanoic Acid

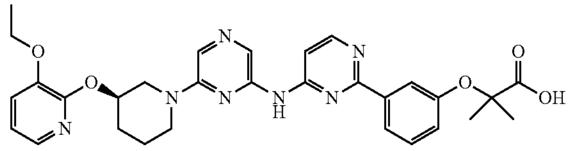

The title compound was obtained in a similar manner to Example 1 by using (R)-2-chloro-6-(3-((3-ethoxypyridin-2-yl)oxy)piperidin-1-yl)pyrazine (53.3 mg, 0.159 mmol) prepared in Preparation Example 3 and ethyl 2-(3-(4-aminopyrimidin-2-yl)phenoxy)-2-methylpropanoate (48.0 mg, 0.159 mmol) prepared in Preparation Example 95. (2 step yield 51%)

$^1$H-NMR (CHLOROFORM-D) δ 9.22 (s, 1H), 8.47 (d, J=5.8 Hz, 1H), 8.20-8.05 (m, 2H), 7.83-7.68 (m, 2H), 7.39 (t, J=7.9 Hz, 1H), 7.12 (d, J=7.3 Hz, 1H), 6.95 (d, J=7.6 Hz, 1H), 6.87 (s, 1H), 6.82 (dd, J=7.6, 4.9 Hz, 1H), 6.55 (d, J=5.8 Hz, 1H), 5.28-5.17 (1H), 4.05-3.77 (m, 4H), 3.77-3.66 (m, 1H), 3.66-3.56 (m, 1H), 2.24-2.10 (m, 1H), 2.10-1.96 (m, 2H), 1.76-1.63 (m, 7H), 1.27 (t, J=7.0 Hz, 3H)

Example 176: (R)-2-(3-(2-((6-(3-(2-ethoxyphenoxy)piperidin-1-yl)pyrazin-2-yl)amino)pyrimidin-4-yl)phenoxy)-2-methylpropanoic Acid

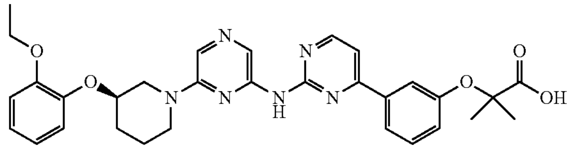 [SMILES: CCOc1ccccc1O[C@@H]1CCCN(c2cncc(Nc3nccc(-c4cccc(OC(C)(C)C(=O)O)c4)n3)n2)C1]

The title compound was obtained in a similar manner to Example 1 by using (R)-2-chloro-6-(3-(2-ethoxyphenoxy)piperidin-1-yl)pyrazine (107 mg, 0.322 mmol) prepared in Preparation Example 1 and ethyl 2-(3-(2-aminopyrimidin-4-yl)phenoxy)-2-methylpropanoate (97.0 mg, 0.322 mmol) prepared in Preparation Example 68. (2 step yield 62%)

$^1$H-NMR (400 MHz, CHLOROFORM-D) δ 9.29 (s, 1H), 8.52 (d, J=5.5 Hz, 1H), 8.09 (t, J=1.8 Hz, 1H), 7.69 (s, 1H), 7.65 (s, 1H), 7.55 (d, J=7.8 Hz, 1H), 7.37 (t, J=7.8 Hz, 1H), 7.29 (d, J=5.0 Hz, 1H), 7.19-7.07 (m, 1H), 7.07-6.94 (m, 2H), 6.94-6.80 (m, 2H), 4.41-4.23 (m, 1H), 4.12-4.05 (m, 1H), 4.05-3.88 (m, 2H), 3.80 (q, J=4.4 Hz, 1H), 3.67-3.51 (1H), 3.44 (t, J=9.6 Hz, 1H), 2.16-2.08 (m, 1H), 2.07-1.96 (1H), 1.95-1.82 (m, 1H), 1.68-1.53 (7H), 1.38 (t, J=6.9 Hz, 3H)

Example 177: (R)-2-(4-(6-((6-(3-(2-ethoxy-4-fluorophenoxy)piperidin-1-yl)pyrazin-2-yl)amino)pyridin-2-yl)phenoxy)-2-methylpropanoic Acid

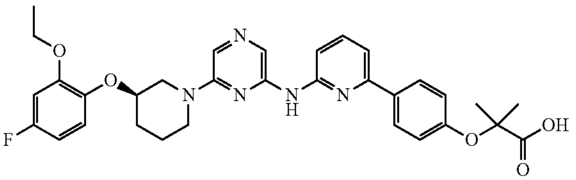 [SMILES: CCOc1cc(F)ccc1O[C@@H]1CCCN(c2cncc(Nc3cccc(-c4ccc(OC(C)(C)C(=O)O)cc4)n3)n2)C1]

The title compound was obtained in a similar manner to Example 1 by using (R)-2-chloro-6-(3-(2-ethoxy-4-fluorophenoxy)piperidin-1-yl)pyrazine (94.0 mg, 0.266 mmol) prepared in Preparation Example 118 and ethyl 2-(4-(6-aminopyridin-2-yl)phenoxy)-2-methylpropanoate (80.0 mg, 0.266 mmol) prepared in Preparation Example 97. (2 step yield 59%)

$^1$H-NMR (400 MHz, CHLOROFORM-D) δ 8.05 (s, 1H), 7.82-7.64 (m, 4H), 7.64-7.46 (1H), 7.14 (d, J=7.8 Hz, 1H), 7.09-6.96 (m, 2H), 6.88 (t, J=7.1 Hz, 1H), 6.58 (dd, J=10.1, 2.7 Hz, 1H), 6.53-6.38 (1H), 4.31-4.17 (m, 1H), 4.04 (d, J=11.9 Hz, 1H), 3.99-3.84 (m, 2H), 3.75 (t, J=6.6 Hz, 1H), 3.53 (dd, J=13.0, 7.5 Hz, 1H), 3.47-3.31 (m, 1H), 2.16-2.05 (m, 1H), 2.00 (q, J=3.4 Hz, 1H), 1.94-1.82 (m, 1H), 1.65 (s, 6H), 1.60 (q, J=4.6 Hz, 1H), 1.36 (t, J=7.1 Hz, 3H)

Example 178: (R)-2-(4-(4-((6-(3-(2-ethoxyphenoxy)piperidin-1-yl)pyrazin-2-yl)amino)pyrimidin-2-yl)phenoxy)-2-methylpropanoic Acid

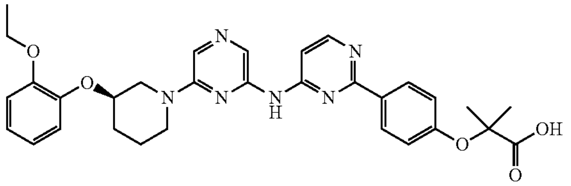

The title compound was obtained in a similar manner to Example 1 by using (R)-2-chloro-6-(3-(2-ethoxyphenoxy)piperidin-1-yl)pyrazine (110 mg, 0.329 mmol) prepared in Preparation Example 1 and methyl 2-(4-(4-aminopyrimidin-2-yl)phenoxy)-2-methylpropanoate (90 mg, 0.299 mmol) prepared in Preparation Example 119. (2 step yield 64%)

$^1$H-NMR (400 MHz, CHLOROFORM-D) δ 8.37 (d, J=5.9 Hz, 1H), 8.25-8.07 (m, 3H), 7.79 (s, 1H), 7.75 (s, 1H), 7.23 (d, J=5.9 Hz, 1H), 7.00-6.88 (4H), 6.88-6.77 (2H), 4.39-4.27 (m, 1H), 4.06-3.86 (m, 3H), 3.76-3.67 (m, 1H), 3.67-3.58 (m, 1H), 3.45 (t, J=9.4 Hz, 1H), 2.18-2.09 (m, 1H), 2.02-1.96 (m, 1H), 1.96-1.86 (m, 1H), 1.68 (s, 6H), 1.65-1.56 (m, 1H), 1.31 (q, J=7.5 Hz, 3H)

Example 179: (R)-2-(4-(4-((6-(3-((3-ethoxypyridin-2-yl)oxy)piperidin-1-yl)pyrazin-2-yl)amino)pyrimidin-2-yl)phenoxy)-2-methylpropanoic Acid

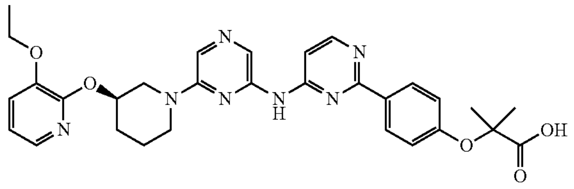 [SMILES: CCOc1cccnc1O[C@@H]1CCCN(c2cncc(Nc3ccnc(-c4ccc(OC(C)(C)C(=O)O)cc4)n3)n2)C1]

The title compound was obtained in a similar manner to Example 1 by using (R)-2-chloro-6-(3-((3-ethoxypyridin-2-yl)oxy)piperidin-1-yl)pyrazine (98 mg, 0.292 mmol) prepared in Preparation Example 3 and methyl 2-(4-(4-aminopyrimidin-2-yl)phenoxy)-2-methylpropanoate (80 mg, 0.265 mmol) prepared in Preparation Example 119. (2 step yield 66%)

$^1$H-NMR (400 MHz, CHLOROFORM-D) δ 8.42-8.29 (m, 1H), 8.15 (d, J=8.2 Hz, 3H), 7.80 (s, 1H), 7.75 (s, 1H), 7.65 (dd, J=4.8, 1.6 Hz, 1H), 7.24-7.15 (1H), 7.04-6.94 (m, 2H), 6.91 (dd, J=7.8, 1.4 Hz, 1H), 6.78-6.67 (1H), 5.22 (q, J=3.2 Hz, 1H), 4.01-3.91 (m, 1H), 3.91-3.76 (m, 3H), 3.68 (d, J=5.9 Hz, 1H), 3.60-3.45 (m, 1H), 2.23-2.08 (m, 1H), 2.00 (t, J=5.0 Hz, 2H), 1.71 (d, J=30.2 Hz, 6H), 1.58 (s, 1H), 1.25 (td, J=7.0, 5.2 Hz, 3H)

Experimental Example: Measurement of Inhibitory Effect Against DGAT2 Enzyme Activity The inhibitory effect against the DGAT2 enzyme activity was investigated by performing the following experiment on the compounds of Formula (1) according to the present invention.

1. Preparation of DGAT2 Expression Vector

In order to prepare the pBacPAK9-DGAT2, which is DGAT2 expression vector, the human DGAT2 gene amplified by polymerase chain reaction (PCR) was cloned into the EcoR1 and Xho1 sites of the pBacPAK9 (clonctech) vector. The nucleotide sequence of the primers used in PCR was the forward primer 5' CTATAAATACGGATCCCGGGAATTCATGGACTACAAGGACGACGATGACAAGCTTAAGACCCTCATAGCCGCC (SEQ. ID. NO: 1) and the reverse primer 5' TAAGCGGCCGCCCTGCAGGCCTCGAGTCAGTTCACCTCCAGGAC (SEQ. ID. NO: 2). The composition of the reaction solution was to contain 50 ng of cDNA clone (OriGene), 200 μM of dATP, dCTP, dTTP, dGTP, 200 nM of each primer, 1 unit of Tag DNA Polymerase (Toyobo), 1×PCR buffer, and the final volume was adjusted to 20 μl. The reaction conditions were denatured at 95° C. for 5 minutes, followed by 30 times of 94° C. for 20 seconds, 60° C. for 20 seconds, and 72° C. for 90 seconds, followed by further reaction at 72° C. for 7 minutes.

2. DGAT2 Expression and Preparation of Membrane Protein

Recombinant human DGAT2 protein was expressed in Sf-21 cells, which are insect cells, by using the BacPack baculovirus expression system (Clontech). The brief manufacturing process is as follows. First, the pBacPAK9-DGAT2 expression vector was transfected with BacPAK6 virus DNA (Bsu36I digest) into sf21 cells using Bacfectin to prepare a recombinant DGAT2 expressing baculovirus. The thus prepared baculovirus was infected with Sf-21 cells at 10 MOI (multiplicity of infection), and after 72 hours, infected insect cells were collected and membrane proteins were isolated. For membrane protein separation, the cell pellet was dissolved in a sucrose solution containing 250 mM sucrose, 10 mM Tris (pH 7.4), and 1 mM ethylenediaminetetraacetic acid (EDTA), and then homogenized by using a dounce homogenizer, and the supernatant was taken by centrifuging at 600×g for 15 minutes, and centrifuged at 100,000×g for 1 hour to discard the supernatant, and the remaining pellet was resuspended in 20 mM HEPES buffer (pH 7.4). The prepared DGAT2 overexpressing membrane protein was dispensed in 100 μl and stored at −80° C. until use. Protein concentration was quantified by using the BCA Protein Assay Kit (Thermo Scientific).

3. Measurement of Inhibitory Effect Against DGAT2 Enzyme Activity

In vitro DGAT2 analysis was performed using a Phospholipid Flash Plate (PerkinElmer) based on the principle of SPA (Scintilation Proximity Assay). First, DGAT2 inhibition compounds serially diluted 5 times from 3 nM to 10 μM (final concentration, 1% DMSO) were mixed in a buffer solution containing 2 μg DGAT2-membrane protein and 20 mM HEPES, 20 mM $MgCl_2$, 1 mg/mL BSA, 50 μM 1,2 sn-oleoyl glycerol (Sigma), put in a 96-well flash plate (FlashPlate) and reacted at 37° C. for 20 minutes, and then 1 μM [14C] ole oil CoA (PerkinElmer, NEC651050UC) was added to be a final volume of 100 μL and further reacted at 37° C. for 15 minutes. After the enzymatic reaction was completed, 100 μL of isopropanol was added, the plate was sealed with a film, and the plate was shaken slowly in a plate shaker. The next day, the amplified scintillation signal (cpm) in Topcounter (Packard) was measured to measure the degree of production of [14C]-labeled triacyl glycerol (TG) as a reaction product. The measured value when the compound was not treated was used as a positive control, and the measured value of the compound treated group was calculated as a relative % to measure the inhibition effect of the compound on TG production. The $IC_{50}$ value, which is the concentration of the compound that inhibits TG production by 50%, was determined by treating the response value according to the compound concentration with a nonlinear regression curve using PRISM (Graphpad Inc.).

As a result of measuring the inhibition effect on the DGAT2 enzyme action for the compound of formula (1), specific $IC_{50}$ values of the individual Example compounds were as shown in Table 1 below.

TABLE 1

| Example | $IC_{50}$ (μM) |
|---|---|
| 1 | 6.2 |
| 2 | 6.5 |
| 3 | 6.3 |
| 4 | >10 |
| 5 | 13.0 |
| 6 | 10.0 |
| 7 | 8.8 |
| 8 | 0.55 |
| 9 | 2.3 |
| 10 | 0.25 |
| 11 | 0.059 |
| 12 | 3.4 |
| 13 | 0.96 |
| 14 | 3.1 |
| 15 | 7.3 |
| 16 | >10 |
| 17 | 1.3 |
| 18 | 1.1 |
| 19 | 1.7 |

TABLE 1-continued

| Example | $IC_{50}$ (μM) |
|---|---|
| 20 | >10 |
| 21 | >10 |
| 22 | 1.3 |
| 23 | 0.27 |
| 24 | 5.5 |
| 25 | 10 |
| 26 | 6.7 |
| 27 | >10 |
| 28 | >10 |
| 29 | 6.4 |
| 30 | 2.4 |
| 31 | 0.13 |
| 32 | >10 |
| 33 | >10 |
| 34 | >10 |
| 35 | 0.44 |
| 36 | >10 |
| 37 | >10 |
| 38 | >10 |
| 39 | 2.7 |
| 40 | 1.7 |
| 41 | 0.6 |
| 42 | 3.7 |
| 43 | 3.1 |
| 44 | 4 |
| 45 | 0.77 |
| 46 | 1.8 |
| 47 | >10 |
| 48 | 1.8 |
| 49 | >10 |
| 50 | 7.2 |
| 51 | 1.9 |
| 52 | 0.73 |
| 53 | 0.51 |
| 54 | 0.91 |
| 55 | 0.86 |
| 56 | 0.13 |
| 57 | 0.33 |
| 58 | 0.31 |
| 59 | 3.7 |
| 60 | 0.22 |
| 61 | 0.091 |
| 62 | 0.17 |
| 63 | 0.071 |
| 64 | 0.13 |
| 65 | 1.5 |
| 66 | 3.5 |
| 67 | 2.4 |
| 68 | 3.3 |
| 69 | 1.1 |
| 70 | >10 |
| 71 | 0.67 |
| 72 | 0.14 |
| 73 | 0.89 |
| 74 | 0.98 |
| 75 | 0.89 |
| 76 | 0.3 |
| 77 | 0.25 |
| 78 | 0.29 |
| 79 | 0.27 |
| 80 | 0.31 |
| 81 | 0.20 |
| 82 | 0.12 |
| 83 | 0.5 |
| 84 | 0.4 |
| 85 | 0.22 |
| 86 | 0.3 |
| 87 | 0.5 |
| 88 | 1.3 |
| 89 | 1.2 |
| 90 | 1.2 |
| 91 | 0.34 |
| 92 | 0.3 |
| 93 | 0.17 |
| 94 | 0.23 |
| 95 | 0.083 |
| 96 | 0.087 |
| 97 | 0.9 |

TABLE 1-continued

| Example | $IC_{50}$ (μM) |
|---|---|
| 98 | 0.49 |
| 99 | 0.57 |
| 100 | 0.43 |
| 101 | 0.19 |
| 102 | 0.14 |
| 103 | 0.3 |
| 104 | 0.17 |
| 105 | 0.5 |
| 106 | 0.49 |
| 107 | 0.26 |
| 108 | 0.35 |
| 109 | 1.5 |
| 110 | 0.17 |
| 111 | 2.2 |
| 112 | 0.2 |
| 113 | 0.24 |
| 114 | >10 |
| 115 | 0.17 |
| 116 | 0.41 |
| 117 | >10 |
| 118 | 2 |
| 119 | 3.2 |
| 120 | 0.89 |
| 121 | 0.59 |
| 122 | 6.1 |
| 123 | 5.5 |
| 124 | 0.34 |
| 125 | 1.8 |
| 126 | 0.8 |
| 127 | 2.9 |
| 128 | 0.16 |
| 129 | 0.8 |
| 130 | 2.1 |
| 131 | >10 |
| 132 | 6.7 |
| 133 | 3.6 |
| 134 | 0.025 |
| 135 | 0.074 |
| 136 | 0.3 |
| 137 | 0.15 |
| 138 | 0.78 |
| 139 | >10 |
| 140 | 0.15 |
| 141 | 1.6 |
| 142 | 0.38 |
| 143 | 0.2 |
| 144 | 0.23 |
| 145 | 1.7 |
| 146 | 0.39 |
| 147 | 0.15 |
| 148 | 3.1 |
| 149 | 5 |
| 150 | 1.2 |
| 151 | 0.17 |
| 152 | 0.81 |
| 153 | 0.16 |
| 154 | 0.18 |
| 155 | 0.55 |
| 156 | 1.2 |
| 157 | 0.72 |
| 158 | 1.1 |
| 159 | 0.56 |
| 160 | 0.13 |
| 161 | 0.19 |
| 162 | 0.23 |
| 163 | 0.86 |
| 164 | 0.32 |
| 165 | 0.064 |
| 166 | 0.47 |
| 167 | 0.67 |
| 168 | 0.42 |
| 169 | 0.26 |
| 170 | 0.25 |
| 171 | 0.24 |
| 172 | 0.25 |
| 173 | 0.22 |
| 174 | 0.48 |
| 175 | 1.1 |

TABLE 1-continued

| Example | $IC_{50}$ (μM) |
|---|---|
| 176 | 0.59 |
| 177 | 0.38 |
| 178 | 0.49 |
| 179 | 0.59 |

cloalkyl, carboxyalkoxy-heterocycloalkyl, carboxyalkyl-amino-aryl, carboxyalkyl-aryl-oxy or carboxyalkyl-heteroaryl;

wherein the alkyl, alkoxy, cycloalkyl, aryl, heterocycloalkyl, heteroaryl or heteroarylene is optionally substituted with one or more substituents selected from halo, —COOH, alkyl, alkoxy, haloalkyl, alkylsulfonyl and heteroaryl-alkyl; and

The invention claimed is:

1. A compound of the following Formula (1), or a pharmaceutically acceptable salt or stereoisomer:

[Formula (1)]

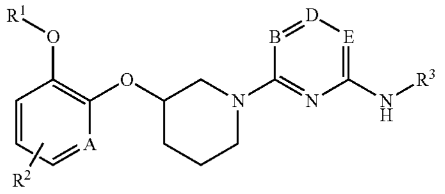

wherein

A and D are each independently CH or N;

B and E are each independently CH, C-halogen, $C_1$-$C_7$-haloalkyl 1 or N;

$R^1$ is $C_1$-$C_{10}$ alkyl, $C_3$-$C_{10}$ cycloalkyl or $C_1$-$C_7$-haloalkyl;

$R^2$ is hydrogen, halogen or $C_1$-$C_{10}$ alkyl;

$R^3$ is -G-J;

wherein G is $C_5$-$C_{12}$ aryl, $C_5$-$C_{12}$ arylene, $C_6$-$C_{10}$ arylene-$C_1$-$C_7$ alkylene, heteroaryl or heteroarylene;

J is hydrogen, amino, aminocarbonyl, alkoxy-alkyl, $C_3$-$C_{10}$ cycloalkyl, cycloalkyl-oxy, heterocycloalkyl, $C_5$-$C_{12}$ aryl, aryl-oxy, aryl-alkoxy, heteroaryl, heteroaryl-amino, carboxy-$C_1$-$C_7$ alkyl, carboxy-$C_2$-$C_7$ alkenyl, carboxyalkyl-aryl, carboxyalkoxy-aryl, carboxyalkyl-heterocycloalkyl, carboxyalkenyl-heterocythe heterocycloalkyl, heteroaryl and heteroarylene are a 3- to 12-membered heterocycloalkyl, heteroaryl and heteroarylene and include one or more heteroatoms selected from N, O and S.

2. The compound, or a pharmaceutically acceptable salt or stereoisomer thereof according to claim 1, wherein A and D are each independently CH or N;

B and E are each independently CH, C-halogen, C-halo-$C_1$-$C_7$ alkyl or N;

$R^1$ is $C_1$-$C_7$ alkyl, $C_3$-$C_7$ cycloalkyl or halo-$C_1$-$C_7$ alkyl;

$R^2$ is hydrogen, halogen or $C_1$-$C_7$ alkyl;

$R^3$ is -G-J;

wherein G is $C_6$-$C_{10}$ aryl, $C_6$-$C_{10}$ arylene, $C_6$-$C_{10}$ arylene-$C_1$-$C_7$ alkylene, 5- to 12-membered heteroaryl or 5- to 12-membered heteroarylene;

J is hydrogen, amino, aminocarbonyl, $C_1$-$C_7$ alkoxy-$C_1$-$C_7$ alkyl, $C_3$-$C_{10}$ cycloalkyl, $C_3$-$C_{10}$ cycloalkyl-oxy, 5- to 12-membered heterocycloalkyl, $C_6$-$C_{10}$ aryl, $C_6$-$C_{10}$ aryl-oxy, $C_6$-$C_{10}$ aryl-$C_1$-$C_7$ alkoxy, 5- to 12-membered heteroaryl, 5- to 12-membered heteroaryl-amino, carboxy-$C_1$-$C_7$ alkyl, carboxy-$C_2$-$C_7$ alkenyl, carboxy-$C_1$-$C_7$ alkyl-$C_6$-$C_{10}$ aryl, carboxy-$C_1$-$C_7$ alkoxy-$C_6$-$C_{10}$ aryl, carboxy-$C_1$-$C_7$ alkyl-5- to 12-membered heterocycloalkyl, carboxy-$C_2$-$C_7$ alkenyl-5- to 12-membered heterocycloalkyl, carboxy-$C_1$-$C_7$ alkoxy-5- to 12-membered heterocycloalkyl, carboxy-$C_1$-$C_7$ alkyl-amino-$C_6$-$C_{10}$ aryl, carboxy-$C_1$-$C_7$ alkyl-$C_6$-$C_{10}$ aryl-oxy or carboxy-$C_1$-$C_7$ alkyl-5- to 12-membered heteroaryl;

wherein the alkyl, alkoxy, cycloalkyl, aryl, heterocycloalkyl, heteroaryl or heteroarylene is optionally substituted with 1 to 4 substituents selected from halo, —COOH, $C_1$-$C_7$ alkyl, $C_1$-$C_7$ alkoxy, halo-$C_1$-$C_7$ alkyl, $C_1$-$C_7$ alkylsulfonyl and 5- to 12-membered heteroaryl-$C_1$-$C_7$ alkyl; and the heterocycloalkyl, heteroaryl and heteroarylene include 1 to 5 heteroatoms selected from N, O and S.

3. The compound, or a pharmaceutically acceptable salt or stereoisomer thereof according to claim 1, wherein the compound is selected from the following group:

(R)-2-((6-(3-(2-ethoxyphenoxy)piperidin-1-yl)pyrazin-2-yl)amino)thiazole-5-carboxylic acid;

(R)—N-(6-(3-(2-ethoxyphenoxy)piperidin-1-yl)pyrazin-2-yl)-4,5-dimethylthiazol-2-amine;

(R)—N-(6-(3-(2-ethoxyphenoxy)piperidin-1-yl)pyrazin-2-yl)thiazol-2-amine;

(R)—N-(6-(3-(2-ethoxyphenoxy)piperidin-1-yl)pyrazin-2-yl)-4-phenylthiazol-2-amine;

(R)—N-(6-(3-(2-ethoxyphenoxy)piperidin-1-yl)pyrazin-2-yl)benzo[d]thiazol-2-amine;

(R)—N-(6-(3-(2-ethoxyphenoxy)piperidin-1-yl)pyrazin-2-yl)-6-methoxybenzo[d]thiazol-2-amine;

(R)—N-(6-(3-(2-ethoxyphenoxy)piperidin-1-yl)pyrazin-2-yl)-6-(methanesulfonyl)benzo[d]thiazol-2-amine;

(R)—N-(6-(3-(2-ethoxyphenoxy)piperidin-1-yl)pyrazin-2-yl)-3-(1-(2-methoxyethoxy)-2-methylpropan-2-yl)isooxazol-5-amine;

(R)—N-(6-(3-(2-ethoxyphenoxy)piperidin-1-yl)pyrazin-2-yl)-4-phenyloxazol-2-amine;

(R)—N-(6-(3-(2-ethoxyphenoxy)piperidin-1-yl)pyrazin-2-yl)benzo[d]oxazol-2-amine;

(R)-5-chloro-N-(6-(3-(2-ethoxyphenoxy)piperidin-1-yl)pyrazin-2-yl)benzo[d]oxazol-2-amine;

(R)-2-(2-((6-(3-(2-ethoxyphenoxy)piperidin-1-yl)pyrazin-2-yl)amino)benzo[d]oxazol-5-yl)acetic acid;

(R)-2-(2-((6-(3-(2-ethoxyphenoxy)piperidin-1-yl)pyrazin-2-yl)amino)benzo[d]oxazol-5-yl)-2-methylpropanoic acid;

(R)-3-(2-((6-(3-(2-ethoxyphenoxy)piperidin-1-yl)pyrazin-2-yl)amino)benzo[d]oxazol-5-yl)-2,2-dimethylpropanoic acid;

(R,E)-3-(2-((6-(3-(2-ethoxyphenoxy)piperidin-1-yl)pyrazin-2-yl)amino)benzo[d]oxazol-5-yl)acrylic acid;

(R)-3-(2-((6-(3-(2-ethoxyphenoxy)piperidin-1-yl)pyrazin-2-yl)amino)benzo[d]oxazol-5-yl)propanoic acid;

(R)-2-(2-((6-(3-(2-ethoxyphenoxy)piperidin-1-yl)pyrazin-2-yl)amino)benzo[d]oxazol-6-yl)-2-methylpropanoic acid;

(R)-3-(2-((6-(3-(2-ethoxyphenoxy)piperidin-1-yl)pyrazin-2-yl)amino)benzo[d]oxazol-6-yl)propanoic acid;

(R)-6-(3-(2-ethoxyphenoxy)piperidin-1-yl)-N-(1H-pyrazol-3-yl)pyrazin-2-amine;

(R)-2-(3-((6-(3-(2-ethoxyphenoxy)piperidin-1-yl)pyrazin-2-yl)amino)-1H-pyrazol-1-yl)acetic acid;

(R)-3-(3-((6-(3-(2-ethoxyphenoxy)piperidin-1-yl)pyrazin-2-yl)amino)-1H-pyrazol-1-yl)-2,2-dimethylpropanoic acid;

(R)-3-(3-(6-((4-(3-(2-ethoxyphenoxy)piperidin-1-yl)-5-fluoropyrimidin-2-yl)amino)pyridin-2-yl)phenyl)-2,2-dimethylpropanoic acid;

(R)-6-(3-(2-ethoxyphenoxy)piperidin-1-yl)-N-(1-methyl-1H-tetrazol-5-yl)pyrazin-2-amine;

(R)—N-6-(3-(2-ethoxyphenoxy)piperidin-1-yl)-N-phenylpyrazin-2-amine;

(R)—N-(4-((6-(3-(2-ethoxyphenoxy)piperidin-1-yl)pyrazin-2-yl)amino)phenyl)methanesulfonamide;

(R)-2-(4-((6-(3-(2-ethoxyphenoxy)piperidin-1-yl)pyrazin-2-yl)amino)phenyl)-N-(pyridin-4-ylmethyl)acetamide;

(R)-2-(4-((6-(3-(2-ethoxyphenoxy)piperidin-1-yl)pyrazin-2-yl)amino)phenyl)-2-methylpropanoic acid;

(R)-2-(4-((6-(3-(2-ethoxyphenoxy)pyridin-1-yl)pyrazin-2-yl)amino)phenyl)-2-methylpropanoic acid;

(R)-2-(3-((6-(3-(2-ethoxyphenoxy)piperidin-1-yl)pyrazin-2-yl)amino)phenyl)-2-methylpropanoic acid;

(R)-3-(3'-((6-(3-(2-ethoxyphenoxy)piperidin-1-yl)pyrazin-2-yl)amino)-[1,1'-biphenyl]-4-yl)-2,2-dimethylpropanoic acid;

(R)-6-(3-(2-ethoxyphenoxy)piperidin-1-yl)-N-(pyridin-2-yl)pyrazin-2-amine;

(R)-6-((6-(3-(2-ethoxyphenoxy)piperidin-1-yl)pyrazin-2-yl)amino)nicotinic acid;

(R)-2-((6-(3-(2-ethoxyphenoxy)piperidin-1-yl)pyrazin-2-yl)amino)isonicotinic acid;

(R)-2-((6-(3-(2-ethoxyphenoxy)piperidin-1-yl)pyrazin-2-yl)amino)nicotinic acid;

(R)-2-(2-((6-(3-(2-ethoxyphenoxy)piperidin-1-yl)pyrazin-2-yl)amino)pyridin-4-yl)-2-methylpropanoic acid;

(R)-2-(6-((6-(3-(2-ethoxyphenoxy)piperidin-1-yl)pyrazin-2-yl)amino)pyridin-3-yl)acetic acid;

(R,E)-3-(6-((6-(3-(2-ethoxyphenoxy)piperidin-1-yl)pyrazin-2-yl)amino)pyridin-3-yl)acrylic acid;

(R)-3-(6-((6-(3-(2-ethoxyphenoxy)piperidin-1-yl)pyrazin-2-yl)amino)pyridin-3-yl)propanoic acid;

(R)-3-(2-((6-(3-(2-ethoxyphenoxy)piperidin-1-yl)pyrazin-2-yl)amino)pyridin-4-yl)-2,2-dimethylpropanoic acid;

(R)-6-(3-(2-ethoxyphenoxy)piperidin-1-yl)-N-(5-phenylpyridin-2-yl)pyrazin-2-amine;

(R)-6-(3-(2-ethoxyphenoxy)piperidin-1-yl)-N-(4-phenylpyridin-2-yl)pyrazin-2-amine;

(R)-2-(3-(2-((6-(3-(2-ethoxyphenoxy)piperidin-1-yl)pyrazin-2-yl)amino)pyridin-4-yl)phenyl)-2-methylpropanoic acid;

(R)-2-(3-(2-((6-(3-(2-ethoxyphenoxy)piperidin-1-yl)pyrazin-2-yl)amino)pyridin-4-yl)phenyl)-2-methylpropanoic acid;

(R)-3-(3-(2-((6-(3-(2-ethoxyphenoxy)piperidin-1-yl)pyrazin-2-yl)amino)pyridin-4-yl)phenyl)-2,2-dimethylpropanoic acid;

(R)-3-(4-(2-((6-(3-(2-ethoxyphenoxy)piperidin-1-yl)pyrazin-2-yl)amino)pyridin-4-yl)phenyl)-2,2-dimethylpropanoic acid;

(R)-3-(3-(2-((6-(3-(2-ethoxyphenoxy)piperidin-1-yl)pyrazin-2-yl)amino)pyridin-4-yl)phenyl)propanoic acid;

(R)-3-(3-(5-((6-(3-(2-ethoxyphenoxy)piperidin-1-yl)pyrazin-2-yl)amino)pyridin-3-yl)phenyl)-2,2-dimethylpropanoic acid;

(R)-3-(3-(5-((6-(3-(2-ethoxyphenoxy)piperidin-1-yl)pyrazin-2-yl)amino)pyridin-2-yl)phenyl)-2,2-dimethylpropanoic acid;

(R)-2-(6-((6-(3-(2-ethoxyphenoxy)piperidin-1-yl)pyrazin-2-yl)amino)pyridin-3-yl)phenyl)-2-methylpropanoic acid;

(R)-2-(6-((6-(3-(2-ethoxyphenoxy)piperidin-1-yl)pyrazin-2-yl)amino)pyridin-2-yl)-2-methylpropanoic acid;

(R)-3-(6-((6-(3-(2-ethoxyphenoxy)piperidin-1-yl)pyrazin-2-yl)amino)pyridin-2-yl)-2,2-dimethylpropanoic acid;

1-(6-((6-((R)-3-(2-ethoxyphenoxy)piperidin-1-yl)pyrazin-2-yl)amino)pyridin-2-yl)pyrrolidine-3-carboxylic acid;
1-(6-((6-((R)-3-(2-ethoxyphenoxy)piperidin-1-yl)pyrazin-2-yl)amino)pyridin-2-yl)-3-methylpyrrolidine-3-carboxylic acid;
1-(6-((6-((R)-3-(2-ethoxyphenoxy)piperidin-1-yl)pyrazin-2-yl)amino)pyridin-2-yl)piperidine-3-carboxylic acid;
(R)-1-(6-((6-((R)-3-(2-ethoxyphenoxy)piperidin-1-yl)pyrazin-2-yl)amino)pyridin-2-yl)piperidine-3-carboxylic acid;
(R)-1-(6-((6-(3-(2-ethoxyphenoxy)piperidin-1-yl)pyrazin-2-yl)amino)pyridin-2-yl)piperidine-4-carboxylic acid;
(R)-2-(1-(6-((6-(3-(2-ethoxyphenoxy)piperidin-1-yl)pyrazin-2-yl)amino)pyridin-2-yl)piperidin-4-yl)acetic acid;
(R)-2-(1-(6-((6-(3-(2-ethoxyphenoxy)piperidin-1-yl)pyrazin-2-yl)amino)pyridin-2-yl)piperidin-4-yl)-2-methylpropanoic acid;
2-(((S)-1-(6-((6-((R)-3-(2-ethoxyphenoxy)piperidin-1-yl)pyrazin-2-yl)amino)pyridin-2-yl)piperidin-3-yl)acetic acid;
(R)-2-(3-(6-((6-(3-(2-ethoxyphenoxy)piperidin-1-yl)pyrazin-2-yl)amino)pyridin-2-yl)phenyl)-2-methylpropanoic acid;
(R)-2-(4-(6-((6-(3-(2-ethoxyphenoxy)piperidin-1-yl)pyrazin-2-yl)amino)pyridin-2-yl)phenyl)-2-methylpropanoic acid;
(R)-2-(4-(6-((6-(3-((3-ethoxypyridin-2-yl)oxy)piperidin-1-yl)pyrazin-2-yl)amino)pyridin-2-yl)phenyl)-2-methylpropanoic acid;
(R)-3-(3-(6-((6-(3-(2-ethoxyphenoxy)piperidin-1-yl)pyrazin-2-yl)amino)pyridin-2-yl)phenyl)-2,2-dimethylpropanoic acid;
(R)-3-(3-(6-((6-(3-((3-ethoxypyridin-2-yl)oxy)piperidin-1-yl)pyrazin-2-yl)amino)pyridin-2-yl)phenyl)-2,2-dimethylpropanoic acid;
(R)-3-(3-(6-((6-(3-(2-ethoxyphenoxy)piperidin-1-yl)pyridin-2-yl)amino)pyridin-2-yl)phenyl)-2,2-dimethylpropanoic acid;
(R)-3-(3-(6-((2-(3-(2-ethoxyphenoxy)piperidin-1-yl)pyrimidin-4-yl)amino)pyridin-2-yl)phenyl)-2,2-dimethylpropanoic acid;
(R)-3-(3-(6-((6-(3-(2-ethoxyphenoxy)piperidin-1-yl)pyrimidin-2-yl)amino)pyridin-2-yl)phenyl)-2,2-dimethylpropanoic acid;
(R)-3-(3-(6-((4-(3-((3-ethoxypyridin-2-yl)oxy)piperidin-1-yl)pyrimidin-2-yl)amino)pyridin-2-yl)phenyl)-2,2-dimethylpropanoic acid;
(R)-3-(3-((6-(3-(2-ethoxyphenoxy)piperidin-1-yl)pyrazin-2-yl)amino)-1H-pyrazol-1-yl)phenyl)-2,2-dimethylpropanoic acid;
(R)-3-(3-(6-((2-(3-(2-ethoxyphenoxy)piperidin-1-yl)-5-(trifluoromethyl)pyrimidin-4-yl)amino)pyridin-2-yl)phenyl)-2,2-dimethylpropanoic acid;
(R)-3-(3-(6-((4-(3-(2-ethoxyphenoxy)piperidin-1-yl)-5-(trifluoromethyl)pyrimidin-2-yl)amino)pyridin-2-yl)phenyl)-2,2-dimethylpropanoic acid;
(R)-3-(4-(6-((6-(3-(2-ethoxyphenoxy)piperidin-1-yl)pyrazin-2-yl)amino)pyridin-2-yl)phenyl)-2,2-dimethylpropanoic acid;
(R)-(4-(6-((6-(3-(2-ethoxyphenoxy)piperidin-1-yl)pyrazin-2-yl)amino)pyridin-2-yl)phenyl)glycine;
(R)-(4-(6-((6-(3-((3-ethoxypyridin-2-yl)oxy)piperidin-1-yl)pyrazin-2-yl)amino)pyridin-2-yl)phenyl)glycine;
(R)-(4-(6-((2-(3-(2-ethoxyphenoxy)piperidin-1-yl)pyrimidin-4-yl)amino)pyridin-2-yl)phenyl)glycine;
(R)-(4-(6-((4-(3-(2-ethoxyphenoxy)piperidin-1-yl)pyrazin-2-yl)amino)pyridin-2-yl)phenyl)glycine;
(R)-2-((4-(6-((6-(3-(2-ethoxyphenoxy)piperidin-1-yl)pyrazin-2-yl)amino)pyridin-2-yl)phenyl)amino)-2-methylpropanoic acid;
(R)-3-(3-(6-((6-(3-(2-ethoxyphenoxy)piperidin-1-yl)pyrazin-2-yl)amino)pyridin-2-yl)-4-fluorophenyl)-2,2-dimethylpropanoic acid;
(R)-3-(3-(6-((6-(3-((3-ethoxypyridin-2-yl)oxy)piperidin-1-yl)pyrazin-2-yl)amino)pyridin-2-yl)-4-fluorophenyl)-2,2-dimethylpropanoic acid;
(R)-2-(3-(6-((6-(3-(2-ethoxyphenoxy)piperidin-1-yl)pyrazin-2-yl)amino)pyridin-2-yl)phenoxy)-2-methylpropanoic acid;
(R)-2-(3-(6-((6-(3-((3-ethoxypyridin-2-yl)oxy)piperidin-1-yl)pyrazin-2-yl)amino)pyridin-2-yl)phenoxy)-2-methylpropanoic acid;
(R)-2-(4-(6-((6-(3-(2-ethoxyphenoxy)piperidin-1-yl)pyrazin-2-yl)amino)pyridin-2-yl)phenoxy)-2-methylpropanoic acid;
(R)-2-(4-(6-((6-(3-((3-ethoxypyridin-2-yl)oxy)piperidin-1-yl)pyrazin-2-yl)amino)pyridin-2-yl)phenoxy)-2-methylpropanoic acid;
(R)-2-(3-(6-((6-(3-(2-ethoxyphenoxy)piperidin-1-yl)pyrazin-2-yl)amino)pyridin-2-yl)-4-fluorophenoxy)-2-methylpropanoic acid;
(R)-2-(3-(6-((6-(3-((3-ethoxypyridin-2-yl)oxy)piperidin-1-yl)pyrazin-2-yl)amino)pyridin-2-yl)-4-fluorophenoxy)-2-methylpropanoic acid;
(R)-3-(4-(6-((6-(3-(2-ethoxyphenoxy)piperidin-1-yl)pyrazin-2-yl)amino)pyridin-2-yl)-1H-pyrazol-1-yl)-2,2-dimethylpropanoic acid;
(R)-3-((6-((6-(3-(2-ethoxyphenoxy)piperidin-1-yl)pyrazin-2-yl)amino)pyridin-2-yl)oxy)benzoic acid;
(R)-3-((6-((6-(3-((3-ethoxypyridin-2-yl)oxy)piperidin-1-yl)pyrazin-2-yl)amino)pyridin-2-yl)oxy)benzoic acid;
(R)-4-((6-((6-(3-(2-ethoxyphenoxy)piperidin-1-yl)pyrazin-2-yl)amino)pyridin-2-yl)oxy)benzoic acid;
(R)-4-((6-((6-(3-((3-ethoxypyridin-2-yl)oxy)piperidin-1-yl)pyrazin-2-yl)amino)pyridin-2-yl)oxy)benzoic acid;
(R)-2-(3-((6-((6-(3-(2-ethoxyphenoxy)piperidin-1-yl)pyrazin-2-yl)amino)pyridin-2-yl)oxy)phenyl)-2-methylpropanoic acid;
(R)-2-(3-((6-((6-(3-((3-ethoxypyridin-2-yl)oxy)piperidin-1-yl)pyrazin-2-yl)amino)pyridin-2-yl)oxy)phenyl)-2-methylpropanoic acid;
(R)-2-(4-((6-((6-(3-(2-ethoxyphenoxy)piperidin-1-yl)pyrazin-2-yl)amino)pyridin-2-yl)oxy)phenyl)-2-methylpropanoic acid;
(R)-2-(4-((6-((6-(3-((3-ethoxypyridin-2-yl)oxy)piperidin-1-yl)pyrazin-2-yl)amino)pyridin-2-yl)oxy)phenyl)-2-methylpropanoic acid;
(R)-2-(3-((6-((6-(3-(2-ethoxyphenoxy)piperidin-1-yl)pyrazin-2-yl)amino)pyridin-2-yl)oxy)phenyl)acetic acid;
(R)-2-(3-((6-((6-(3-((3-ethoxypyridin-2-yl)oxy)piperidin-1-yl)pyrazin-2-yl)amino)pyridin-2-yl)oxy)phenyl)acetic acid;
(R)-2-(4-((6-((6-(3-(2-ethoxyphenoxy)piperidin-1-yl)pyrazin-2-yl)amino)pyridin-2-yl)oxy)phenyl)acetic acid;
(R)-2-(4-((6-((6-(3-((3-ethoxypyridin-2-yl)oxy)piperidin-1-yl)pyrazin-2-yl)amino)pyridin-2-yl)oxy)phenyl)acetic acid;

(R)-4-(((6-((6-(3-(2-ethoxyphenoxy)piperidin-1-yl)pyrazin-2-yl)amino)pyridin-2-yl)oxy)methyl)benzoic acid;
(R)-3-(3-(6-((6-(3-(2-ethoxyphenoxy)piperidin-1-yl)pyrazin-2-yl)amino)-5-fluoropyridin-2-yl)phenyl)-2,2-dimethylpropanoic acid;
(R)-3-(3-(6-((6-(3-((3-ethoxypyridin-2-yl)oxy)piperidin-1-yl)pyrazin-2-yl)amino)-5-fluoropyridin-2-yl)phenyl)-2,2-dimethylpropanoic acid;
(R)-3-(3-(6-((6-(3-(2-ethoxyphenoxy)piperidin-1-yl)pyrazin-2-yl)amino)-3-fluoropyridin-2-yl)phenyl)-2,2-dimethylpropanoic acid;
(R)-3-(3-(6-((6-(3-((3-ethoxypyridin-2-yl)oxy)piperidin-1-yl)pyrazin-2-yl)amino)-3-fluoropyridin-2-yl)phenyl)-2,2-dimethylpropanoic acid;
(R)-2-(3-(6-((6-(3-((3-ethoxypyridin-2-yl)oxy)piperidin-1-yl)pyrazin-2-yl)amino)-5-fluoropyridin-2-yl)phenoxy)-2-methylpropanoic acid;
(R)-2-(3-(6-((6-(3-((3-ethoxypyridin-2-yl)oxy)piperidin-1-yl)pyrazin-2-yl)amino)-3-fluoropyridin-2-yl)phenoxy)-2-methylpropanoic acid;
(R)-3-(3-(6-((6-(3-((3-ethoxypyridin-2-yl)oxy)piperidin-1-yl)pyrazin-2-yl)amino)-3-fluoropyridin-2-yl)-4-fluorophenyl)-2,2-dimethylpropanoic acid;
(R)-3-(3-(6-((6-(3-(2-ethoxyphenoxy)piperidin-1-yl)pyrazin-2-yl)amino)-5-fluoropyridin-2-yl)-4-fluorophenyl)-2,2-dimethylpropanoic acid;
(R)-3-(3-(6-((6-(3-((3-ethoxypyridin-2-yl)oxy)piperidin-1-yl)pyrazin-2-yl)amino)-5-fluoropyridin-2-yl)-4-fluorophenyl)-2,2-dimethylpropanoic acid;
(R)-2-(4-(6-((6-(3-(2-ethoxyphenoxy)piperidin-1-yl)pyrazin-2-yl)amino)-3-(trifluoromethyl)pyridin-2-yl)phenyl)-2-methylpropanoic acid;
(R)-3-(3-(6-((6-(3-(2-ethoxyphenoxy)piperidin-1-yl)pyrazin-2-yl)amino)-4-(trifluoromethyl)pyridin-2-yl)phenyl)-2,2-dimethylpropanoic acid;
(R)-3-(3-(6-((6-(3-(2-ethoxyphenoxy)piperidin-1-yl)pyrazin-2-yl)amino)-3-methylpyridin-2-yl)phenyl)-2,2-dimethylpropanoic acid;
(R)-3-(3-(6-((6-(3-(2-ethoxyphenoxy)piperidin-1-yl)pyrazin-2-yl)amino)pyrazin-2-yl)phenyl)-2,2-dimethylpropanoic acid;
(R)—N-(6-(3-(2-ethoxyphenoxy)piperidin-1-yl)pyrazin-2-yl)pyrimidin-2-amine;
(R)-2-((6-(3-(2-ethoxyphenoxy)piperidin-1-yl)pyrazin-2-yl)amino)pyrimidine-5-carboxylic acid;
(R)-2-(2-((6-(3-(2-ethoxyphenoxy)piperidin-1-yl)pyrazin-2-yl)pyrimidin-4-yl)-2-methylpropanoic acid;
(R)-2-(2-((4-(3-((3-ethoxypyridin-2-yl)oxy)piperidin-1-yl)pyrimidin-2-yl)pyrimidin-4-yl)-2-methylpropanoic acid;
(2-((6-((R)-3-(2-ethoxyphenoxy)piperidin-1-yl)pyrazin-2-yl)amino)pyrimidin-4-yl)-L-proline;
1-(2-((6-((R)-3-(2-ethoxyphenoxy)piperidin-1-yl)pyrazin-2-yl)amino)pyrimidin-4-yl)pyrrolidine-3-carboxylic acid;
1-(2-((6-((R)-3-(2-ethoxyphenoxy)piperidin-1-yl)pyrazin-2-yl)amino)pyrimidin-4-yl)-3-methylpyrrolidine-3-carboxylic acid;
1-(2-((6-((R)-3-(2-ethoxyphenoxy)piperidin-1-yl)pyrazin-2-yl)amino)pyrimidin-4-yl)piperidine-3-carboxylic acid;
(R)-1-(2-((6-((R)-3-(2-ethoxyphenoxy)piperidin-1-yl)pyrazin-2-yl)amino)pyrimidin-4-yl)piperidine-3-carboxylic acid;
1-(2-((6-((R)-3-(2-ethoxyphenoxy)piperidin-1-yl)pyrazin-2-yl)amino)pyrimidin-4-yl)-3-methylpiperidine-3-carboxylic acid;
(R)-1-(2-((6-(3-(2-ethoxyphenoxy)piperidin-1-yl)pyrazin-2-yl)amino)pyrimidin-4-yl)piperidine-4-carboxylic acid;
5-(2-((6-((R)-3-(2-ethoxyphenoxy)piperidin-1-yl)pyrazin-2-yl)amino)pyrimidin-4-yl)bicyclo[2.2.1]heptane-2-carboxylic acid;
(R)-2-(1-(2-((6-(3-(2-ethoxyphenoxy)piperidin-1-yl)pyrazin-2-yl)amino)pyrimidin-4-yl)piperidin-4-yl)acetic acid;
(R)-2-(1-(2-((6-(3-(2-ethoxyphenoxy)piperidin-1-yl)pyrazin-2-yl)amino)pyrimidin-4-yl)piperidin-4-yl)-2-methylpropanoic acid;
(R)-2-(4-(2-((6-(3-(2-ethoxyphenoxy)piperidin-1-yl)pyrazin-2-yl)amino)pyrimidin-4-yl)piperazin-1-yl)acetic acid;
2-((S)-1-(2-((6-((R)-3-(2-ethoxyphenoxy)piperidin-1-yl)pyrazin-2-yl)amino)pyrimidin-4-yl)piperidin-3-yl)acetic acid;
(E)-3-((S)-1-(2-((6-((R)-3-(2-ethoxyphenoxy)piperidin-1-yl)pyrazin-2-yl)amino)pyrimidin-4-yl)piperidin-3-yl)acrylic acid;
3-((S)-1-(2-((6-((R)-3-(2-ethoxyphenoxy)piperidin-1-yl)pyrazin-2-yl)amino)pyrimidin-4-yl)piperidin-3-yl)propanoic acid;
2-(((S)-1-(2-((6-((R)-3-(2-ethoxyphenoxy)piperidin-1-yl)pyrazin-2-yl)amino)pyrimidin-4-yl)piperidin-3-yl)oxy)acetic acid;
2-(((R)-1-(2-((6-((R)-3-(2-ethoxyphenoxy)piperidin-1-yl)pyrazin-2-yl)amino)pyrimidin-4-yl)piperidin-3-yl)oxy)acetic acid;
2-(((R)-1-(2-((6-((R)-3-(2-ethoxyphenoxy)piperidin-1-yl)pyrazin-2-yl)amino)pyrimidin-4-yl)piperidin-3-yl)oxy)-2-methylpropanoic acid;
(R)-4-(2-((6-(3-(2-ethoxyphenoxy)piperidin-1-yl)pyrazin-2-yl)amino)pyrimidin-4-yl)oxy)cyclohexane-1-carboxylic acid;
(1R,4r)-4-((2-((6-((R)-3-(2-ethoxyphenoxy)piperidin-1-yl)pyrazin-2-yl)amino)pyrimidin-4-yl)oxy)cyclohexane-1-carboxylic acid;
(1R,4r)-4-((2-((6-((R)-3-((3-ethoxypyridin-2-yl)oxy)piperidin-1-yl)pyrazin-2-yl)amino)pyrimidin-4-yl)oxy)cyclohexane-1-carboxylic acid;
(1S,4s)-4-((2-((6-((R)-3-(2-ethoxyphenoxy)piperidin-1-yl)pyrazin-2-yl)amino)pyrimidin-4-yl)oxy)cyclohexane-1-carboxylic acid;
(1S,4s)-4-((2-((6-((R)-3-((3-ethoxypyridin-2-yl)oxy)piperidin-1-yl)pyrazin-2-yl)amino)pyrimidin-4-yl)oxy)cyclohexane-1-carboxylic acid;
(R)-6-(2-((6-(3-(2-ethoxyphenoxy)piperidin-1-yl)pyrazin-2-yl)amino)pyrimidin-4-yl)picolinic acid;
(R)-2-(3-(2-((6-(3-(2-ethoxyphenoxy)piperidin-1-yl)pyrazin-2-yl)amino)pyrimidin-4-yl)phenyl)acetic acid;
(R)-2-(3-(2-((6-(3-(2-ethoxyphenoxy)piperidin-1-yl)pyrazin-2-yl)amino)pyrimidin-4-yl)phenyl)-2-methylpropanoic acid;
(R)-2-(3-(2-((6-(3-((3-ethoxypyridin-2-yl)oxy)piperidin-1-yl)pyrazin-2-yl)amino)pyrimidin-4-yl)phenyl)-2-methylpropanoic acid;
(R)-2-(4-(2-((6-(3-(2-ethoxyphenoxy)piperidin-1-yl)pyrazin-2-yl)amino)pyrimidin-4-yl)phenyl)-2-methylpropanoic acid;
(R)-2-(4-(2-((6-(3-((3-ethoxypyridin-2-yl)oxy)piperidin-1-yl)pyrazin-2-yl)amino)pyrimidin-4-yl)phenyl)-2-methylpropanoic acid;

(R)-3-(3-(2-((6-(3-(2-ethoxyphenoxy)piperidin-1-yl)pyrazin-2-yl)amino)pyrimidin-4-yl)phenyl)propanoic acid;

(R)-3-(3-(2-((6-(3-(2-ethoxyphenoxy)piperidin-1-yl)pyrazin-2-yl)amino)pyrimidin-4-yl)phenyl)-2,2-dimethylpropanoic acid;

(R)-3-(3-(2-((6-(3-((3-ethoxypyridin-2-yl)oxy)piperidin-1-yl)pyrazin-2-yl)amino)pyrimidin-4-yl)phenyl)-2,2-dimethylpropanoic acid;

(R)-3-(3-(2-((6-(3-(2-ethoxyphenoxy)piperidin-1-yl)pyridin-2-yl)amino)pyrimidin-4-yl)phenyl)-2,2-dimethylpropanoic acid;

(R)-3-(3-(2-((2-(3-(2-ethoxyphenoxy)piperidin-1-yl)pyrimidin-4-yl)amino)pyrimidin-4-yl)phenyl)-2,2-dimethylpropanoic acid;

(R)-3-(3-(2-((4-(3-(2-ethoxyphenoxy)piperidin-1-yl)pyrimidin-2-yl)amino)pyrimidin-4-yl)phenyl)-2,2-dimethylpropanoic acid;

(R)-2-(4-(2-((6-(3-(2-ethoxyphenoxy)piperidin-1-yl)pyrazin-2-yl)amino)pyrimidin-4-yl)phenyl)acetic acid;

(R)-2-(4-(2-((6-(3-((3-ethoxypyridin-2-yl)oxy)piperidin-1-yl)pyrazin-2-yl)amino)pyrimidin-4-yl)phenyl)acetic acid;

(R)-3-(4-(2-((6-(3-(2-ethoxyphenoxy)piperidin-1-yl)pyrazin-2-yl)amino)pyrimidin-4-yl)phenyl)-2,2-dimethylpropanoic acid;

(R)-3-(4-(2-((6-(3-((3-ethoxypyridin-2-yl)oxy)piperidin-1-yl)pyrazin-2-yl)amino)pyrimidin-4-yl)phenyl)-2,2-dimethylpropanoic acid;

(R)-3-(4-(2-((2-(3-(2-ethoxyphenoxy)piperidin-1-yl)pyrimidin-4-yl)amino)pyrimidin-4-yl)phenyl)-2,2-dimethylpropanoic acid;

(R)-3-(4-(2-((4-(3-(2-ethoxyphenoxy)piperidin-1-yl)pyrimidin-2-yl)amino)pyrimidin-4-yl)phenyl)-2,2-dimethylpropanoic acid;

(R)-3-(4-(2-((4-(3-((3-ethoxypyridin-2-yl)oxy)piperidin-1-yl)pyrimidin-2-yl)amino)pyrimidin-4-yl)phenyl)-2,2-dimethylpropanoic acid;

(R)-2-(3-(2-((6-(3-(2-ethoxyphenoxy)piperidin-1-yl)pyrazin-2-yl)amino)pyrimidin-4-yl)phenoxy)-2-methylpropanoic acid;

(R)-2-(3-(2-((6-(3-((3-ethoxypyridin-2-yl)oxy)piperidin-1-yl)pyrazin-2-yl)amino)pyrimidin-4-yl)phenoxy)-2-methylpropanoic acid;

(R)-2-(4-(2-((6-(3-(2-ethoxyphenoxy)piperidin-1-yl)pyrazin-2-yl)amino)pyrimidin-4-yl)phenoxy)-2-methylpropanoic acid;

(R)-2-((4-(2-((6-(3-(2-ethoxyphenoxy)piperidin-1-yl)pyrazin-2-yl)amino)pyrimidin-4-yl)phenyl)amino)-2-methylpropanoic acid;

(R)-2-(4-((2-((6-(3-(2-ethoxyphenoxy)piperidin-1-yl)pyrazin-2-yl)amino)pyrimidin-4-yl)oxy)phenyl)acetic acid;

(R)-2-(4-((2-((6-(3-((3-ethoxypyridin-2-yl)oxy)piperidin-1-yl)pyrazin-2-yl)amino)pyrimidin-4-yl)phenyl)acetic acid;

(R)-3-(3-(2-((6-(3-(2-ethoxyphenoxy)piperidin-1-yl)pyrazin-2-yl)amino)-5-fluoropyrimidin-4-yl)phenyl)-2,2-dimethylpropanoic acid;

(R)-3-(3-(2-((6-(3-((3-ethoxypyridin-2-yl)oxy)piperidin-1-yl)pyrazin-2-yl)amino)-5-(trifluoromethyl)pyrimidin-4-yl)phenyl)-2,2-dimethylpropanoic acid;

(R)-3-(3-(2-((6-(3-((3-ethoxypyridin-2-yl)oxy)piperidin-1-yl)pyrazin-2-yl)amino)-6-(trifluoromethyl)pyrimidin-4-yl)phenyl)-2,2-dimethylpropanoic acid;

(R)-3-(3-(2-((6-(3-(2-ethoxyphenoxy)piperidin-1-yl)pyrazin-2-yl)amino)-6-(trifluoromethyl)pyrimidin-4-yl)phenyl)-2,2-dimethylpropanoic acid;

(R)-2-(3-(4-((6-(3-(2-ethoxyphenoxy)piperidin-1-yl)pyrazin-2-yl)amino)pyrimidin-2-yl)phenyl)-2-methylpropanoic acid;

(R)-2-(4-(4-((6-(3-(2-ethoxyphenoxy)piperidin-1-yl)pyrazin-2-yl)amino)pyrimidin-2-yl)phenyl)-2-methylpropanoic acid;

(R)-3-(3-(4-((6-(3-(2-ethoxyphenoxy)piperidin-1-yl)pyrazin-2-yl)amino)pyrimidin-2-yl)phenyl)-2,2-dimethylpropanoic acid;

(R)-3-(3-(4-((6-(3-((3-ethoxypyridin-2-yl)oxy)piperidin-1-yl)pyrazin-2-yl)amino)pyrimidin-2-yl)phenyl)-2,2-dimethylpropanoic acid;

(R)-3-(4-(4-((6-(3-(2-ethoxyphenoxy)piperidin-1-yl)pyrazin-2-yl)amino)pyrimidin-2-yl)phenyl)-2,2-dimethylpropanoic acid;

(R)-3-(4-(4-((6-(3-((3-ethoxypyridin-2-yl)oxy)piperidin-1-yl)pyrazin-2-yl)amino)pyrimidin-2-yl)phenyl)-2,2-dimethylpropanoic acid;

(R)-2-(3-(4-((6-(3-(2-ethoxyphenoxy)piperidin-1-yl)pyrazin-2-yl)amino)pyrimidin-2-yl)phenoxy)-2-methylpropanoic acid;

(R)-2-(3-(4-((6-(3-((3-ethoxypyridin-2-yl)oxy)piperidin-1-yl)pyrazin-2-yl)amino)pyrimidin-2-yl)phenoxy)-2-methylpropanoic acid;

(R)-2-(3-(2-((6-(3-(2-ethoxyphenoxy)piperidin-1-yl)pyrazin-2-yl)amino)pyrimidin-4-yl)phenoxy)-2-methylpropanoic acid;

(R)-2-(4-(6-((6-(3-(2-ethoxy-4-fluorophenoxy)piperidin-1-yl)pyrazin-2-yl)amino)pyridin-2-yl)phenoxy)-2-methylpropanoic acid;

(R)-2-(4-(4-((6-(3-(2-ethoxyphenoxy)piperidin-1-yl)pyrazin-2-yl)amino)pyrimidin-2-yl)phenoxy)-2-methylpropanoic acid; and (R)-2-(4-(4-((6-(3-((3-ethoxypyridin-2-yl)oxy)piperidin-1-yl)pyrazin-2-yl)amino)pyrimidin-2-yl)phenoxy)-2-methylpropanoic acid.

4. A pharmaceutical composition comprising an effective amount of the compound of Formula (1), or a pharmaceutically acceptable salt or stereoisomer thereof as defined in claim 1 as an active ingredient, together with a pharmaceutically acceptable carrier.

5. A method of treating a metabolic disease associated with DGAT2, comprising administering the pharmaceutical composition of claim 4 to a subject in need thereof, wherein the metabolic disease associated with DGAT2 is selected from the group consisting of fatty liver, nonalcoholic steatohepatitis (NASH), nonalcoholic fatty liver disease (NAFLD), diabetes, obesity, hyperlipidemia, atherosclerosis and hypercholesterolemia.

* * * * *

SEQUENCE LISTING

<160> NUMBER OF SEQ ID NOS: 2

<210> SEQ ID NO 1
<211> LENGTH: 73
<212> TYPE: DNA
<213> ORGANISM: Artificial Sequence
<220> FEATURE:
<223> OTHER INFORMATION: forward primer

<400> SEQUENCE: 1
ctataaatac ggatcccggg aattcatgga ctacaaggac gacgatgaca agcttaagac 60
cctcatagcc gcc 73

<210> SEQ ID NO 2
<211> LENGTH: 44
<212> TYPE: DNA
<213> ORGANISM: Artificial Sequence
<220> FEATURE:
<223> OTHER INFORMATION: reverse primer

<400> SEQUENCE: 2
taagcggccg ccctgcaggc ctcgagtcag ttcacctcca ggac 44